US012383688B2

(12) United States Patent
Galgali et al.

(10) Patent No.: US 12,383,688 B2
(45) Date of Patent: Aug. 12, 2025

(54) NASAL SEAL, MASK AND RESPIRATORY INTERFACE ASSEMBLY

(71) Applicant: Fisher & Paykel Healthcare Limited, Auckland (NZ)

(72) Inventors: Amit Galgali, Auckland (NZ); Bruno Sintive, Auckland (NZ); Callum Ross Gordon, Auckland (NZ); Mark Andrew Thompson, Auckland (NZ); Ryan Anthony Graham, Auckland (NZ); Mark Arvind McLaren, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1117 days.

(21) Appl. No.: 17/237,659

(22) Filed: Apr. 22, 2021

(65) Prior Publication Data

US 2021/0244905 A1 Aug. 12, 2021

Related U.S. Application Data

(63) Continuation of application No. 15/757,148, filed as application No. PCT/IB2016/055369 on Sep. 9, 2016, now Pat. No. 11,013,877.

(Continued)

(51) Int. Cl.
*A61M 16/06* (2006.01)
*A61M 16/08* (2006.01)
(Continued)

(52) U.S. Cl.
CPC ........ *A61M 16/0616* (2014.02); *A61M 16/06* (2013.01); *A61M 16/0605* (2014.02);
(Continued)

(58) Field of Classification Search
CPC .......... A61M 16/0063; A61M 16/0069; A61M 16/06; A61M 16/0605; A61M 16/0611;
(Continued)

(56) References Cited

U.S. PATENT DOCUMENTS

| 5,724,965 A | * 3/1998 | Handke ............ A61M 16/0605 128/207.18 |
| 6,119,694 A | 9/2000 | Correa et al. |

(Continued)

FOREIGN PATENT DOCUMENTS

| CN | 103732281 | 4/2014 |
| EP | 2145645 | 1/2010 |

(Continued)

OTHER PUBLICATIONS

International Search Report, PCT/IB2016/055369, dated Nov. 18, 2016, 12 pages.

*Primary Examiner* — Annette Dixon
(74) *Attorney, Agent, or Firm* — VIA LLP

(57) ABSTRACT

A nasal seal, mask or an interface assembly have a seal body defining a breathing chamber. A nasal port is provided in the seal body. The nasal port has a central portion straddled by a pair of lateral portions. The nasal port further has an upper edge and a lower edge. The upper edge defines an inwardly projecting portion within the central portion. The lower edge defines an inwardly protection portion within the central portion. Thus, the nasal port can be generally bean-shaped or bowtie-shaped. The mask can include a frame having a central portion that supports the seal and a pair of arm portions that extend rearwardly of the seal and are configured to connect to headgear. The central portion can be more rigid than the arm portions. The mask can be configured to reduce noise transmitted through a bias flow vent.

22 Claims, 118 Drawing Sheets

Related U.S. Application Data

(60) Provisional application No. 62/381,496, filed on Aug. 30, 2016, provisional application No. 62/310,549, filed on Mar. 18, 2016, provisional application No. 62/300,578, filed on Feb. 26, 2016, provisional application No. 62/217,656, filed on Sep. 11, 2015.

(51) Int. Cl.
   *A61M 16/00* (2006.01)
   *A61M 16/10* (2006.01)
   *A61M 16/16* (2006.01)

(52) U.S. Cl.
   CPC .... *A61M 16/0683* (2013.01); *A61M 16/0816* (2013.01); *A61M 16/0825* (2014.02); *A61M 16/0875* (2013.01); *A61M 2016/0039* (2013.01); *A61M 16/0069* (2014.02); *A61M 16/0666* (2013.01); *A61M 16/1085* (2014.02); *A61M 16/109* (2014.02); *A61M 16/1095* (2014.02); *A61M 16/16* (2013.01); *A61M 2202/0225* (2013.01); *A61M 2205/3368* (2013.01); *A61M 2205/42* (2013.01); *A61M 2205/44* (2013.01); *A61M 2205/581* (2013.01); *A61M 2205/582* (2013.01); *A61M 2205/583* (2013.01); *A61M 2205/584* (2013.01); *A61M 2205/588* (2013.01); *A61M 2205/6045* (2013.01); *A61M 2207/00* (2013.01); *A61M 2210/0618* (2013.01)

(58) Field of Classification Search
   CPC .......... A61M 16/0616; A61M 16/0622; A61M 16/0627; A61M 16/0633; A61M 16/0644; A61M 16/0666; A61M 16/0683; A61M 16/0816; A61M 16/0825; A61M 16/0858; A61M 16/0875; A61M 16/1085; A61M 16/109; A61M 16/1095; A61M 16/16; A61M 2016/0039; A61M 2202/0085; A61M 2202/0208; A61M 2202/0225; A61M 2205/3368; A61M 2205/42; A61M 2205/44; A61M 2205/581; A61M 2205/582; A61M 2205/583; A61M 2205/584; A61M 2205/588; A61M 2205/6045; A61M 2207/00; A61M 2210/0606; A61M 2210/0618
   See application file for complete search history.

(56) References Cited

U.S. PATENT DOCUMENTS

| | | | |
|---|---|---|---|
| 6,907,882 B2 | 6/2005 | Ging et al. | |
| 7,201,169 B2 | 4/2007 | Wilkie et al. | |
| 7,624,735 B2 | 12/2009 | Ho et al. | |
| 7,640,933 B1 | 1/2010 | Ho | |
| 11,013,877 B2 * | 5/2021 | Galgali | A61M 16/0605 |
| 2003/0196658 A1 | 10/2003 | Ging et al. | |
| 2008/0190432 A1 | 8/2008 | Blochlinger | |
| 2009/0120442 A1 | 5/2009 | Ho | |
| 2013/0037033 A1 * | 2/2013 | Hitchcock | A61M 16/0622 128/206.24 |
| 2014/0261435 A1 | 9/2014 | Rothermel | |
| 2014/0283842 A1 | 9/2014 | Bearne et al. | |
| 2017/0246411 A1 | 8/2017 | Mashal et al. | |
| 2018/0001044 A1 * | 1/2018 | Stephens | A61M 16/0063 |

FOREIGN PATENT DOCUMENTS

| | | |
|---|---|---|
| WO | WO 2000/078381 | 12/2000 |
| WO | WO 2014/062070 | 4/2014 |
| WO | WO 2014/062070 A1 | 4/2014 |
| WO | WO 2014/077708 | 5/2014 |
| WO | WO 2014/077708 A1 | 5/2014 |
| WO | WO 2014/129913 | 8/2014 |
| WO | WO 2014/181214 | 11/2014 |
| WO | WO 2014/183167 A1 | 11/2014 |
| WO | 2015020535 A1 | 2/2015 |
| WO | WO 2015/097265 A2 | 7/2015 |
| WO | WO 2015/193821 | 12/2015 |

* cited by examiner

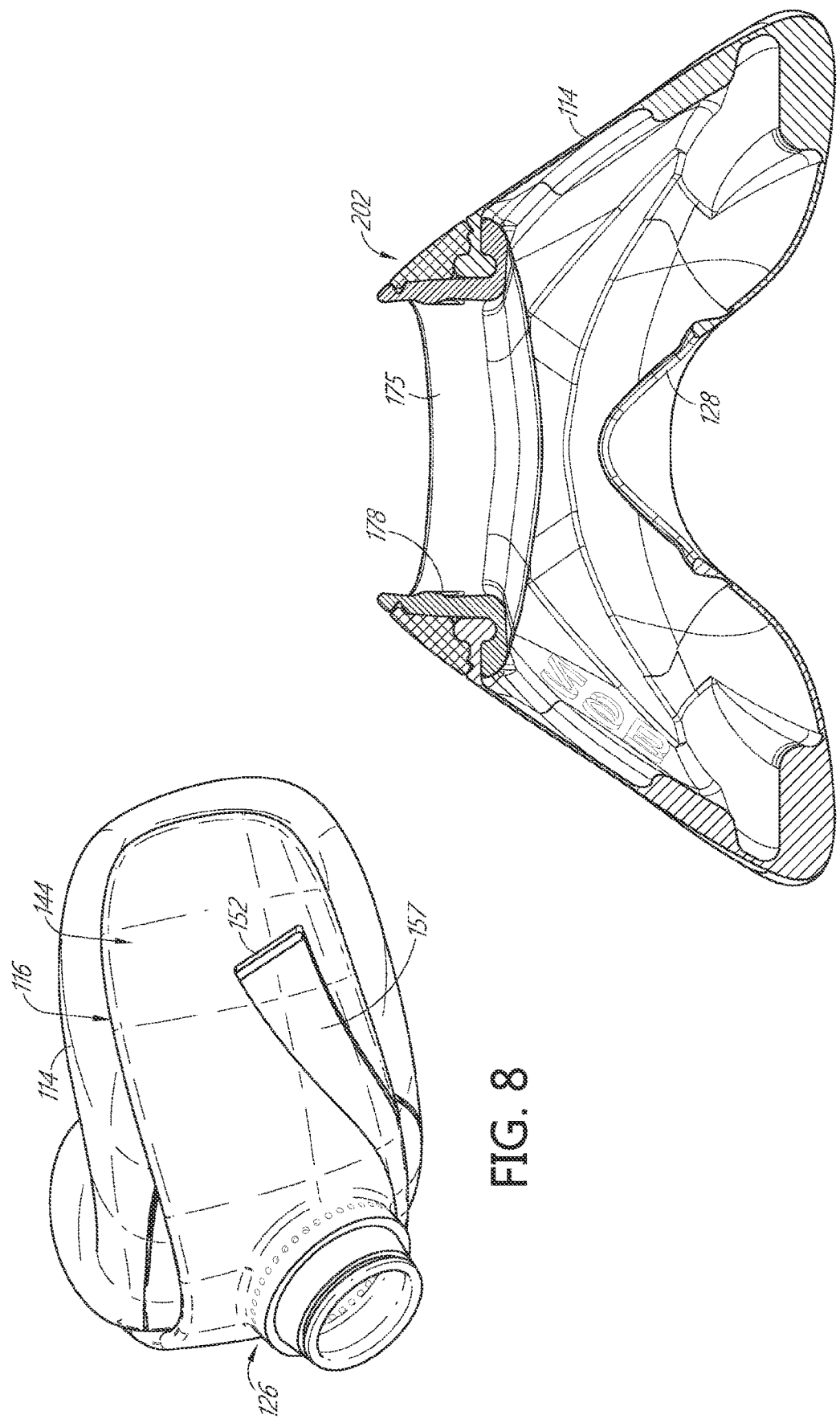

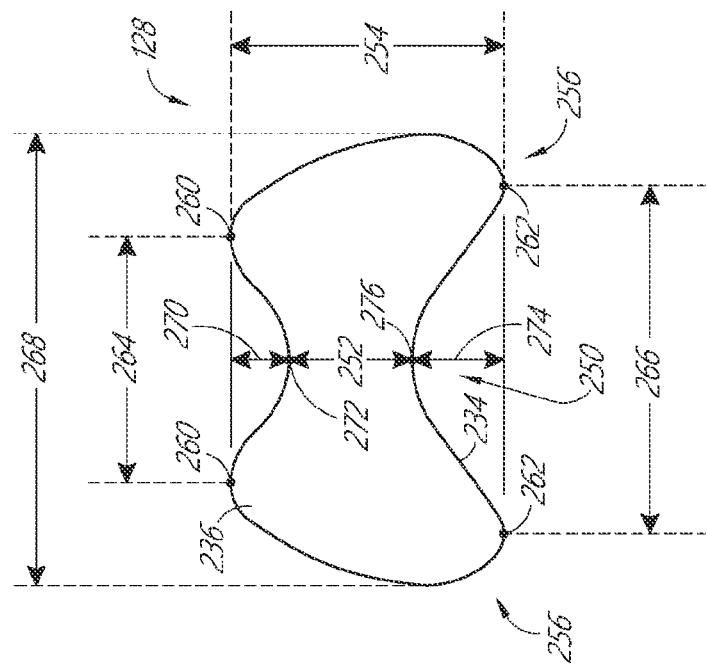
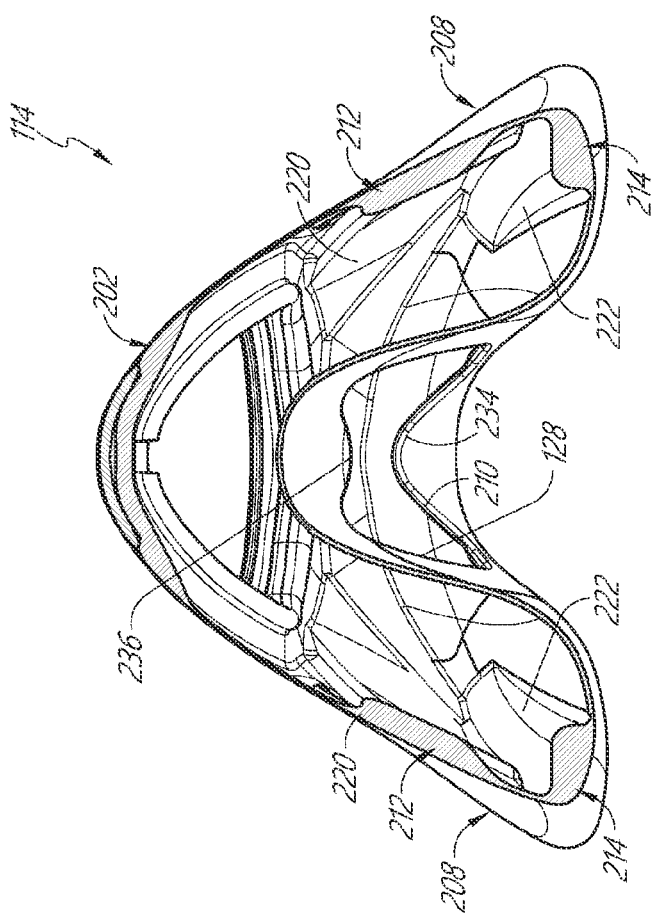
FIG. 16
FIG. 15

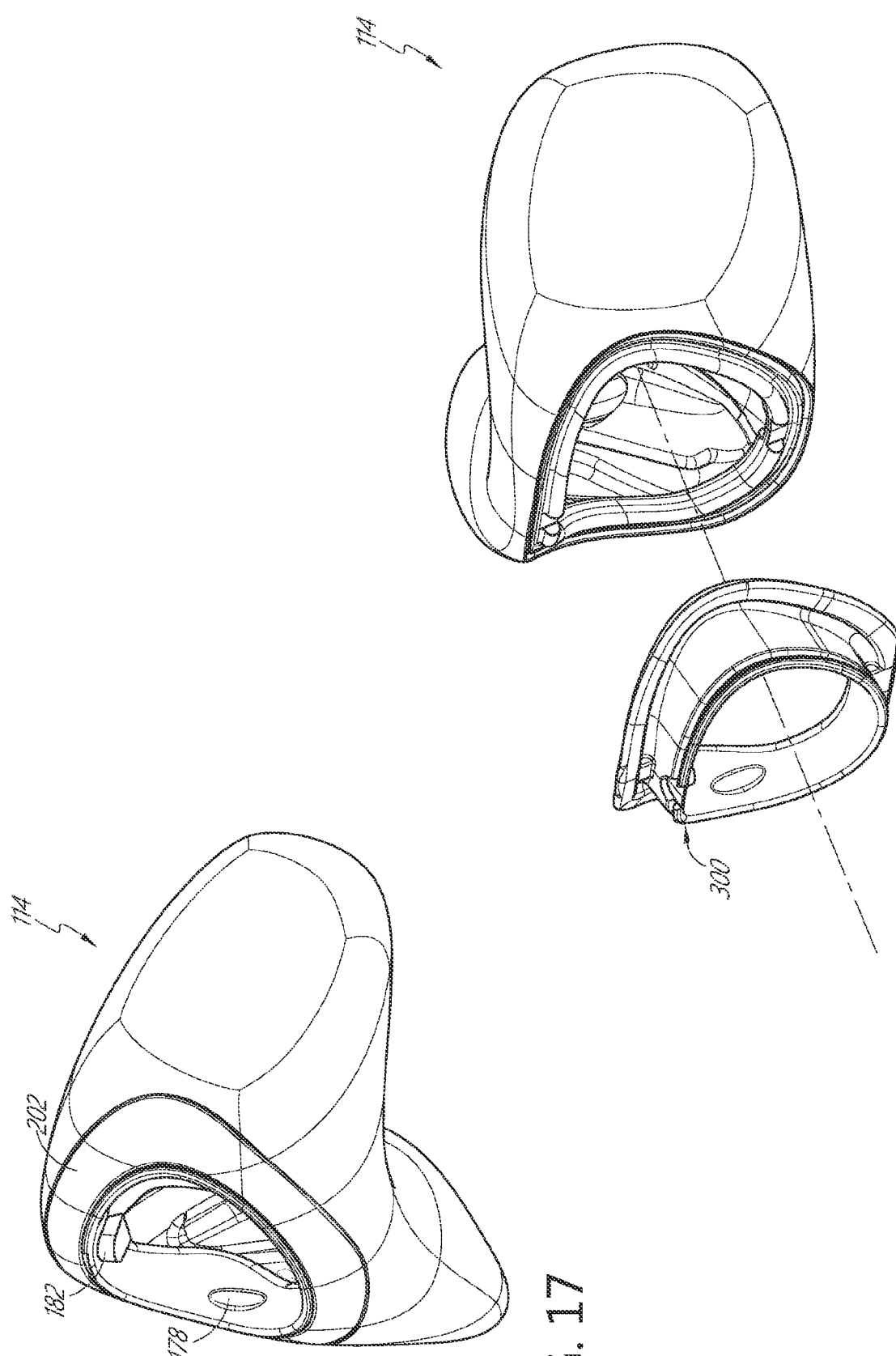

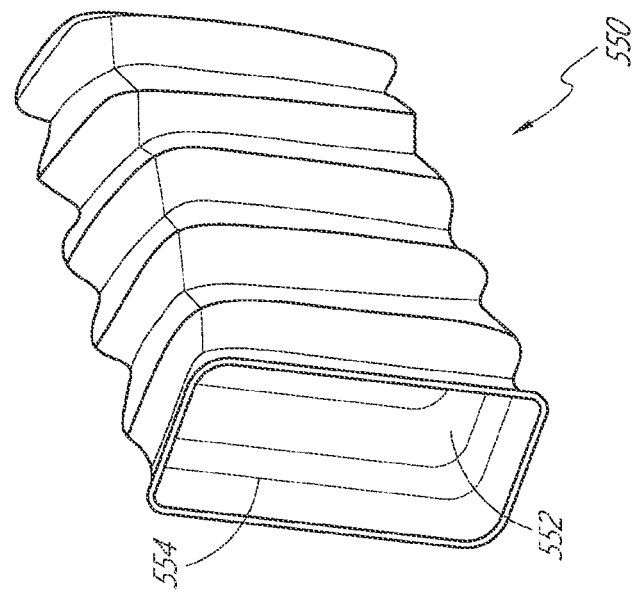
FIG. 36D
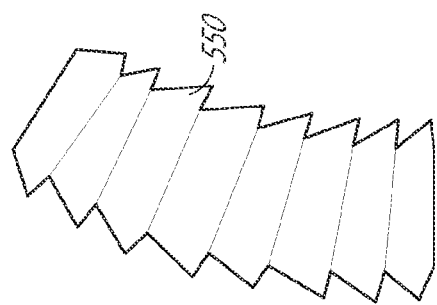
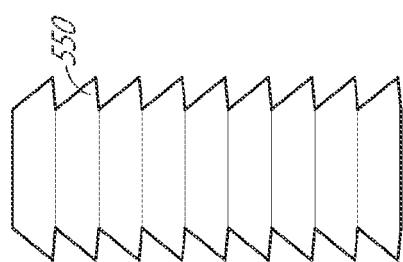
FIG. 36C

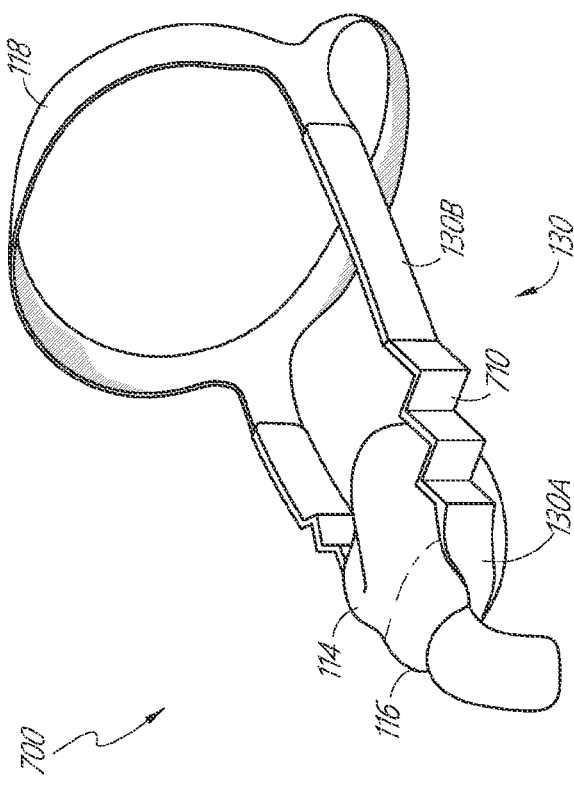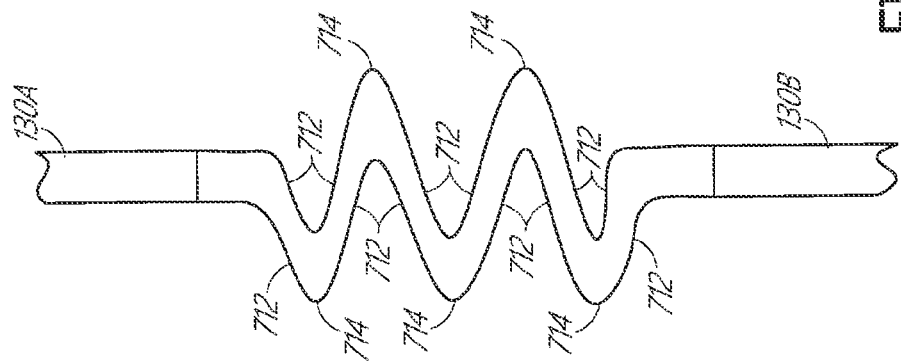

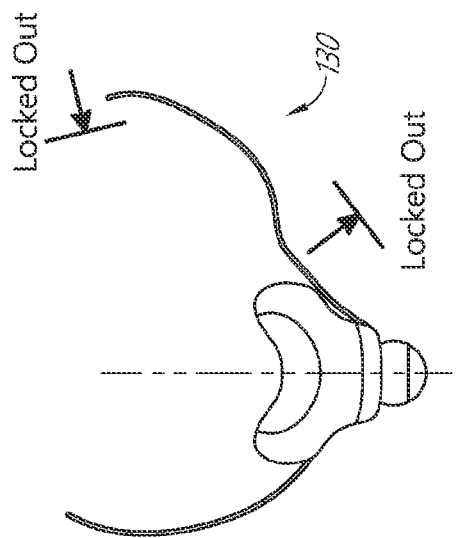
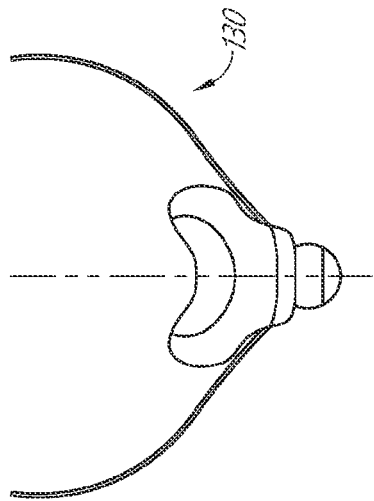
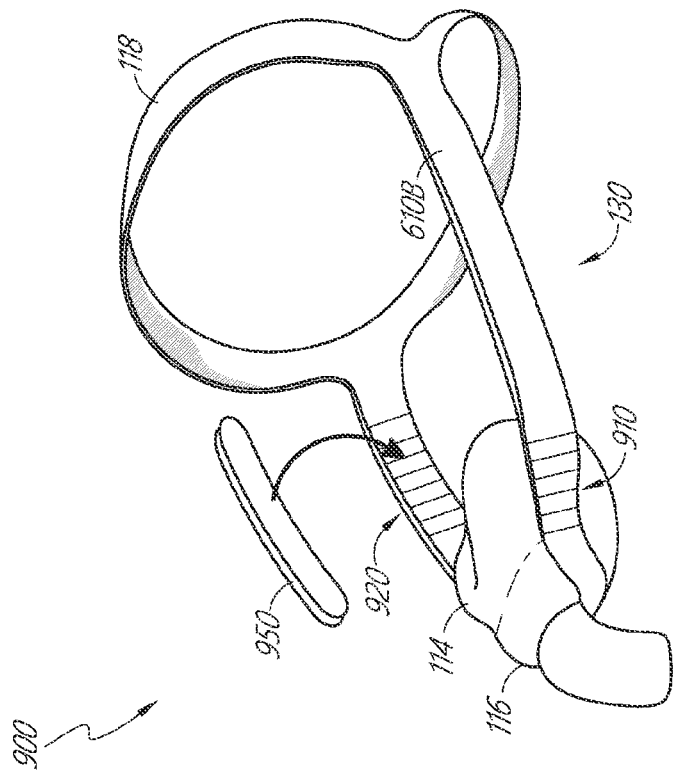
FIG. 40A
FIG. 40B
FIG. 40C

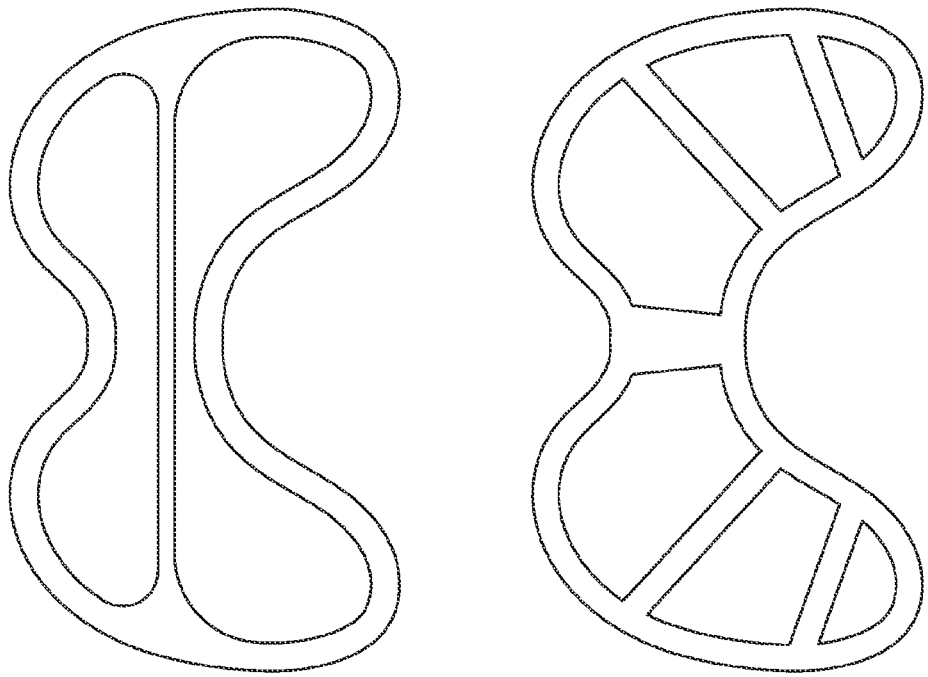
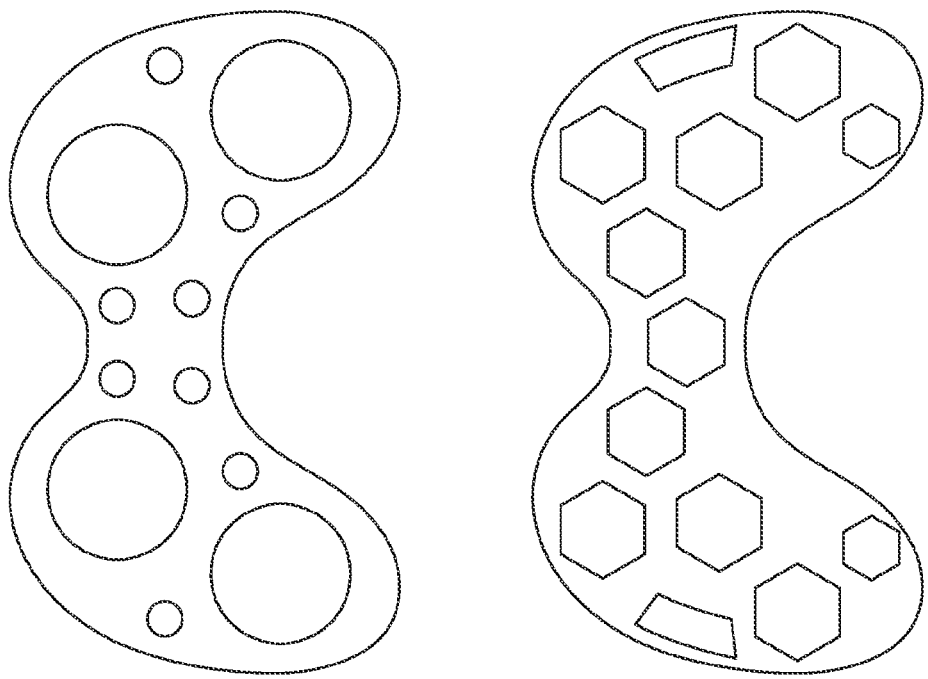
FIG. 45E

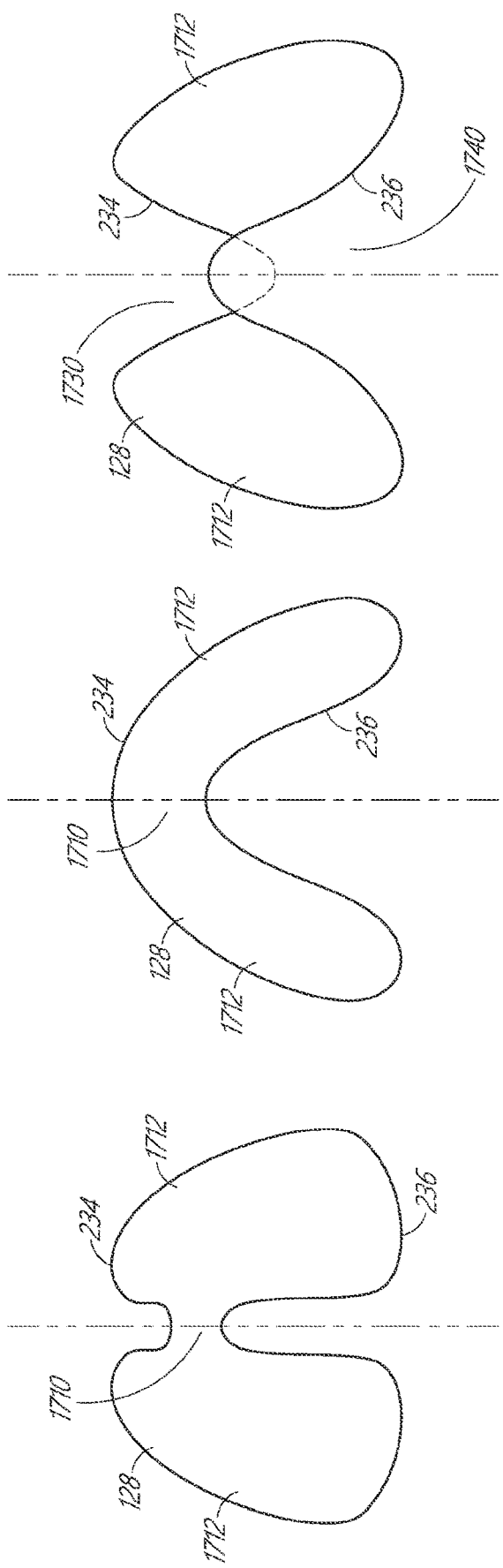
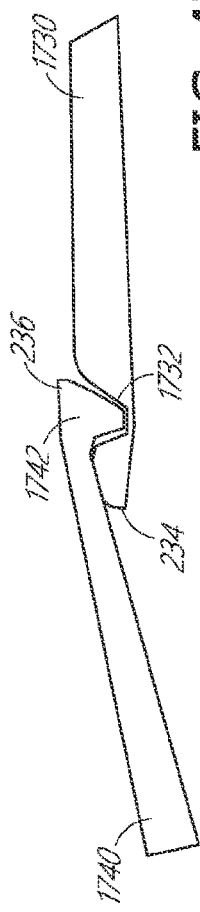
FIG. 47D
FIG. 47E
FIG. 47F
FIG. 47G

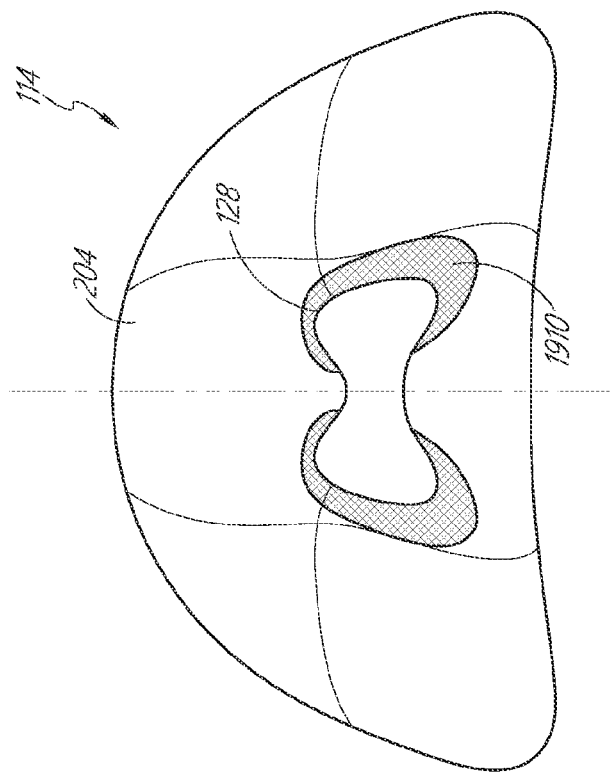
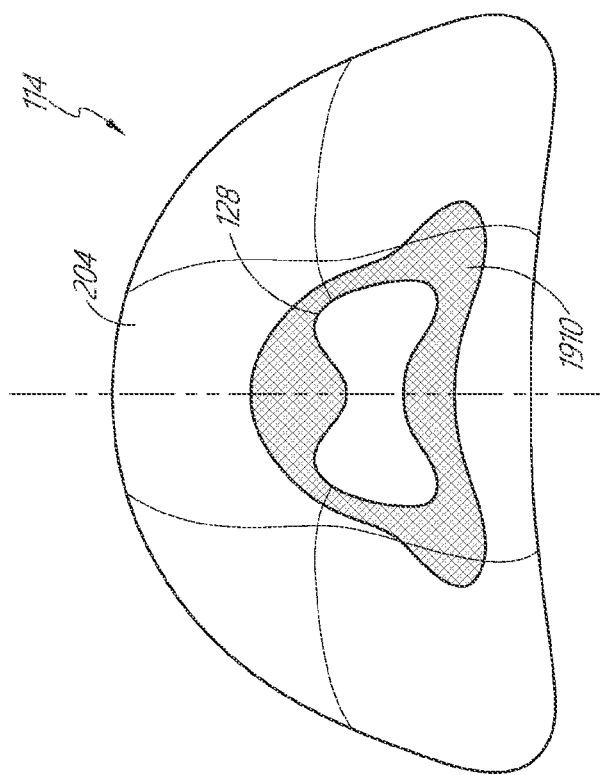
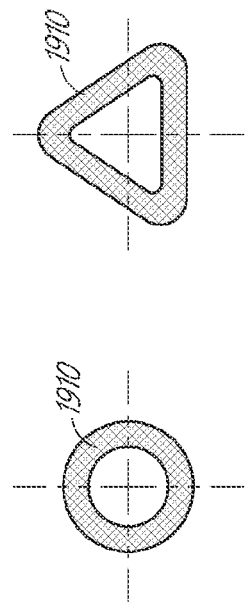
FIG. 48H
FIG. 48I
FIG. 48G

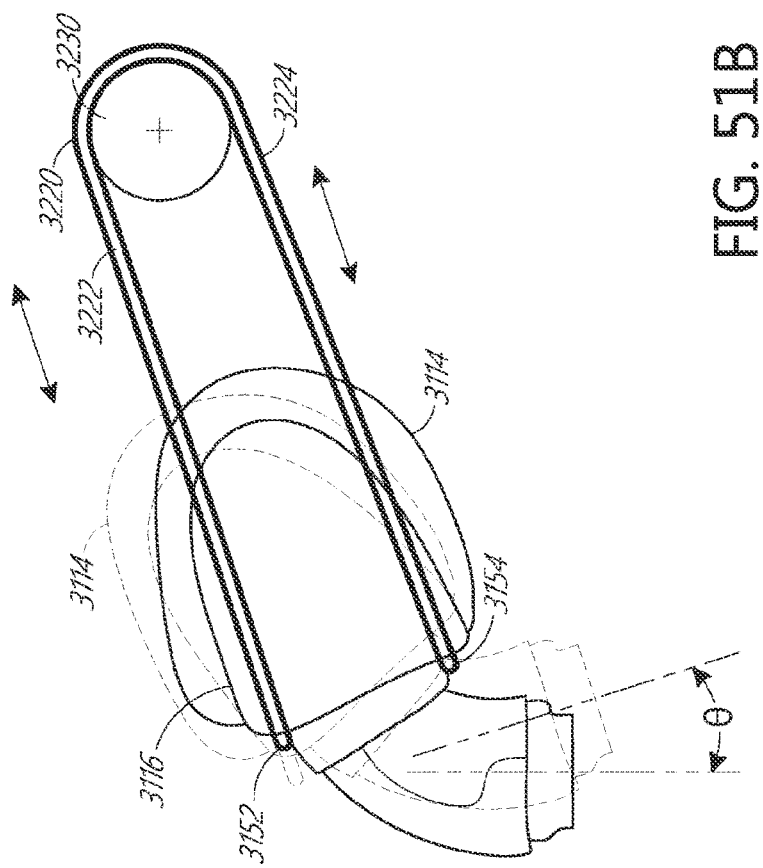
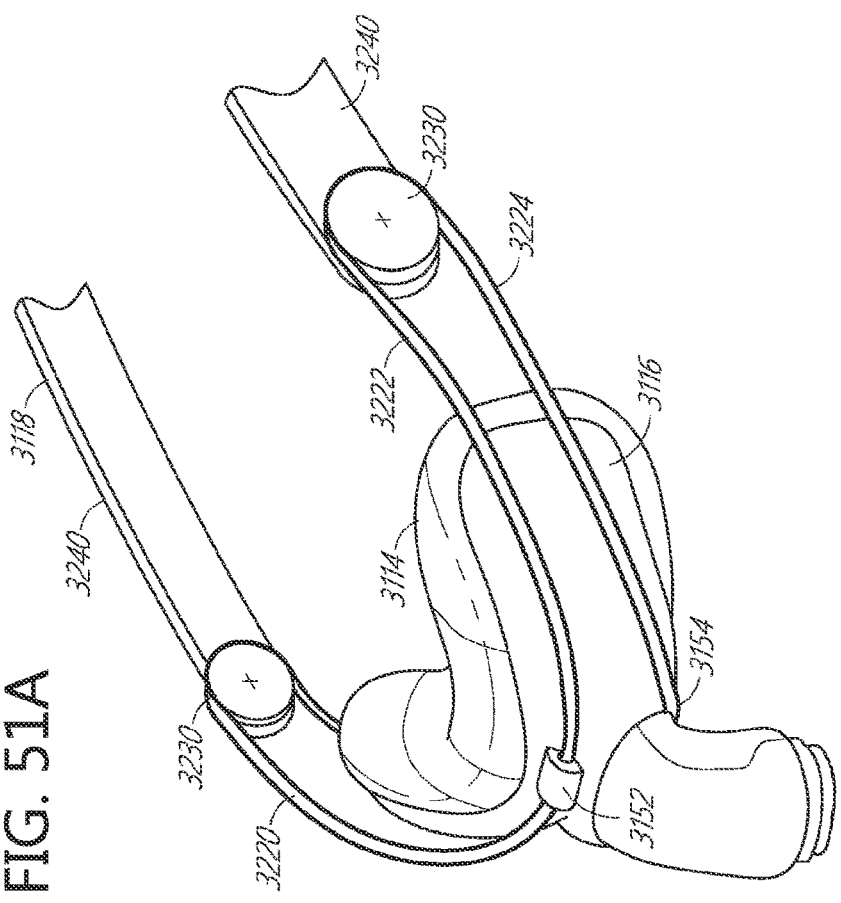

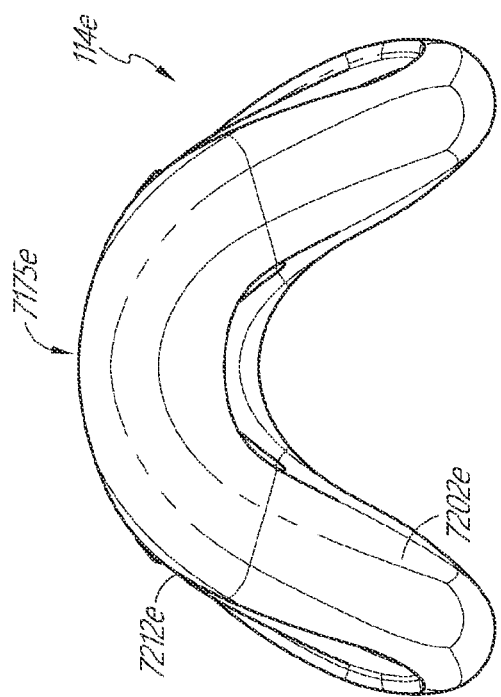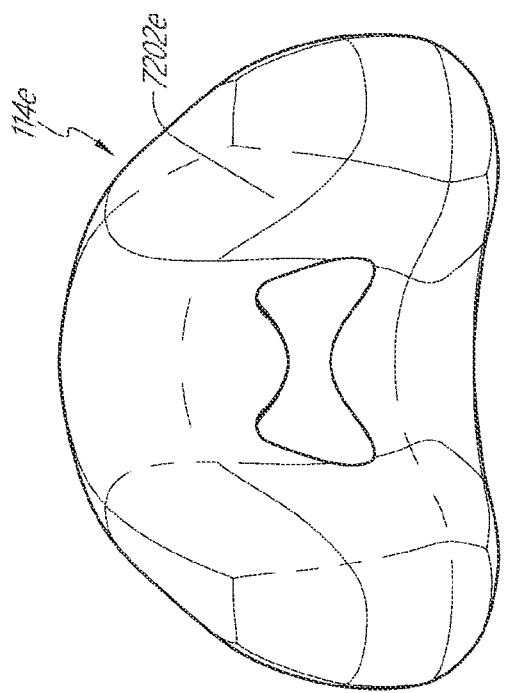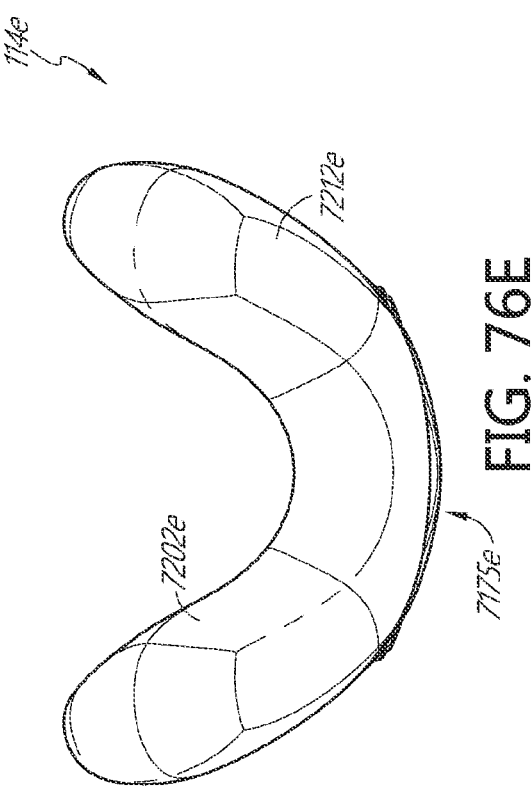

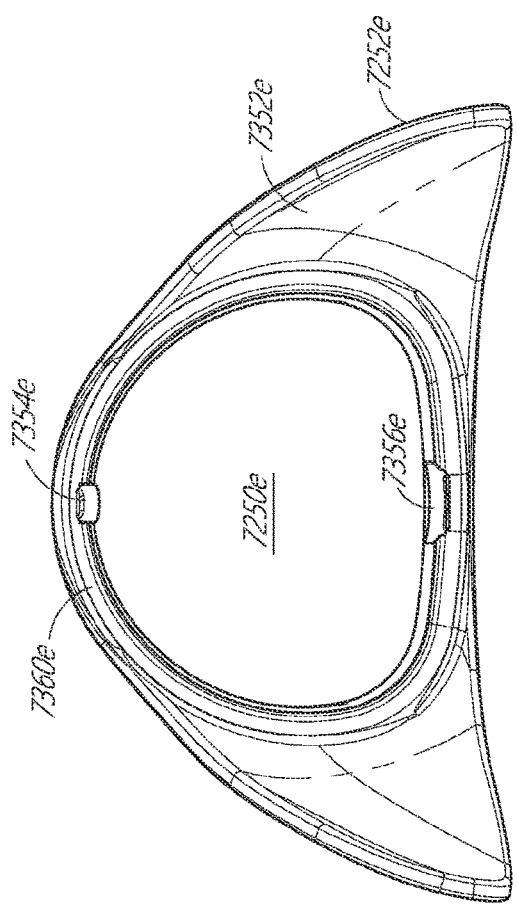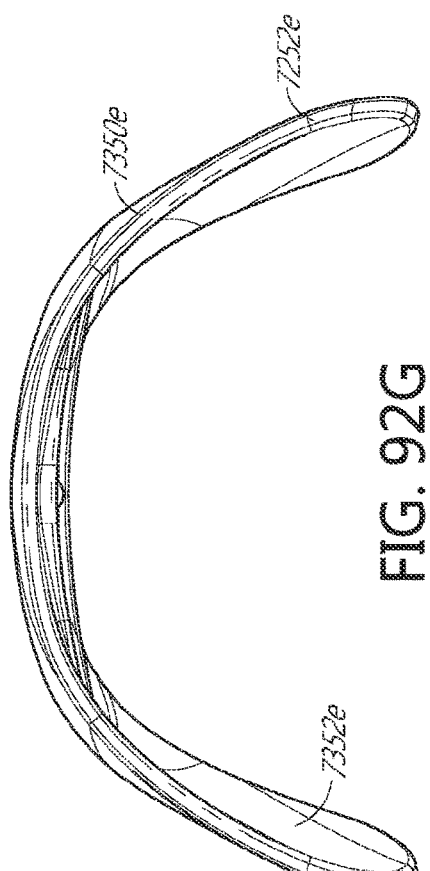

NASAL SEAL, MASK AND RESPIRATORY INTERFACE ASSEMBLY

INCORPORATION BY REFERENCE TO PRIORITY APPLICATIONS

This application is a continuation application of U.S. patent application Ser. No. 15/757,148, filed Mar. 2, 2018, which is a national stage application under 35 U.S.C. § 371 (c) of PCT Application No. PCT/IB2016/055369, filed Sep. 9, 2016, which is related to and claims priority to U.S. Provisional Application Nos. 62/381,496, filed Aug. 30, 2016, 62/310,549, filed Mar. 18, 2016, 62/300,578, filed Feb. 26, 2016, and, 62/217,656, filed Sep. 11, 2015, the entireties of which are hereby incorporated by reference herein and made a part of the present disclosure.

BACKGROUND

Field

The disclosure generally relates to a nasal seal for a respiratory interface, and to an interface including the nasal seal, comprising either a mask or a mask and headgear.

Description of Related Art

Respiratory interfaces are used to provide respiratory gas or gases, such as air in continuous positive airway pressure (CPAP) therapy, to a user under positive pressure. A nasal interface delivers gas to the nose.

The seal of an indirect nasal interface contacts the upper lip, the face on either side of the nose, and the bridge of the nose, and substantially encloses the nose. An indirect nasal interface may be relatively large on the face, may put pressure on the bridge of the nose, and the frame of the interface may include a T-piece connecting to headgear at the wearer's forehead which typically obstructs also wearing spectacles for example.

A direct nasal interface is typically smaller on the face, and does not comprise a T-piece, and is thus less obstructive. However a direct nasal interface typically comprises nasal pillows or similar which enter into the nares of the wearer to ensure an effective seal.

CPAP is a therapy for sleep apnea (e.g., obstructive sleep apnea). Patients being treated with CPAP for sleep apnea wear a face or nasal mask during sleep. It is desirable that respiratory interfaces be comfortable to wear while maintaining a good seal between the respiratory interface and the user.

SUMMARY

The systems, methods and devices described herein have innovative aspects, no single one of which is indispensable or solely responsible for their desirable attributes. Without limiting the scope of the claims, some of the advantageous features will now be summarized.

In some configurations, a nasal seal includes a seal body defining a breathing chamber. A nasal port is provided in the seal body. The nasal port comprises a central portion straddled by a pair of lateral portions. The nasal port further comprises an upper edge and a lower edge. The upper edge defines an inwardly projecting portion within the central portion. The lower edge defines an inwardly protection portion within the central portion.

In some configurations, the inwardly projection portions of one or both of the upper edge and the lower edge is curved.

In some configurations, the nasal port is generally bean-shaped or bowtie-shaped.

In some configurations, the nasal seal further comprises a thickened rim portion extending around a portion or an entirety of a periphery of the nasal port, the thickened rim portion having a larger wall thickness than a portion of the seal immediately adjacent the thickened rim portion.

In some configurations, the seal body comprises a central portion straddled by a pair of lateral portions, wherein in use the seal body is configured such that the lateral portions move inwardly when pressure is applied to the central portion by a user.

In some configurations, a user-facing surface of the nasal seal comprises a thinned wall portion. In some configurations, the thinned wall portion of the user-facing surface has or is equal to the smallest wall thickness of the seal body.

In some configurations, the nasal seal further comprises a pair of thickened wall portions that, in use, contact the user's cheeks. In some configurations, the thickened wall portions have or are equal to the largest wall thickness of the seal body.

In some configurations, the thickened wall portions each comprise a groove within the thickened wall portion that allows decoupled movement of portions of the thickened wall portion on either side of the groove.

In some configurations, the nasal seal further comprises a connector configured to allow the nasal seal to be coupled to a frame, wherein the connector comprises a first portion within the seal body and a second portion outside of the seal body, wherein the first portion and the second portion are coupled to one another.

In some configurations, the first portion comprises a flange and a hub, wherein the hub extends through an aperture of the seal body and wherein the second portion is coupled to the hub of the first portion.

In some configurations, the seal body comprises a rim extending partially or entirely around the aperture, wherein the rim is captured between the first portion and the second portion.

In some configurations, the rim comprises a generally T-shaped cross-section having a base, a first lobe extending in a first direction from the base and a second lobe extending in a second direction from the base opposite the first direction.

In some configurations, each of the first portion and the second portion of the connector comprises a recess configured to receive a respective one of the first lobe and the second lobe.

In some configurations, the seal and the connector comprise interfering portions that inhibit or prevent relative rotation between the seal and the connector.

In some configurations, the seal body has a first texture on a user-contacting side and a second texture on the opposite side, wherein the second texture is different from the first texture.

In some configurations, a nasal mask comprises the nasal seal of any of the preceding paragraphs and a frame, wherein the frame comprises a central portion and a pair of arm portions that extend rearwardly from the central portion, wherein the arm portions are configured for connection to a headgear.

In some configurations, the central portion of the frame is shaped to correspond to a side of the seal body that faces the central portion.

In some configurations, the central portion is more rigid than the arm portions.

In some configurations, the pair of arm portions are overmolded onto the central portion.

In some configurations, each of the pair of arm portions comprises a hinge portion that permits rearward ends of the arm portions to flex relative to the central portion of the frame.

In some configurations, the central portion comprises a seal connector portion configured to removably receive the seal.

In some configurations, the central portion comprises a conduit connector portion that supports a conduit connector.

In some configurations, the conduit connector comprises an elbow.

In some configurations, a bias flow vent is located on the conduit connector portion.

In some configurations, the nasal mask further comprises an expansion within a flow passage defined between an upstream end of the conduit connector portion and the breathing chamber of the seal body, wherein the bias flow vent is located upstream of the expansion.

In some configurations, a mask tube is coupled to the conduit connector, an upstream end of the mask tube comprising a connector configured to be connected to a gases supply conduit of an associated respiratory therapy system, wherein an interior of the connector is the same size and shape as an interior of the mask tube.

In some configurations, an end of the connector abuts against the upstream end of the mask tube and the connector and mask tube are coupled by a coupling sleeve. In some configurations, the coupling sleeve is overmolded onto the mask tube and the connector.

In some configurations, a pad is positioned on an inward-facing surface of each of the pair of arm portions.

In some configurations, the pad and the arm portion are joined by an overmolding process.

In some configurations, the pad comprises a textured surface finish.

In some configurations, the pad comprises a fabric outer layer.

In some configurations, an interface assembly comprises the nasal mask as described in any one of the preceding paragraphs and a headgear comprising an upper strap, a rear strap and forward strap extensions that connect to the arm portions of the frame.

In some configurations, at least the upper strap and the forward strap extensions are inextensible. In some configurations, the rear strap is extensible.

In some configurations, the forward strap extensions and the arm portions are adjustably connected to one another.

In some configurations, the forward strap extensions and the arm portions have a plurality of discrete adjustment positions.

In some configurations, one of the forward strap extension and the arm portion includes a plurality of posts and the other of the forward strap extension and the arm portion includes a plurality of recesses, each configured to receive one of the posts.

In some configurations, an interface assembly includes a nasal mask, a frame attached to the nasal mask, a headgear, and side arms connecting the frame and the headgear. The side arms are rigid in a vertical plane and movable in a horizontal plane with respect to a user's face.

In some configurations, the side arms include a hinge.

In some configurations, the side arms are formed from modular segments.

In some configurations, the side arms include an accordion spring.

In some configurations, the side arms have kerfing on surfaces of the side arms.

In some configurations, ends of the side arms have a hook connector that engages a toothed post disposed on the frame.

In some configurations, the side arms include leaf springs configured to bias the frame between the side arms.

In some configurations, a central portion is connected to ends of the side arms, and a channel is disposed on the frame. The central portion is positioned within the channel such that the frame is movably supported by the central portion.

In some configurations, the side arms are extensible.

In some configurations, the nasal seal further includes a seal body defining a breathing chamber, and a nasal port positioned on the seal body. The nasal port includes a central portion straddled by a pair of lateral portions, the nasal port further includes an upper edge and a lower edge. The nasal seal also includes a flange extending towards the breathing chamber from the upper edge, wherein the flange is configured to contact the user's nose when the user's nose is inserted into the nasal port.

In some configurations, the nasal seal further includes through-holes positioned in the flange.

In some configurations, a nasal seal includes a seal body defining a breathing chamber, a nasal port positioned on the seal body, the nasal port further comprising an upper edge and a lower edge, and a nose obstructing member configured to contact a user's nose that is inserted into the nasal port.

In some configurations, the nose obstructing member is disposed on the nasal port and includes a woven mesh attached to and spanning across the nasal port.

In some configurations, the nose obstructing member is disposed on the nasal port and includes through-holes extending through the nose obstructing member.

In some configurations, the nose obstructing member is disposed on the nasal port and includes tethers attached to a bottom surface of the breathing chamber.

In some configurations, the nose obstructing member extends from a bottom surface of the breathing chamber towards the nasal port.

In some configurations, a distance between the upper and lower edges is narrowest at a midpoint along a width of the nasal port.

In some configurations, wherein the nasal port includes a thickened bead positioned along the upper edge of the nasal port.

In some configurations, a nasal seal includes a seal body defining a breathing chamber, and a nasal port positioned on the seal body. The nasal port further includes outer lateral portions and a central portion positioned between the outer lateral portions. The central portion of the nasal port is narrower than the outer lateral portions of the nasal port. The central portion is configured to contact a user's nose that is inserted into the nasal port.

In some configurations, a distance between an upper edge of the nasal port and a lower edge of the nasal port is narrowest at a lateral midpoint of nasal port.

In some configurations, the outer lateral portions further comprises ovular ports and the central portion further comprises a throat portion, wherein the throat portion connects the ovular ports.

In some configurations, the ovular ports are angled toward each other.

In some configurations, the throat portion is closer to lower-most edges of the ovular ports than upper-most edges of the ovular ports.

In some configurations, the throat portion is closer to upper-most edges of the ovular ports than lower-most edges of the ovular ports.

In some configurations, the nasal port is crescent-shaped.

In some configurations, the nasal port is kidney-shaped.

In some configurations, the outer lateral portions comprise ovular ports that are separated by the central portion.

In some configurations, an upper portion of the nasal port and a lower portion of the nasal port overlap.

In some configurations, the upper portion has a recess and the lower portion has a protrusion, wherein the protrusion is positioned within the recess.

In some configurations, a nasal seal includes a seal body defining a breathing chamber, a nasal port positioned on the seal body, and a marking positioned on the seal body configured to indicate a position of the user's nose over the nasal port.

In some configurations, the marking are printed onto the seal body.

In some configurations, the marking are scented.

In some configurations, the marking is formed from frosted silicone.

In some configurations, the marking is deformable.

In some configurations, an interface assembly including a nasal mask, a frame attached to the nasal mask, a headgear, an upper connecting member rotatably connected to an upper portion of the frame and the headgear, and a lower connecting member connecting a lower portion of the frame and the headgear. Relative movement between the upper and lower connecting members cause rotation of the frame.

In some configurations, the upper and lower connecting are connected to the headgear by pulleys.

In some configurations, a nasal seal includes a seal body defining a breathing chamber, and a downwardly-deflectable upper portion. The downwardly-deflectable upper portion rolls in a downward direction relative to a lower portion of the seal.

In some configurations, the nasal seal further includes an upwardly-deflectable lower portion. The upwardly-deflectable lower portion rolls in an upward direction relative to a lower portion of the seal.

In some configurations, a nasal seal includes a seal body defining a breathing chamber, a nasal port positioned on the seal body, and a deformable nose interfacing portion formed around the nasal port. The deformable nose interfacing portion deforms in an inward direction into the breathing chamber and expands in an outward direction from the breathing chamber.

In some configurations, a stiffened region surrounds the nasal port. The stiffened region has a thickness that is greater than the deformable nose interfacing portion.

In some configurations, a nasal seal includes a front wall having a rim that circumferentially surrounds a gas inlet opening. The front wall extends proximally from the rim and joins a rear wall, forming a breathing chamber disposed between the front and rear walls. A central portion of the rear wall extends distal to first and second lateral portions of the rear wall, forming a recess. A nasal aperture in the recess communicates with the breathing chamber.

In some aspects, the front wall has a first region having a first thickness and a second region having a second thickness, the first thickness being at least three times greater than the second thickness. In some configurations, the front wall extends to the second wall without passing through an inflection point. In some aspects, the nasal seal further comprises a connector that is secured to the rim of the front wall. In some configurations, the connector comprises arms that extend proximally along the front wall.

In some configurations, at least a portion of the nasal aperture is disposed closer to a distal-most point of the front wall than to a proximal-most point of the front wall. In some embodiments, the entire nasal aperture is closer to the distal-most point of the front wall than to the proximal-most point of the front wall.

In some aspects, the nasal seal comprises a bottom wall that extends from the gas inlet opening to the recess. The bottom wall has a front portion that is distal to a back portion. The back portion has a thickness that is greater than the thickness of the front portion. In some embodiments, the bottom wall further comprises a central portion disposed between the front and back portions. The central portion has a thickness that is less than the thickness of the front portion.

In some embodiments, the rear wall comprises a thickened portion that surrounds the nasal aperture. In certain configurations, the thickened portion extends away from the nasal aperture by a maximum width that is less than three times a maximum thickness of the thickened portion. In some embodiments, the thickened portion extends away from the nasal aperture by a maximum width that is more than three times the maximum thickness of the thickened portion.

In some embodiments, the gas inlet opening comprises a truncated region and a non-truncated region, a distance between the central point of the opening and the truncated region being less than a distance between the central point of the opening and the non-truncated region.

Further aspects of the presently disclosed subject matter, which should be considered in all its novel aspects, will become apparent to those skilled in the art upon reading of the following description which provides at least one example of a practical application of the invention.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 8 is a perspective view of the mask with the portion shown in FIGS. 6 and 7 removed.

FIG. 9 is a sectional view of the portion of the mask shown in FIG. 8 taken along a horizontal plane.

FIG. 14 is a sectional view of the seal taken along the line 14-14 in

FIG. 13.

FIG. 15 is a sectional view of the seal taken along the line 15-15 in

FIG. 13.

FIG. 16 is an outline of an aperture of the seal.

FIG. 17 is a perspective view of the seal illustrated features of a connector configured to connect to the frame.

FIG. 18 is a perspective view of the seal with a portion of the connector removed.

FIG. 36C is a top view of a concertina cover of the interface of FIG. 36A shown in bent and unbent positions.

FIG. 36D is perspective view of the concertina cover of the interface of FIG. 36A.

FIG. 38A is perspective view of an interface having a spring-loaded side arm arrangement.

FIG. 38B is a close-up top view of a spring portion of the interface of FIG. 38A.

FIG. 40A is perspective view of an interface having a side arm arrangement with kerfing.

FIG. 40B is a top view of the interface of FIG. 40A illustrating the side arms in an unbent and undeformed orientation.

FIG. 40C is a top view of the interface of FIG. 40A illustrating the maximum articulation of the side arms.

FIG. 45E illustrates aperture covers having a variety of hole arrangements.

FIG. 47D illustrates an alternative configuration of an aperture for a seal that prevents or inhibits the user's nose from being inserted into the aperture.

FIG. 47E illustrates an alternative configuration of an aperture for a seal that prevents or inhibits the user's nose from being inserted into the aperture.

FIG. 47F illustrates an alternative configuration of an aperture for a seal that prevents or inhibits the user's nose from being inserted into the aperture.

FIG. 47G is side cross-sectional view of the aperture arrangement in FIG. 47F.

FIG. 48G is a rear view of a nasal seal arrangement having frosted markings to visually indicate correct nose alignment and position.

FIG. 48H is a rear view of a nasal seal arrangement having frosted markings to visually indicate correct nares position.

FIG. 48I depicts alternative frosted marking arrangements.

FIG. 51A is a perspective view of an alternative interface arrangement having pulleys to allow rotation of a nasal seal.

FIG. 51B is a side view of the alternative interface arrangement of FIG. 51A illustrating the rotation of the nasal seal.

FIG. 52B is a side perspective cross-sectional view of the rolling nasal seal in FIG. 52A illustrating an undeformed orientation.

FIG. 52C is a side perspective cross-sectional view of the rolling nasal seal in FIG. 52A illustrating a rolled orientation.

FIG. 53A is a perspective view of a rolling nasal seal having upper and lower rolling sections.

FIG. 53B is a schematic side view illustrating user nose angles and upper lip angles.

FIG. 53C is a side view of the rolling nasal seal of FIG. 53A illustrating an undeformed orientation.

FIG. 53D is a side view of the rolling nasal seal of FIG. 53A illustrating a rolled orientation.

FIG. 53E is a perspective view of an alternative rolling nasal seal having a spring steel section.

FIG. 54A is a perspective view of a nasal seal having a bellowing region.

FIG. 54B is a side perspective cross-sectional view of the nasal seal in FIG. 54A.

FIG. 54C is a schematic side view illustrating the nasal seal in FIG. 54A fitted to users with a longer and shorter nose.

FIG. 54D is a schematic side view illustrating the nasal seal in FIG. 54A fitted to a user having a level plane longer nose.

FIG. 54E is a schematic side view illustrating the nasal seal in FIG. 54A fitted to a user having a downwardly angled longer nose.

Figure 54C:
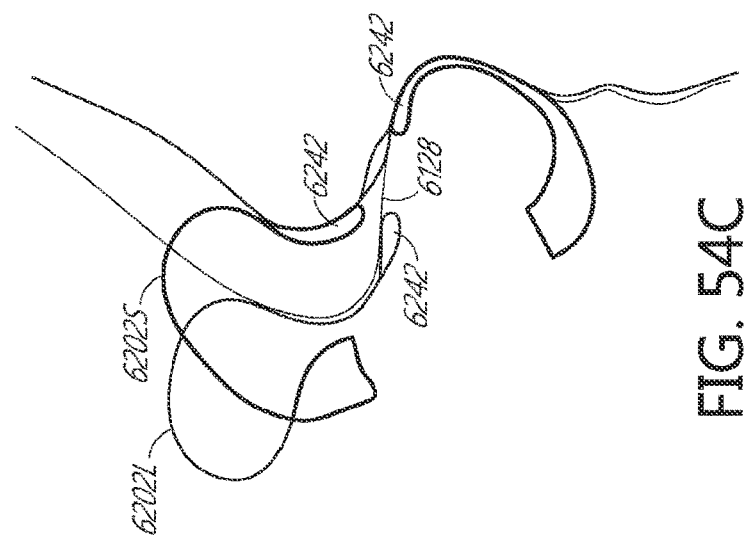
Figure 54B:
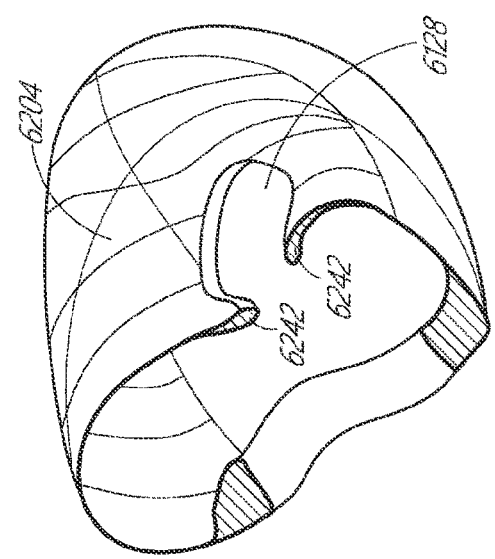
Figure 54A:
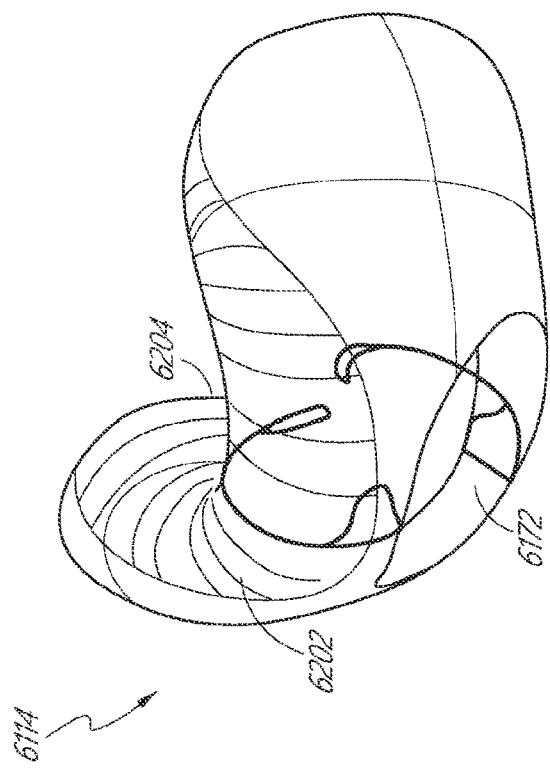
Figure 54E:
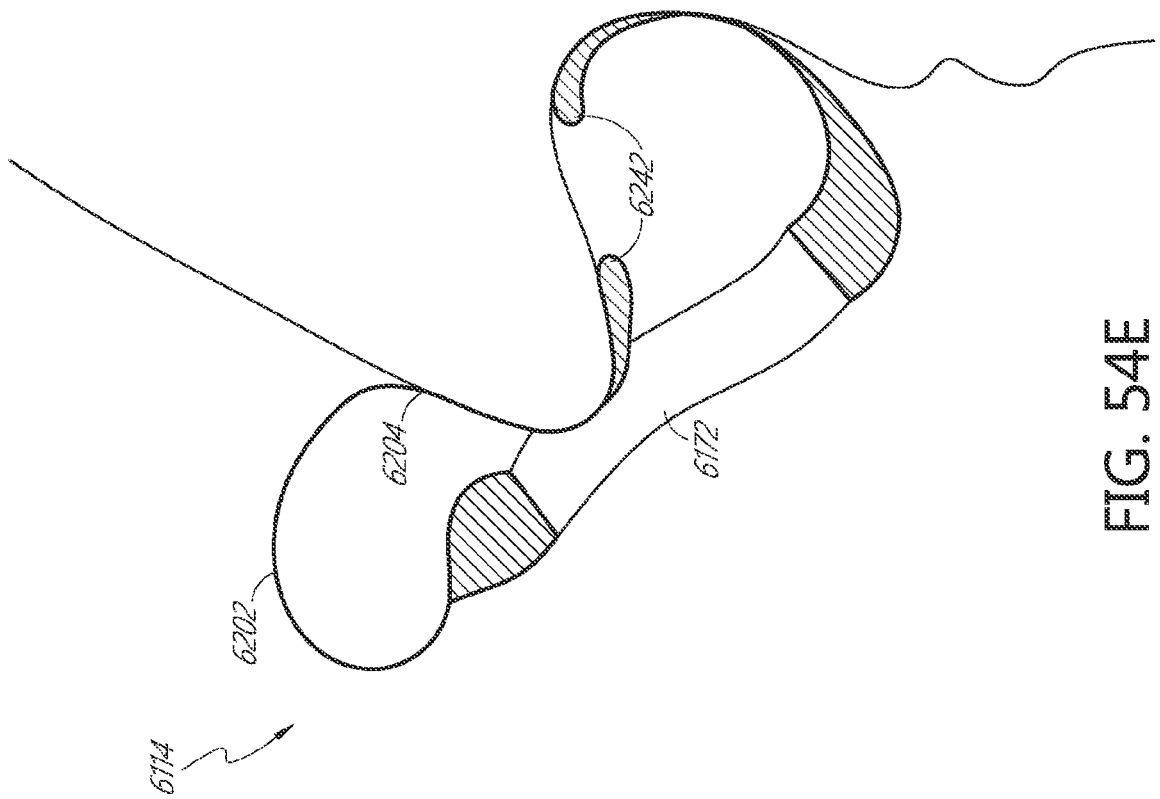
Figure 54D:
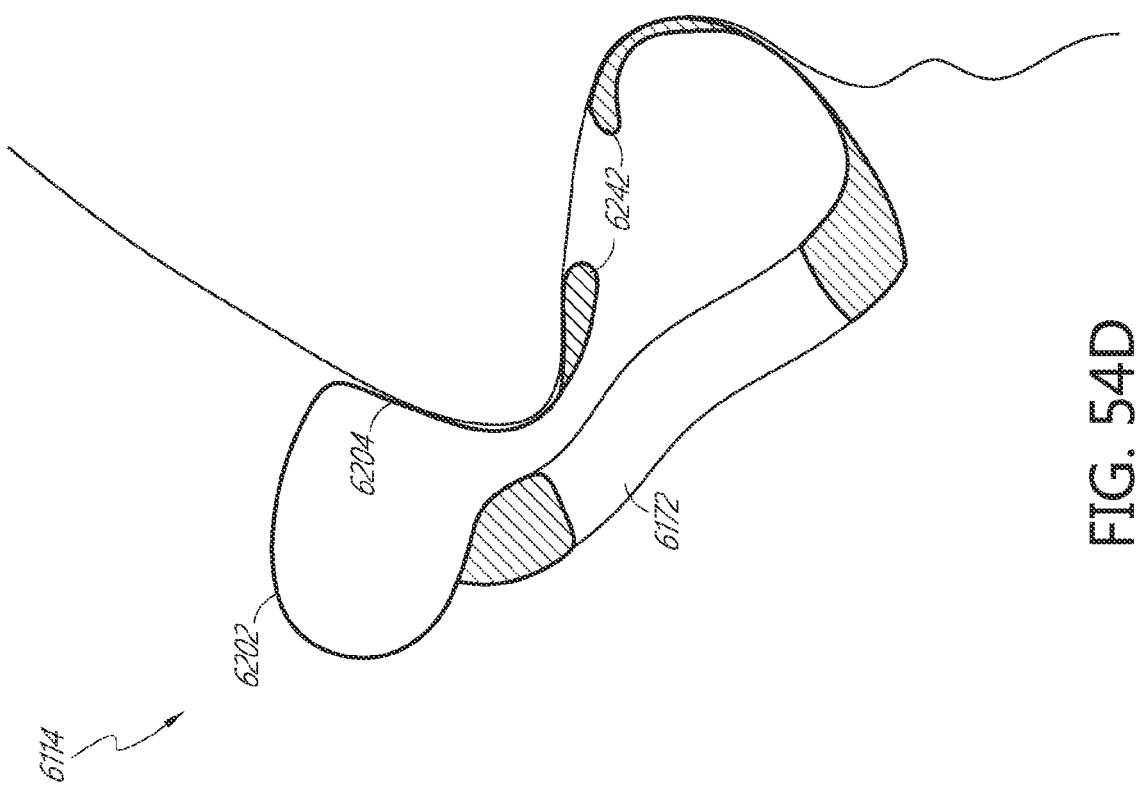
Figure 54G:
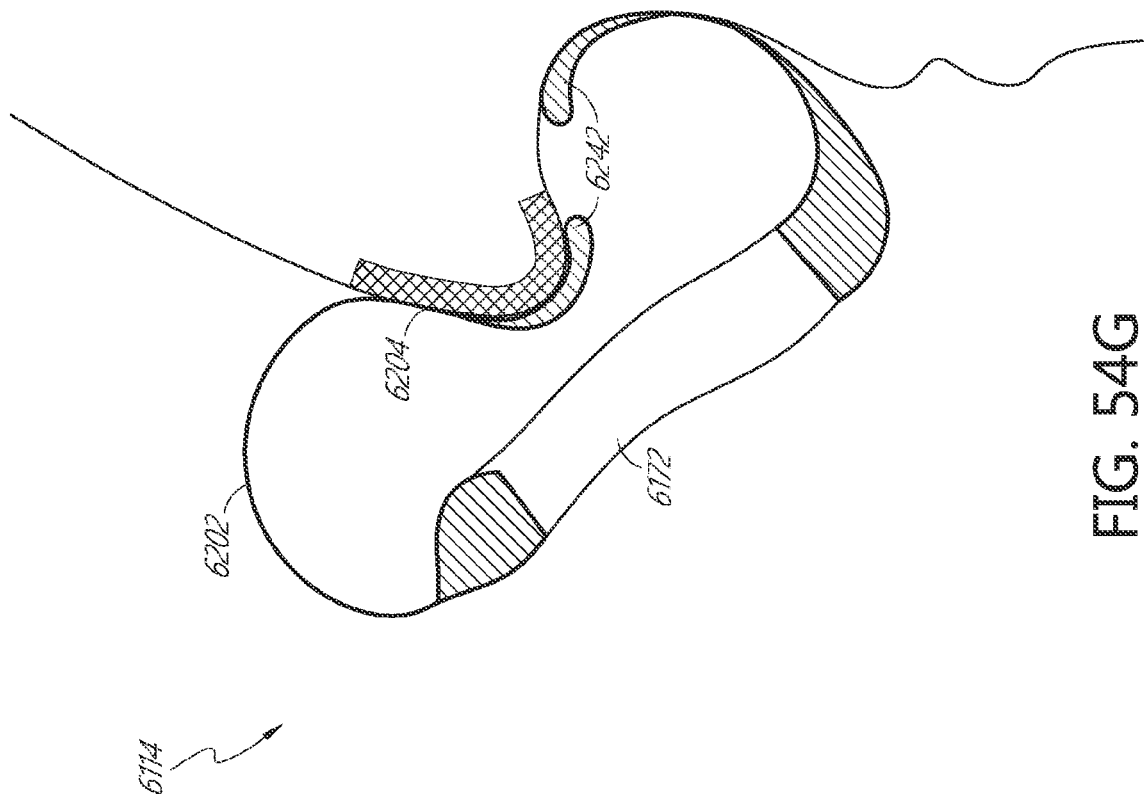
Figure 54F:
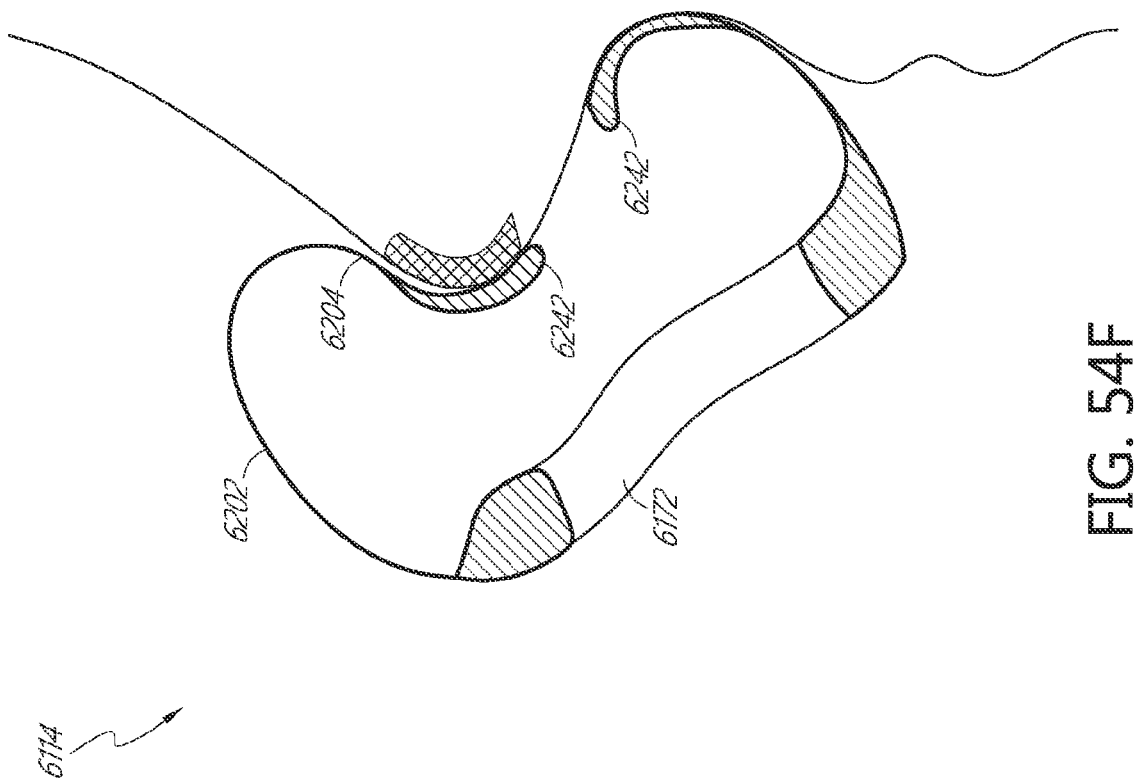

FIG. 54F is a schematic side view illustrating the nasal seal in FIG. 54A fitted to a user having an upwardly angled shorter nose.

FIG. 54G is a schematic side view illustrating the nasal seal in FIG. 54A fitted to a user having a downwardly angled shorter nose.

Figure 1:
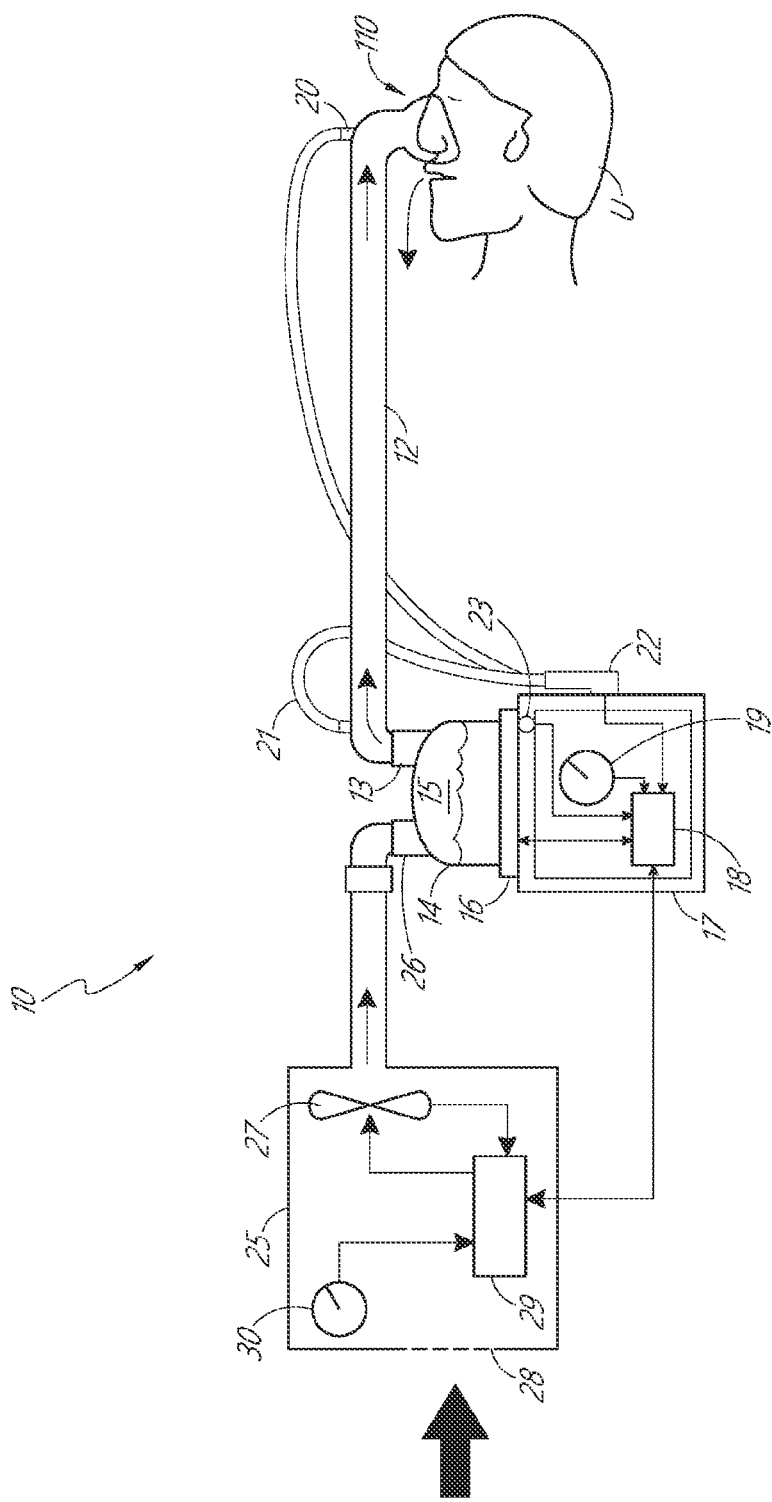
FIG. 1 is a view of a respiratory system comprising a flow generator, a humidifier and a user interface.
Figure 55:
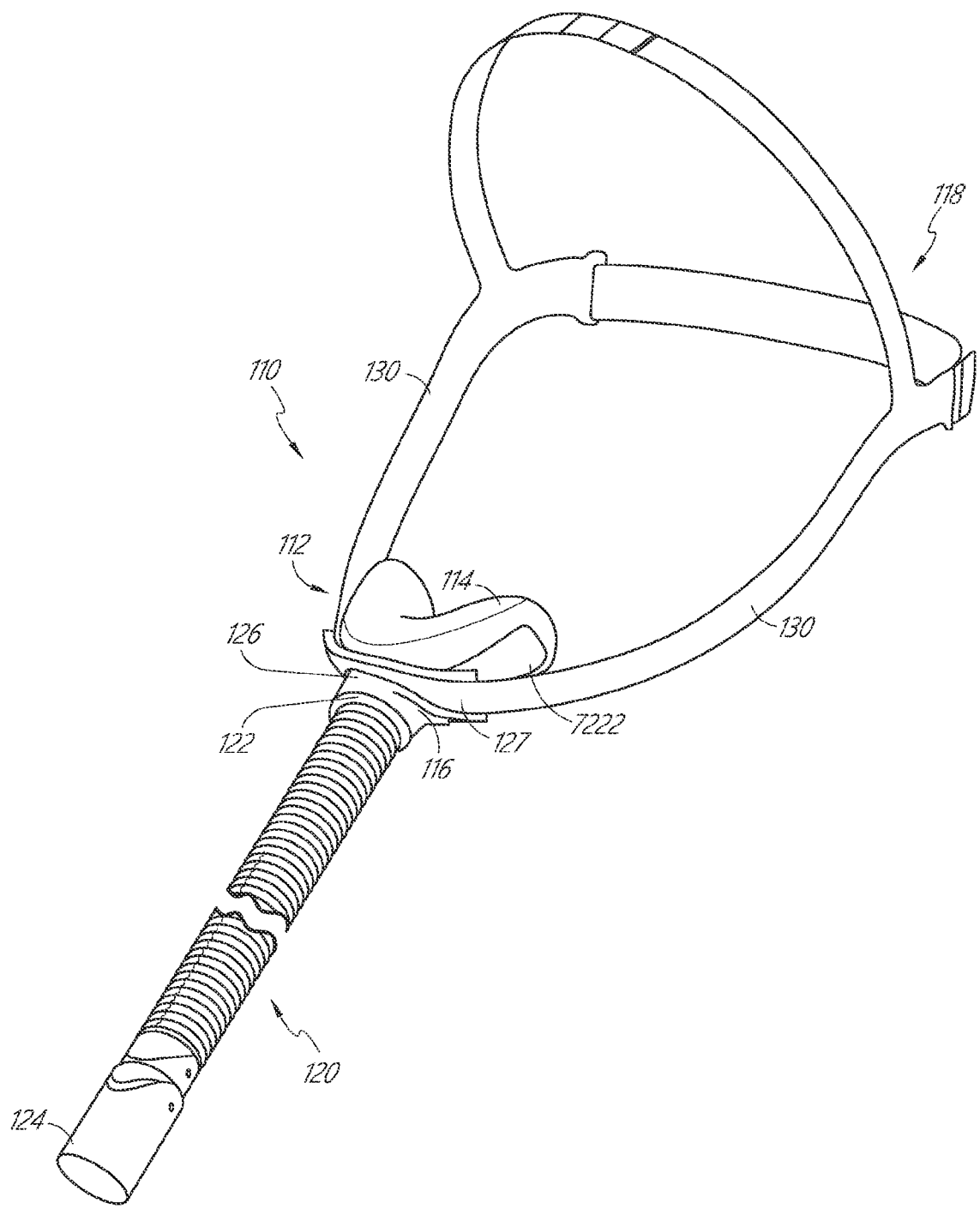

FIG. 55 is a perspective view of a user interface, comprising a patient interface and a beadgear, which is suitable for use with the respiratory system of FIG. 1.

Figure 56:
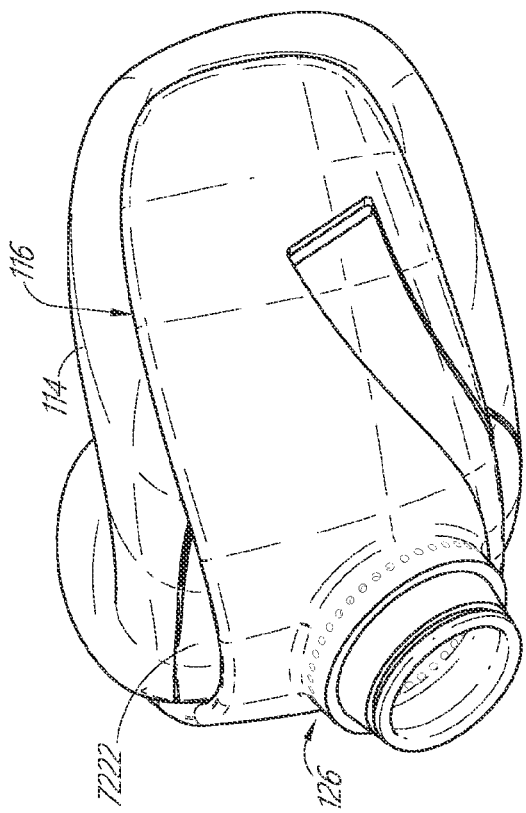

FIG. 56 is a perspective view of a seal and a frame of the patient interface.

Figure 57:
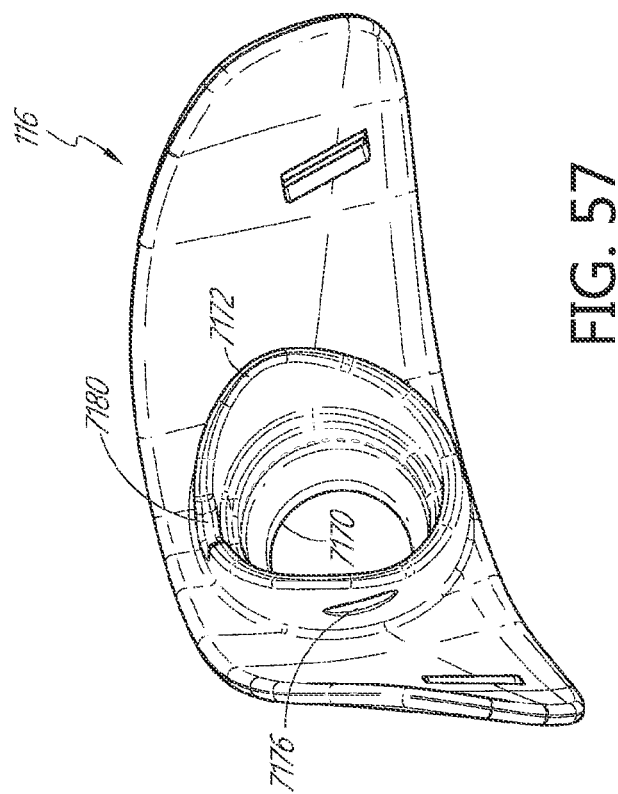

FIG. 57 is a rear perspective view of the frame of FIG. 56.

Figure 58B:
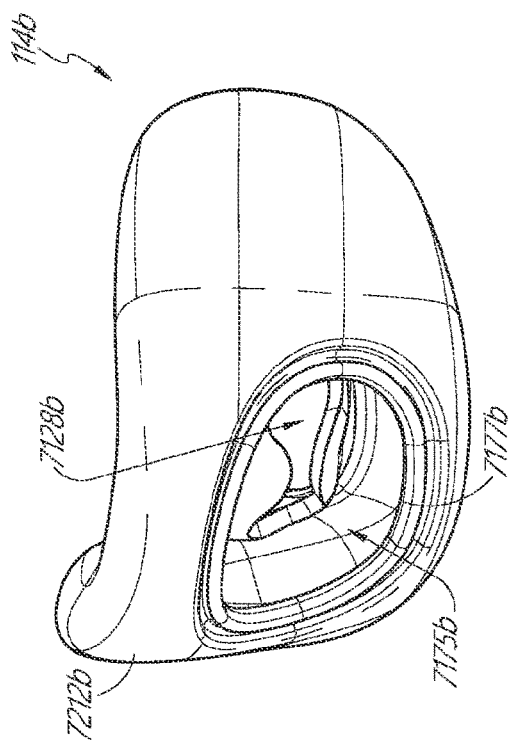
Figure 58C:
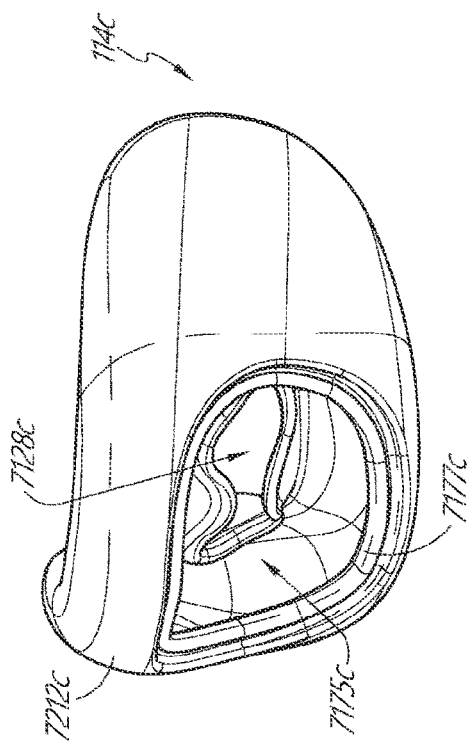
Figure 58A:
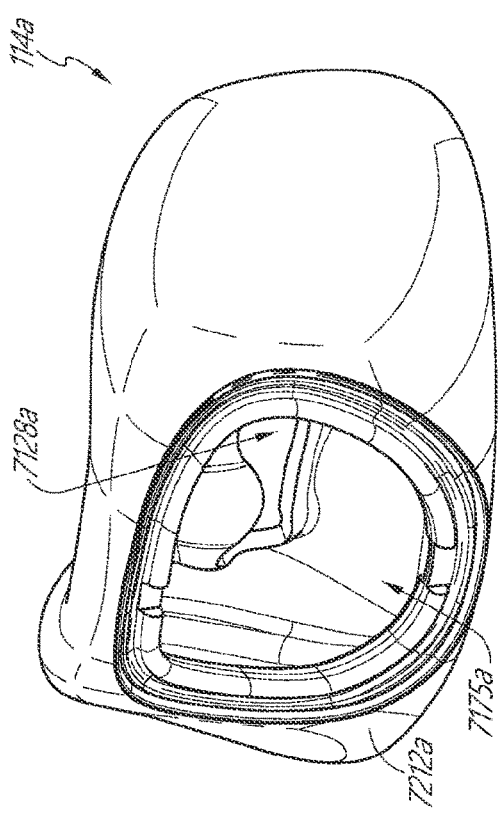

FIG. 58A is a perspective view of an embodiment of a nasal seal.

FIG. 58B is a perspective view of an embodiment of a nasal seal.

FIG. 58C is a perspective view of an embodiment of a nasal seal.

Figure 59A:
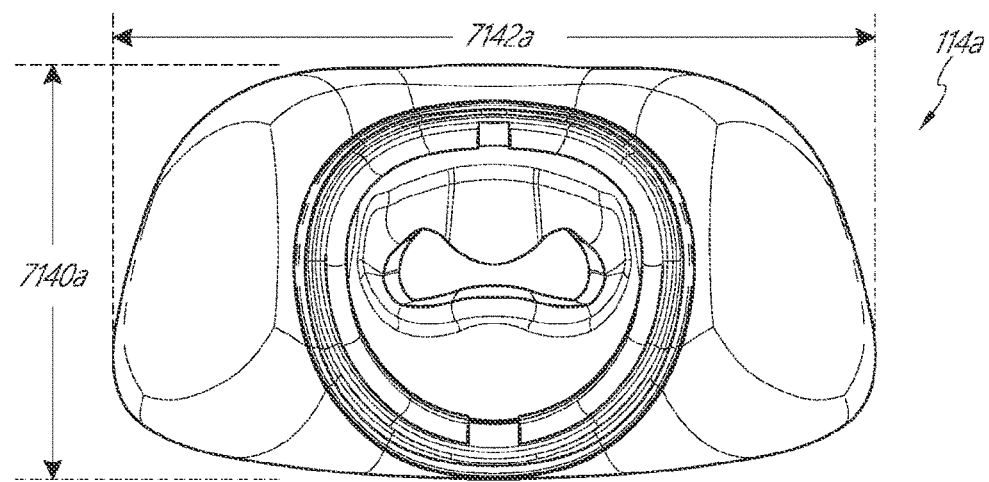

FIG. 59A is a front view of the nasal seal of FIG. 58A.

Figure 59B:
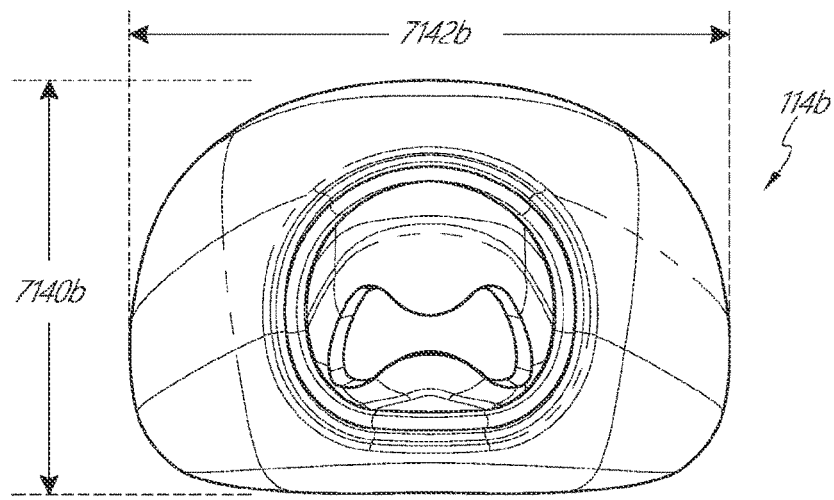

FIG. 59B is a front view of the nasal seal of FIG. 58B.

Figure 59C:
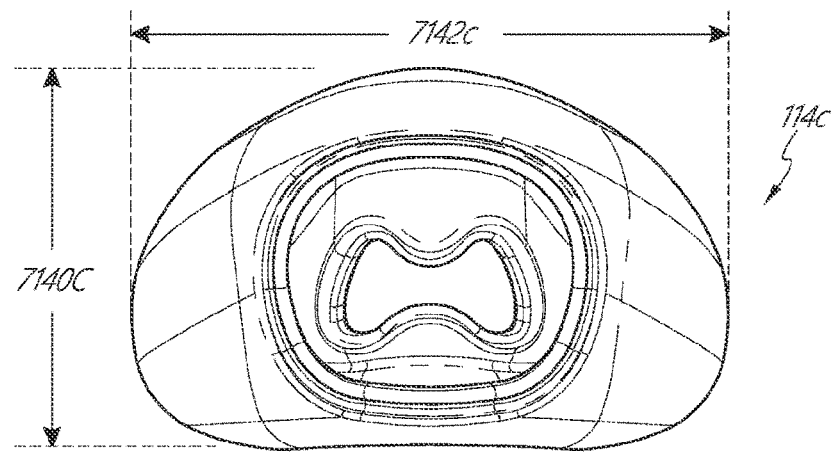

FIG. 59C is a front view of the nasal seal of FIG. 58C.

Figure 60A:
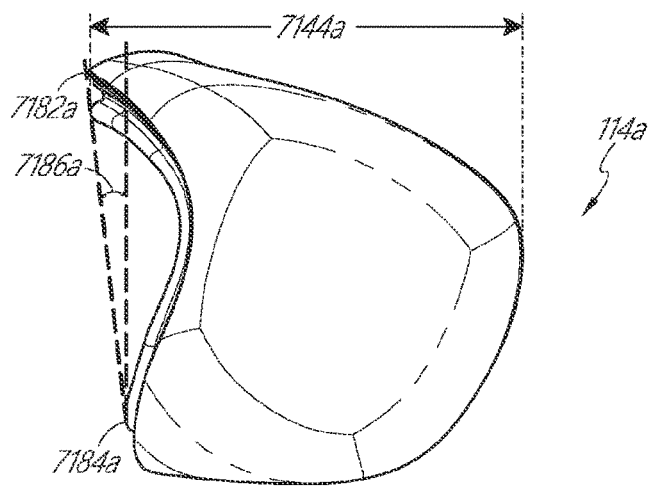

FIG. 60A is a left side view of the nasal seal of FIG. 58A.

Figure 60B:
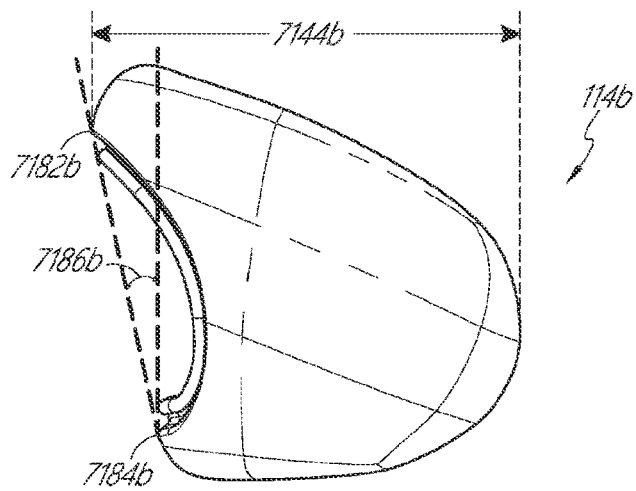

FIG. 60B is a left side view of the nasal seal of FIG. 58B.

Figure 60C:
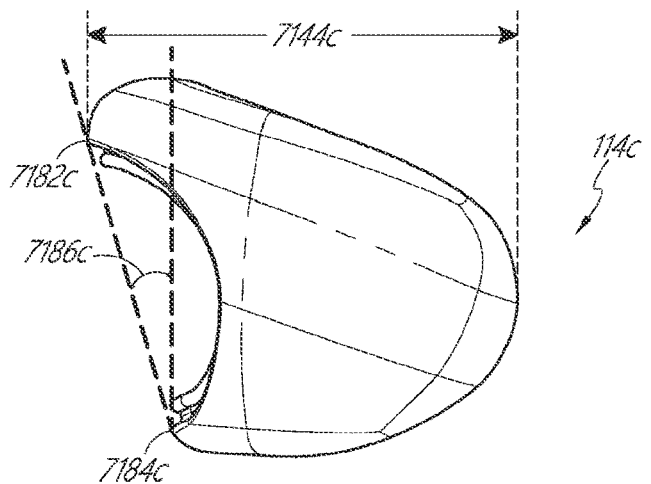

FIG. 60C is a left side view of the nasal seal of FIG. 58C.

Figure 61A:
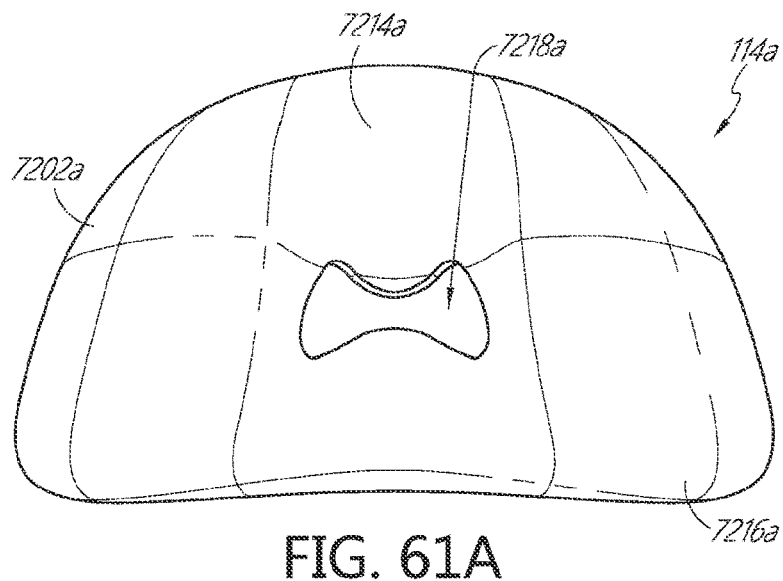

FIG. 61A is a rear view of the nasal seal of FIG. 58A.

Figure 61B:
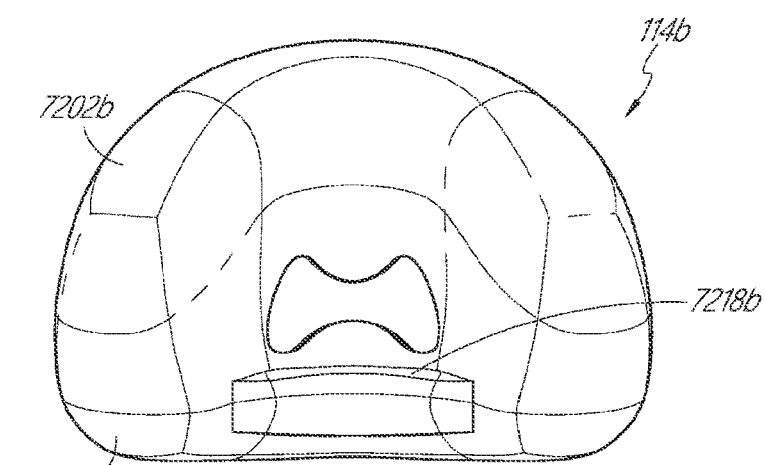

FIG. 61B is a rear view of the nasal seal of FIG. 58B.

Figure 61C:
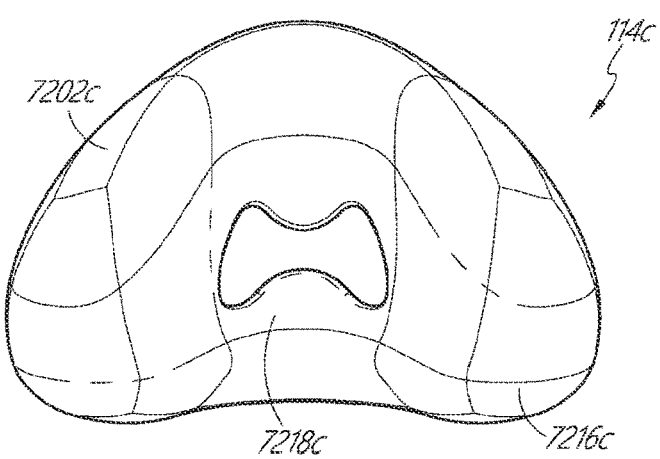

FIG. 61C is a rear view of the nasal seal of FIG. 58C.

Figure 62A:
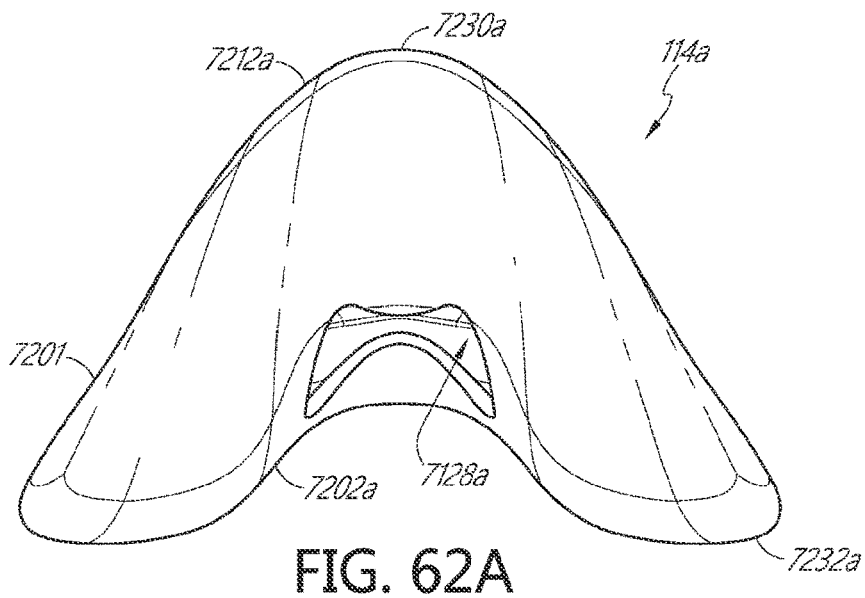

FIG. 62A is a top view of the nasal seal of FIG. 58A.

Figure 62B:
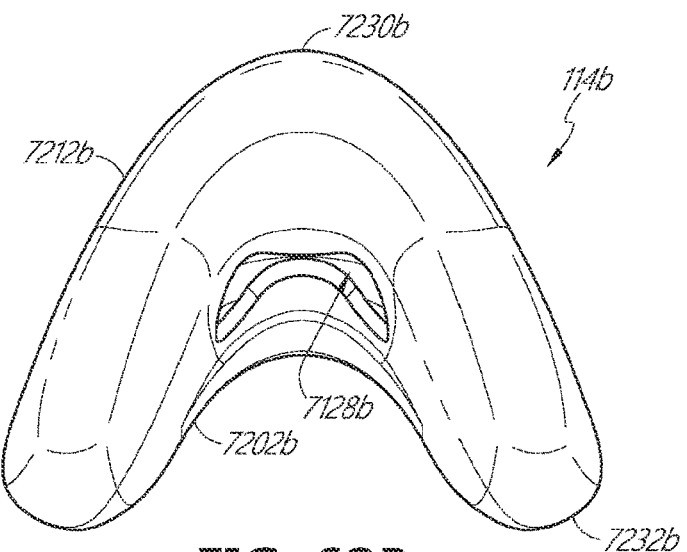

FIG. 62B is a top view of the nasal seal of FIG. 58B.

Figure 62C:
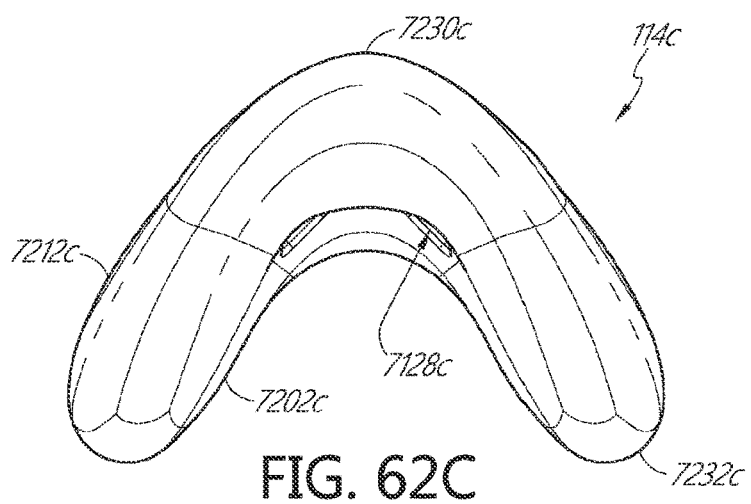

FIG. 62C is a top view of the nasal seal of FIG. 58C.

Figure 63A:
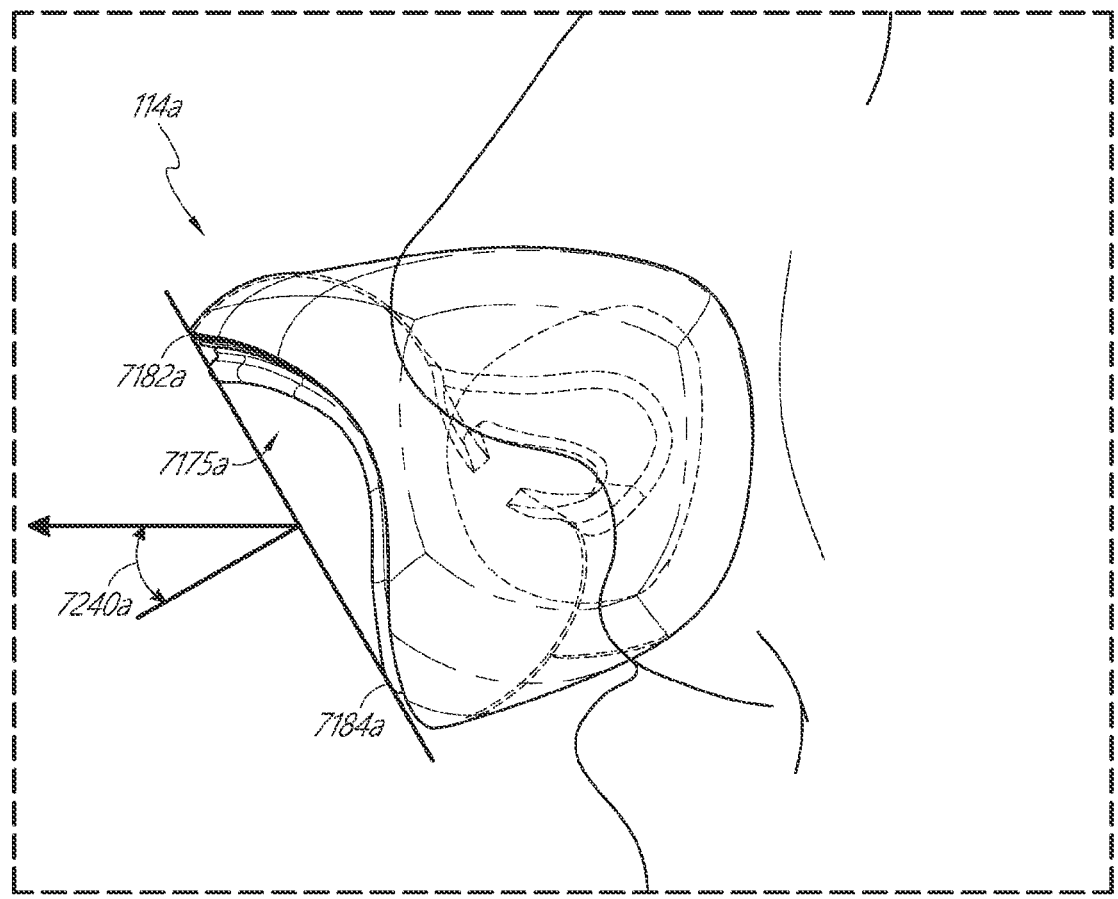

FIG. 63A is a left side view of the nasal seal of FIG. 58A in use.

Figure 63B:
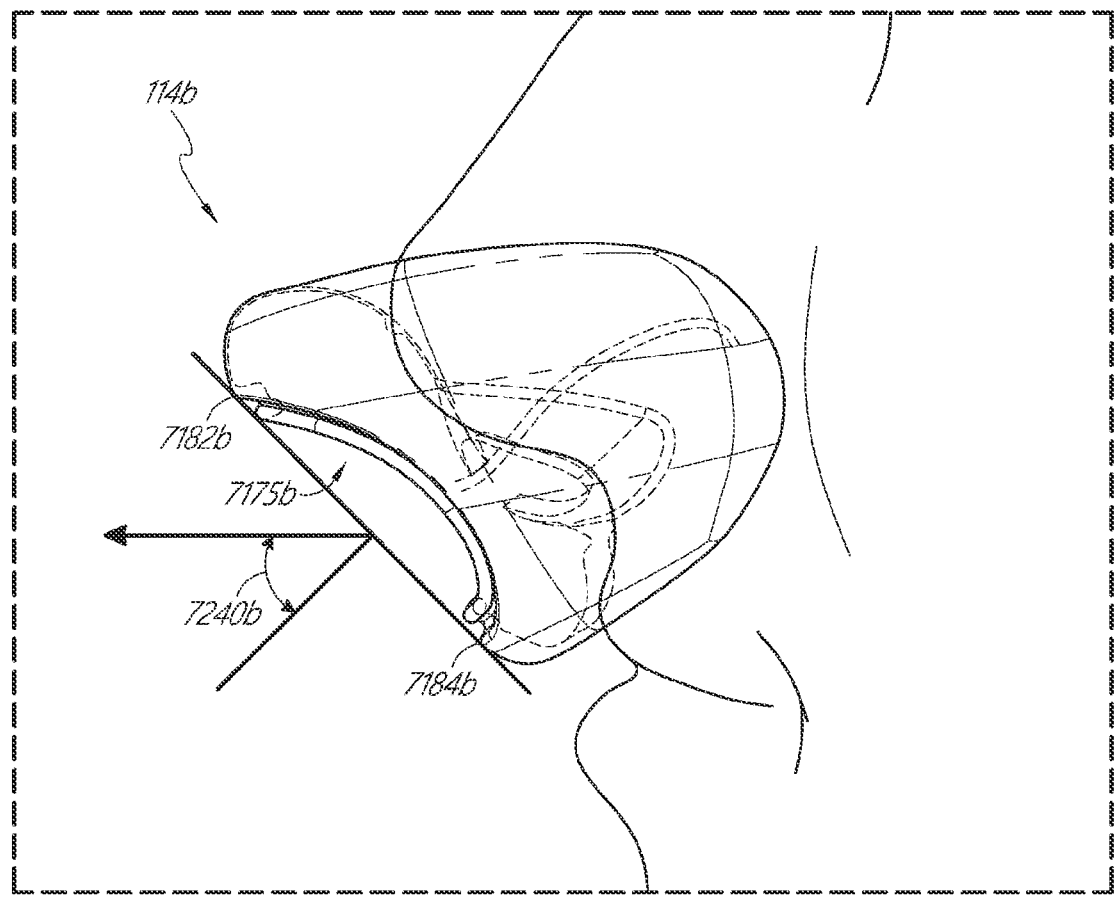

FIG. 63B is a left side view of the nasal seal of FIG. 58B in use.

Figure 63C:
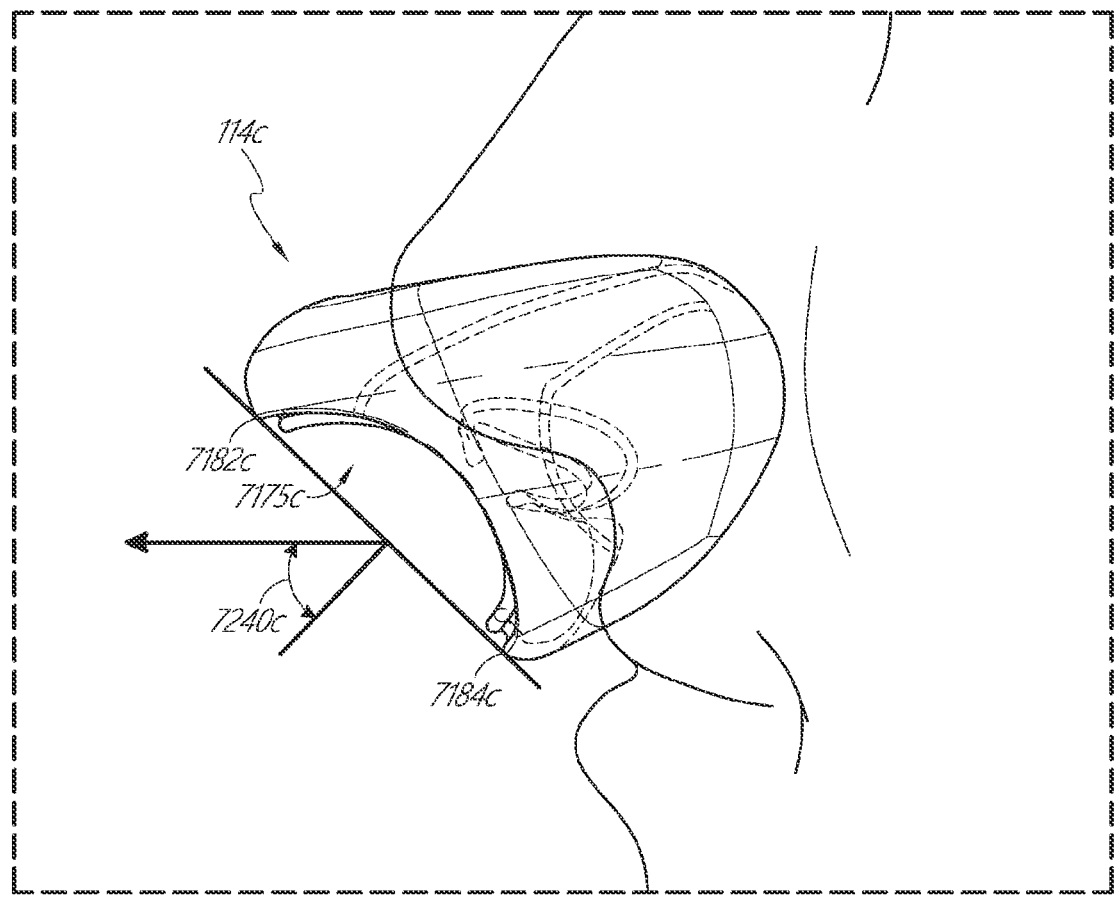

FIG. 63C is a left side view of the nasal seal of FIG. 58C in use.

Figure 64:
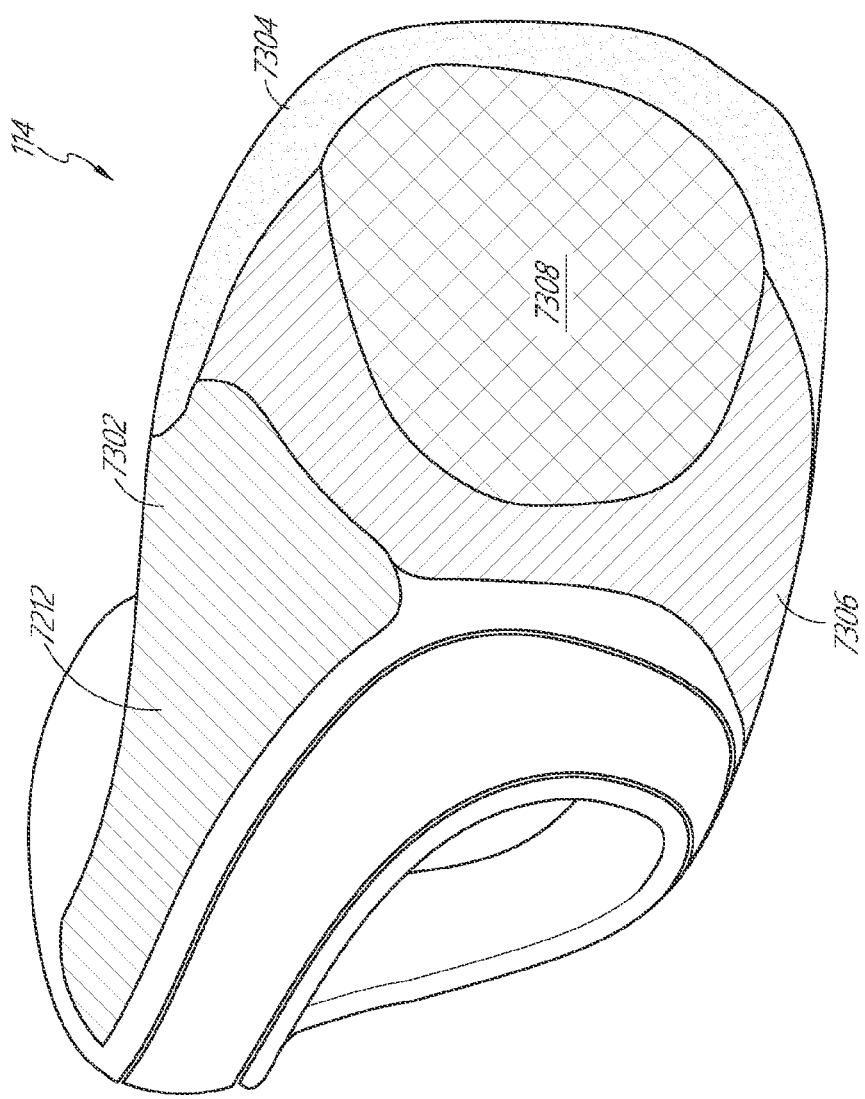

FIG. 64 is a perspective view of an embodiment of a nasal seal.

Figure 65B:
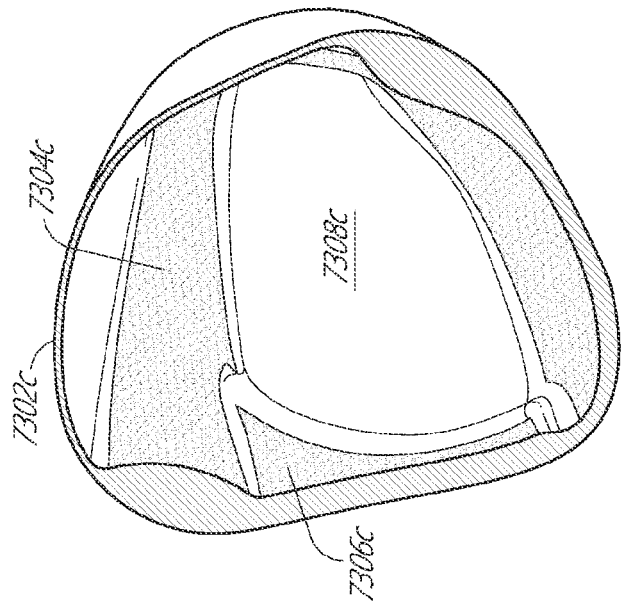
Figure 65A:
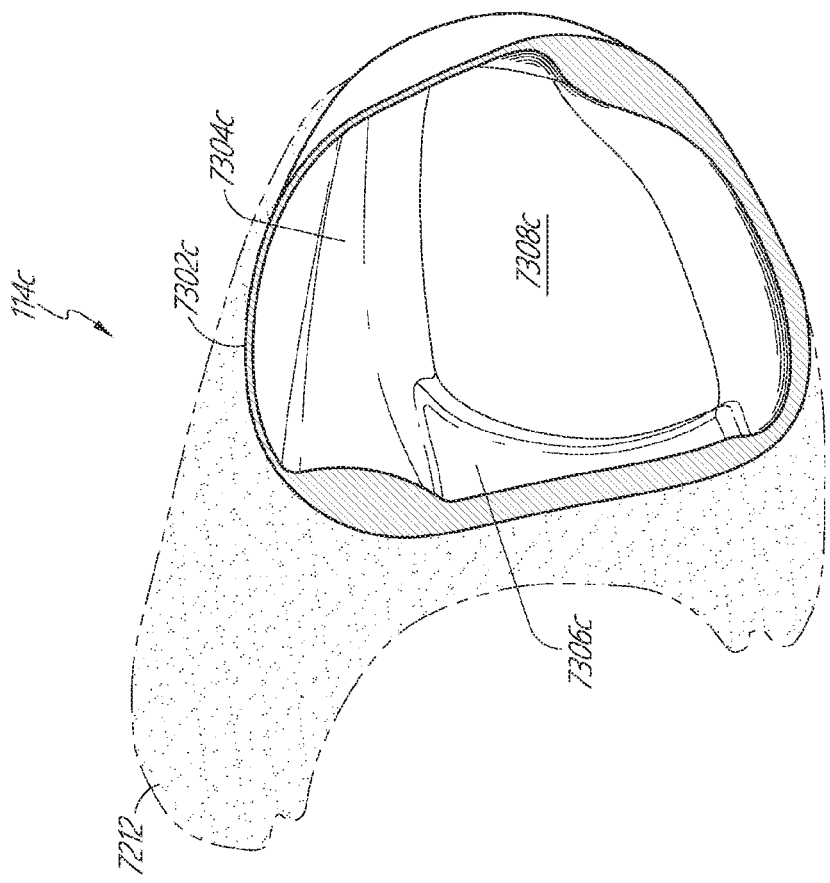

FIG. 65A is a partial cross-sectional view of the nasal seal of FIG. 58C.

FIG. 65B is a partial cross-sectional view of the nasal seal of FIG. 58C.

Figure 66C:
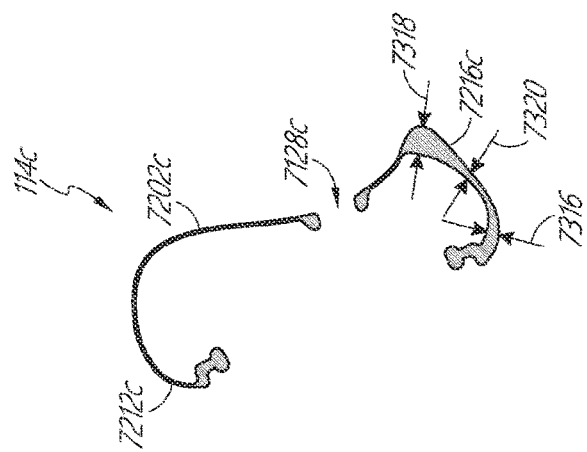
Figure 66B:
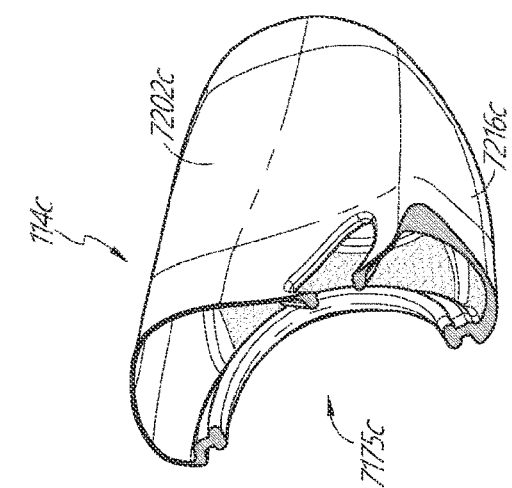
Figure 66A:
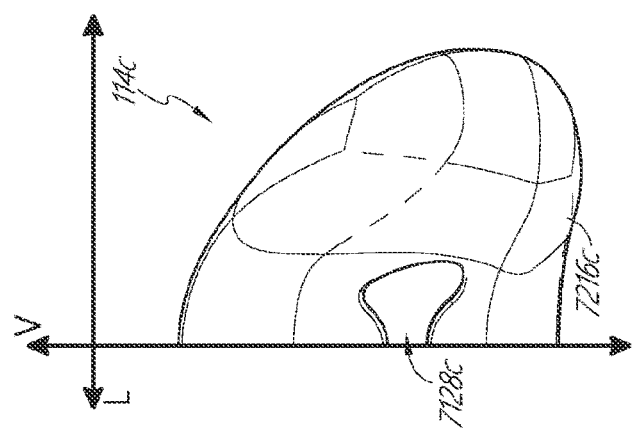

FIG. 66A is a partial rear view of the nasal seal of FIG. 58C.

FIG. 66B is a partial sagittal cross-sectional view of the nasal seal of FIG. 58C.

FIG. 66C is a sagittal cross-sectional view of the nasal seal of FIG. 58C.

Figure 67A:
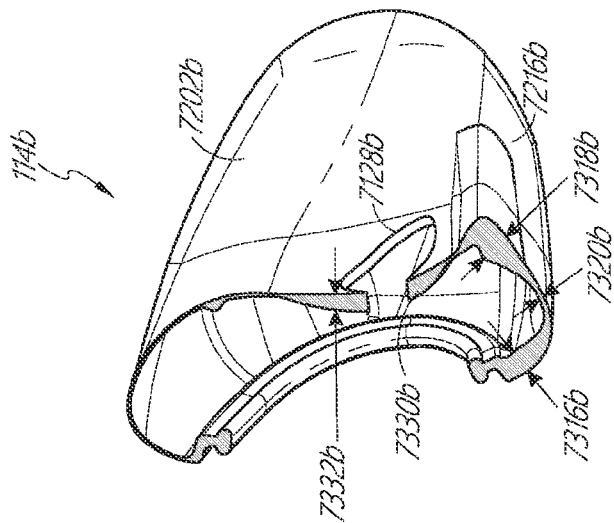

FIG. 67A is a partial sagittal cross-sectional view of the nasal seal of FIG. 58A.

Figure 67B:
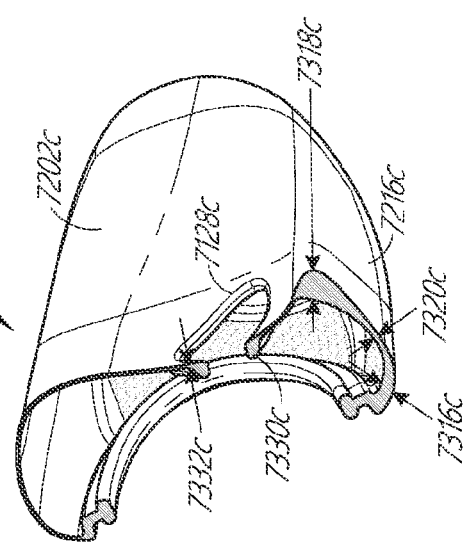

FIG. 67B is a partial sagittal cross-sectional view of the nasal seal of FIG. 58B.

Figure 67C:
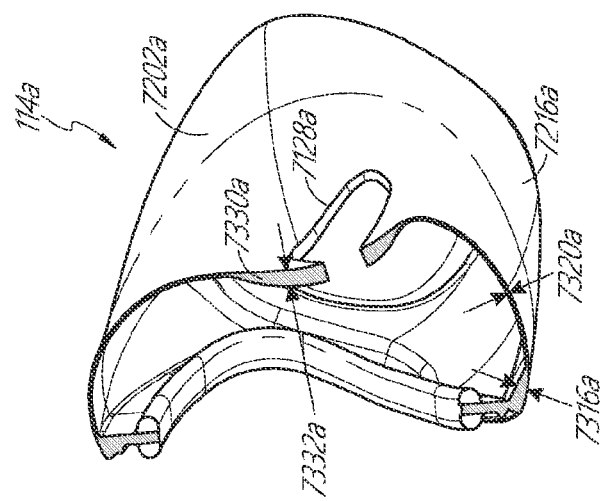

FIG. 67C is a partial sagittal cross-sectional view of the nasal seal of FIG. 58C.

Figure 68:
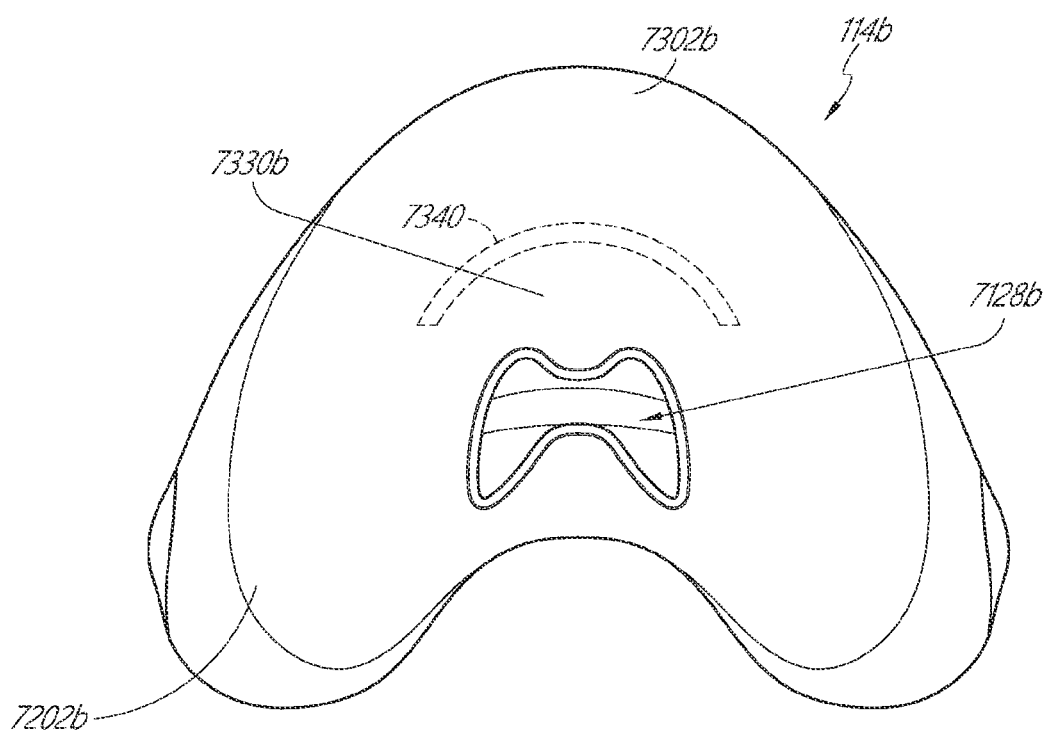

FIG. 68 is a rear view of an embodiment of a nasal seal.

Figure 69:
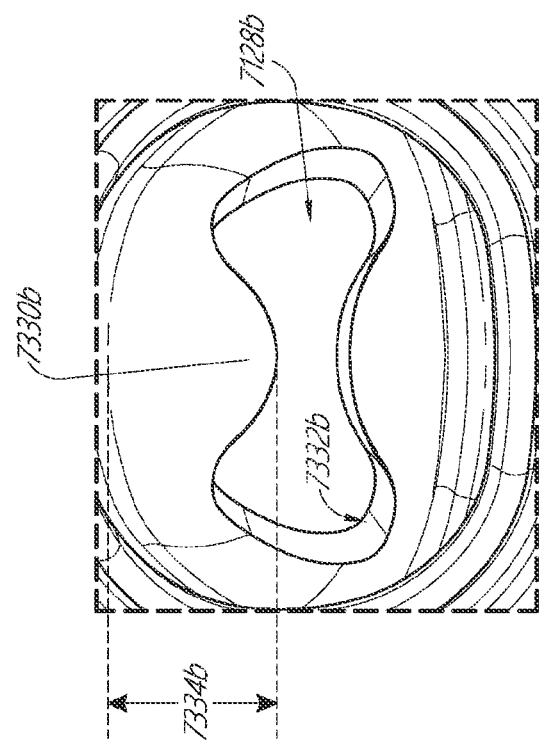

FIG. 69 is a partial rear view of the nasal seal of FIG. 58B.

Figure 70:
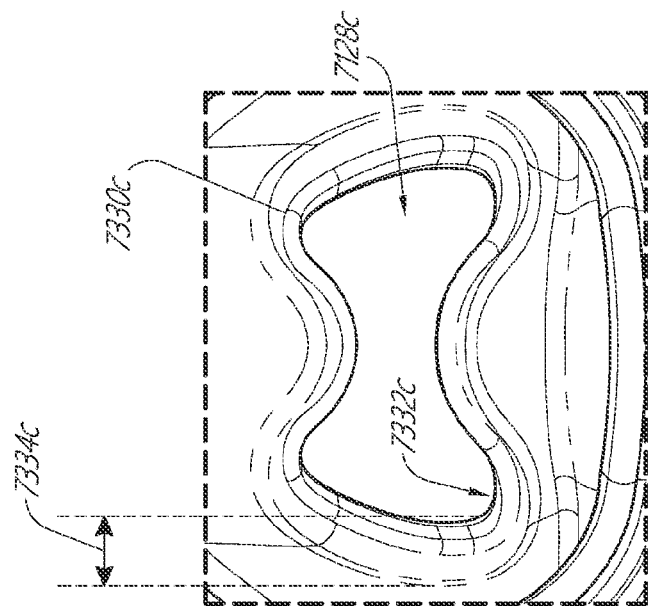

FIG. 70 is a partial rear view of the nasal seal of FIG. 58C.

Figure 71B:
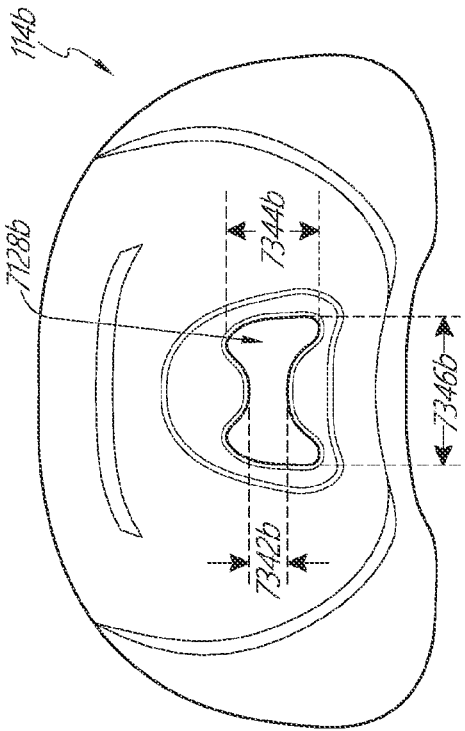
Figure 71A:
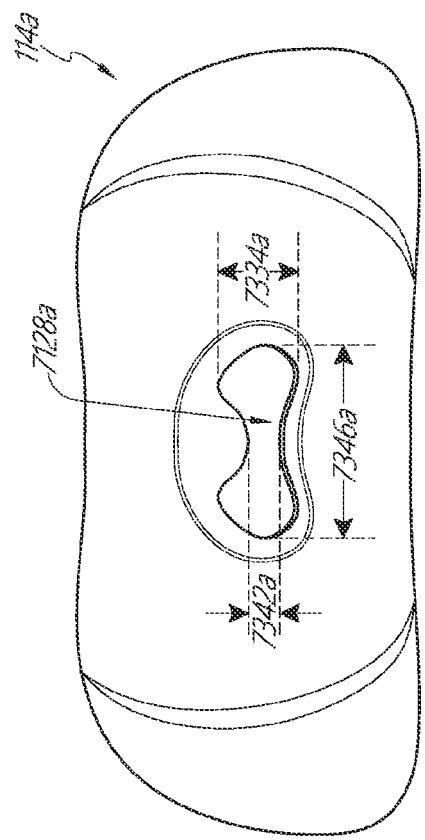

FIG. 71A is a rear view of the nasal seal of FIG. 58A.

FIG. 71B is a rear view of the nasal seal of FIG. 58B.

Figure 71C:
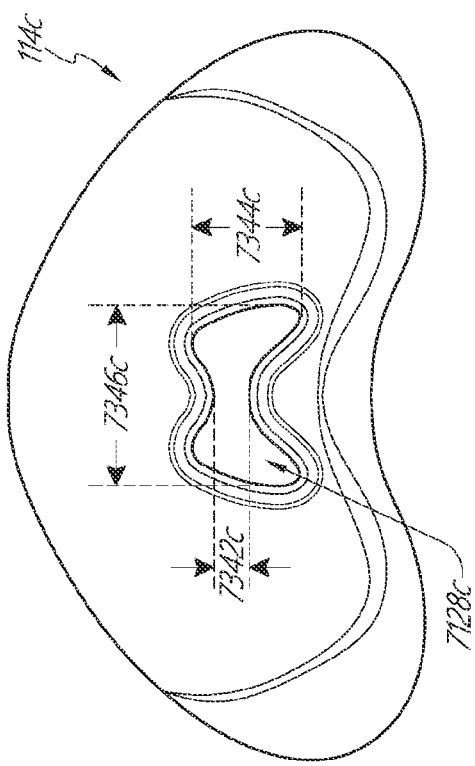

FIG. 71C is a rear view of the nasal seal of FIG. 58C.

Figure 72:
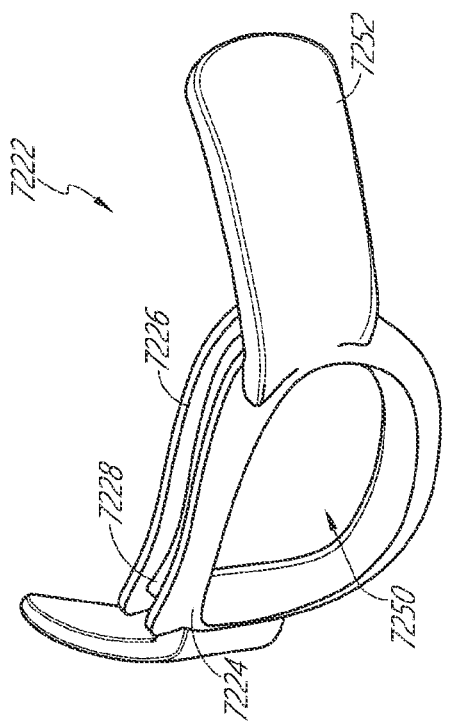

FIG. 72 is a perspective view of an embodiment of a connector.

Figure 73:
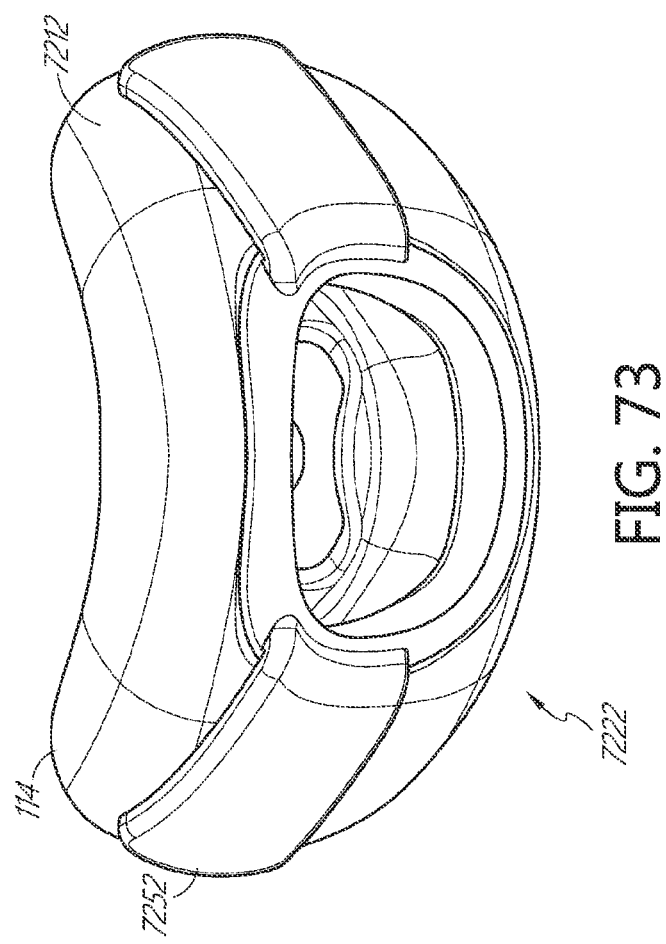

FIG. 73 is a perspective view of the connector of FIG. 72 on a nasal seal.

Figure 74:
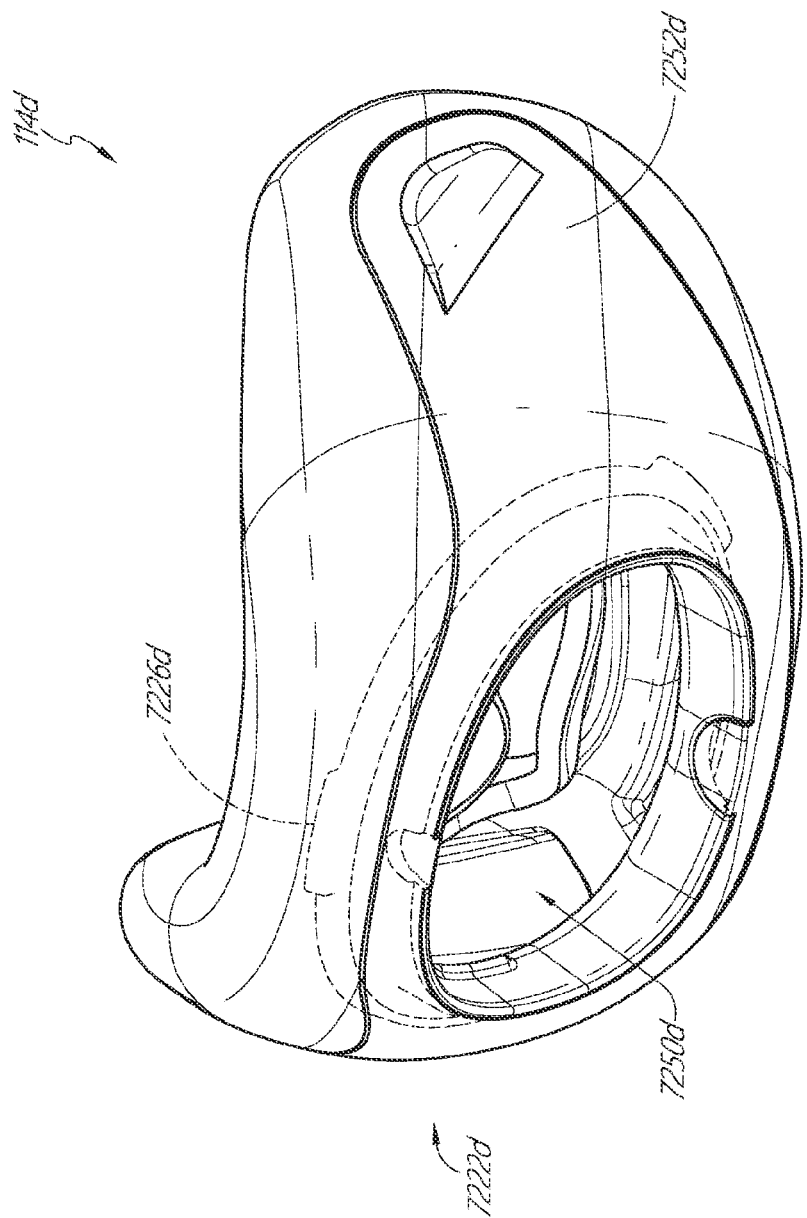

FIG. 74 is a front perspective view of an embodiment of a connector attached to a nasal seal.

Figure 75:
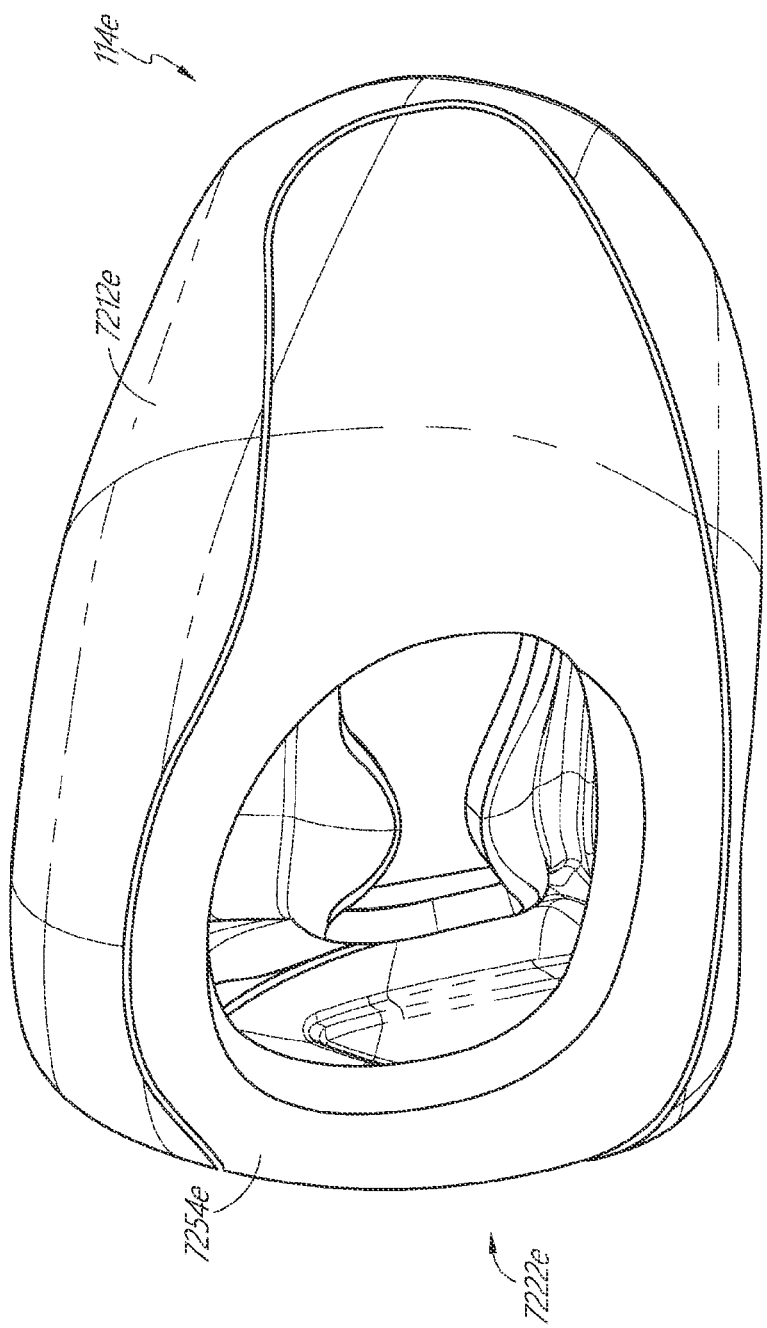

FIG. 75 is a front perspective view of an embodiment of a connector attached to a nasal seal.

Figure 76B:
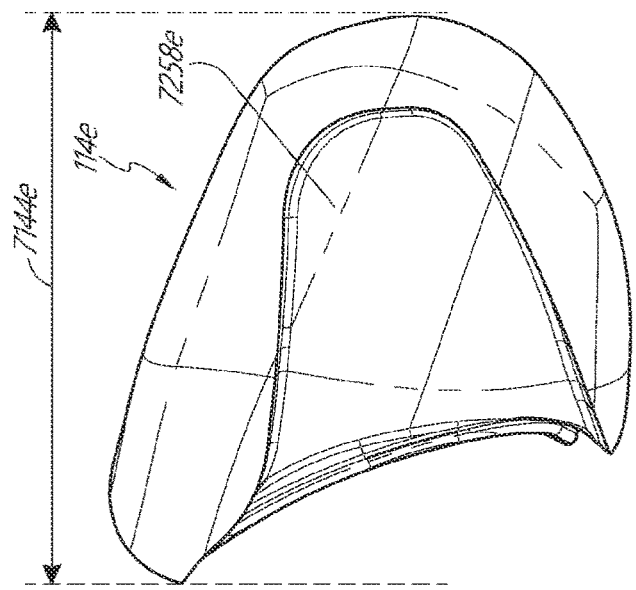
Figure 76A:
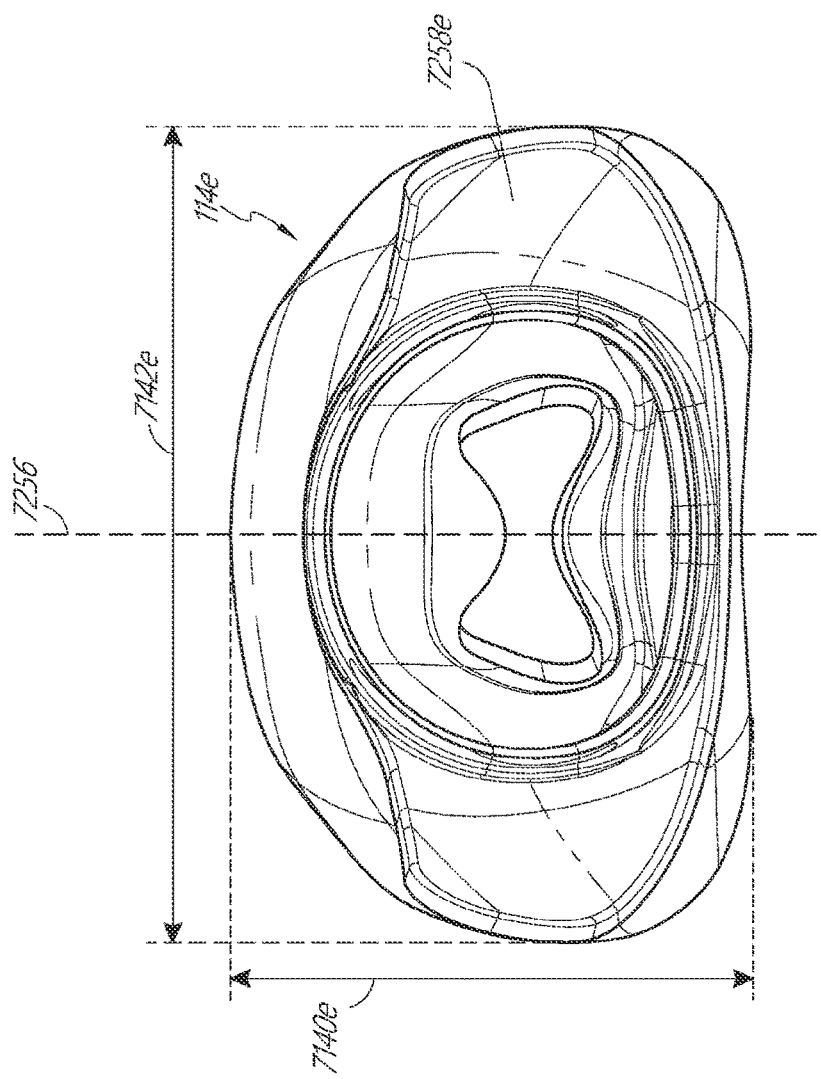

FIG. 76A is a front view of an embodiment of a nasal seal.

FIG. 76B is a left side view of the nasal seal of FIG. 76A.

FIG. 76C is a rear view of the nasal seal of FIG. 76A.

FIG. 76D is a top view of the nasal seal of FIG. 76A.

FIG. 76E is a bottom view of the nasal seal of FIG. 76A.

Figure 77:
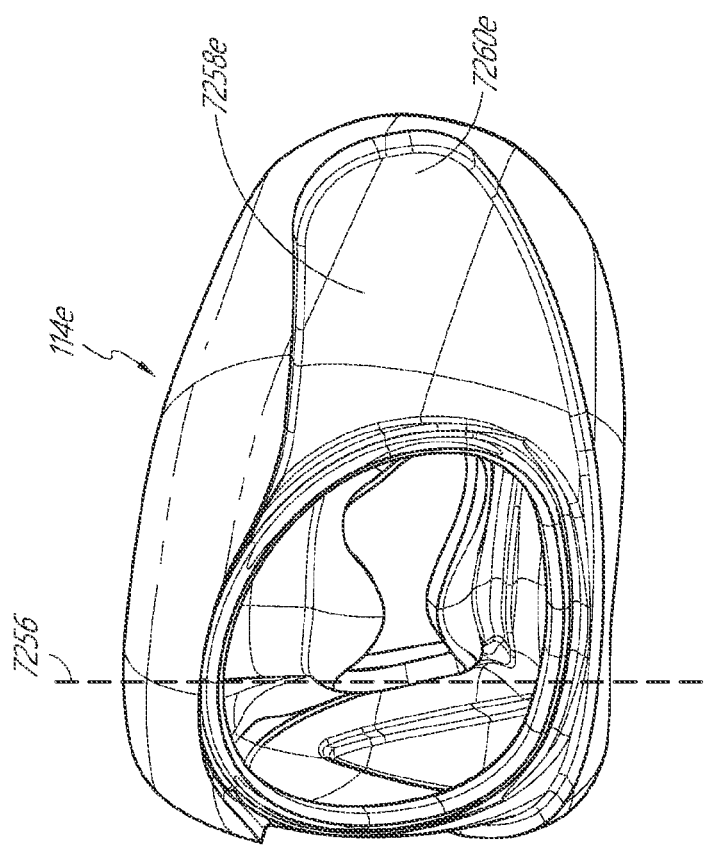

FIG. 77 is a perspective view of an embodiment of a medium-sized nasal seal.

Figure 78:
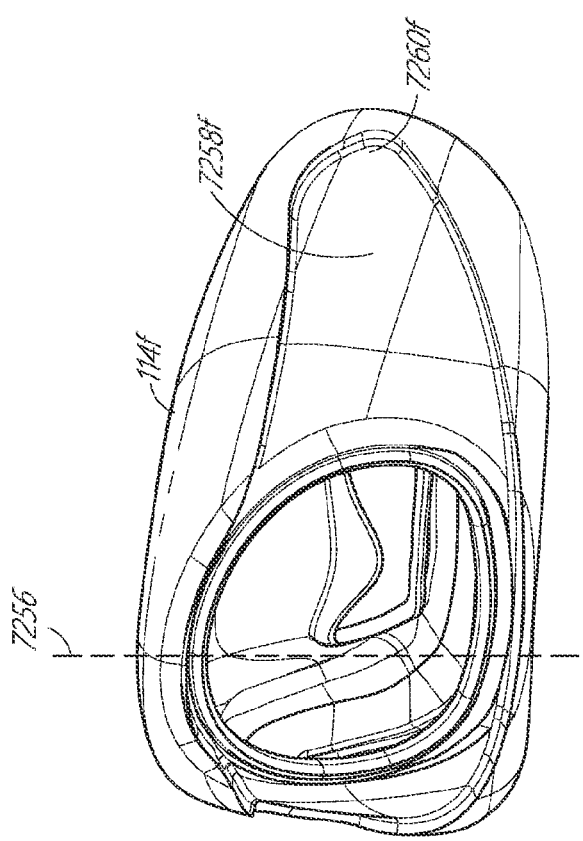

FIG. 78 is a perspective view of an embodiment of a wide-sized nasal seal.

Figure 79B:
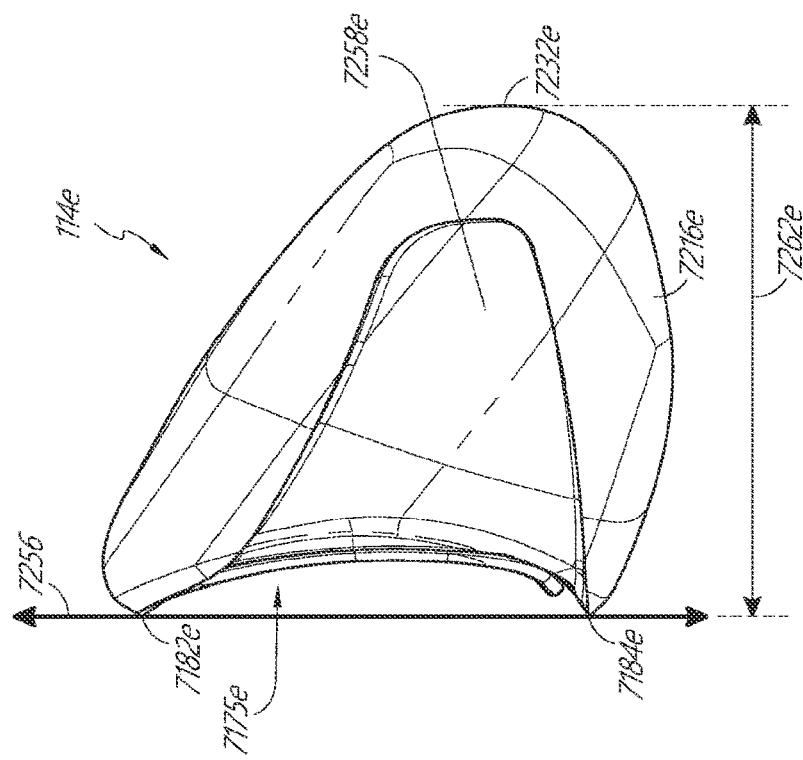
Figure 79A:
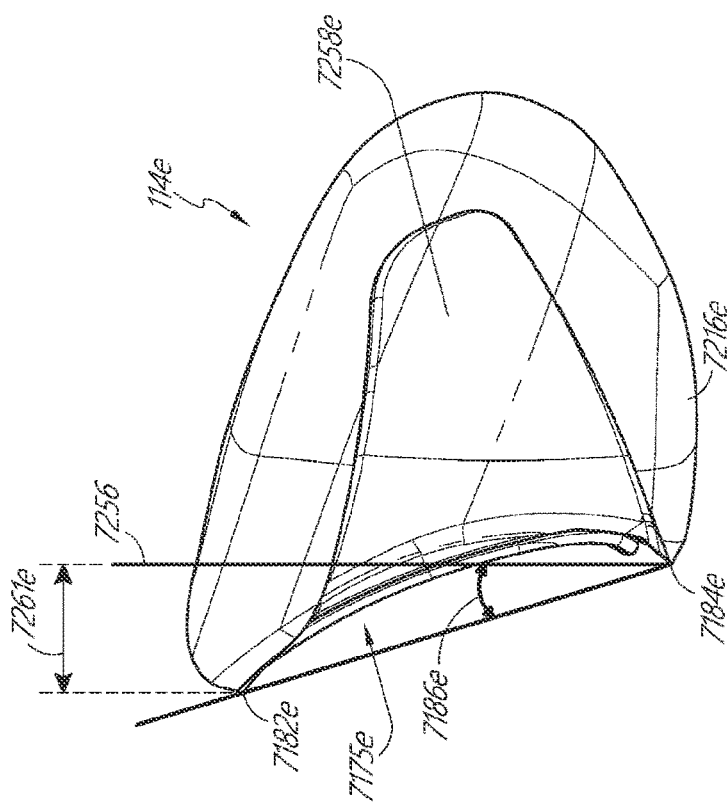

FIG. 79A is a left side view of the nasal seal of FIG. 76A.

FIG. 79B is a left side view of the nasal seal of FIG. 76A.

Figure 80:
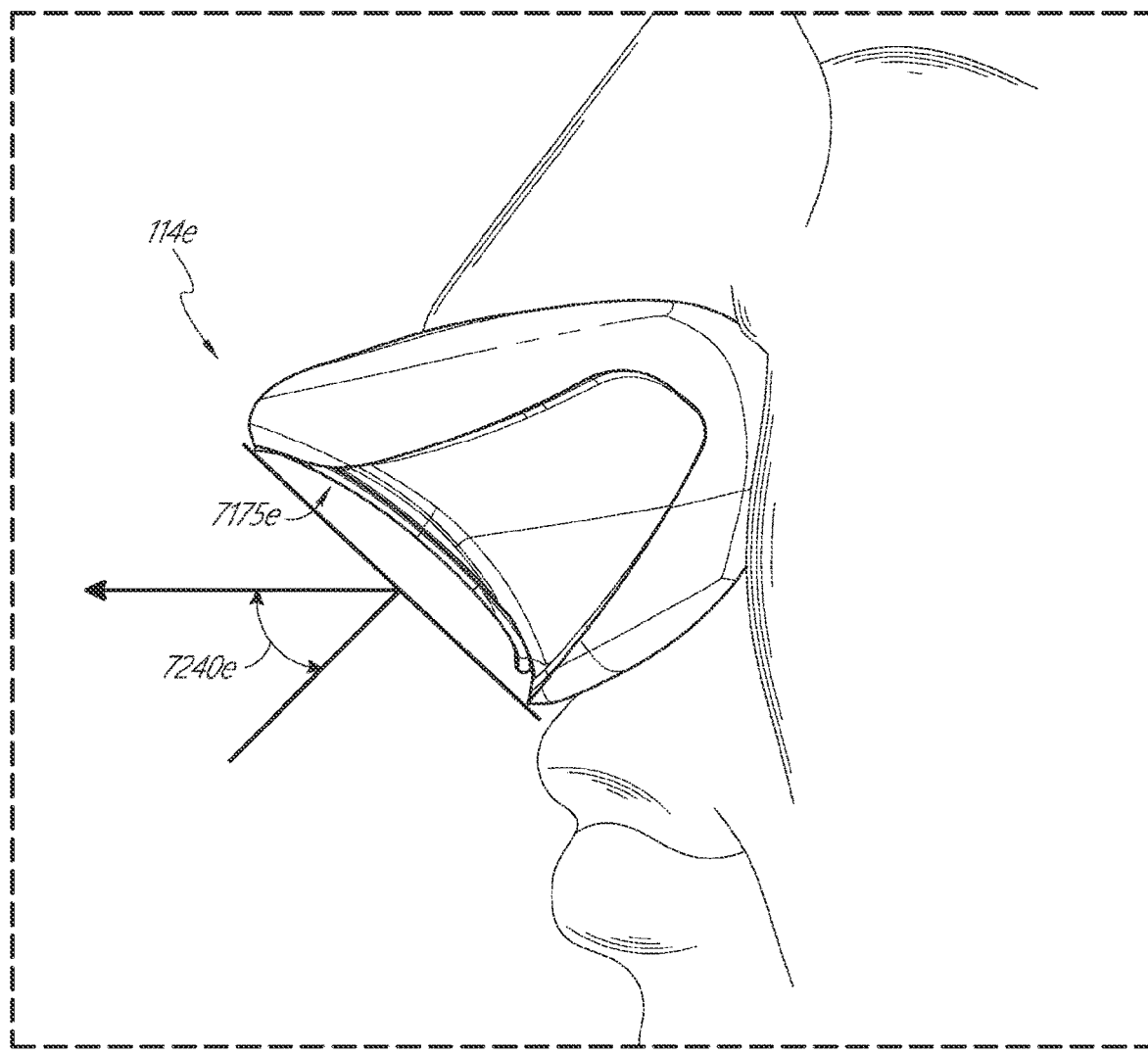

FIG. 80 is a side view of the nasal seal of FIG. 76A positioned on the nose of a user.

Figure 81:
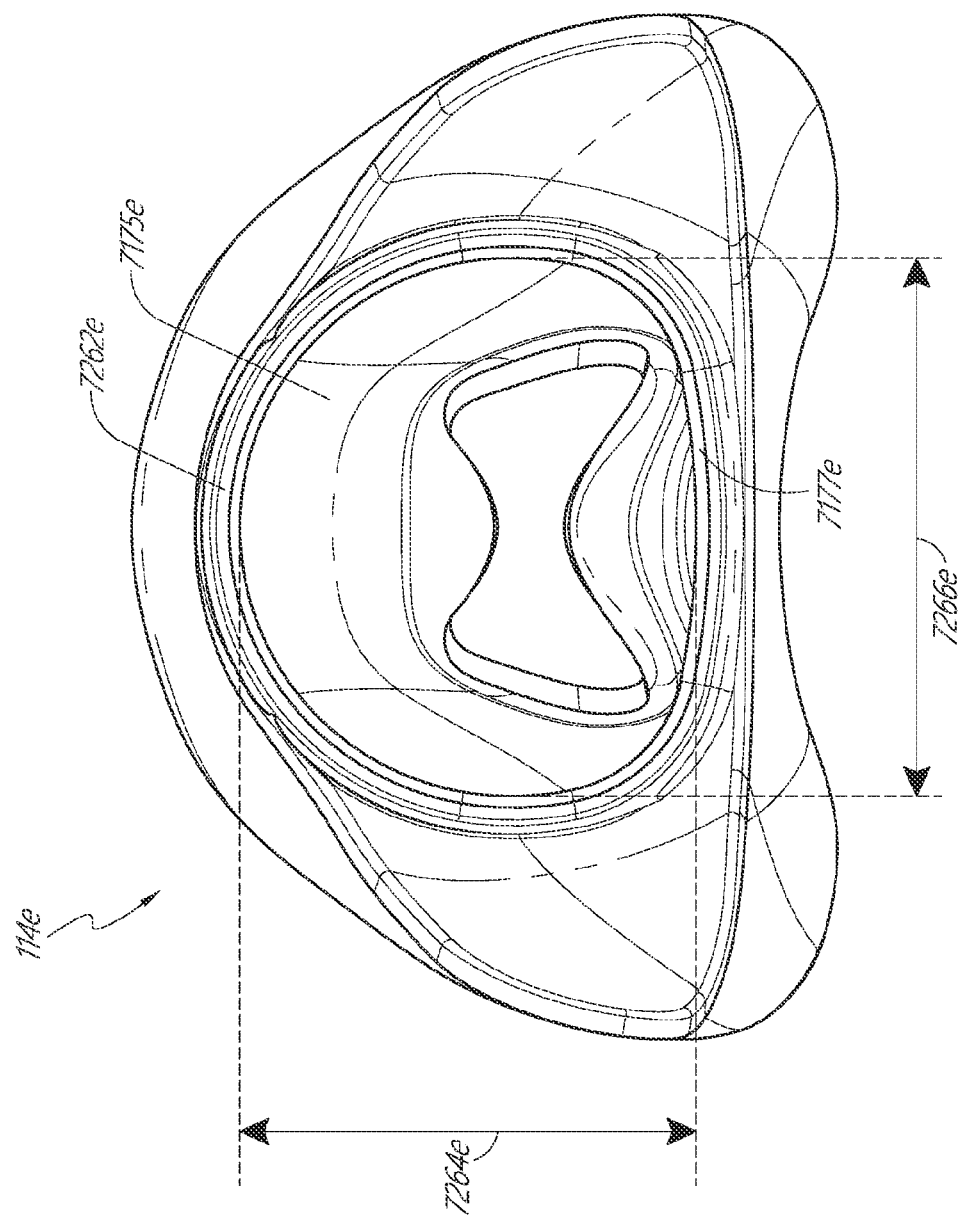

FIG. 81 is a front view of the nasal seal of FIG. 76A.

Figure 82B:
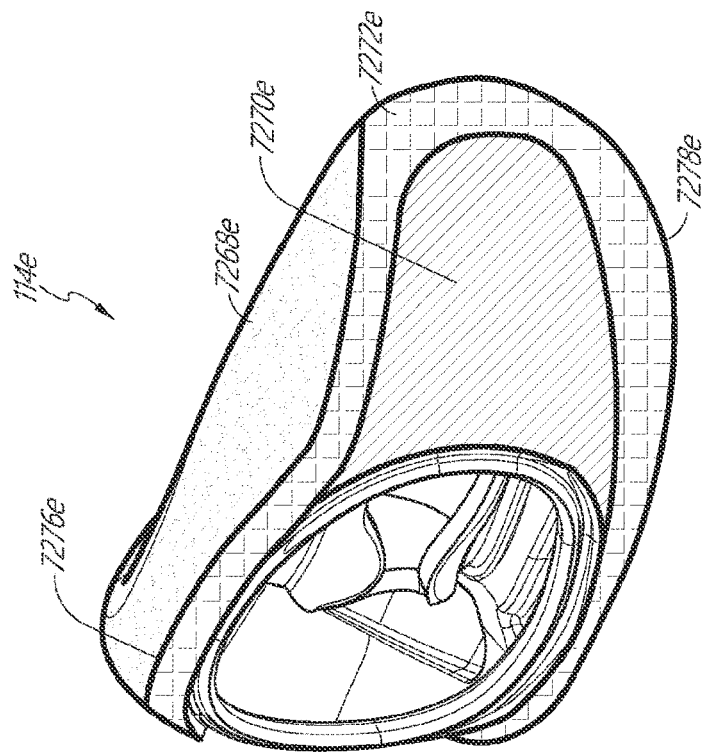
Figure 82A:
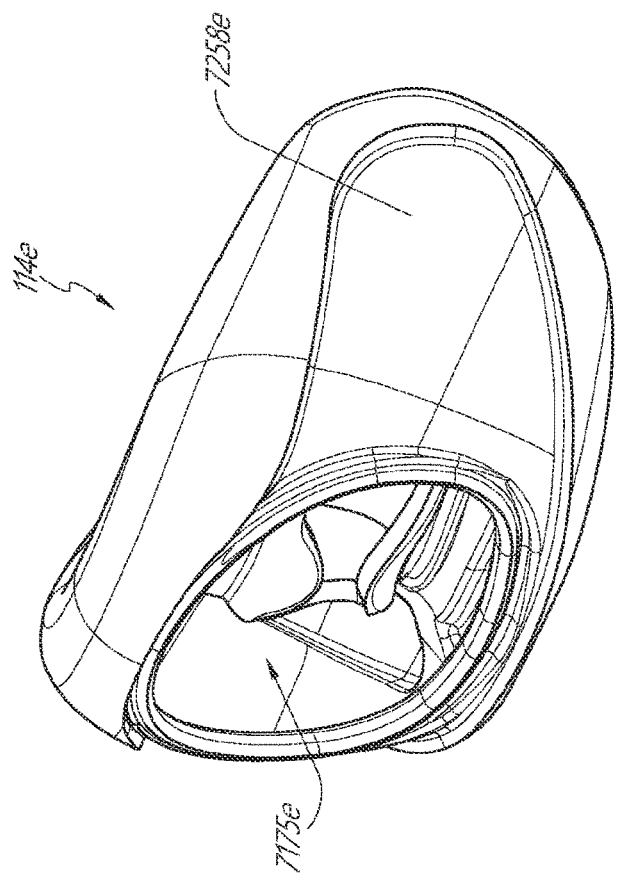

FIG. 82A is a front perspective view of an embodiment of a nasal seal.

FIG. 82B is a front perspective view of the nasal seal of FIG. 82A illustrating the position on the seal of different regions of wall thickness.

Figure 83:
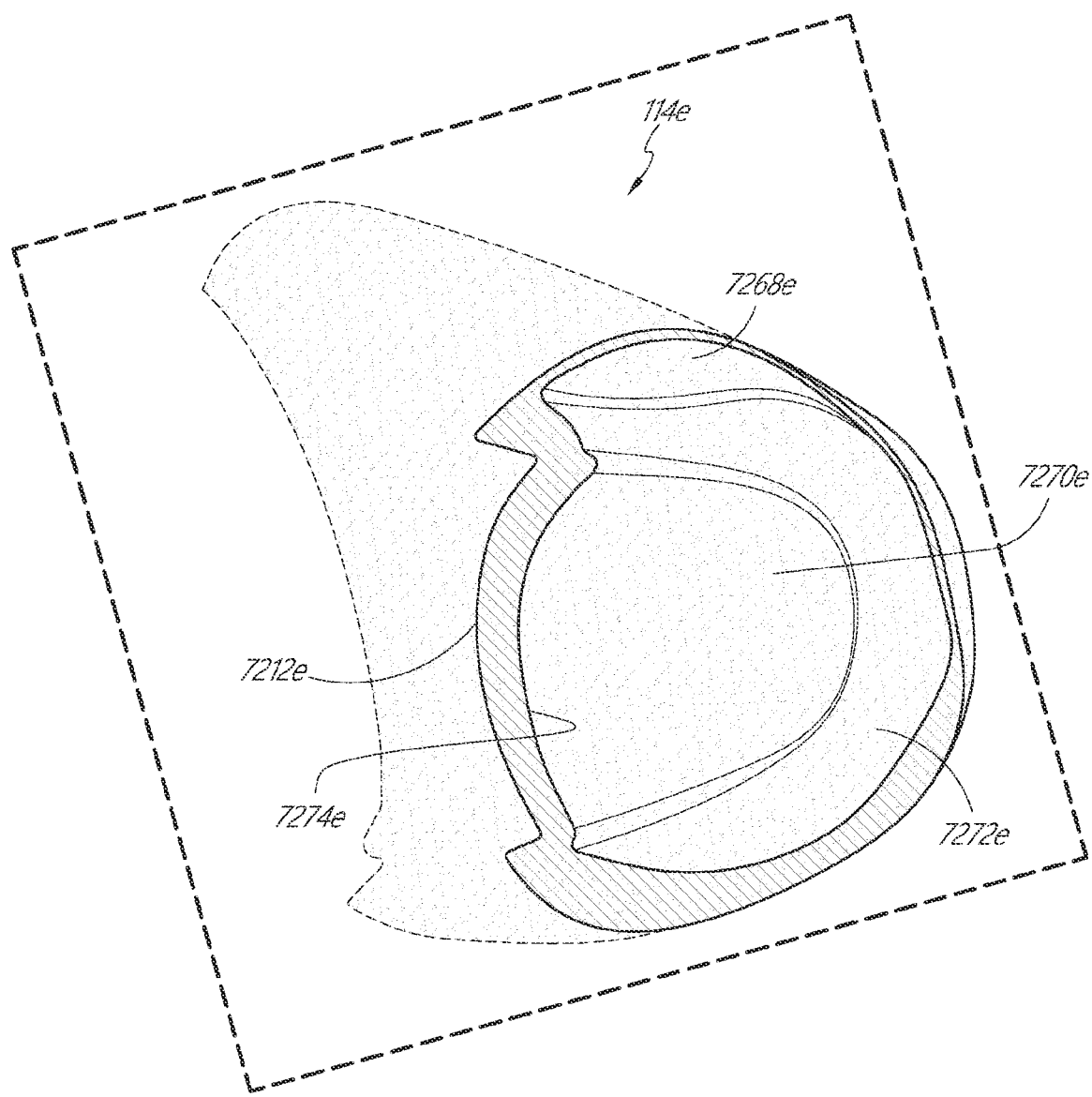

FIG. 83 is a partial cross-section of an embodiment of the nasal seal.

Figure 84:
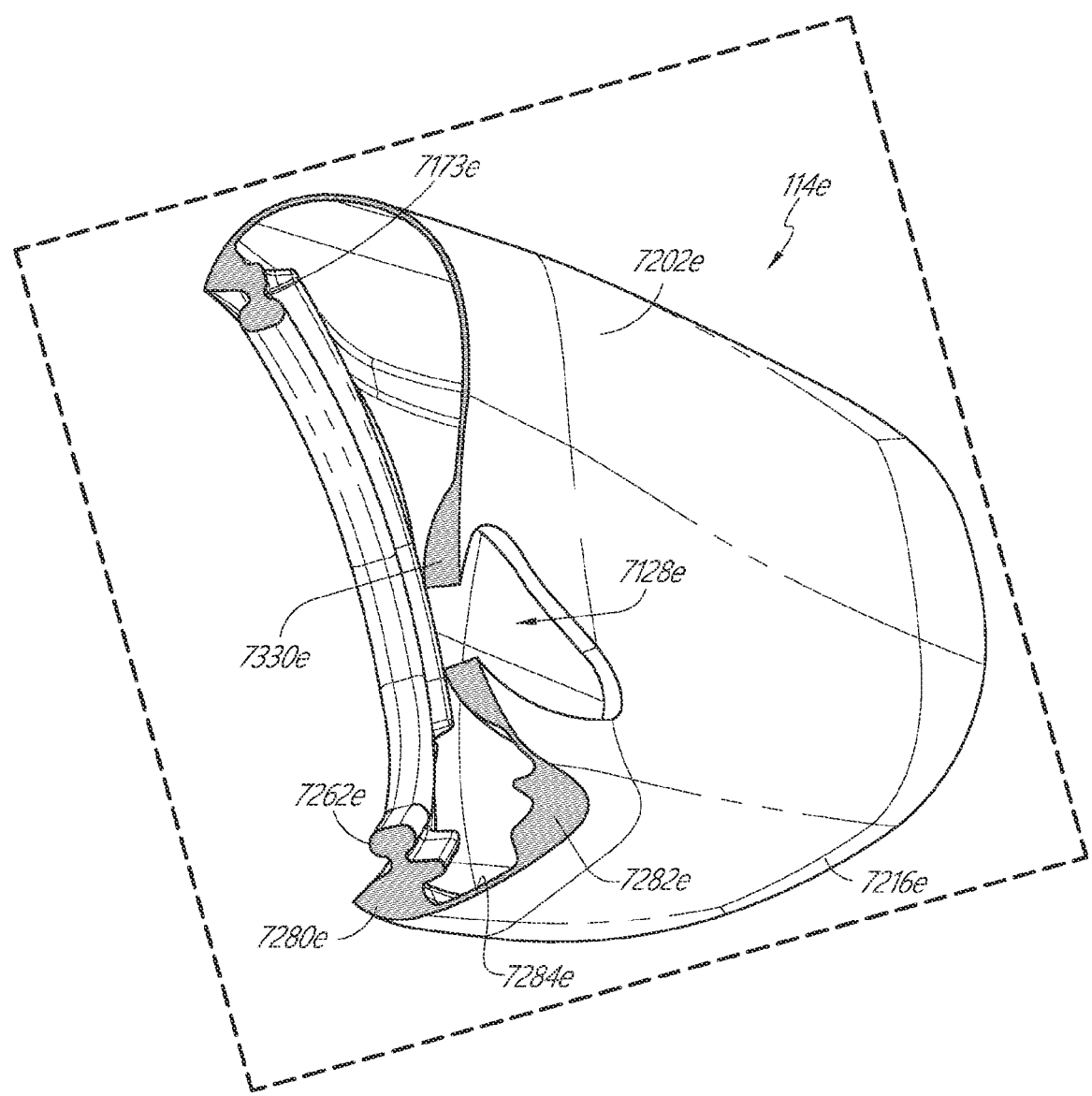

FIG. 84 is a sagittal cross-section of an embodiment of the nasal seal.

Figure 85:
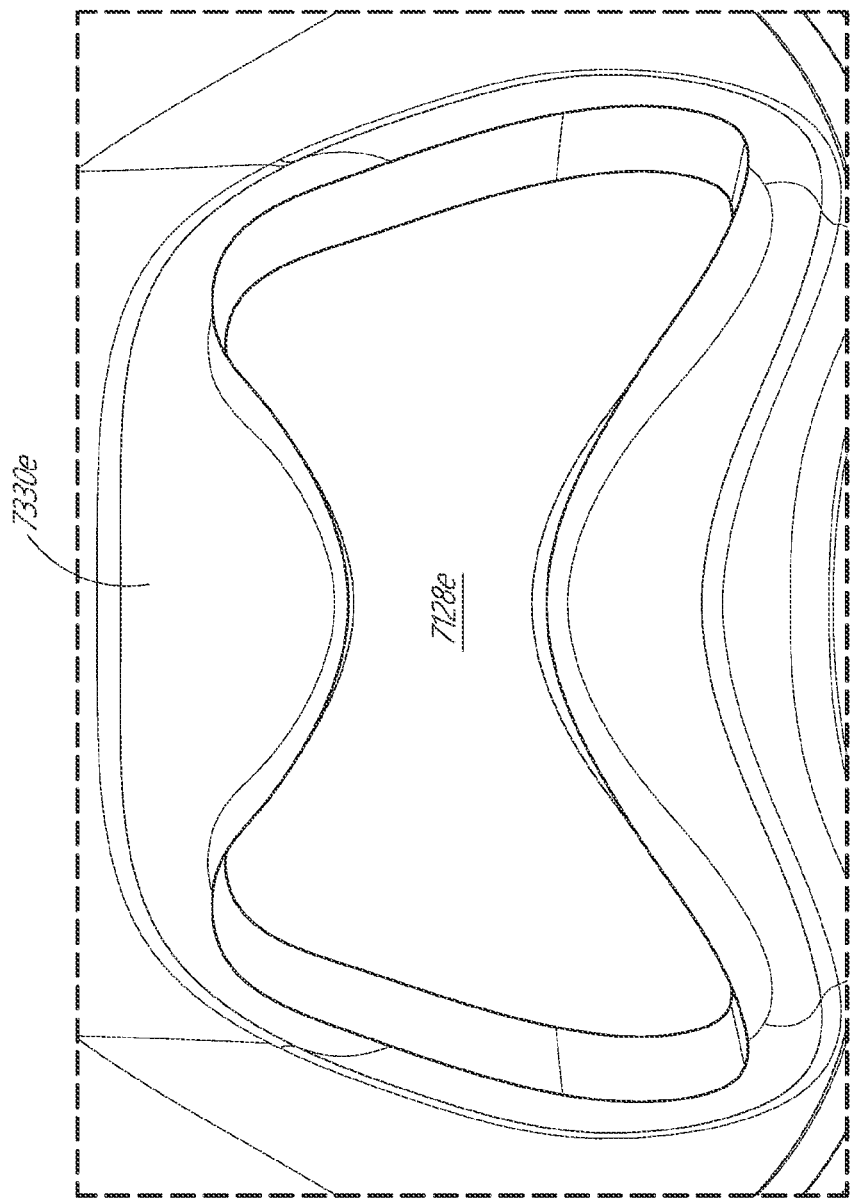

FIG. 85 is a front view of the inner surface of the rear wall of an embodiment of the nasal seal illustrating the thickened portion that surrounds the nasal aperture.

Figure 86:
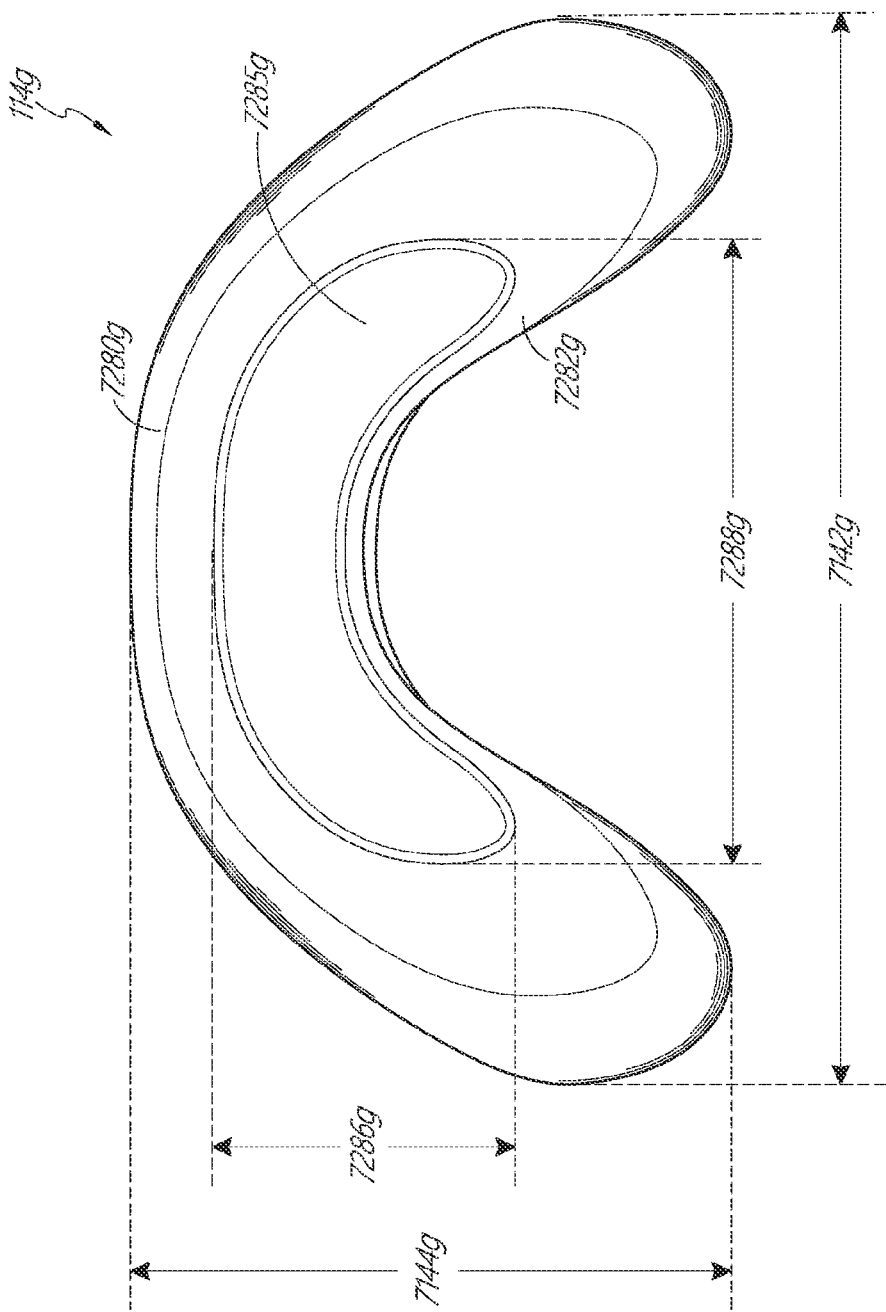

FIG. 86 is a bottom view of an embodiment of a nasal seal having a sub-nasal window.

Figure 87:
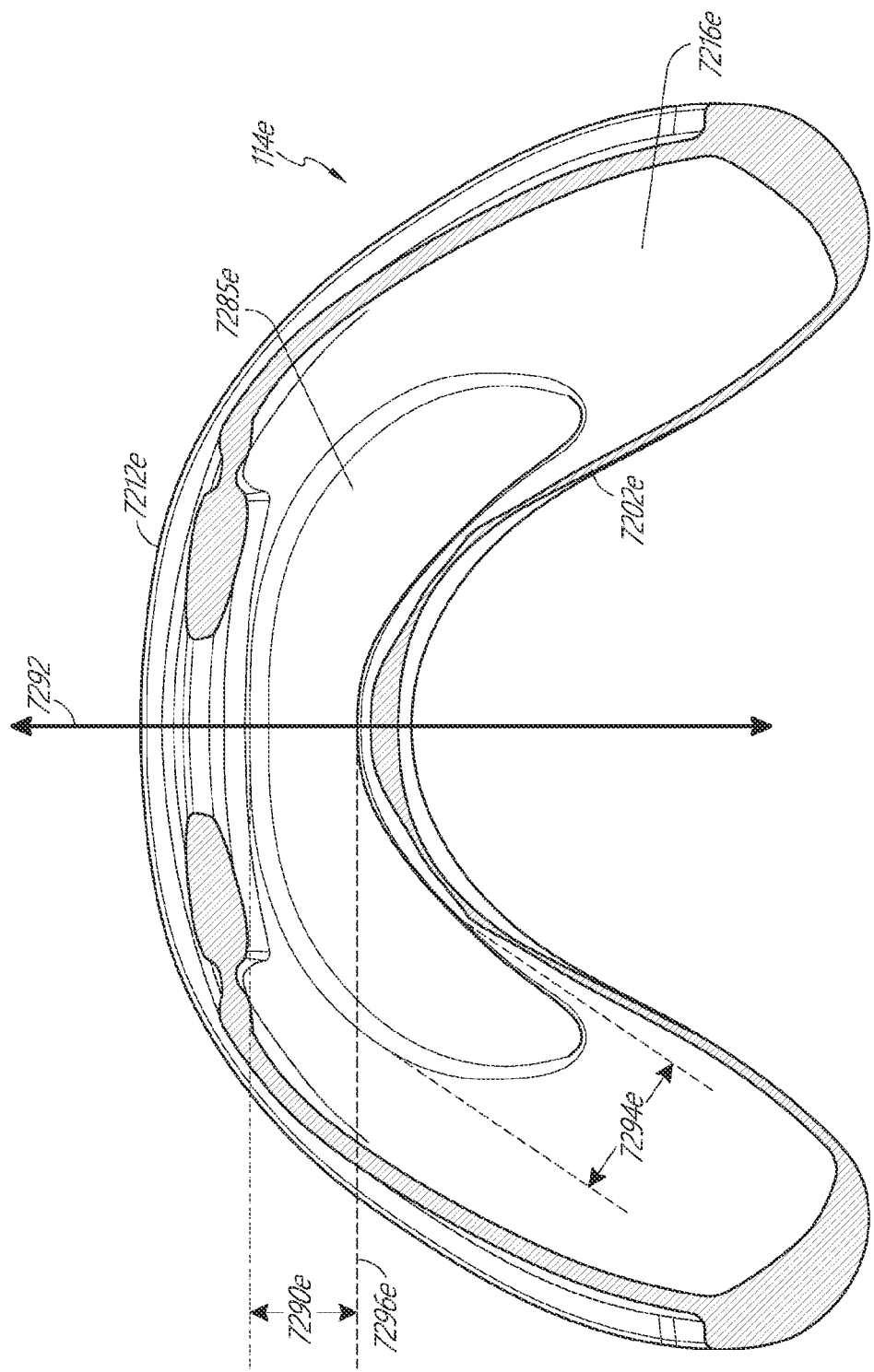

FIG. 87 is a cross-sectional top view of an embodiment of a nasal seal having a sub-nasal window.

Figure 88:
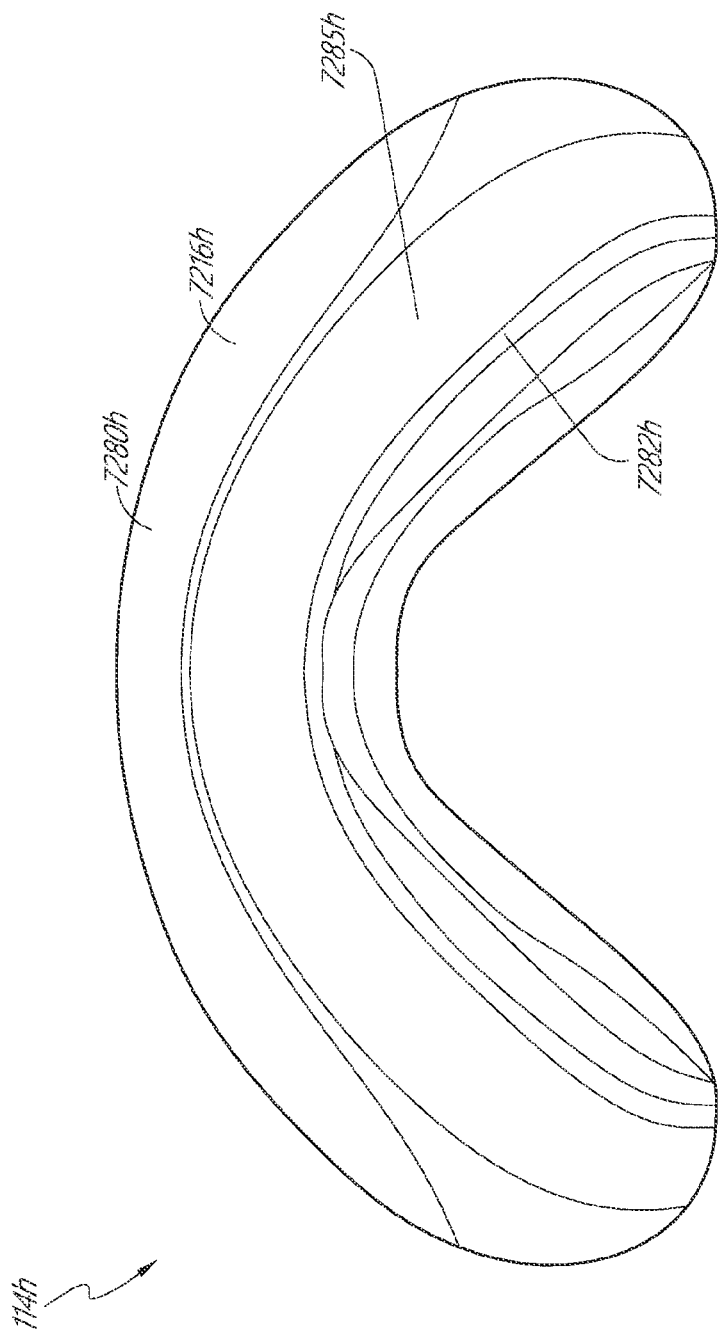

FIG. 88 is a bottom view of an embodiment of a nasal seal having a sub-nasal window that extends across the bottom wall of the seal.

Figure 89:
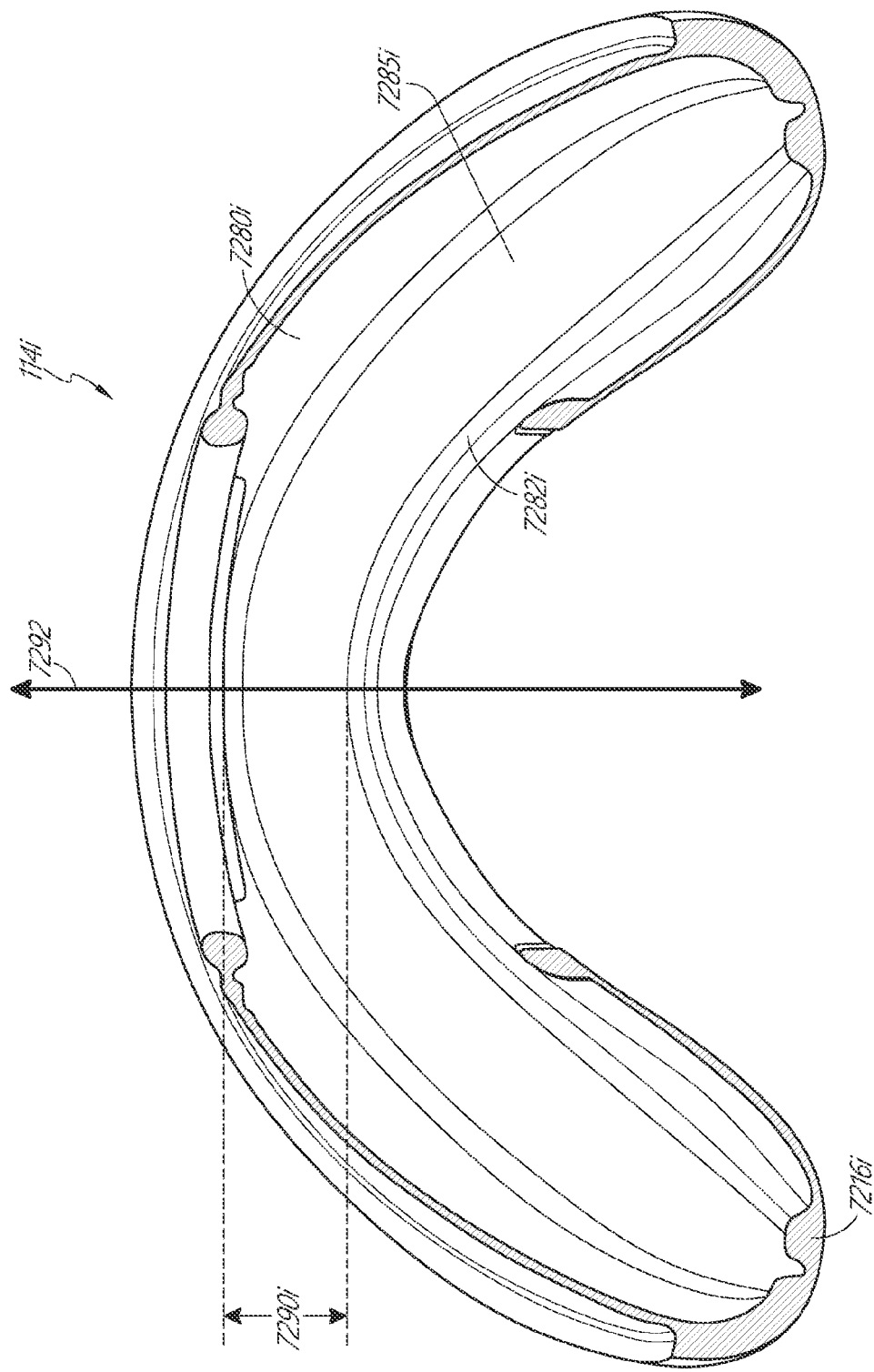

FIG. 89 is a cross-sectional top view of an embodiment of a nasal seal having a sub-nasal window that extends across the bottom wall of the seal.

Figure 90:
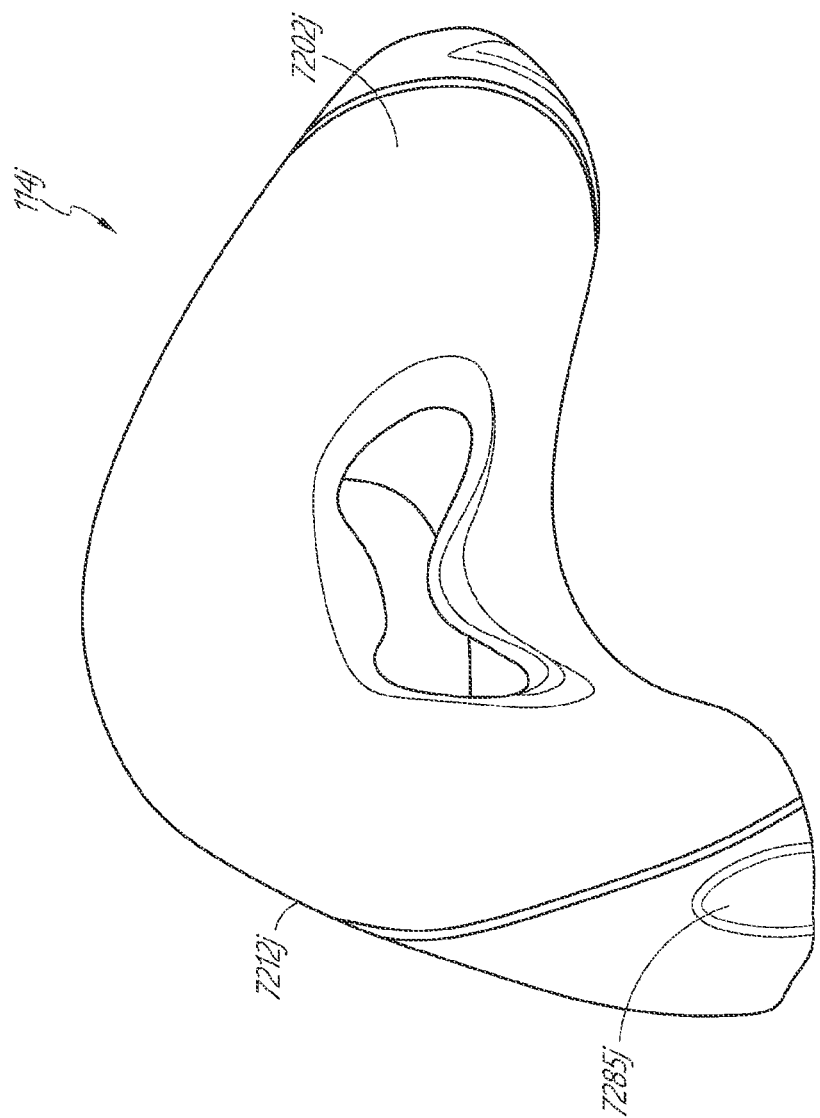

FIG. 90 is a rear perspective view of an embodiment of a nasal seal having a sub-nasal window that extends across the bottom wall of the seal.

Figure 91:
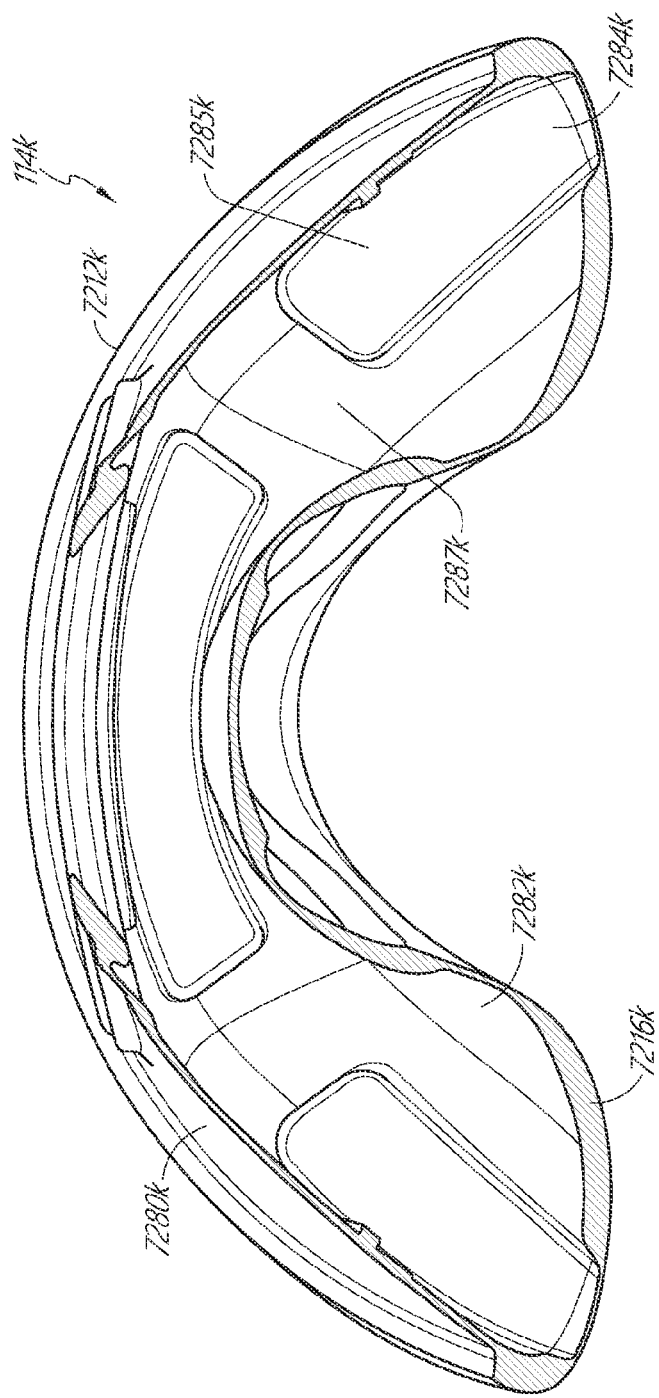

FIG. 91 is a cross-sectional top view of an embodiment of a nasal seal having a partitioned sub-nasal window.

Figure 92A:
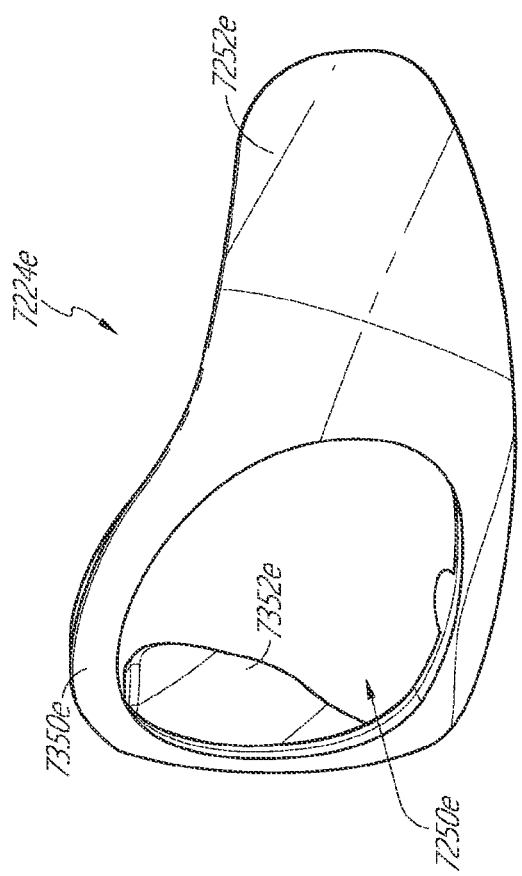

FIG. 92A is a front perspective view of an embodiment of a front flange of a connector.

Figure 92B:
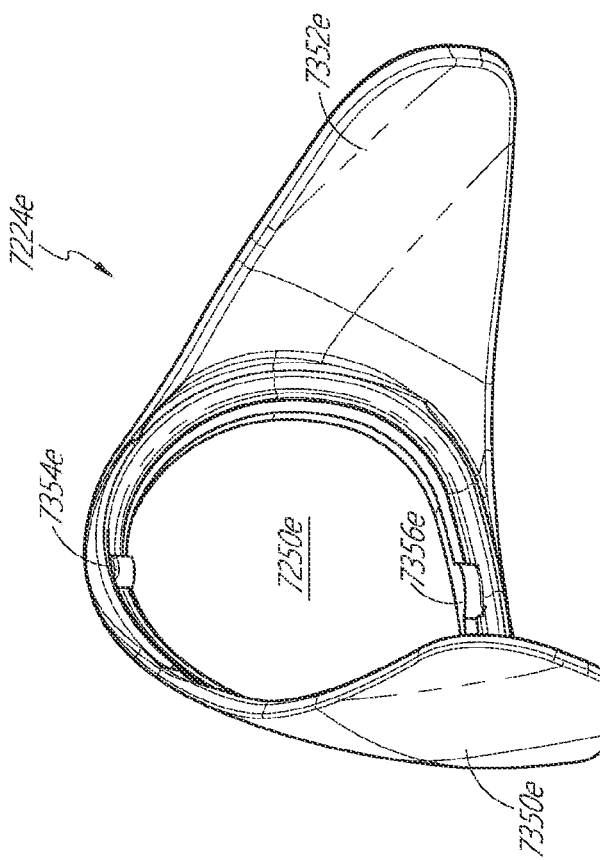

FIG. 92B is a rear perspective view of the front flange of FIG. 92A.

Figure 92C:
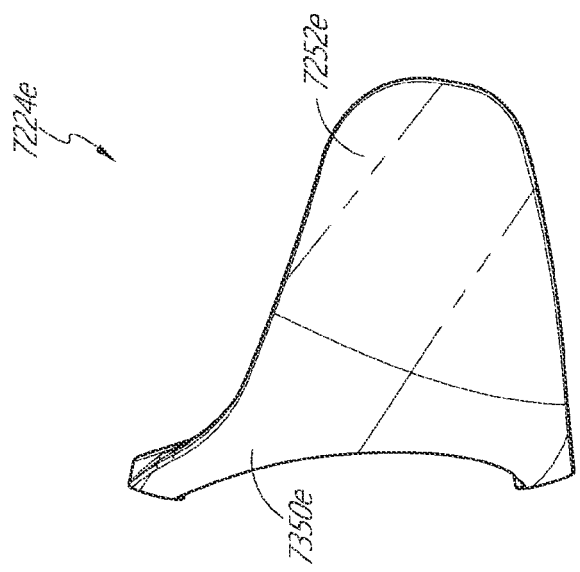

FIG. 92C is a front view of the front flange of FIG. 92A.

Figure 92D:
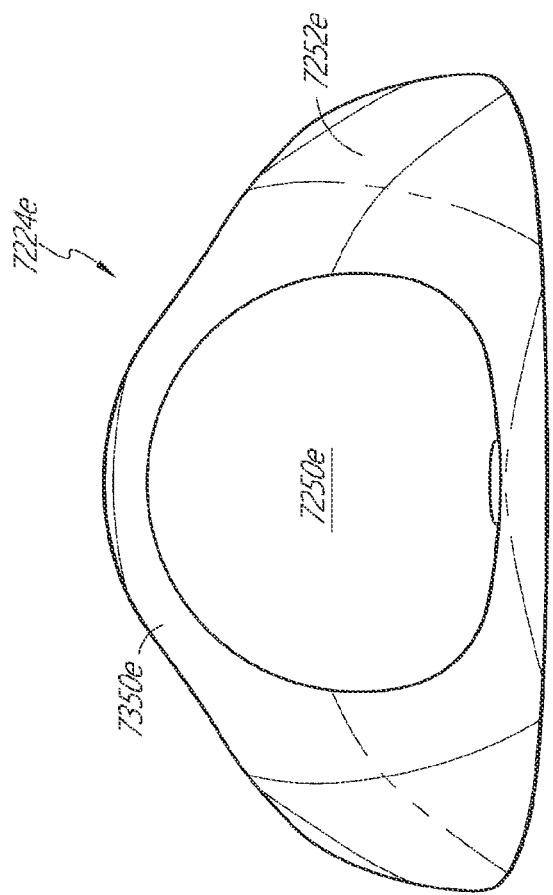

FIG. 92D is a left side view of the front flange of FIG. 92A.

FIG. 92E is a rear view of the front flange of FIG. 92A.

FIG. 92F is a top view of the front flange of FIG. 92A.

FIG. 92G is a bottom view of the front flange of FIG. 92A.

Figure 93B:
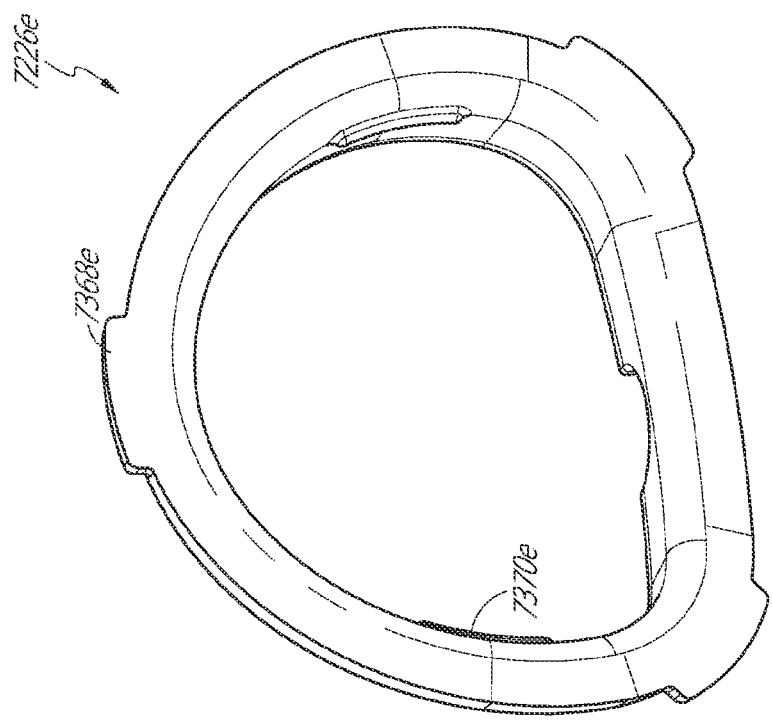
Figure 93A:
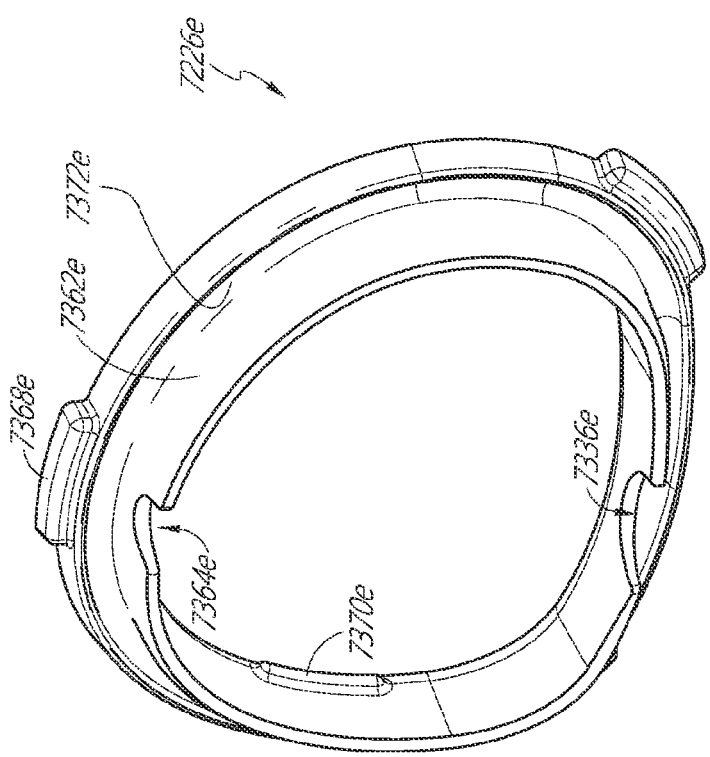

FIG. 93A is a front perspective view of an embodiment of a rear flange of a connector.

FIG. 93B is a rear perspective view of the rear flange of FIG. 93A.

Figure 93D:
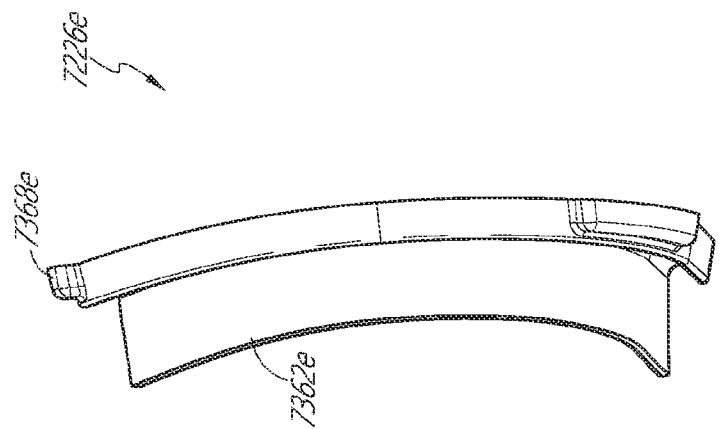
Figure 93C:
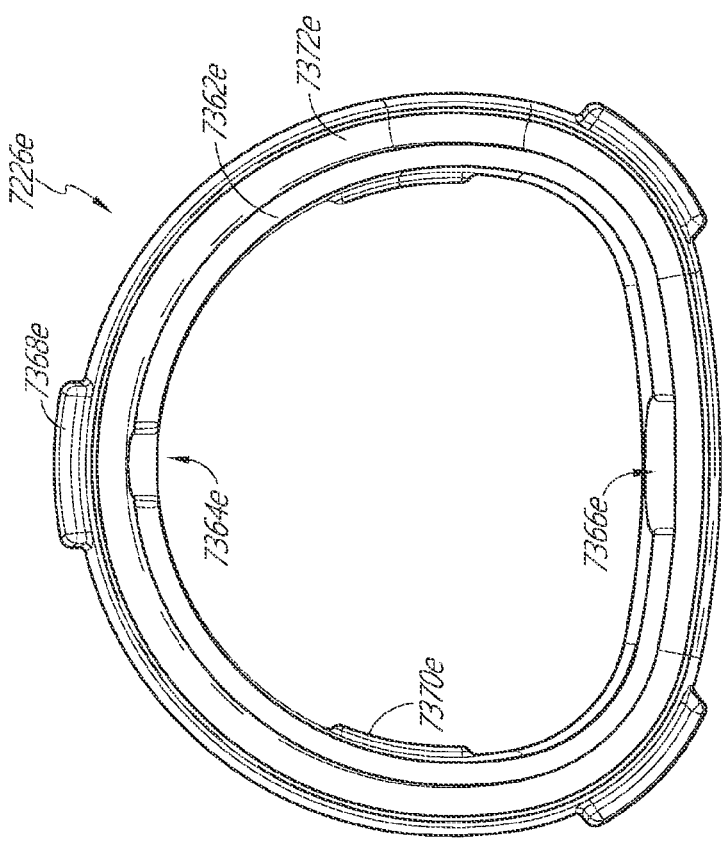

FIG. 93C is a front view of the rear flange of FIG. 93A.

FIG. 93D is a left side view of the rear flange of FIG. 93A.

FIG. 93B is a rear view of the rear flange of FIG. 93A.

Figure 93F:
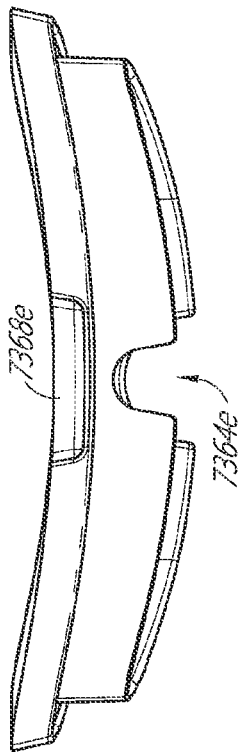

FIG. 93F is a top view of the rear flange of FIG. 93A.

Figure 93G:
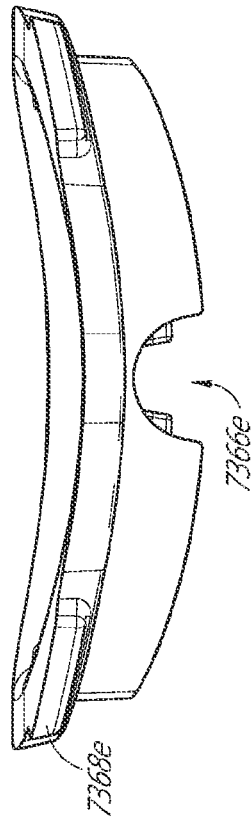

FIG. 93G is a bottom view of the rear flange of FIG. 93A.

Figure 94:
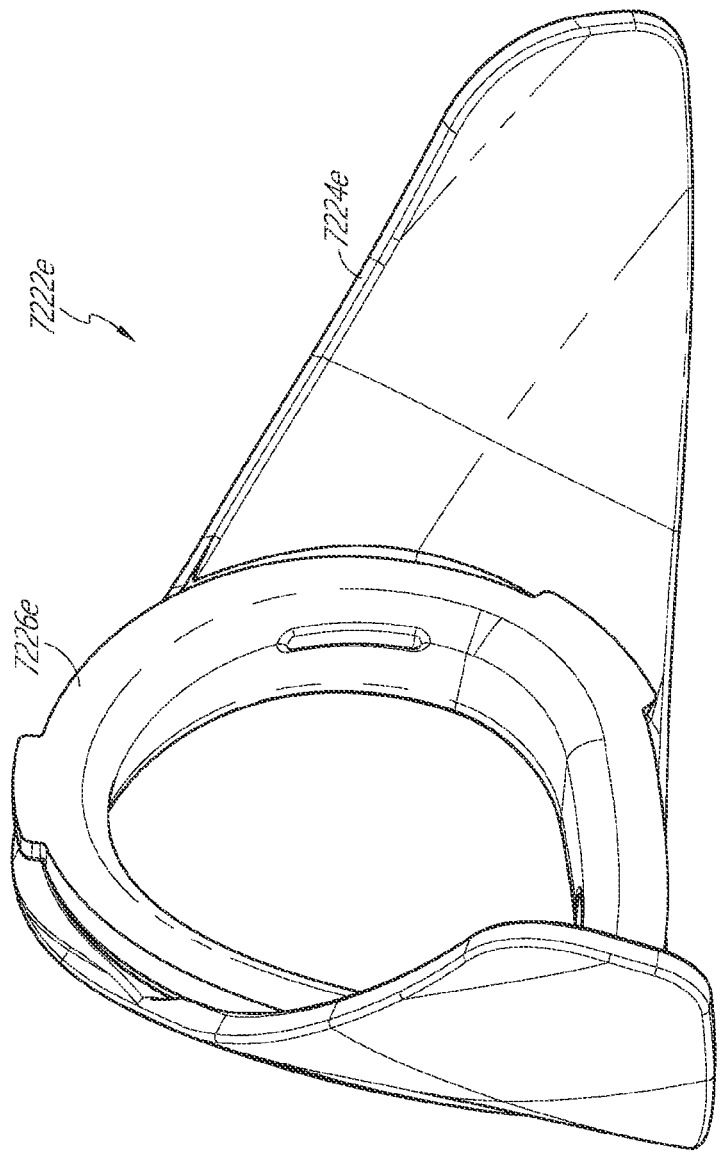

FIG. 94 is a rear perspective view of an assembly of the front flange of FIG. 92A connected to the rear flange of FIG. 93A.

Figure 95:
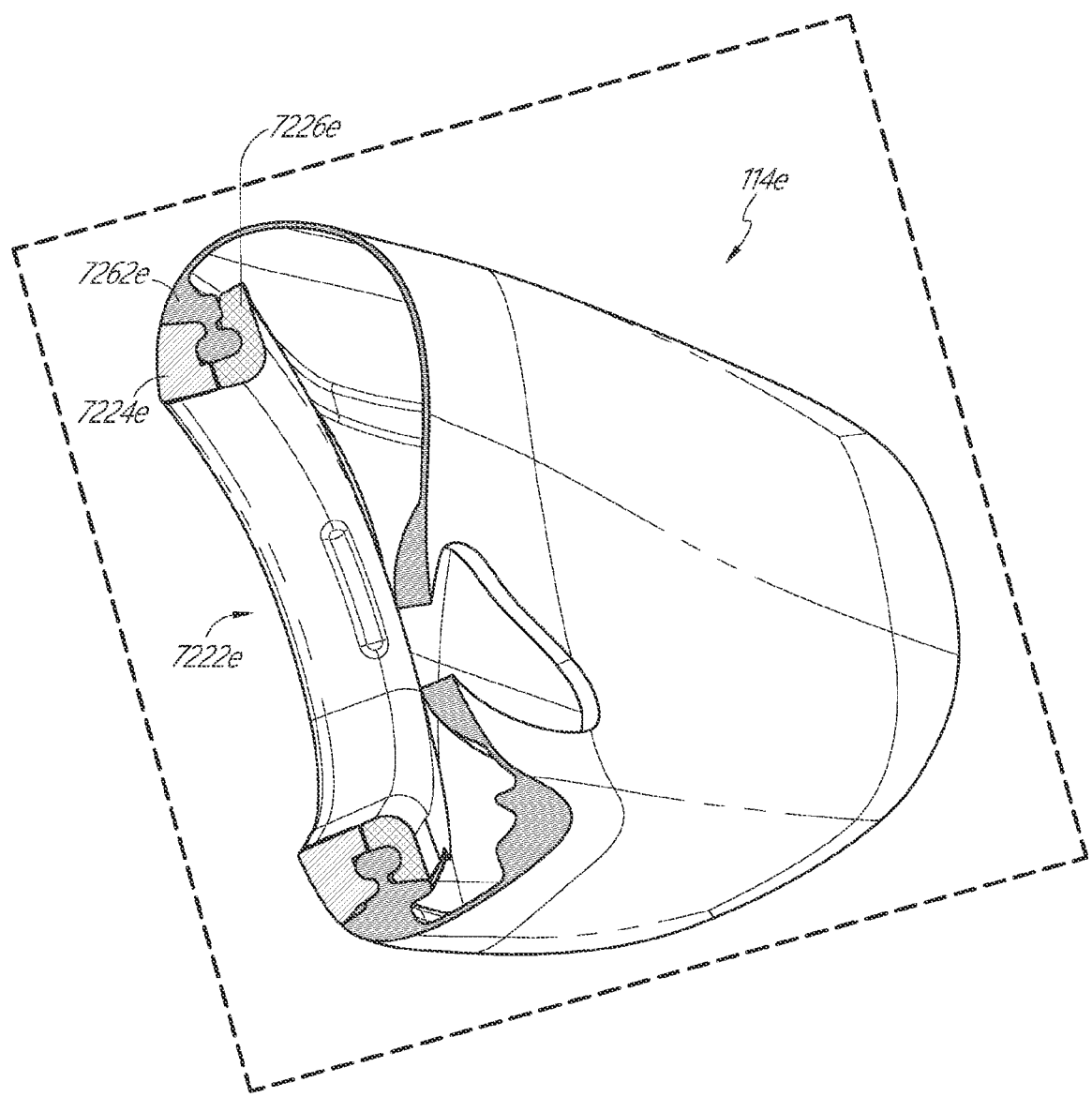

FIG. 95 is a sagittal cross-sectional view of an embodiment of a connector attached to a nasal seal.

Figure 96:
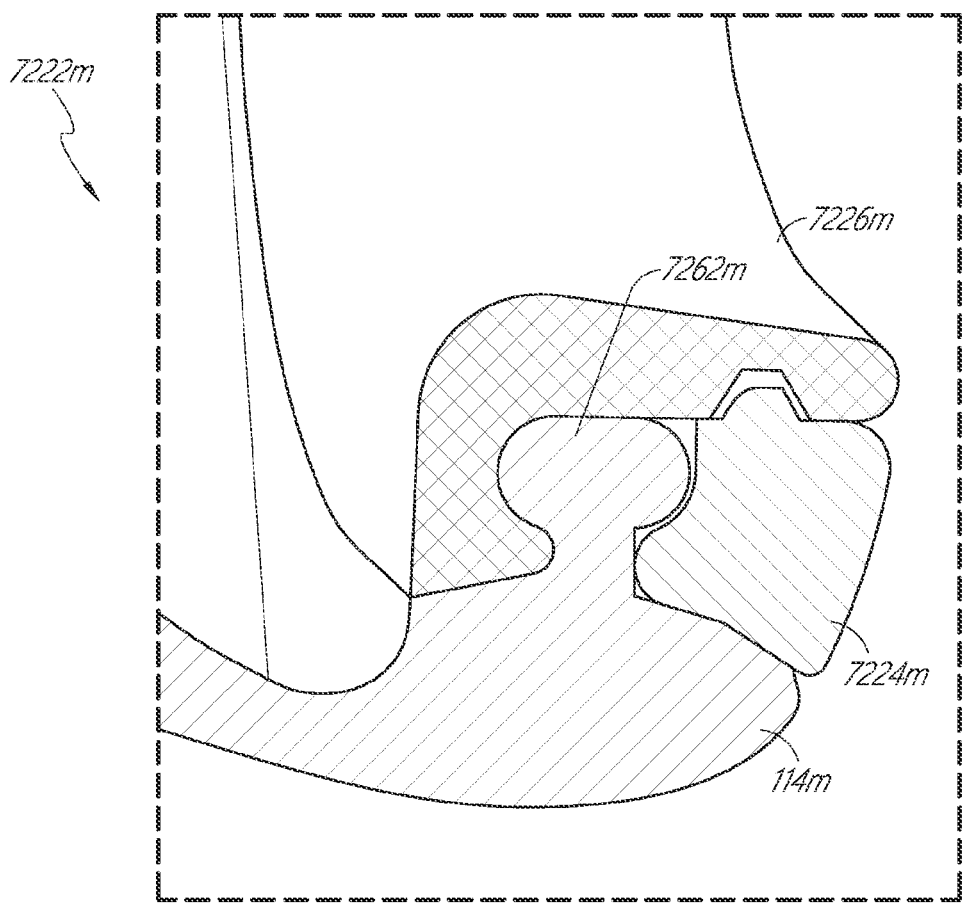

FIG. 96 is a sagittal cross-sectional view of a portion of an embodiment of a connector attached to a nasal seal.

Figure 97:
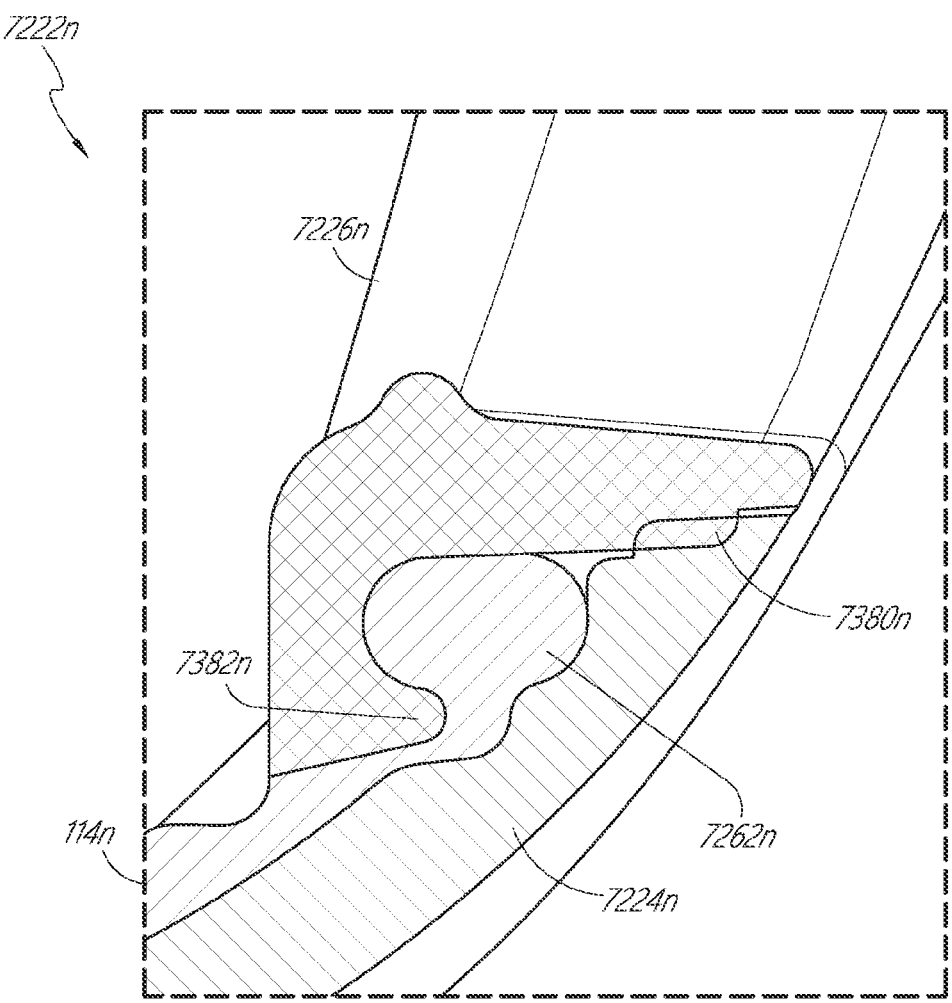

FIG. 97 is a sagittal cross-sectional view of a portion of another embodiment of a connector attached to a nasal seal.

Figure 98:
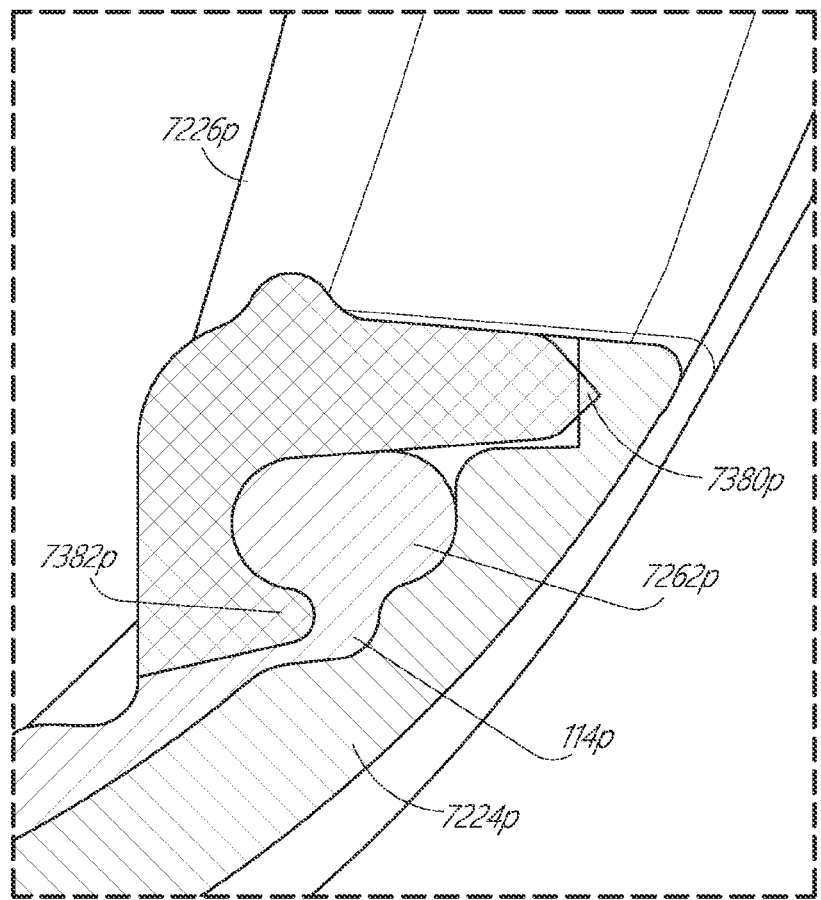

FIG. 98 is a sagittal cross-sectional view of a portion of yet another embodiment of a connector attached to a nasal seal.

Figure 99:
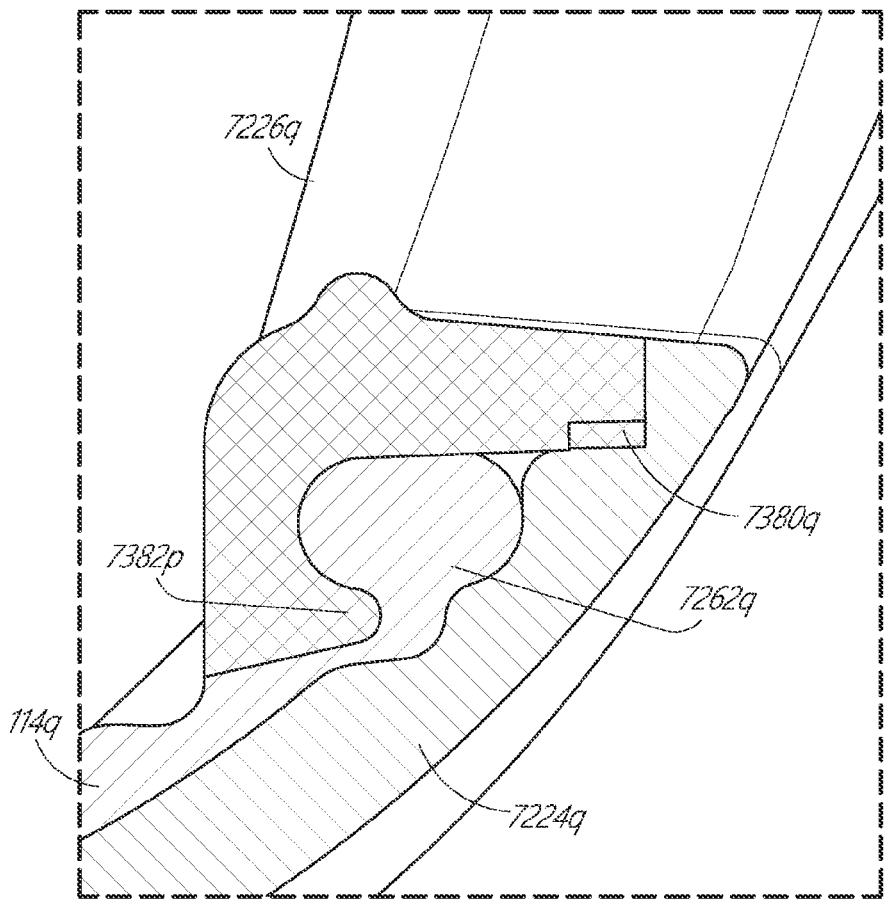

FIG. 99 is a sagittal cross-sectional view of a portion of still another embodiment of a connector attached to a nasal seal.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

FIG. 1 is a schematic diagram of a positive pressure respiratory therapy system in the form of a continuous positive airway pressure (CPAP) system 10 for providing a heated and humidified air stream to a user U through an interface 110 worn by the user, and which is connected to CPAP system 10 by a conduit or tube 12. A humidification chamber 14 has a heat conductive base in contact with a heater plate 16 of a humidifier 17 to humidify the air stream. The conduit 12 is connected to an outlet 13 of the humidification chamber 14 to convey humidified air to the user interface 110. The humidifier 17 comprises a controller 18, such as a microprocessor-based controller that executes computer software commands stored in an associated memory, for example but without limitation. The controller 18 receives input commands from multiple sources, including a user input interface 19 such as a dial or touch screen, which enables the setting of a predetermined value of humidity, temperature, or other characteristic of the humidified air supplied to the user U. The controller 18 also may receive input from one or more other sources, such as for example temperature and/or flow velocity sensors 20 and 21, which are connected through a connector 22 to communicate with the controller 18, and/or a heater plate temperature sensor 23. In response to the selected humidity or temperature value, the controller 18 determines when and/or to what level the heater plate 16 should be energized to suitably heat the water contained in the humidification chamber 14.

As the volume of water in the chamber is heated, water vapour begins to fill the volume of the chamber above a surface of the water. The water vapour passes out of the outlet 13 of the humidification chamber with a flow of air that is provided from a supply 25, such as a blower 27, and which enters the humidification chamber 30 through an inlet 26. The blower 27 can be a variable speed fan, or can include a variable pressure regulator. The blower 27 draws air through an inlet 28. The blower can be controlled by a controller 29 or by the controller 18, for example. The controller 18 or 29 may control blower speed, regulated pressure, or the like according to any suitable criteria. For example, the controller 29 may respond to inputs from controller 18 and a user set value (e.g., a preset value) of pressure and/or fan speed, which can be set with a user interface 30 (e.g., a dial).

The conduit 12 may comprise a heater such as a heater wire for example, to heat the walls of the conduit to reduce condensation of humidified gases within the conduit.

The seal and interfaces of the disclosure can be used in such a CPAP system as described whether humidified or not, or alternatively in other forms of respiratory systems, such as for example VPAP (Variable Positive Airway Pressure) systems, BiPAP (Bi level Positive Airway Pressure) systems, or with a ventilator, and are described herein generally with reference to CPAP therapy by way of example only.

Figure 2:
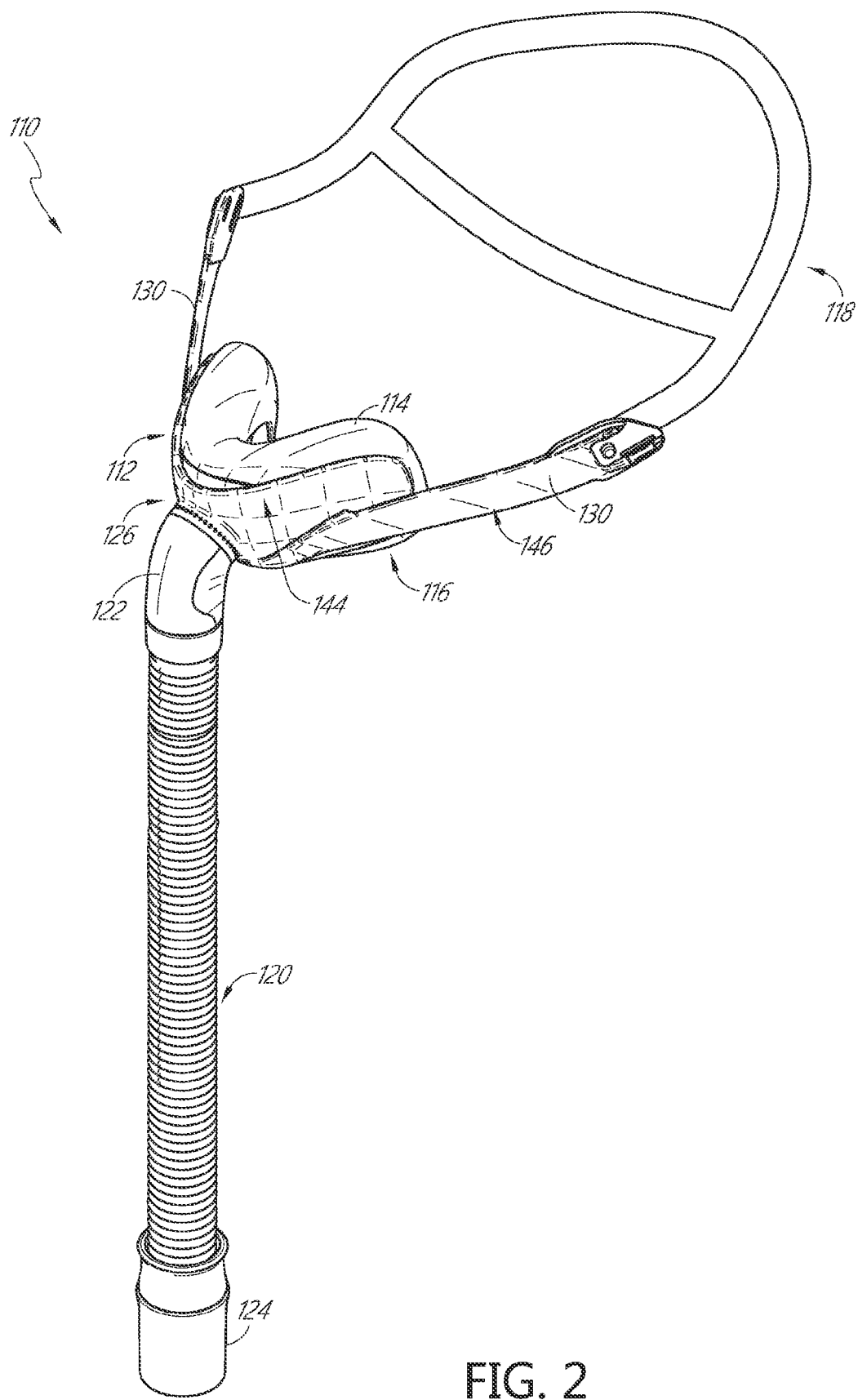
FIG. 2 is a perspective view of a user interface, comprising a mask and a headgear, which is suitable for use with the respiratory system of FIG. 1.
Figure 3:
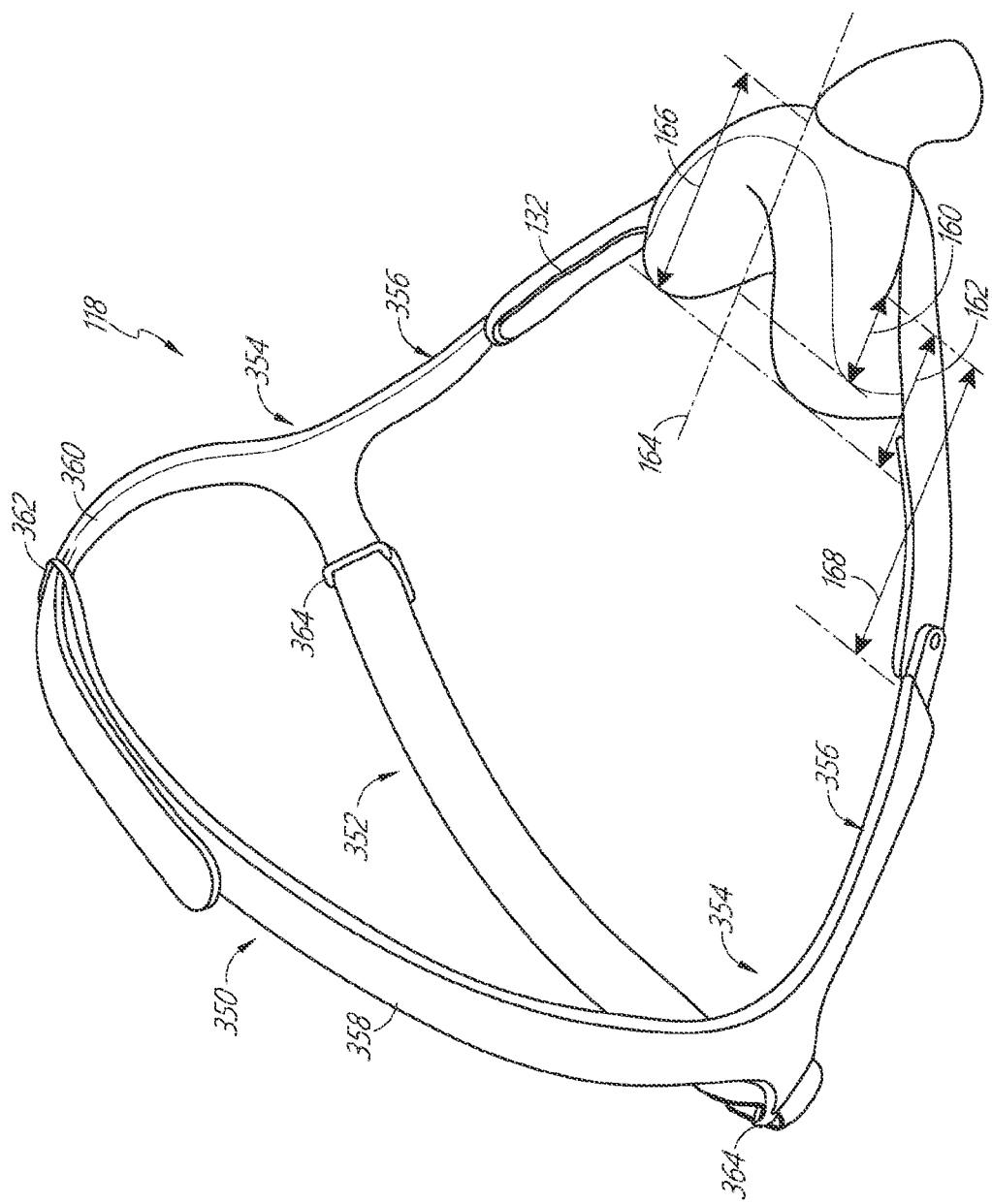
FIG. 3 is another perspective view of the user interface of FIG. 2.
Figure 4:
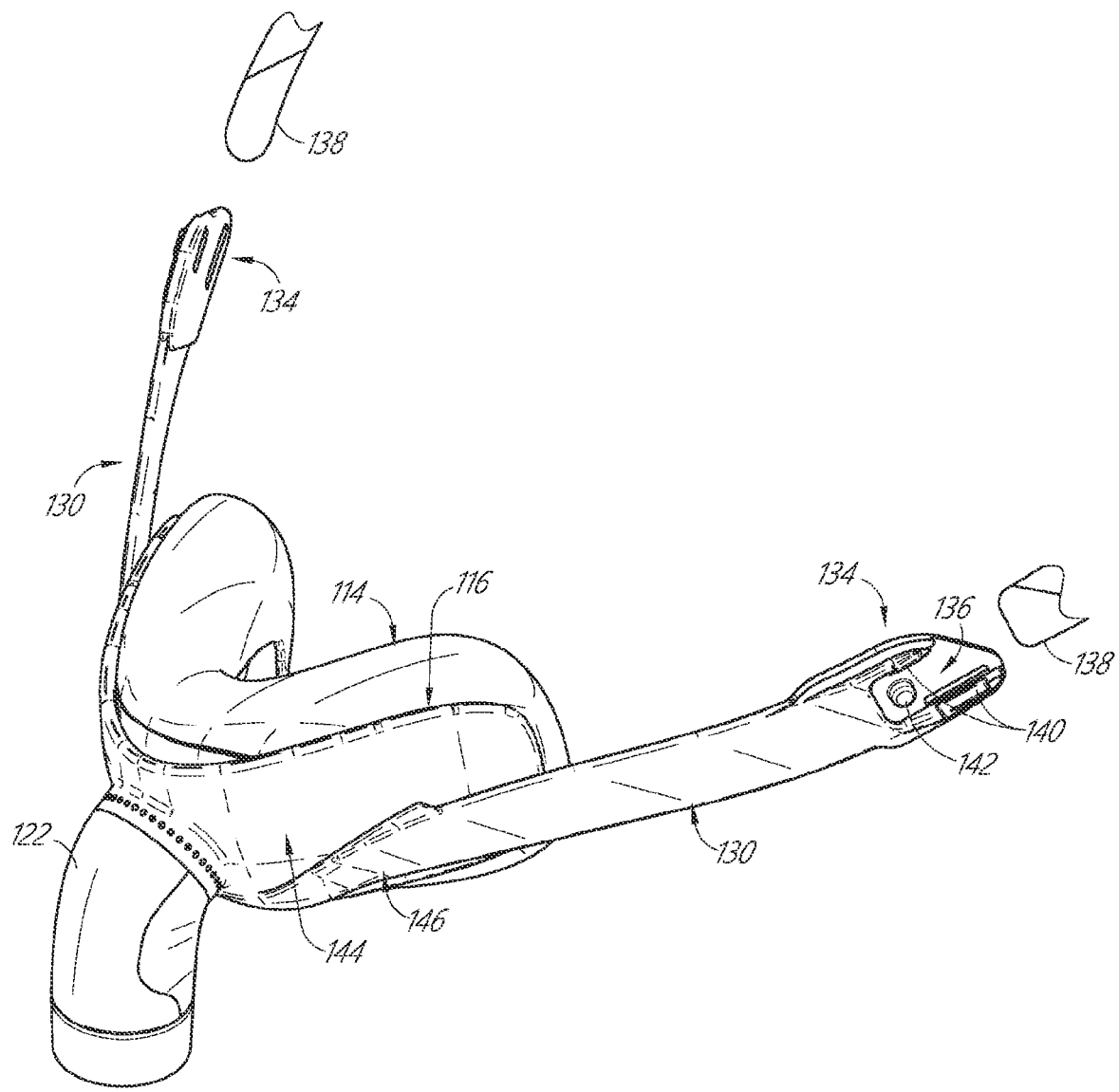
FIG. 4 is a perspective view of the mask of the user interface of FIG. 2, which comprises a frame and a seal.

FIGS. 2 and 3 are perspective views of an example of the interface assembly or interface 110 of the system 10 of FIG. 1. The interface 110 comprises a mask 112, which in some configurations includes a seal 114 and a frame assembly or frame 116. The interface 110 also includes headgear 118 for securing the mask 112 to the user. In preferred embodiments, the interface 110 does not comprise a T-piece from the frame 116 extending upwardly (when worn) to connect to the headgear 118 at the user's forehead. However, if desired, aspects, features or components of the disclosed interface 110 can be utilized in a design that incorporates a T-piece.

In some configurations, the interface 110 also comprises a short flexible supply conduit or tube 120 extending from the mask 112, such as from a central connection at the front of the mask 112, which connects to the supply conduit 12 of the CPAP system 10 or other respiratory system. The conduit 120 is connected to the mask 112 either directly or via a suitable connector, such as a hollow elbow 122. In some configurations, the elbow 122 can swivel about one or more swivel axes relative to the mask 112 so that the path of the conduit 120 relative to the positioning of the mask 112 on the face of the user can adapt to the sleeping position of the user. However, in other arrangements, the elbow 122 can be integral or unitary with the mask 112. The end of the conduit 120 opposite the elbow 122 can comprise a suitable connector 124 for connecting the conduit 120 to the supply conduit 12. In some configurations, the connector 124 can be or comprise a swivel connector that allows relative rotation between the conduit 120 and the supply conduit 12.

The interface 110 preferably includes a limited flow outlet or bias flow vent 126 for providing gas washout from the interface 110. In some configurations, the bias flow vent 126 is in the form of a collection of small apertures. The bias flow vent 126 may be provided in the frame 116, as shown, in the elbow 122 or elsewhere on the interface 110.

As described above, the mask 112 can comprise a seal 114 and a frame 116. In some configurations, the frame 116 (and, if desired, the elbow 122) can be stiffer than at least a portion of the seal 114, such as the portion that defines a user-contacting surface. In some configurations, the seal 114 is removably coupled to the frame 116 around a passage through the frame 116 from the interior of elbow 122. Thus, the seal 114 and the frame 116 together form an enclosure having a gas flow inlet from the CPAP system 10 and an aperture 128 through the seal 114 to the user.

In some configurations, the frame 116 comprises side arms 130 that extend outwardly (away from each other), rearwardly and upwardly at a shallow angle, past left and right extremities of the seal 114 and along the left and right cheeks and in particular cheekbones of a user to connect to the headgear 118 for holding the seal 114 on the face of a user. Such side arms 130 may be longer than they are deep or thick and may be resiliently flexibly connected to the frame and/or resiliently flexible along their length (widthwise but not heightwise). In some configurations, the side arms 130 extend toward or to a location between the ears and eyes of the user and/or to or near the temple of the user, where the side arms 130 connect to the headgear 118. In some configurations, a length of the side arms 130 is between about 100 mm and about 150 mm. The shape of the side arms 130 and/or angle between them is such that the side arms 130 rest on the left and right cheeks and in particular cheekbones of the user to assist in stabilizing the interface 110 against rotation about a horizontal axis when worn.

The side arms may be resiliently flexible towards and away from the face of the user in an approximately horizontal plane (when worn), to accommodate different face sizes, but are relatively inflexible in an approximately vertical plane. The illustrated side arms 130 are solid, but other versions of the side arms could include one or more apertures or cut-outs extending lengthwise of the side arms to increase the resilient flexibility of the side arms towards and away from the face of the user, but to retain relative inflexibility in an approximately vertical plane (when worn).

In some configurations, the side arms 130 can comprise a softer material on a portion or an entirety of at least the user-facing surfaces of the side arms 130, or fully around the side arms 130, for softening contact of the side arms 130 with the face of the user. If desired, an interior surface of the side arms 130 can include pads 132 that face and/or contact the face of the user, as illustrated in FIG. 3. The pads 132 can be removable for cleaning or replacement. The pads 132 and the side arms 130 can be connected by an overmolding or welding process. The pads 132 can have a textured and/or fabric outer surface. The textured surface can increase friction to keep the side arms 130 in place on the user's face and the fabric material can promote comfort.

At their outer or free ends the side arms 130 comprise connector portions 134 for detachably connecting the side arms 130 to the headgear 118. In some configurations, each of the connector portions 134 comprises a recess or receptacle 136 configured to receive a complementary connector 138 of the headgear 118. The connector 138 of the headgear 118 can be retained within the receptacle 136 of the side arms 130 by any suitable mechanism, such as a snap-fit arrangement, for example. In some configurations, the connector 138 has orientation features. In some configurations, the receptacle 136 has orientation features. The orientation feature may allow the left-side of the headgear 118 to only connect to the left-side side arm 130 and the right-side of the headgear 118 to only connect to the right-side side arm 130. In some configurations, the orientation features may allow the left-side of the headgear 118 to connect to the right-side side arm 130 and the right-side of the headgear 118 to connect to the left-side side arm 130, only in the manner that the headgear 118 is turned inside-out. In the illustrated arrangement, each connector portion 134 includes at least one protrusion or latch member 140, such as a pair of latch members 140 each of which is positioned on opposing sides of the receptacle 136. The latch members 140 can retain the connector 138 within the receptacle 136 in at least one direction, such as in a direction moving outwardly away from the connector portion 134 and in a direction of rotation. The latch members 140 can guide the connector 140 into connected position, for example, when the connector 138 is inserted from the end. In some configurations, the connector portion 134 comprises one or more additional retention elements, such as a protrusion or boss 142. In the illustrated arrangement, the boss 142 extends outwardly from an outer surface of the receptacle 136 and engages a complementary opening of the connector 138 of the headgear 118 to retain the connector 138 within the receptacle 136 in response to forces tending to move the connector 138 rearwardly or in a longitudinal direction of the side arm 130. In some configurations, the boss 142 has a chamfer on one side (not shown in the drawings), facilitating the connector 138 clipping into position.

In some configurations, the side arms 130 may be unitarily-formed with another portion or a remainder of the frame 116 by injection moulding from a plastics material, for example. However, in the illustrated arrangement, the frame 116 comprises a central or base portion (referred to herein as a "base") 144 that supports the seal 114 and a connector portion or connector 146, which includes the side arms 130. The base 144 and the connector 146 can be permanently or removably coupled to one another. In some configurations, each of the side arms 130 could include its own connector 146 that could be separately attached to the base 144.

The illustrated connector 146 is a generally U-shaped member from a top view comprising the side arms 130 and a central portion 148 that connects the two side arms 130 to one another. In the illustrated arrangement, the central portion 148 passes below the elbow 122 and extends upwardly on each side to a respective one of the side arms 130. The central portion 148 can also be configured to connect to the base 144, such as via a snap-fit connection, for example. In the illustrated arrangement, the central portion 148 comprises a pair of spaced-apart protrusions 150 that engage a respective one of a pair of complementary slots 152 of the base 144. In other configurations, this arrangement could be reversed or other suitable connection arrangements could be utilized. The central portion 148 can be removable from the base 144. That is, the protrusions 150 can be removable from the slots 152. In other configurations, the central portion 148 and/or side arms 130 can be integrated with the base 144, such as by a two-shot or over-molding process, for example.

The central portion 148 comprises an inner surface 154 that faces or rests against the base 144. In some configurations, the central portion 148 includes a shelf or shoulder 156 upon which the base 144 or another portion of the frame assembly 116 or seal 114 rests. In the illustrated arrangement, a lower edge of the base 144 rests upon the shoulder 156 such that a portion of the connector 146 below the shoulder 156 is positioned below the base 144. The illustrated shoulder 156 is curved in shape with outer ends being lower than a central portion relative to an orientation of the mask 112 in use. In other arrangements, the shoulder 156 could have other shapes, such as curved in an opposite direction (i.e., concave) or flat, for example. In addition, a forward surface of the base 144 defines a recess 157 that accommodates the central portion 148 of the connector 146. The recess 157 can extend partially or entirely between the slots 152 of the base 144.

The laterally-outward or rearward portions of the central portion 148 of the connector 138 connect to the side arms 130. In the illustrated arrangement, the side arms 130 are unitarily-formed with the central portion 148. However, in other arrangements, the side arms 130 could be formed separately, with the same or different materials, and coupled to the central portion 148, such as via mechanical fasteners, adhesives, welding process or by a two-shot molding process (e.g., over-moulding), for example.

In some configurations, the laterally-outward or rearward portions of the central portion 148 can be configured to support the side arms 130 in a spaced relationship to the base 144 and/or seal 114. In the illustrated arrangement, the laterally-outward or rearward portions of the central portion 148 have a greater wall thickness in a direction perpendicular to the inner surface 154 than a center of the central portion 148. The wall thickness increases progressively in a forward-rearward direction of the laterally-outward or rearward portions of the central portion 148. As a result, the forward ends of the side arms 130 are spaced outwardly from the inner surface 154, base 144 and/or seal 114 by a distance 158. The distance 158 can be, for example, between 3-15 mm, 5-10 mm or about 5 mm. The attachment points of the central portion 148 defined by, for example, the protrusions 150 with the base 144 can define hinges or hinge points of the frame assembly that promotes flexibility of the side arms 130 relative to the central portion 148 and/or the base 144. The reduced thickness of the forward ends of the side arms 130 relative to the greater wall thickness of the rearward portions of the central portion 148 can facilitate the flexibility of the side arms 130 relative to the central portion 148 and/or the base 144.

In some configurations, the protrusions 150 are located at or near and end of the laterally-outward or rearward portions of the central portion 148. With such an arrangement, the central portion 148 of the connector 146 is coupled to the base 144 while the side arms 130 are not directly coupled to the base 144 and are free to move or flex relative to the base 144. In some configurations, the connector 146 is overmolded onto the base 144 or the connector 146 and base are otherwise joined by an overmolding process. In other arrangements, the connector 146 can be otherwise coupled to the base 144, preferably on at the central portion 148 such that the side arms 130 are free to flex or move relative to the base 144. In some configurations, the base 144 is constructed from a material that is more rigid than the material of the connector 146 or at least more rigid than the side arms 130 of the connector 146. In addition or in the alternative, the side arms 130 can be otherwise configured to be less rigid than the base 144, such as by reduced material thickness, hinges, cut-outs or other suitable arrangements. In some configurations, the central portion 148 terminates prior to a rearward edge of one or both of the base 144 and seal 114 on each side of the mask 112. Accordingly, portions of the side arms 130 forward of the rearward edge of one or both of the base 144 and seal 114 can move or flex relative to the base 144 and/or seal 114.

In some configurations, termination points of the central portion 148 are spaced from a rearward edge of the base 144 by a distance 160 and from a rearward edge of the seal 114 by a distance 162 on each side of the mask 112 as measured along a central axis 164 of the mask 112 that extends in a forward-rearward direction and bisects the mask 112. The distance 160 can be between one-quarter and one-half of a total length 166 of the mask 112 as measured along the central axis 164. In some configurations, the distance 160 is between one-third and three-eighths of the total length 166 of the mask 112. The distance 162 can be between one-third and five-eighths of the total length 166, between two-fifths and nine-sixteenths of the total length 166. In some configurations, a length 168 of the side arms 130 can be at least as long as, at least 1.5 times or at least twice the total length 166 of the mask 112 as measured along the central axis 164 depending on where the forward ends of the side arms 130 are located relative to the mask 112. Such an arrangement provides a desirable level of support to the base 144 and seal 114, while also permitting a desirable level of movement of the side arms 130 to accommodate a variety of facial geometries.

In an alternative arrangement, instead of the side arms 130 as shown (or with shorter side arms), the ends of headgear 118 may attach to the mask frame 116 (or shorter side arms) on either (left and right) sides via stiffer strap ends, which terminate at the mask 112 by an attachment mechanism which allows movement in an approximately horizontal plane but not in an approximately vertical plane, such as a hook which engages into a vertical upright slot (e.g., slot 152) on the mask frame 116 (e.g., base 144).

As described above, in some configurations, the seal 114 is removably coupled to the frame 116. The seal 114 can be configured to surround a passage through the frame 116 from the interior of elbow 122. Thus, the seal 114 and/or the frame 116 can form a chamber having a gas flow inlet from the CPAP system 10 and an aperture 128 through the seal 114 to the user. In the illustrated arrangement, the base 144 of the frame 116 defines a generally U-shape when viewed from above. A central portion of the base 144 defines an aperture 170 through which gases can flow. A first annular wall surrounds the aperture 170 and projects in a rearward direction to define a support or connector 172 for the seal 114. A second annular wall surrounds the aperture and projects in a forward direction to define a support or connector 174 for the elbow 122.

The seal 114 defines an aperture 175 configured to receive the connector 172 of the base 144. The seal 114 and the base 144 can be removably coupled by any suitable arrangement, such as a friction-fit or snap-fit, for example. In the illustrated arrangement, the connector 172 includes one or more recesses 176 configured to receive a corresponding protrusion 178 of the seal 114 to create a snap-fit engagement between the seal 114 and the base 144. However, this arrangement could also be reversed. Moreover, the entire arrangement could be reversed between the seal 114 and the base 144 in that the seal 114 could include a male connector portion and the base 144 could include a corresponding female connector portion.

Preferably, the seal 114 and the base 144 include an alignment or key arrangement such that the seal 114 and the base 144 can only be assembled in the correct orientation relative to one another. Any suitable arrangement can be used. In the illustrated arrangement, the seal connector 172 includes a recess 180 configured to receive a key or protrusion 182 of the seal 114 (FIG. 17). The illustrated recess 180 and protrusion 182 are located on an upper, central portion of the aperture 170; however, other locations along the circumference of the aperture 170 could also be used. This arrangement could also be reversed. Moreover, other suitable arrangements could also be used, such as a non-circular shape of the connector 172 and aperture 176, for example.

The elbow 122 can connect to the elbow connector 174 in any suitable manner. In the illustrated arrangement, the elbow 122 is removably connected to the elbow connector 174 such that the elbow 122 can be removed, such as for cleaning. In the illustrated arrangement, the elbow 122 and the elbow connector 174 are coupled by a snap-fit connection; however, other suitable connections (e.g., friction-fit) can also be used. In some configurations, the elbow connector 174 comprises a recess 184 configured to receive a protrusion 186 of the elbow 122. In the illustrated arrangement, the recess 184 is an annular recess that extends around the entire circumference of the elbow connector 174 so that the elbow 122 is rotatable relative to the frame 116 on the elbow connector 174. The protrusion 186 of the elbow 122 can be annular or interrupted around the circumference of the elbow 122. This arrangement could also be reversed. In alternative arrangements, the connection of the elbow 122 to the frame 116 can provides for both rotation and pivoting of the elbow 122 relative to the frame 116. For example, the connection may comprise a ball joint connection to the frame 116 so that the elbow 122 can pivot about axes parallel to and perpendicular to its connection with the frame 116. The elbow 122 may include a ball end that snap fits into a socket opening in the frame 116. The elbow 122 preferably defines an angle between flow in the conduit 120, and flow through the aperture 170 of between 0° and 90° or between 30° and 60°. Alternatively, as described above, the elbow 122 could be unitarily or integrally formed with the frame 116. In other configurations, the elbow 122 could be omitted entirely and the tube 120 or other breathing circuit could be directly connected to the frame 116.

In the illustrated arrangement, the bias flow vent 126 is defined by the frame 116. In particular, the bias flow vent 126 is defined by the elbow connector 174 of the base 144 of the frame 116. The illustrated elbow connector 174 comprises an enlarged diameter portion closest to the U-shaped body of the base 144 that defines a surface or shoulder 188 that faces or contacts an end surface of the elbow 122. The bias flow vent 126 comprises a plurality of openings or vent boles 190 that extend in a generally radial direction through the enlarged diameter portion of the elbow connector 174. Accordingly, the elbow 122 does not cover the vent holes 190 when the elbow 122 is connected to the base 144 and the vent holes 190 are located between the elbow 122 and the U-shaped body of the base 144. In the illustrated arrangement, a longitudinal axis of the individual vent holes 190 are canted or angled in a forward direction when moving along the axis in a direction from an interior of the elbow connector 174 toward an exterior of the elbow connector 174. Such an arrangement can direct the flow of exhaust gases away from the face of the user. Alternatively, the bias flow vent 126 can be located on the elbow 122, the frame 116 or at another suitable location.

FIGS. 12-15 illustrate features that allow the mask 112 to transfer force from the seal 114 to the frame 116. The illustrated mask 112 comprises a seal support, which can be a base, housing, shell or connector 202, for example. The seal 114 is attached to the connector 202 such that the connector 202 provides some amount of support for the seal 114. The connector 202 permits the mask 112 to be connected to the frame 116. The illustrated connector 202 is generally annular in shape and, in at least some configurations, does not cover a substantial portion of a forward-facing surface of the seal 114.

The connector 202 can be constructed from a relatively rigid, semi-rigid or rigid material, such as polycarbonate, for example. Thus, in at least some configurations, the connector 202 is more rigid than the seal 114. The material from which at least the thin-walled supple center portion of the seal 114 is formed may be a soft stretchable material such as a silicone material, or a TPE (thermoplastic elastomer), for example. In some configurations, the seal 114 is a one piece component all of the described parts and portions of which are integrally formed by injection moulding, for example. In an alternative arrangement, however, only a wearer side of the seal 114 may be formed of such a material, and may be bonded to a more rigid shell (rather than the connector 202), which couples to or is integrally formed with the frame 116 of the interface. Alternatively or additionally, the seal 114 may be a foam or gel-filled seal.

The illustrated mask 112 has a hollow interior which is filled with air under positive pressure in use and is configured to seal under the nose of the user, along a portion of the face extending lateral to the nose, as well as along the upper lip of the user. The mask 112 advantageously does not require contact with the bridge of the nose of the user. In the illustrated configuration, the mask 112 does not extend over the bridge of the nose of the user. More particularly, the illustrated mask 112 does not contact the bridge of the nose of the user.

The mask 112 may or may not extend over the tip of the nose of the user. Thus, in some configurations, the mask 112 covers the tip of the nose. In some configurations, the seal 114 of the mask 112 covers the tip of the nose. In some configurations, the illustrated mask 112 preferably does not enshroud the tip of the nose of the user. In some configurations or with some facial geometries, the tip of the nose of the user extends over the adjoining portion of the mask 112. In some configurations, the frame 116 and other portions of the mask 112 can accommodate deflection of the seal 114 by portions (e.g., the tip) of the user's nose such that the interface can accommodate a variety of nasal lengths.

As illustrated, the mask 112 preferably is adapted to extend around and seal over the wing or alar of the nose, which flares out to form a rounded eminence around the nostril. The illustrated mask 112 is adapted to seal around the surfaces that define the opening to the nostril, which may include a portion or entirety of the fleshy external end of the nasal septum, sometimes called the columella. In some configurations, the mask 112 is adapted to extend upwardly to seal along at least a portion of the left and right dorsal side walls of the nose of the user. In some configurations, the mask 112 is adapted to extend upwardly along at least a portion of the left and right dorsal side walls without extending upwardly to the region of the bridge of the nose of the user. In some configurations, a primary sealing surface of the mask 112 contacts the underside of the nose of the user, the upper lip and/or a transition region between the underside of the nose and the upper lip. A secondary sealing surface of the mask can contact the side surfaces of the nose of the user, possibly along with the cheeks at a location near the nose. Such primary and secondary sealing surfaces may not make contact with the face of all users; however, such an arrangement can provide a suitable seal with a relatively large range of facial geometries.

As described above, the seal 114 comprises at least one nasal opening or aperture 128. In some configurations, the seal 114 can comprise more than one nasal aperture 128. In some configurations, the seal 114 can comprise apertures 128 defined within superstructures, such as pillows, prongs or the like. In some configurations, the nasal aperture 128 can be defined by a nasal cushion or insert, which can be over-moulded or otherwise secured to a base structure of the seal 114. Examples of suitable arrangements of the seal 114 are disclosed in Applicant's publication no. WO 2014/077708, the entirety of which is incorporated by reference herein.

The seal 114 comprises an inward or rearward-facing central portion 204 that faces or contacts the user during use of the mask 112. The seal 114 also comprises a pair of opposing inner lateral portions 206 and a pair of opposing outer lateral portions 208. The inner lateral portions 206 are configured to contact the sides of the nose and/or the portion of the user's face on either side of the nose. The inner lateral portions 206 can comprise both inward-facing surfaces and rearward-facing surfaces. That is, each of the inner lateral portions 206 can wrap from an inward-facing surface of the seal 114 toward or to a rearward-facing surface of the seal 114. The outer lateral portions 208 can comprise both rearward-facing surfaces and outward-facing surfaces. The rearward-facing surfaces of the outer lateral portions 208 can contact the face of the user during use of the mask 112. The seal 114 can also comprise a nasal opening support or thickened rim 210 that partially or completely surrounds and provides support to the nasal aperture 128. Preferably, the outer lateral portions 208 are not connected to the frame 116 such that the outer lateral portions 208 and/or the inner lateral portions 206 can move inwardly in response to pressure exerted on the central portion 204 of the seal 114 by the user. Such an arrangement allows the lateral portions of the seal 114 to move inwardly to facilitate sealing with the user's face.

The seal 114 can comprise regions of varying thickness to provide the seal 114 with different properties or characteristics within the different regions. For example, the central portion 204 can have a relatively low thickness to allow the central portion 204 to conform to the particular facial geometry of the user. In some configurations, the relatively low thickness can allow the central portion 204 to stretch. In some configurations, the central portion 204 can have a thickness between 0.3 mm and 0.5 mm or 0.6 mm. In some configurations, the thickness of the central portion 204 is 0.3 mm. If desired, the central portion 204 could have a thickness as low as 0.15 mm. However, it has been determined that lower thicknesses can result in or increase the likelihood of creasing for some facial geometries and/or under some operational gas pressures. Keeping the thickness at or above 0.3 mm in a substantial portion or an entirety of the central portion 204 can reduce the incidence of creasing over a substantial range of operational pressures, which may comprise an entire range of normal operating pressures.

The inner lateral portions 206 can have a thickness that is greater than the thickness of the central portion 204. In some configurations, the thickness of the inner lateral portions 206 can be between 0.4 mm and 0.6 mm. In some configurations, the thickness of the inner lateral portions 206 is 0.5 mm. The nasal opening support 210 can have a thickness that is greater than one or both of the central portion 204 and the inner lateral portions 206. The relatively greater thickness can protect the seal 114 from tearing at the nasal aperture 128 and can help the nasal aperture 128 maintain an opened shape. In some configurations, the thickness of the nasal opening support 210 is between 1 mm and 2.5 mm. In some configurations, the thickness of the nasal opening support 210 is 1.2 mm. The thicknesses can be constant or varied within any of the central portion 204, inner lateral portions 206 or nasal opening support 210.

Lateral portions 212 of the mask 112, including portions or entireties of the inner lateral portions 206 and the outer lateral portions 208, can be referred to herein as paddles. Paddles 212 can refer to any portion of an interface seal that is positioned alongside the nose of the user during use of the interface. Paddles 212 are disclosed in the context of under-nose interfaces herein, but can be utilized in other types of interfaces, including those that contact, cover or seal against the bridge of the user's nose, unless otherwise indicated.

The outer lateral portions 208 can comprise features that assist in maintaining a shape of the seal 114. In some configurations, the outer lateral portions 208 comprise regions of increased thickness, rigidity or stiffness that assist in maintaining a shape of the seal 114, which are referred to herein as support structures 214. The support structures 214 of the mask 112 can inhibit or prevent overexpansion or undesired expansion of the lateral end portions of the seal 114, which could result in leaks and/or undesirable pressure being applied to the user's nose by the central portion 204 of the seal 114. The support structures 214 can also inhibit or prevent collapse of at least portions of the seal 114 when engaged with a nose in use. For example, the support structures 214 can inhibit or prevent collapse of the nasal region or central portion 204 of the seal 114.

The support structures 214 can also transfer forces from one portion of the seal 114 to another portion of the seal 114. For example, the support structures 214 can transfer force applied to a rear portion of the seal 114 to a front portion of the seal 114. In some configurations, the support structures 214 can transfer force applied to a rearward-facing surface of the seal 114 by the user's face to another portion of the seal 114 that can resist some or all of the transferred force. In some configurations, the support structures 214 transfer force from a rearward-facing or user-contacting surface of the seal 114 to the frame 116 or other structure that supports the seal 114 (e.g., the connector 202). Thus, in some configurations, the support structures 214 extend between a rearward-facing surface of the seal 114 and a surface of the seal 114 that contacts or is overlapped by the frame 116 or other support structure for the seal 114. Preferably, the support structures extend from the rearward-facing surface to the surface that is overlapped by the frame 116 or other support structure. However, as noted above, the support structures 214 can provide structure to the seal 114 and can be utilized to provide such support without necessarily transferring forces.

In some configurations, the frame 116 includes a central portion and lateral portions on each side of the central portion. The lateral portions can function to provide support to the support structures 214 of the seal 114 and can be referred to as paddle covers 216 herein. The lateral portions or paddle covers 216 can be aligned with or overlap the portions of the seal 114 comprising the support structures 214 such that the support structures 214 can transfer loads to the lateral portions 216 of the frame 116.

The supports 214 can extend in a direction generally from the rearward or user-contacting surface of the seal 114 toward its respective lateral portion of cover 216 of the frame 116. In some configurations, each of the supports 214 extends generally or substantially in a longitudinal direction of the seal 114. The supports 214 can extend generally parallel to one another or can be closer at a forward end in comparison to a rearward end. In other words, the supports 214 can converge in a direction moving from the rearward or user-contacting surface of the seal 114 toward a front portion of the seal 114. However, in other configurations, the supports 214 can diverge from rear to front.

In the illustrated arrangement, each support structure 214 is shaped or otherwise configured to follow a portion or an entirety of a peripheral edge of the associated outer lateral portion 208. Each support structure 214 can comprise a general C-shape (or reversed C-shape) when the seal 114 is viewed from the side, which comprises a rearward portion 218, an upper extension or leg 220 and a lower extension or leg 222 that extend forward from the rearward portion 218. In the illustrated arrangement, the support structures 214 are thickened regions of the seal 114, each of which projects inwardly into the interior space of the seal 114. Either one or both of the extensions 220, 222 can extend to and/or contact the connector 202. In the illustrated configuration, only the lower extension 220 extends to the connector 202 and the upper extension 220 is spaced rearward from the connector 202. However, in other configurations, this arrangement could be reversed.

Each of the illustrated support structures 214 comprises a cut-out or relief 224 that provides a region of less thickness, stiffness or rigidity within the support structure 214. In the illustrated arrangement, the relief 224 is a region of less thickness relative to other portions of the support structure 214. The illustrated relief 224 also comprises a general C-shape (or reverse C-shape) when the seal 114 is viewed from the side. In some configurations, the relief 224 also follows a portion or an entirety of a peripheral edge of the associated outer lateral portion 208. However, preferably, the relief 224 is spaced inwardly from the peripheral edge of the outer lateral portion 208. In at least some configurations, the relief 224 is fully contained within the support structure 214. The relief 224 can allow portions of the support structure 214 to move relative to one another. Accordingly, the relief 224 can allow corresponding portions of the seal 114 to move relative to one another. Thus, a portion of the support structure 214 and seal 114 rearward of the relief 224 can move toward a portion of the support structure 214 and seal 114 forward of the relief 224.

The support structure 214 can be of variable thickness to provide different levels of support to the seal 114. For example, the upper extension 220 and/or lower extension 222 can have a thickness that is less than a thickness of at least a portion of the rearward portion 218. In some configurations, a portion of the rearward portion 218 rearward of the relief 224 and/or located on or adjacent a rearward surface of the seal 114 has a thickness that is greater than a portion of the rearward portion 218 forward of the relief 224. The relief 224 can have a thickness that is less than both the portion of the rearward portion 218 forward of the relief 224 and the portion of the rearward portion 218 rearward of the relief 224. Furthermore, a portion of the outer lateral portions 208 outside (e.g., forward) of the support structure 214 can have a thickness that is less than a thickness of any portion of the support structure 214. In some configurations, the thickness of the portion of the outer lateral portions 208 outside of the support structure 214 is equal to or substantially equal to the thickness of the relief 224.

In some configurations, the portion of the rearward portion 218 rearward of the relief 224 and/or located on or adjacent a rearward surface of the seal 114 has a thickness of between 2 mm and 5 mm. In some configurations, the thickness is 4 mm. In some configurations, the portion of the rearward portion 218 forward of the relief 224 has a thickness of between 1.5 mm and 3 mm. In some configurations, the thickness is 2 mm. In some configurations, the relief 224 has a thickness between 0.3 mm and 0.6 mm. In some configurations, the thickness is 0.5 mm. In some configurations, the portion of the outer lateral portions 208 outside of the support structure 214 can have a thickness of between 0.3 mm and 0.6 mm. In some configurations, the thickness is 0.5 mm. The seal 114 can also have thicknesses proportional to those disclosed herein, without having any or all of the particular thicknesses disclosed.

Figure 5:
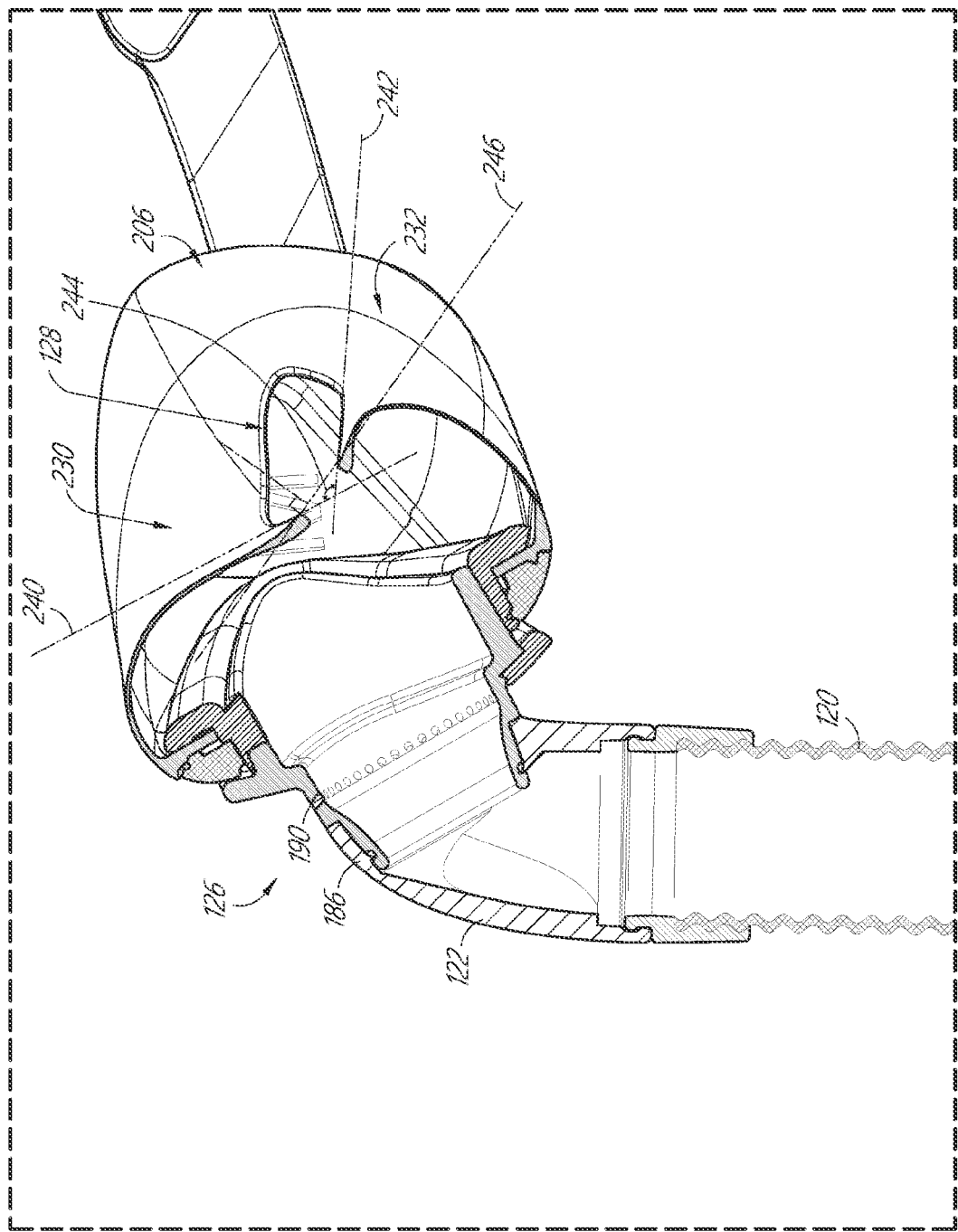
FIG. 5 is a sectional view of the mask of FIG. 4 taken along a central, vertical plane of the mask.
Figure 6:
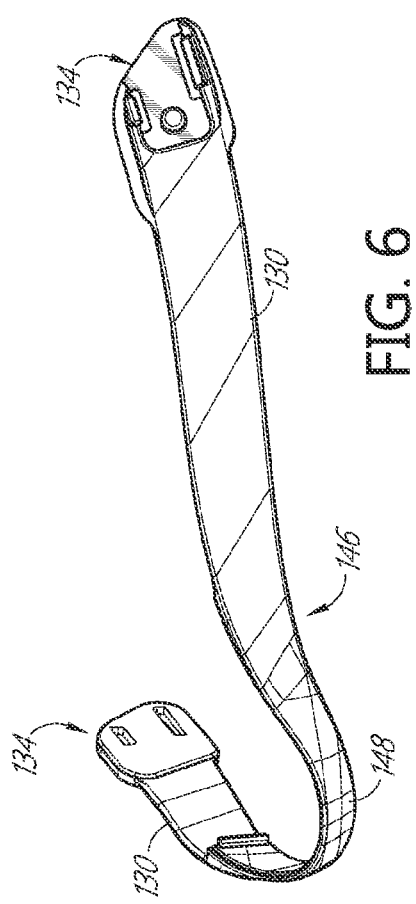
FIG. 6 is a perspective view of a portion of the frame of the mask.
Figure 7:
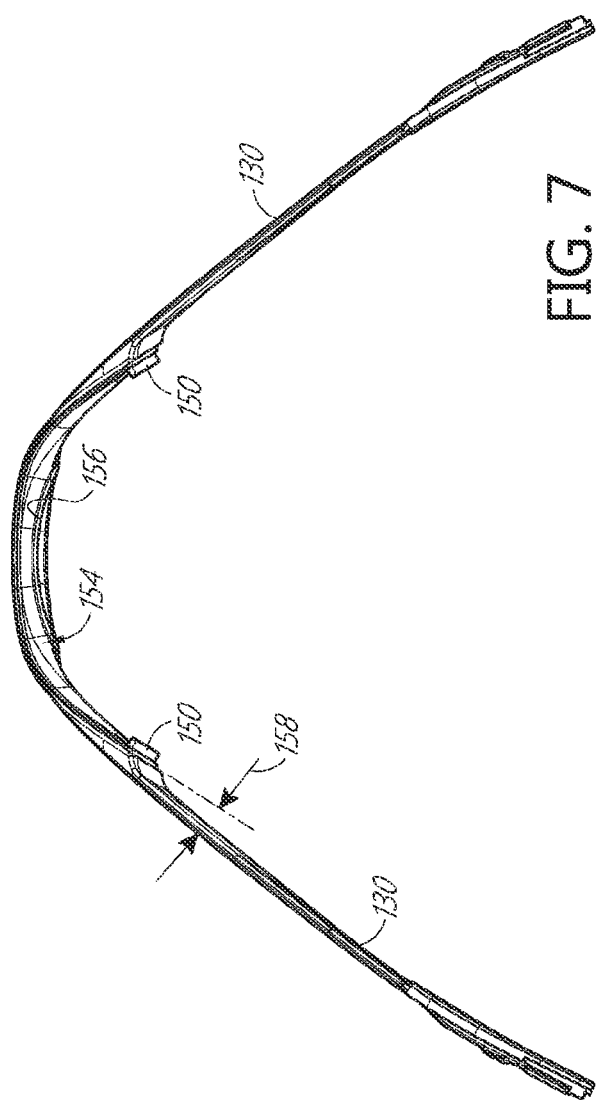
FIG. 7 is a top view of the portion of the frame of FIG. 6.
Figure 11:
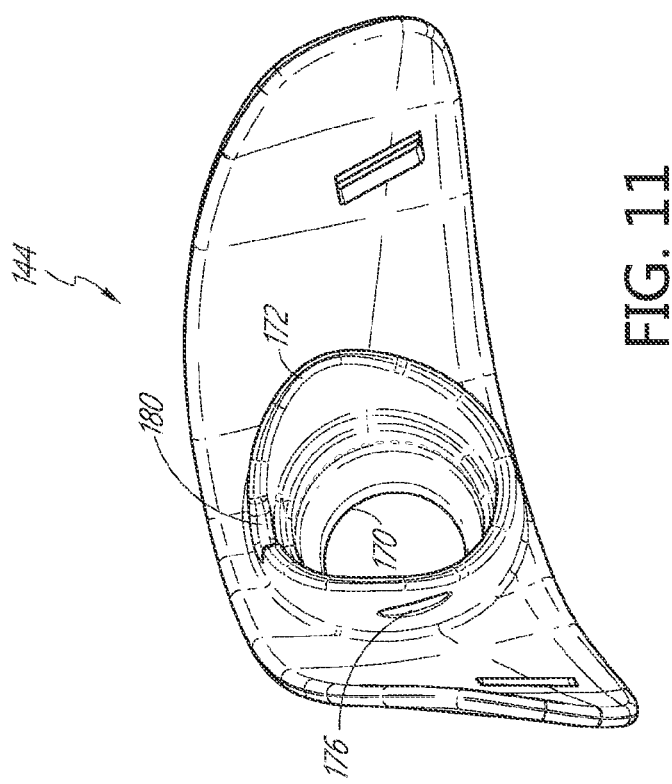
FIG. 11 is a rear perspective view of the portion of the frame of FIG. 10.
Figure 10:
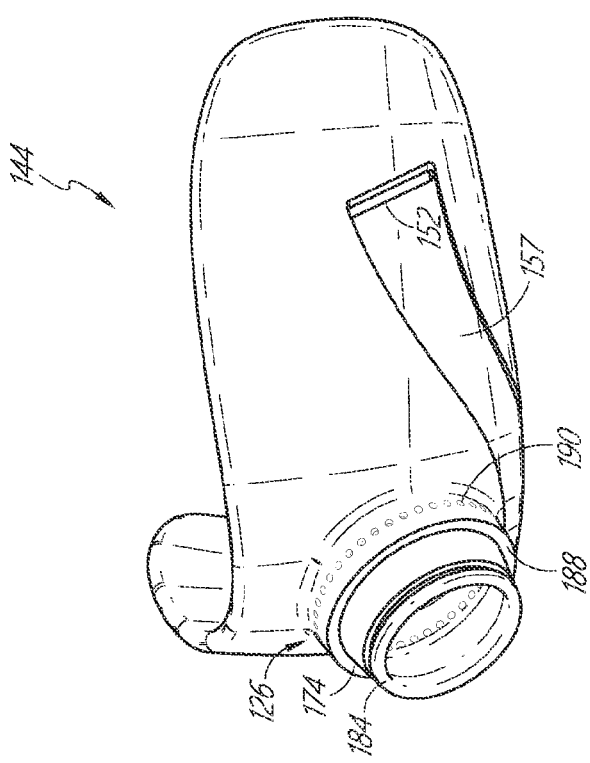
FIG. 10 is a front perspective view of a portion of the frame of the mask.
Figure 12:
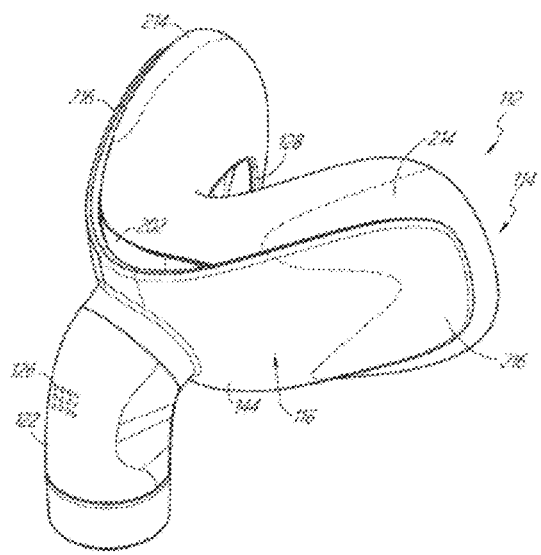
FIG. 12 is another perspective view of the mask illustrating internal structures of the seal in dashed lines.
Figure 14:
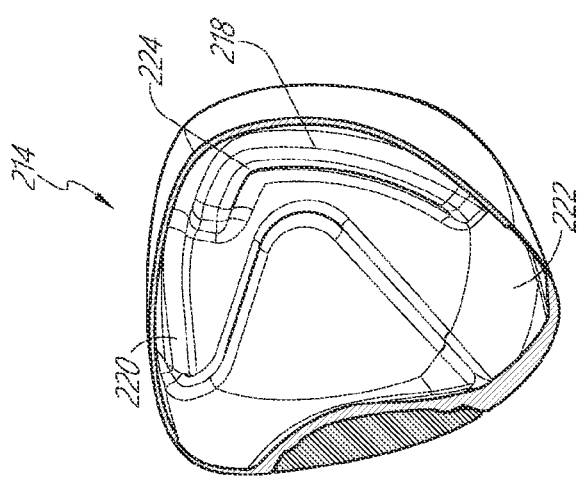
Figure 13:
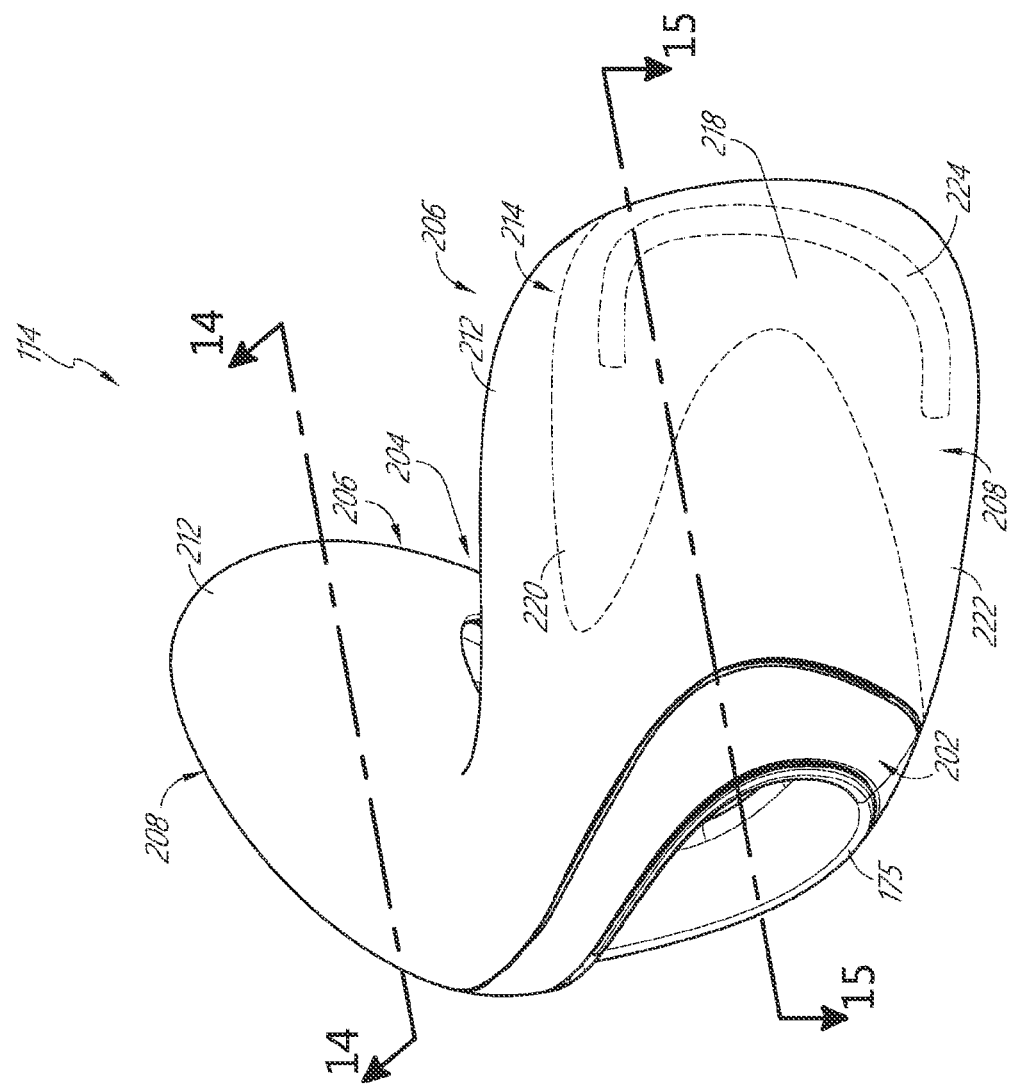
FIG. 13 is a perspective view of the seal separate from the frame.
Figure 20:
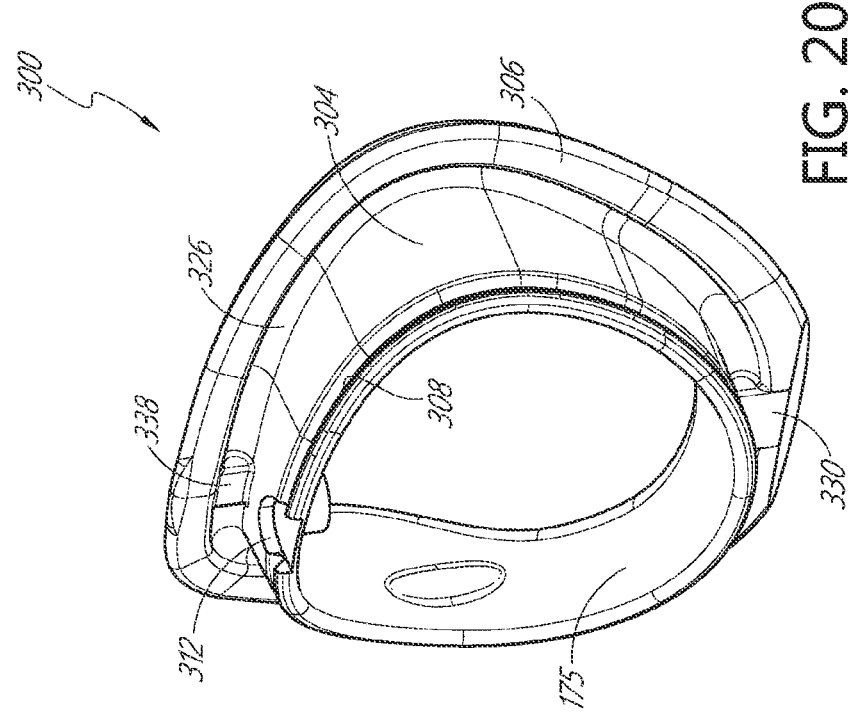
FIG. 20 is a front perspective view of another portion of the connector configured to be connected to the portion of the connector of FIG. 19.
Figure 19:
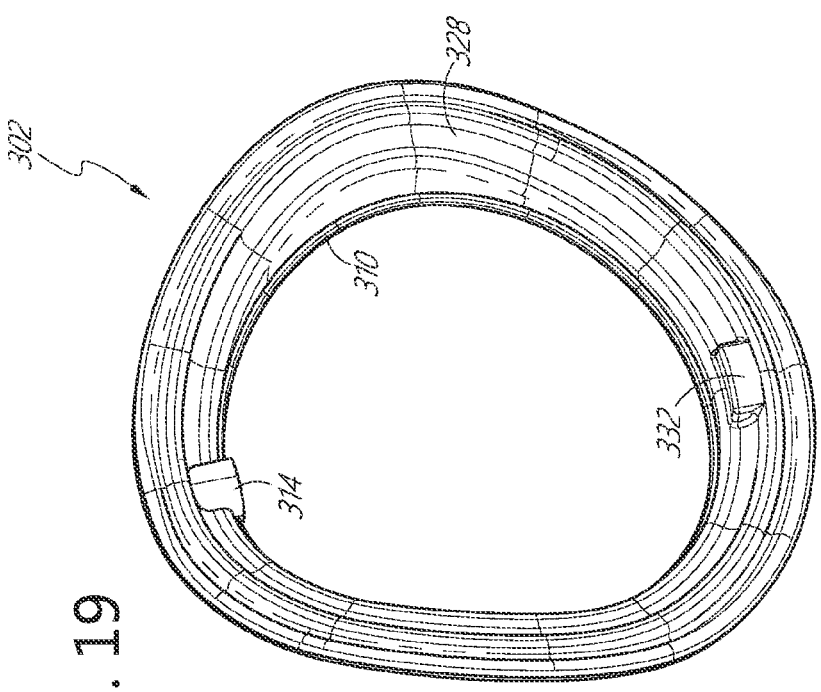
FIG. 19 is a rear perspective view of a portion of the connector.
Figure 21:
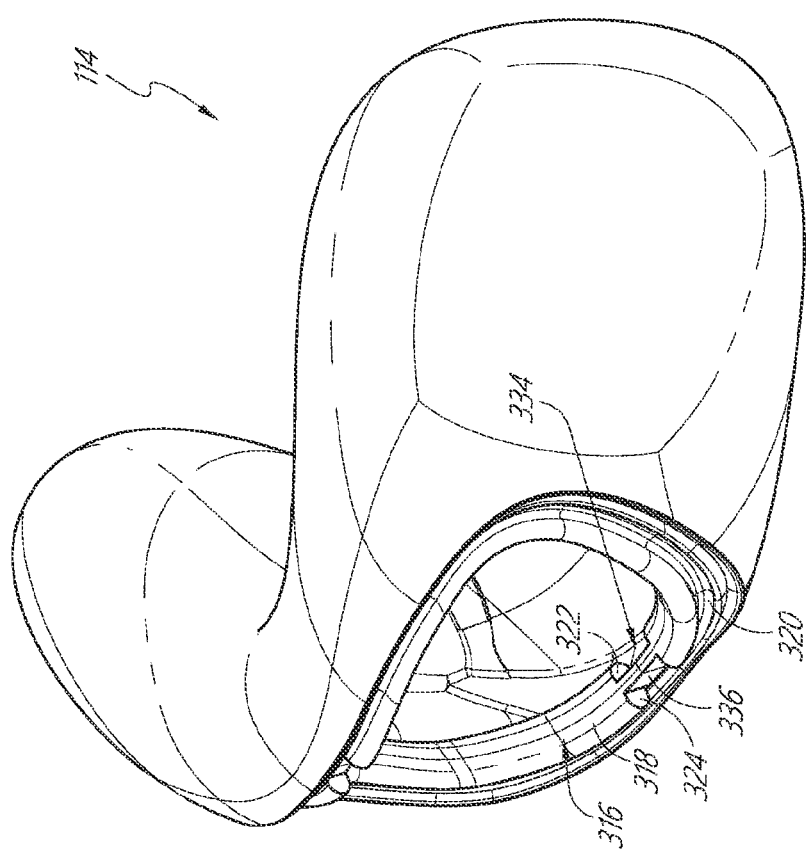
FIG. 21 is a perspective view of the seal with the connector removed.
Figure 22:
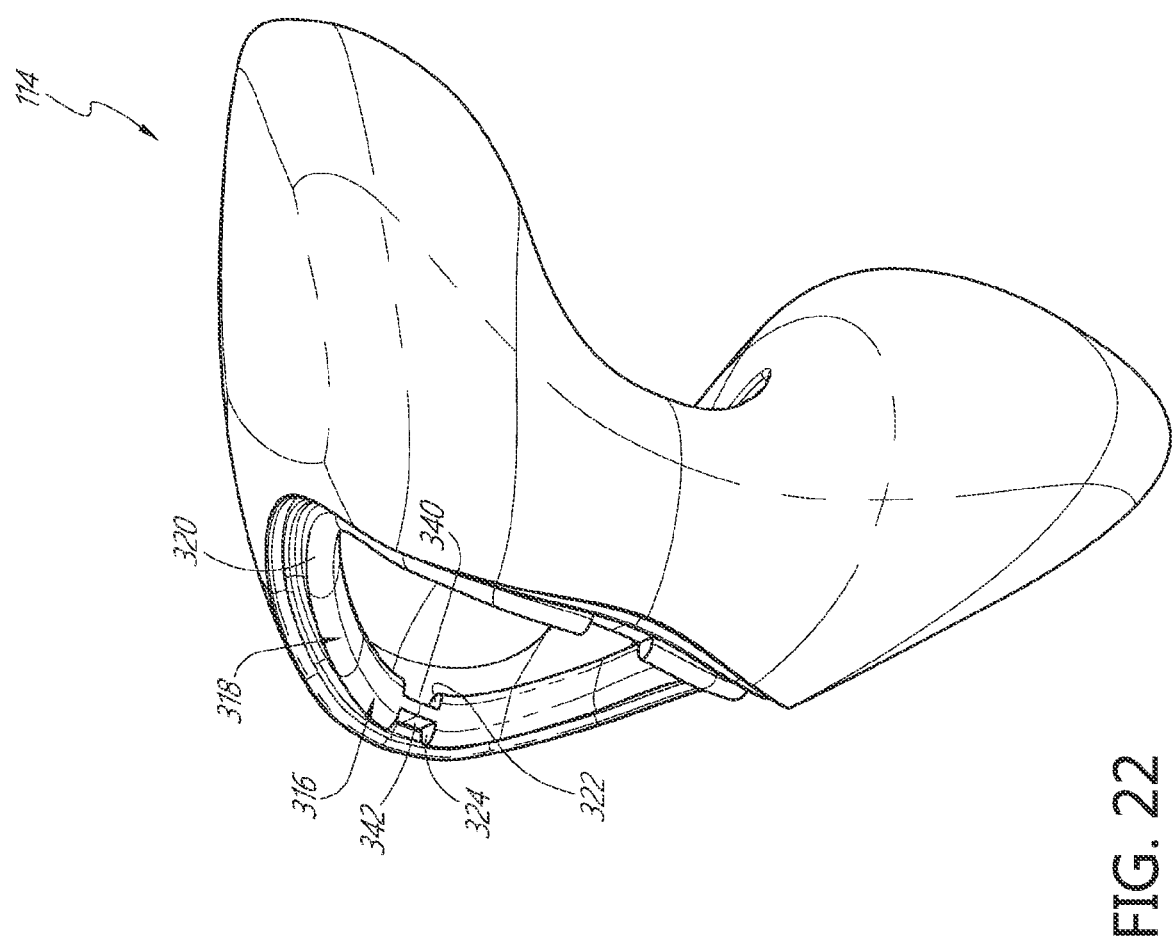
FIG. 22 is a view of the seal with the connector removed showing an upper portion of an aperture of the seal.

As described, a face contacting or wearer side of the seal 114 comprises a supple lower-nose-receiving concave center part shaped to form a seal on the face of the wearer by receiving and sealingly contacting the tip, lower sides, and base of the nose and sealingly contacting the upper lip, and position the aperture 128 for gas flow beneath the nares of wearer. As shown in FIGS. 5 and 16, the lower-nose-receiving supple center part comprises an upper wall portion 230 to contact the tip of the nose of the wearer, a lower wall portion 232 to contact the upper lip below the nose of the wearer, and left and right side wall portions defined by the previously-described inner lateral portions 206 to contact the left and right lower sides of the nose of the wearer. The lower wall portion 232 below the outlet aperture 128 is positioned rearward of or is closer to the left and right rearward-most extremities of the seal 114 than is the upper wall portion 230.

The left and right side wall portions defined by the inner lateral portions 206 extend from the aperture 128 away from one another. An angle between the left and right side wall portions 206 may be between about 20 and about 60 degrees or about 30 and about 50 degrees for example. Typically, the seal 114 has a greater width dimension than a height dimension. In at least some embodiments, the seal 114 may have an overall width of between 5 cm and 10 cm, or 6 cm and t 8 cm. In at least some embodiments, the seal 114 may have an overall height of less than 5 cm, less than 4.5 cm or less than 4 cm. The seal 114 can have a first texture on a user-contacting side and a second texture on the opposite side, which can be different from the first texture. For example, the texture on the user-contacting side can promote sealing with, friction against or comfort for the user's face. The texture on the opposite side can be configured to interact with the base 144 of the frame 116 to increase friction to inhibit relative movement between the seal 114 and the frame 116, decrease friction to promote relative movement between the seal 114 and the frame 116 or reduce adhesion between the seal 114 and the frame 116 so that the lateral portions of the seal 114 are free to move away from and out of contact with the frame 116.

The aperture 128 may be elongate in a width direction of the seal 114. The aperture 128 may be somewhat bean-shaped or bowtie-shaped when viewed from the rear. In the illustrated configuration, a central portion of the aperture 128 has a smaller height than lateral portions of the aperture 128. In addition, because the lower wall portion 232 is positioned rearward of the upper wall portion 230, a lower edge 236 of the aperture 128 is spaced rearward in the depth direction of the seal 114 relative to an upper edge 234 of the aperture 128 with the seal 114 in an orientation as worn by a user with the user's head upright.

FIG. 5 illustrates a sectioned view of the mask 112 taken along a vertical, central plane of the mask 112. A portion of the upper wall portion 230 above and adjacent the aperture 128 can define a line 240 that lies within the central plane. Similarly, a portion of the lower wall portion 232 below and adjacent the aperture 128 can define a line 242 that lies within the central plane. The lines 240 and 242 define an angle 244 between them. In some configurations, the angle 244 is greater than or equal to 90 degrees and less than 180 degrees. In some configurations, the angle 244 is between 120 degrees and 150 degrees. In some configurations, the angle 244 is 135 degrees.

The seal 114 can also define a line 246 that lies in the central plane and extends through a point on the lower edge 236 of the aperture and a point on the upper edge 234 of the aperture 128. FIG. 16A illustrates the aperture 128 viewed from a rear of the seal 114 normal to the line 246. As described above, the aperture 128 can have a bean-shape or a bowtie-shape with the central portion 250 having a smaller height 252 than a height 254 of the lateral portions 256. The aperture 128 can be symmetrical about a central, vertical axis. In the illustrated arrangement, each lateral portion 256 is generally oval in shape, with a long axis of the oval shapes angled inward or toward one another in a direction from the lower edge 236 toward the upper edge 234. The central portion 250 defines curved, concave transitions between the oval shapes of the lateral portions 256 on each of the lower edge 236 and the upper edge 234.

Each lateral portion 256 defines an uppermost point 260 and a lowermost point 262. The uppermost points 260 of the lateral portions 256 are closer to one another and the central axis than the lowermost points 262. The uppermost points 260 define a horizontal distance or width 264 between them that is smaller than a horizontal distance or width 266 between the lowermost points 262. Each of the distances 264, 266 can be equal to or greater than one-half and less than or equal to three-quarters of an overall width 268 of the aperture 128. In some configurations, the distance 264 is between one-third and two-thirds of the width 268, or one-half of the width 268. In some configurations, the distance 266 is between one-half and seven-eighths of the width 268, or three-quarters of the width 268.

The upper edge 234 of the aperture 128 defines a vertical distance 270 between the uppermost points 260 and a lowermost point 272 of the upper edge 234 within the central portion 250, which can be located on the central axis. The vertical distance 270 can also be referred to as a depth of the central portion 250 on the upper edge 234. Similarly, the lower edge 236 of the aperture 128 defines a vertical distance 274 between the lowermost points 262 and an uppermost point 276 of the lower edge 236 within the central portion 250, which can be located on the central axis. The vertical distance 274 can be referred to as a depth of the central portion 250 on the lower edge 236. In some configurations, the vertical distances 270, 274 can be different from one another. In some configurations, the vertical distance 270 is less than the vertical distance 274. In some configurations, the vertical distance 270 is between one-third and two-thirds of the vertical distance 274, or is about one-half of the vertical distance 274. In some configurations, the vertical distance 270 is less than the height 252 of the central portion 250 and/or the height 252 of the central portion 250 is equal to or less than the vertical distance 274.

In some configurations, the overall width 268 of the aperture 128 is between 20-25 mm, between 21-23 mm, or is about 22 mm. In some configurations, the overall height 254 of the aperture 128 is between 10-14 mm, between 11-13 mm, or is about 12 mm. In some configurations, the height 252 of the central portion 250 of the aperture 128 is between 4-6 mm, or is about 5 mm. In some configurations, the distance 270 is between 1.5-2.5 mm, or is about 2 mm. In some configurations, the distance 274 is between 4-6 mm, or is about 5 mm. In some configurations, the distance 264 between the uppermost points 260 of the upper edge 234 is between 8-12 mm, 9-11 mm or is about 10 mm. In some configurations, the distance 266 between the lowermost points 262 of the lower edge 236 is between 15-20 mm, between 16-18 mm, or is about 17 mm.

With particular reference to FIGS. 5, 10 and 17-22, as described above, the illustrated mask 112 comprises the connector 202 that couples the seal 114 to the frame 116. The connector 202 comprises a first portion 300 and a second portion 302 that capture the seal 114 between them. The first portion 300 and the second portion 302 can couple to one another to retain the seal 114 between the first portion 300 and the second portion 302. In some configurations, the first portion 300 can connect to the second portion 302 by a snap-fit arrangement, which can be a permanent or removable connection.

In the illustrated arrangement, the first portion 300 of the connector 202 comprises a hub portion 304 and a flange portion 306. The hub portion 304 comprises an annular wall that extends in an axial direction and defines the aperture 175 that receives the connector 172 of the base 144 portion of the frame 116. The flange portion 306 comprises an annular wall that extends outwardly from the hub portion 304. In some configurations, the flange portion 306 extends in a radial direction and, thus, is perpendicular to the hub portion 304. In the illustrated arrangement, the second portion 302 is an annular member that is sized and shaped to fit onto the hub portion 304 of the first portion 300.

As described above, the first portion 300 and the second portion 302 of the connector 202 are configured to be interlocked with one another in an axial direction. In the illustrated arrangement, an outer surface of the end portion of the hub portion 304 of the first portion 300 defines a recess 308 that extends partially or completely around the hub portion 304 in a circumferential direction. An interior surface of the second portion 302 defines a protrusion 310 that extends partially or completely around the second portion 302 in a circumferential direction and is configured to be received by the recess 308 of the first portion 300. In other configurations, this arrangement could be reversed such that the protrusion 310 can be on the first portion 300 and the recess 308 can be on the second portion 302.

The first portion 300 and the second portion 302 can also be keyed to one another to ensure that the first portion 300 and the second portion 302 can only be connected in a single rotational orientation relative to one another and/or to inhibit or prevent relative rotation once connected. In some configurations, one of the first portion 300 and the second portion 302 comprises a key or protrusion and the other of the first portion 300 and the second portion 302 comprises a slot or recess configured to receive the key or protrusion. In the illustrated arrangement, the hub portion 304 of the first portion 300 comprises a slot or recess 312 and the second portion 302 comprises a key or protrusion 314 that is configured to engage the slot or recess 312. At least a terminal end of the slot or recess 312 is semi-cylindrical in shape and the key or protrusion 314 comprises a complementary semi-cylindrical shape. In the illustrated arrangement, the slot 312 and the protrusion 314 are located on an upper portion of a respective one of the first portion 300 and the second portion 302 of the connector 202. However, in other configurations, this location could be varied. In addition, the location of the recess 312 and the protrusion 314 can be reversed between the first portion 300 and the second portion 302 of the connector 202 from the locations shown.

The seal 114 defines an aperture 316 that receives the first portion 300 and the second portion 302 of the connector 202. When the connector 202 is assembled to the seal 114, the flange portion 306 of the first portion 300 is positioned within an interior of the seal 114 and the hub portion 304 extends through the aperture 316. The second portion 302 of the connector 202 is positioned on the exterior of the seal 114. The seal 114 can comprise an annular rim 318 that encircles the aperture 316 and is configured to be captured by the first portion 300 and the second portion 302 of the connector 202. In particular, the rim 318 comprises a generally T-shaped cross-section having a narrow base 320, a first lobe 322 that extends in a first axial direction from the base 320 and a second lobe 324 that extends in a second axial direction from the base 320 that is opposite the first axial direction. The first portion 300 defines an annular recess 326 configured to receive the first lobe 322 and the second portion 302 defines an annular recess 328 configured to receive the second lobe 324. The base 320 extends between the first portion 300 and the second portion 302 toward a main portion of the seal 114.

In the illustrated arrangement, the connector 202 and the seal 114 comprise interference portions configured to inhibit or prevent rotational movement between the seal 114 and the connector 202. In particular, the hub portion 304 of the first portion 300 comprises a first protrusion 330 and the second portion 302 comprises a second protrusion 332. The first protrusion 330 and the second protrusion 332 face one another with a space between them that is configured to receive a portion of the annular rim 318 between them. The portion of the annular rim 318 defines a first recess 334 and a second recess 336 configured to receive the first protrusion 330 and the second protrusion 332, respectively. In the illustrated arrangement, each of the protrusions 330, 332 and the recesses 334, 336 comprise a generally cuboid shape. The protrusions 330, 332 and the recesses 334, 336 are located on lower portions of the first portion 300 and the second portion 302 of the connector 202. However, in other configurations, these locations could be varied.

In some configurations, the connector 202 and the seal 114 also comprise a second set of interference portions configured to inhibit or prevent rotational movement between the seal 114 and the connector 202. In particular, the first portion 300 comprises a third protrusion 338 and the seal 114 comprises a third recess 340 and a fourth recess 342. The third recess 340 is configured to receive the third protrusion 338. In the illustrated configuration, a portion of the key or protrusion 314 extends into the fourth recess 342. The third protrusion 338, the third recess 340 and the fourth recess 342 are located on an upper portion of a respective one of the connector 202 and the seal 114 and/or opposite the protrusions 330, 332 and the recesses 334, 336. However, in other configurations, the third protrusion 338, the third recess 340 and the fourth recess 342 can be located elsewhere.

Figure 23:
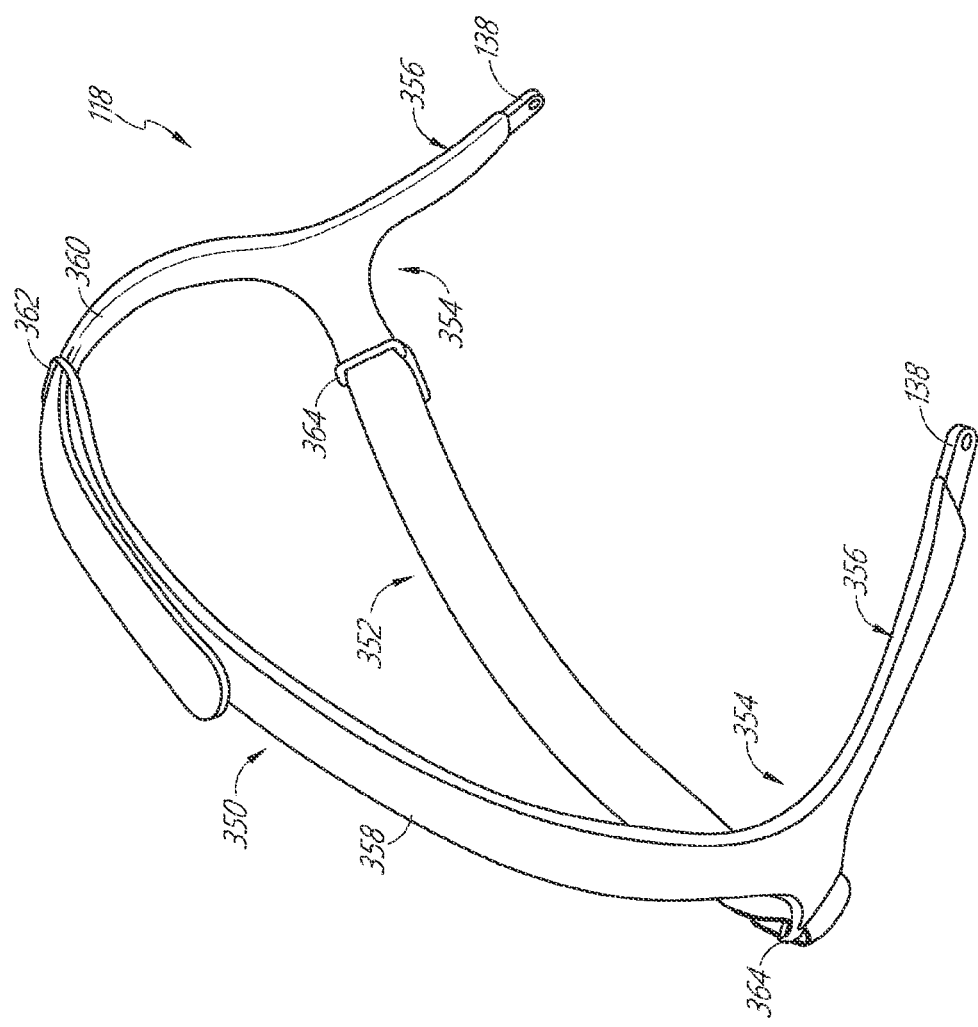
FIG. 23 is a perspective view of the headgear separate from the mask.

With reference to FIGS. 3 and 23, in the illustrated arrangement, the headgear 118 can comprise a bifurcated headgear arrangement having a top or upper strap portion 350 and a rear strap portion 352. The upper strap portion 350 is configured to pass over the top of the user's head from one side to the other. In some configurations, the upper strap portion 350 is a crown strap that lies over the parietal bone or at or near a junction between the parietal bone and the frontal bone. In other configurations, the upper strap portion 350 can comprise a forehead strap that lies over the frontal bone of the user. The rear strap portion 352 passes around the back of the user's head and, in some configurations, lies over the occipital bone of the user. However, in other configurations, the rear strap portion 352 could be positioned higher or lower on the head and/or neck of the user. In the illustrated arrangement, the upper strap portion 350 and the rear strap portion 352 join one another on each side of the headgear 118 at a junction 354. Each one of a pair of forward extension straps 356 extends forwardly from the junction 354 toward and connects to a respective one of the side arms 130 of the frame 116.

In some configurations, at least some portions of the headgear 118 are rigid, semi-rigid, inelastic or substantially inextensible in response to normal or expected forces acting on the headgear 118 and other portion of the headgear 118 are elastic or extensible in response to normal or expected forces. In some configurations, one or more of the upper strap portion 350, junctions 354 and forward extension straps 356 are rigid, semi-rigid, inelastic or substantially inextensible. In the illustrated configuration, each of the upper strap portion 350, junctions 354 and forward extension straps 356 are rigid, semi-rigid, inelastic or substantially inextensible. In the illustrated configuration, the rear strap portion 352 is elastic or extensible. Such an arrangement allows the rear strap portion 352 to stretch to adjust a circumferential length of the headgear 118. The amount of stretch of the rear strap portion 352 can be limited and, thus, the rear strap portion 352 can also be adjustable in length. In some configurations, it is preferable for circumferential length adjustment to occur at the back of the user's head, which is less susceptible to lengthening in response to blow-off forces. The rigid, semi-rigid, inelastic or substantially inextensible nature of the junctions 354 and forward extension straps 356 positioned on the side and forward portions of the user's head assists in maintaining a desired circumferential length of the headgear 118 despite the elastic nature of the rear strap portion 352. In some cases, frictional forces between the portions of the headgear 118 and the side and forward portions of the user's head inhibit movement or lengthening of the headgear 118 in response to blow-off forces. However, in other arrangements, the rear strap portion 352 can be rigid, semi-rigid, inelastic or substantially inextensible and, in such cases, may be adjustable in length.

The upper strap portion 350 can comprise a length adjustment arrangement. In the illustrated arrangement, the upper strap portion 350 comprises a first portion 358 and a second portion 360 that are separate from one another and are capable of being adjustably connected to one another. A free end of the first portion 358 comprises a loop 362 through which the second portion 360 can pass. Thus, the first portion 358 and the second portion 360 can be slid relative to one another to vary an overlapping distance of the portions 358, 360 and, thus, vary a length of the upper strap portion 350. The second portion 360 can be coupled to the first portion 358 to secure the upper strap portion 350 in a desired adjusted length. In the illustrated arrangement, an inner surface of the second portion 360 can comprise a hook portion of a hook-and-loop fastener and the outer surface of the first portion 358 can comprise a loop portion of the hook-and-loop fastener. This arrangement can also be reversed. In some configurations, a material of the upper strap portion 350 can define the loop portion of the hookand-loop fastener. In other words, the loop portion may not be a discrete element of the upper strap portion 350.

With the above-described arrangement, for a particular user, the upper strap portion 350 can be adjusted to an appropriate length such that the junctions 354 and/or forward extension straps 356 sit above the user's ears. Once adjusted, the upper strap portion 350 can be maintained in the adjusted position during donning and doffing of the headgear 118 and associated interface 110. In other words, preferably, the first portion 358 and the second portion 360 do not have to be separated from one another for the user to put on or take off the interface 110. Rather, the headgear 118 allows the interface 110 to be donned ('like a cap') by holding the frame 116 at the seal 114 or near the seal 114 (as one would hold a cap at its peak when lifting or flipping it onto the head) and moving the rear strap portion 352 over and to the rear of the user's head. The stretchable or extensible rear strap portion 352 can facilitate the passing of the headgear 118 over the user's head without opening the headgear 118 by separating the portions 358, 360 of the upper strap portion 350 or separating one or both ends of the rear strap portion 352 from a remainder of the headgear 118. The headgear 118 may be removed or doffed in a reverse action.

In the illustrated configuration, the rear strap portion 352 is connected to each of the junctions 354 by an end portion of the rear strap portion 352 that is passed through a loop 364 carried by the junction 354 and doubled back on itself. The end portion of the rear strap portion 352 can be coupled to a relatively more central portion of the rear strap portion 352 by a suitable fastener, such as a hook-and-loop fastener, for example. The rear strap portion 352 can be adjustable at one or both ends.

In some configurations, the rigid, semi-rigid, inelastic or substantially inextensible portions of the headgear 118 can be constructed by introducing a molten plastic material into a space defined by a textile or fabric material outer cover and allowed to cool to form a plastic core. The plastic material can adhere or be coupled to the textile or fabric material to form an integrated structure. The textile or fabric material can be a tubular structure or separate layers of material, for example. Headgear structures having a plastic core and an outer textile or fabric cover and methods for producing such headgear structures are disclosed in Applicant's U.S. Provisional Application Nos. 62/050,925; 62/159,857; and 62/198,104, the entireties of which are incorporated by reference herein and made a part of the present disclosure. In some arrangements, some or all of the connectors 138 and loops 362, 264 are formed as a unitary structure with the plastic core of the headgear 118.

Seals and masks disclosed herein may be used with headgear in other forms, such as headgear with two straps which attach to the mask on either side, i.e., headgear which comprises left and right side upper and lower straps. The frame of such an interface embodiment may or may not comprise side arms as described above. Left and right upper straps may pass downwardly (when the headgear is worn) between the eyes and ears of the wearer and left and right lower straps may extend from the lower rear of the head and beneath the ears to the mask (and attach to the mask each side below the upper straps). Alternatively, upper and lower straps may join for example in a stiffer yoke before attaching to the mask frame, or which is integral with the mask frame. Such a headgear may have buckle and tongue, loop and tongue or other adjustment in the upper or lower straps or both sides, part way along their length(s) or at the connection of the straps to the mask. In less preferred embodiments, the upper straps may attach to the top of a T-piece extending upwardly from the frame to the wearer's forehead. In another embodiment, again, the headgear may comprise a single strap which passes or loops from the mask on one side around the rear of the head and back to the mask on the other side. Such a headgear strap may be elastic or resiliently stretchable and/or may have a length adjustment device (e.g., buckle and tongue, loop and tongue, etc.) in the rear or at the sides or at the connection of the headgear to the mask on one or both sides. A variant of such headgear may also comprise a crown strap.

Other suitable materials or configurations for the headgear 118 can also be used. For example, in some configurations, the headgear may be formed at least in part from a soft flexible material, which can be a cloth covered foam material, such as a BREATH-O-PRENE material, for example. The headgear 118 may be formed by cutting out the headgear 118 to shape from the sheet material by blade cutting or radio frequency cutting, for example. In one embodiment, the edges of the headgear are thermoformed, i.e., compressing under heat, to form rounded edges. That is, heat and pressure are applied along the headgear edges to compress the opposite outer surfaces of the headgear material towards one another at the edges and heat bond them together. This may be done simultaneously or in the same tool with cutting the headgear to shape for example, by cutting an outline of the headgear shape in the sheet material and theremoforming to define the rounded headgear edges in one operation, or instead by first cutting the headgear to shape and then rounding the edges in a second operation. The rounded edges or any joints in the headgear may alternatively be formed by ultrasonic or radio frequency welding, for example.

As described above, the mask 112 comprises a bias flow vent 126 that allows expired gases from the user to be exhausted from the interface 110. In the illustrated arrangement, the bias flow vent 126 is defined by the frame 116. In particular, the bias flow vent 126 is defined by the elbow connector 174 of the base 144 of the frame 116. The vent holes 190 of the bias flow vent extend in a generally radial direction through the elbow connector 174 between the elbow 122 and the U-shaped body of the base 144. The location of the vent holes 190 can reduce noise produced by the interface 110. In addition, other features of the interface 110 can facilitate noise reduction. Examples of such features and arrangements are disclosed with particular reference to FIGS. 24-29.

Inspiration noise can be defined as the increased level of noise resulting from the breathing in or inspiration of a user wearing a CPAP mask. Inspiration noise is common to CPAP masks, especially smaller nasal masks or nasal pillow masks. Static bias noise can be defined as constant noise with no flow generated by patient breathing and is generally associated with bias hole geometry and can be reduced via a number of different hole shapes, patterns and configurations. Dynamic inspiration noise (which is generally worse on inhalation) can be caused by geometry other than the bias holes. It is believed that this inspiration noise is, however, transmitted or heard through the bias holes and hence is closely associated with bias flow. When a patient is breathing on a CPAP machine, as he or she breathes in, the flow in the CPAP tube increases such that an approximately constant pressure is maintained within the mask. This has the result that bias flow on inhalation and exhalation is approximately constant and hence flow through the bias holes is a function of pressure only.

Dynamic noise, and specifically inspiration noise, occurs when a patient is breathing in and hence when the flow from the CPAP is at a maximum. It is therefore believed that increased flow causes the inspiration noise. Methods to minimize the noise created on inspiration are discussed below. Noise is caused by a restriction in the breathing circuit upstream of the bias flow. The restriction causes increased velocity and turbulence, which in turn generates noise. The noise is heard through the bias holes. It has been determined that having a diameter less than approximately 15 mm within the breathing circuit can result in significant inspiration noise. Therefore, when possible or practical considering other factors, maintaining a diameter greater than approximately 15 mm within the breathing circuit can be desirable when designing a mask system that has reduced, minimal or no inspiration noise issues.

In addition to maintaining a minimum diameter or cross-sectional area within the breathing circuit, another factor is the consideration of turbulence. Turbulence created in the airstream itself creates noise, which is subsequently heard by the patient. Sudden expansions in a pipe cause changes in pipe velocity, turbulence and, hence, noise. Expansion can either be a sudden expansion (wherein the expansion angle is equal to 180 degrees) or a more gradual expansion (wherein the expansion angle is greater than 0 degrees and less than 180 degrees). In order to reduce the noise, either the rate at which the fluid is slowing down can be reduced (i.e., utilize a shallow gradual expansion) or the velocity at which the air is travelling can be reduced. In order to reduce head loss, an expansion should preferably have an angle of $\Theta<30°$ or, alternatively, an angle of $120°\Theta<180°$ or $150°\Theta<180°$.

Figure 24:
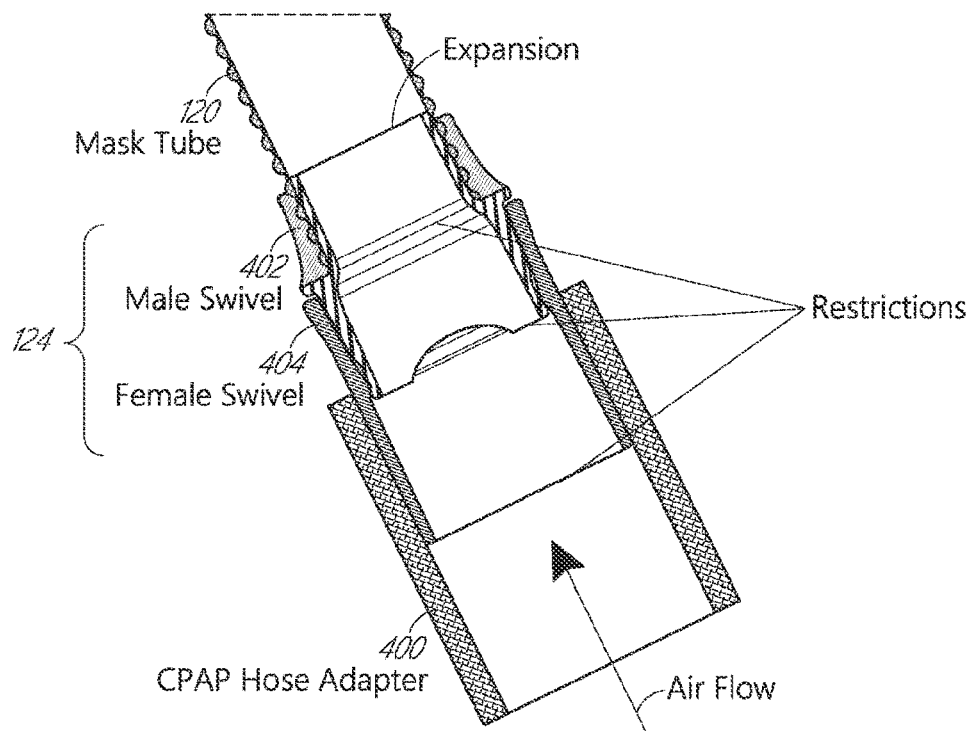
FIG. 24 is a sectional view of a conventional CPAP hose to mask connection.

In practice, noise can be reduced designing cross sections such that the peak air speed is reduced or minimized and/or designing of geometry to reduce or eliminate sudden changes in geometry that cause turbulence and thus noise. In some configurations, noise reductions can be achieved by careful consideration of tube and connection diameters within the breathing circuit. For example, a conventional CPAP hose to mask tube connection is shown in FIG. 24. The actual CPAP hose or breathing circuit is not shown in FIG. 24 (see, however, conduit 12 in FIG. 1), but would be coupled to the upstream end of the CPAP hose adapter 400. The CPAP hose adapter 400 is coupled to the connector 124 of the mask tube 120. The illustrated connector 124 of the mask tube 120 is a swivel connector that comprises a male swivel portion 402 and a female swivel portion 404. The male swivel portion 402 is coupled to the mask tube 120 and the female swivel portion 404 is coupled to the CPAP hose adapter 400. It can be seen in FIG. 24 that there are several restrictions and an expansion within the illustrated CPAP hose to mask tube connection. The restrictions cause the velocity of the air to increase which then causes increased turbulence when the air passes over the expansion. The restrictions are created as a result of several male to female connections between swivels 402, 404 and tube or hoses.

Figure 25:
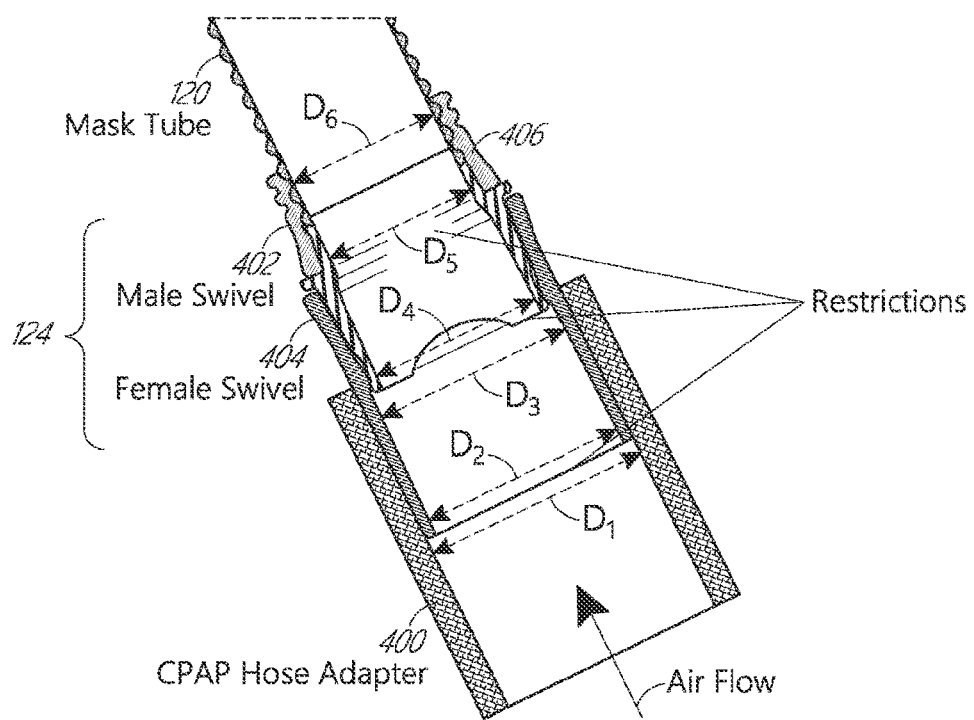
FIG. 25 is a sectional view of a CPAP hose to mask connection of the present disclosure.

With reference to FIG. 25, an improved CPAP hose to mask tube connection reduces one or more of the restrictions, such as by reducing or minimizing the wall thickness of the swivel components and changing the way in which the male swivel 402 is joined to the mask tube 120. In particular, in the illustrated configuration of FIG. 25, the male swivel 402 does not extend inside the mask tube 120. Rather, the male swivel 402 has a minimum diameter that is equal to or substantially equal to the internal diameter of the mask tube 120. In some configurations, this is achieved by using a coupling sleeve 406 or other suitable coupling to couple the male swivel 402 to the mask tube 120. The coupling sleeve 406 can be formed by, for example, overmoulding a material that will chemically bond to the male swivel 402 and the mask tube 120 onto a portion of both the swivel 402 and the tube 120. Such an arrangement reduces the size of the restriction within the male swivel 402 and also removes or substantially eliminates the expansion from the male swivel 402 to the mask tube 120. In the illustrated arrangement, the diameters of the various components are labeled and can be as follows:

Approximate Diameters:
$D1 \approx 22$ mm
$D2 \approx D3 \approx 19$ mm
$D4 \approx 17$ mm
$D5 \approx D6 \approx 15$ mm In other configurations, the diameters may vary from the above values, but the proportions between two or more of the diameters can be the same or substantially the same. Furthermore, the differences between two or more of the diameters can be the same, substantially the same or less than the above values.

In some applications or in some locations within a CPAP system, such as the interface 110, for example, it can be difficult or impractical to avoid sudden changes in geometry. For example, to prevent sudden transitions in cross-sectional area, a small wall angle (e.g., less than) 30° is desirable. Such small wall angles require the transition between diameters or cross-sectional areas to occur over a greater length compared to a more sudden transition, which can increase the overall size of the mask. In many cases, it is desirable for the mask to be as small and unobtrusive as possible or practical, for user comfort. Thus, a sudden transition may be desirable in terms of the smaller mask geometry that it allows.

Figure 26B:
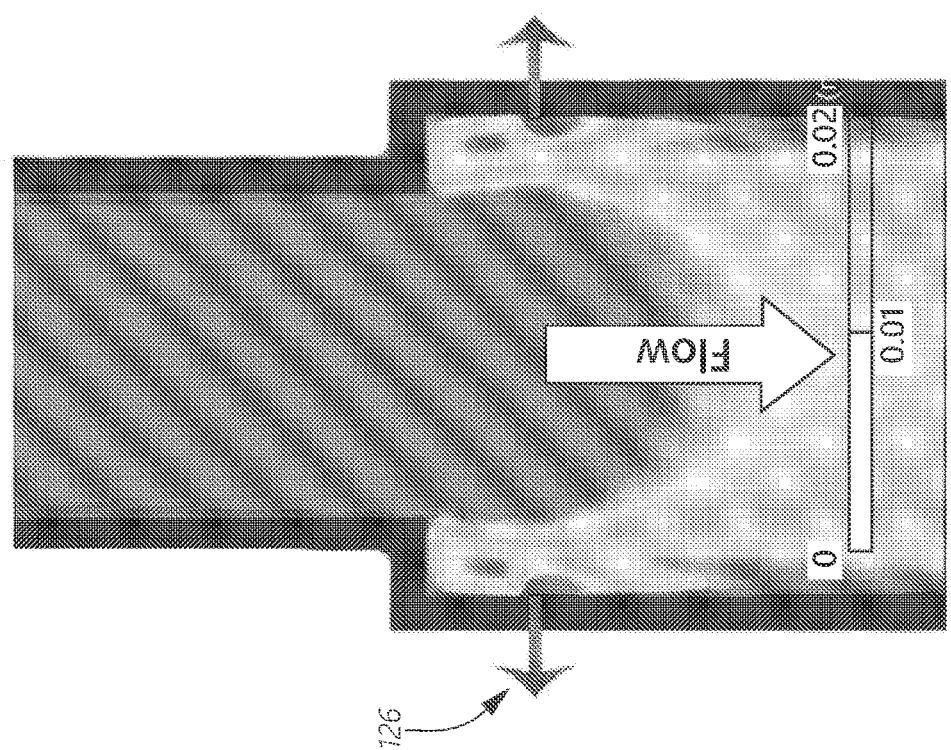
FIGS. 26A and 26B are velocity diagrams of an expansion within a flow passage with a bias flow vent positioned before and after the expansion, respectively.
Figure 26A:
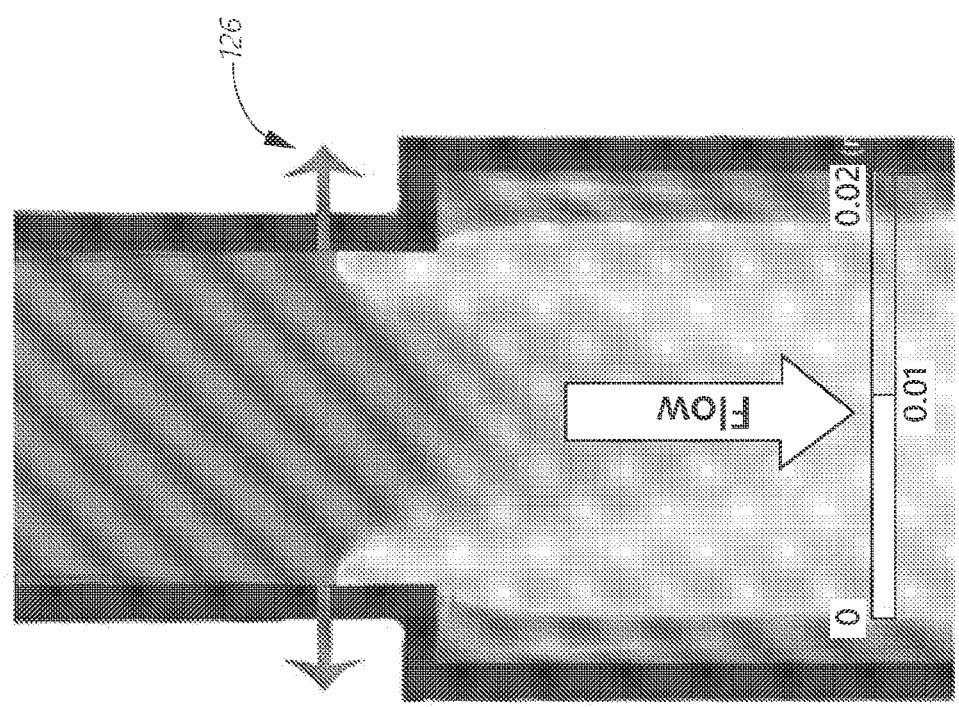
Figure 27B:
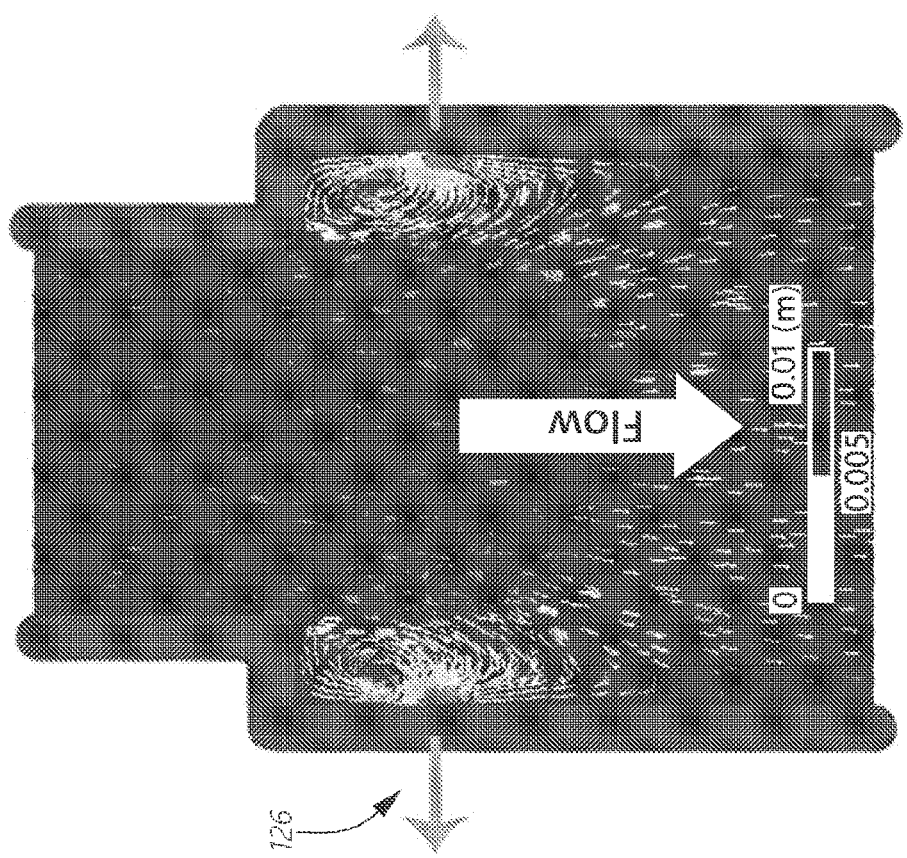
FIGS. 27A and 27B are vector diagrams of the expansion within a flow passage with the bias flow vent positioned before and after the expansion, respectively.
Figure 27A:
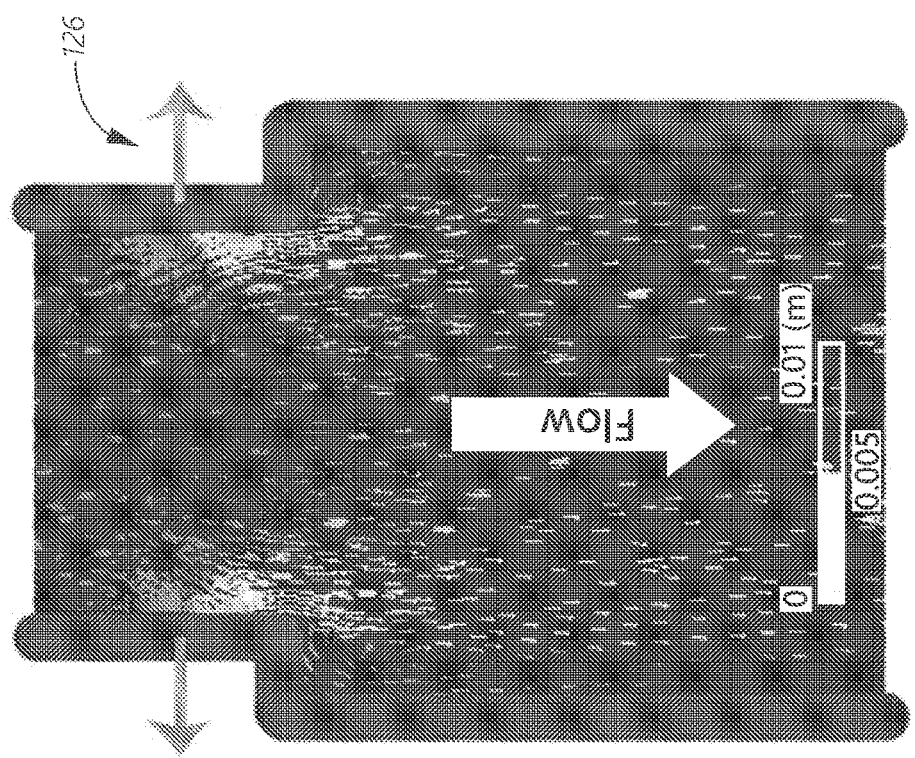

To reduce the noise created over the unavoidable transitions from small diameters to large diameters (expansions), the location of the bias vent can be selected to reduce the flow rate across the transition. The bias flow, which is generally associated with the creation of noise, can actually be used to reduce noise. By having the bias flow on the side of the expansion with the smallest cross sectional area (before the expansion), the inspiration noise can be reduced as the flow rate over the expansion and thus the velocity is now reduced. Such an arrangement creates a less turbulent flow, as shown in FIGS. 26 and 27. FIGS. 26A and 27A illustrate flow at an expansion when the bias flow vent is located before or upstream of the expansion. FIG. 26A is a velocity plot and FIG. 27A is a vector plot. FIGS. 26B and 27B illustrate flow at an expansion when the bias flow vent is located after the expansion. Again, FIG. 26B is a velocity plot and FIG. 27B is a vector plot. Comparing FIGS. 26A and 26B, it is apparent that the velocity at the expansion is lower when the bias flow vent is located before the expansion (FIG. 26A) relative to the velocity at the expansion when the bias flow vent is located after the expansion (FIG. 26B). The dark area in the relative upstream portions of the flows represents areas higher velocity. Thus, with the bias flow vent located before the expansion, velocity is lower and, accordingly, noise is lower. FIGS. 27A and 27B also illustrate that less recirculated flow is present when the bias flow vent is located before the expansion (FIG. 27A) compared to the situation when the bias flow vent is located after the expansion (FIG. 27B). Less recirculated flow means less turbulence, which means less noise.

Figure 28A:
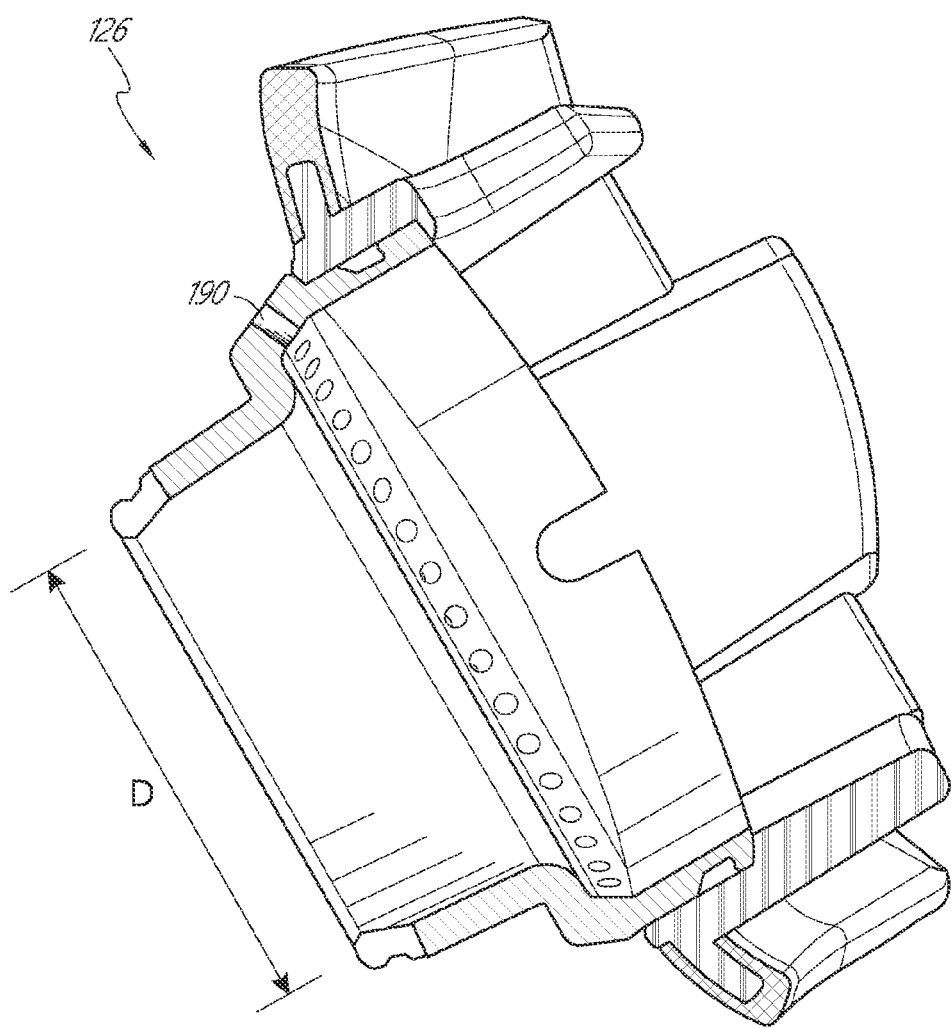
FIGS. 28A, 28B and 28C are sectional views of three different designs of a portion of an interface comprising a bias flow vent.
Figure 28B:
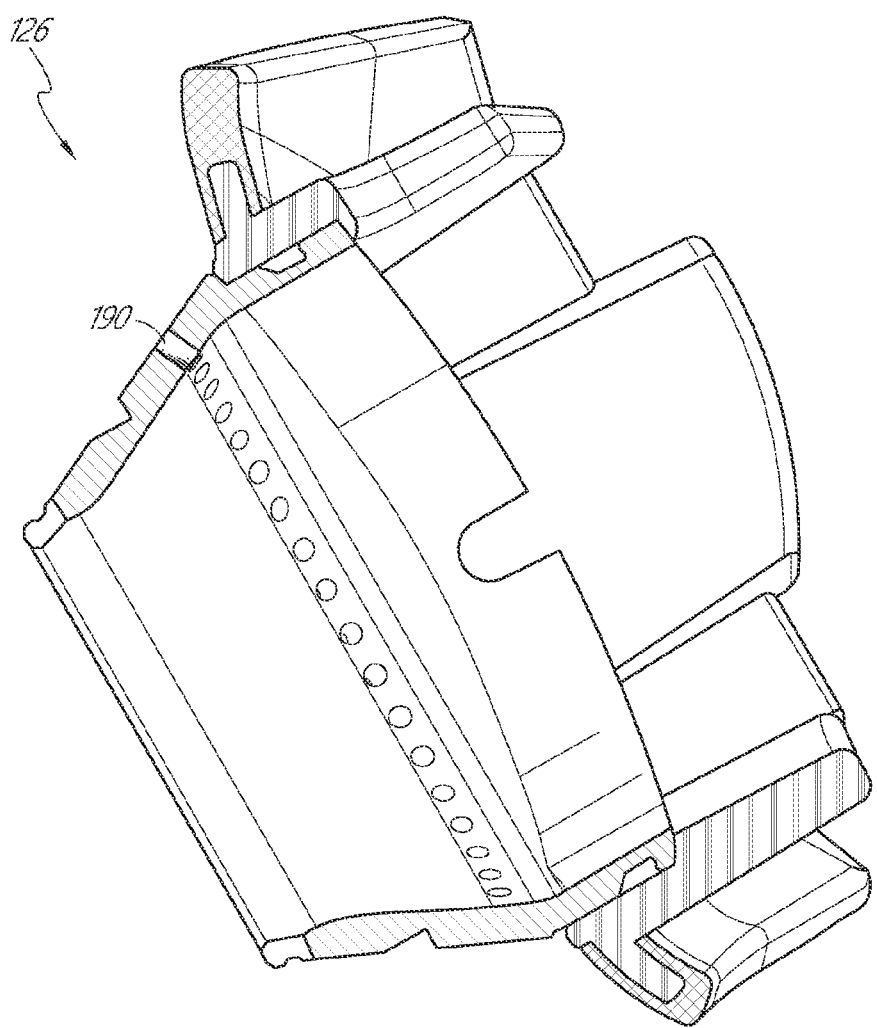
Figure 28C:
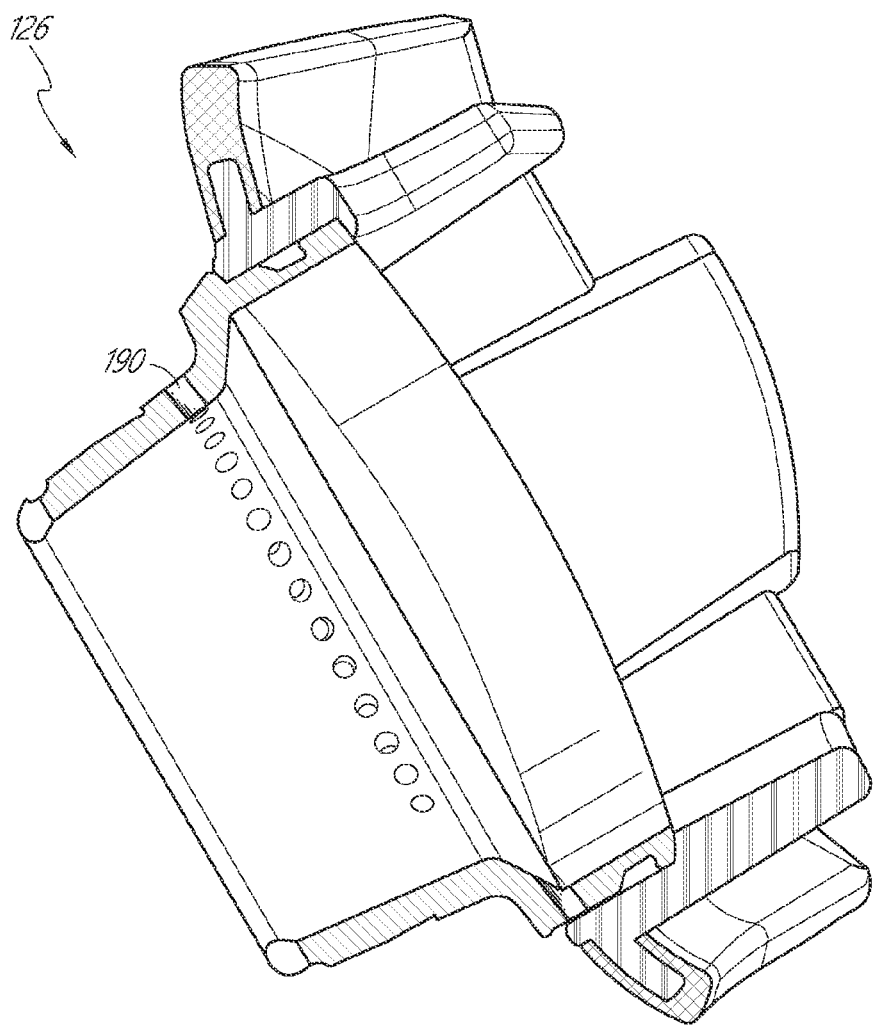
Figure 29:
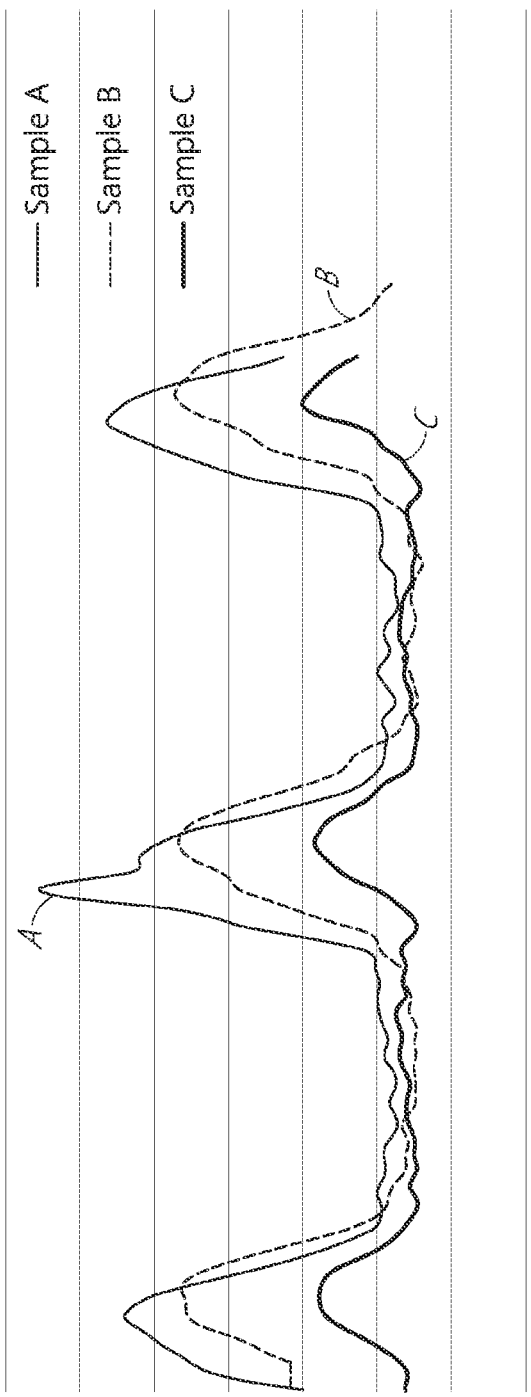
FIG. 29 is a plot of noise level over time for the three designs of FIGS. 28A, 28B and 28C.

Different design options (A, B and C) illustrating how this principle can be implemented in a mask 112 are shown in FIGS. 28A, 28B and 28C. The level of sound in each design option produces over 3 breaths is shown in the plot in FIG. 29. Design C has the lowest peak inspiration noise and Design A has the highest peak inspiration noise, with Design B having a peak inspiration noise between Design C and Design A. Each sample has the same minimum internal diameter D. In the illustrated designs, the bias flow vents 126 are implemented in the elbow connectors 174; however, in other arrangements, the bias flow vents 126 can be in other locations, as well. For example, in some configurations, the bias flow vents 126 can be in the elbow 122, among other possible locations.

In Design A, the vent holes 190 of the bias flow vent 126 are located after a sudden change in geometry. As a result, upon inhalation, there is a high flow rate of air over a sudden expansion which causes turbulence and noise.

In Design B, the vent holes 190 of the bias flow vent 126 are located after a gradual transition in geometry. The angle of the gradual transition in the geometry is greater than 30°. As a result, upon inhalation, some separation of flow from the walls of the flow path occurs due to the high flow over the gradual expansion. This separation of flow causes turbulence, which causes noise.

In Design C, the vent holes 190 of the bias flow vent 126 are located before or upstream of a sudden change in the geometry. This reduces the flow rate and, thus, the velocity of the air passing over the sudden expansion. As the head or pressure loss is proportional to the velocity squared, it is apparent that velocity is a significant factor in the amount of head losses, turbulence and, hence, noise that occurs when the fluid flows over a change in section. This shows the influence the position of the bias flow vent 126 has on the noise and turbulence generated. As there is a reduced velocity passing over the expansion, the turbulence and, hence, the noise is significantly lower in Design C than that observed in Design A.

In an alternative arrangement, the principle illustrated in Design C can be applied to Design B by locating the bias flow vent 126 before or at the start of the gradual expansion. Due to the reduced flow over the gradual expansion, results similar to that in Design C are expected.

The location of the vent holes 190 of the bias flow vent 126 relative to sudden expansions has a greater impact on noise than reducing the angle of the walls at the expansion. This is desirable as it can be impractical to optimize the expansion angle in an actual mask because the use of a desirable (small) angle requires an increased transition length in order to achieve the change in cross-sectional area, which may result in an overly large mask. In order to reduce dynamic (inhalation) noise, turbulence created within the air supply flow path can be reduced or minimized by avoiding, reducing or minimizing restrictions where possible or practical within the flow path from the CPAP machine to the patient. In addition or in the alternative, internal diameters (or cross-sectional areas) of swivels, elbows and/or other parts of the flow path can be increased or maximized, or made as close to the internal diameter (or cross sectional area) of the air supply (CPAP) hose as possible or practical. Such an arrangement will keep the flow velocity and, hence, turbulence to a minimum resulting in the creation of less noise. Design of a transition from a smaller section to a larger section, if required or desirable, is preferably located between the bias flow vent and the patient (after the bias flow) such that the volumetric flow rate over the transition is reduced. Design of a transition from a smaller section to a larger section, if required or desirable, preferably is such that the flow head loss over the transition is minimised. The flow path from the smaller section to the larger section preferably is a gradual expansion, with walls angles at less than 30 degrees. If such an arrangement is not practical, then a sudden transition with walls angled at 180° is preferred.

Figure 30:
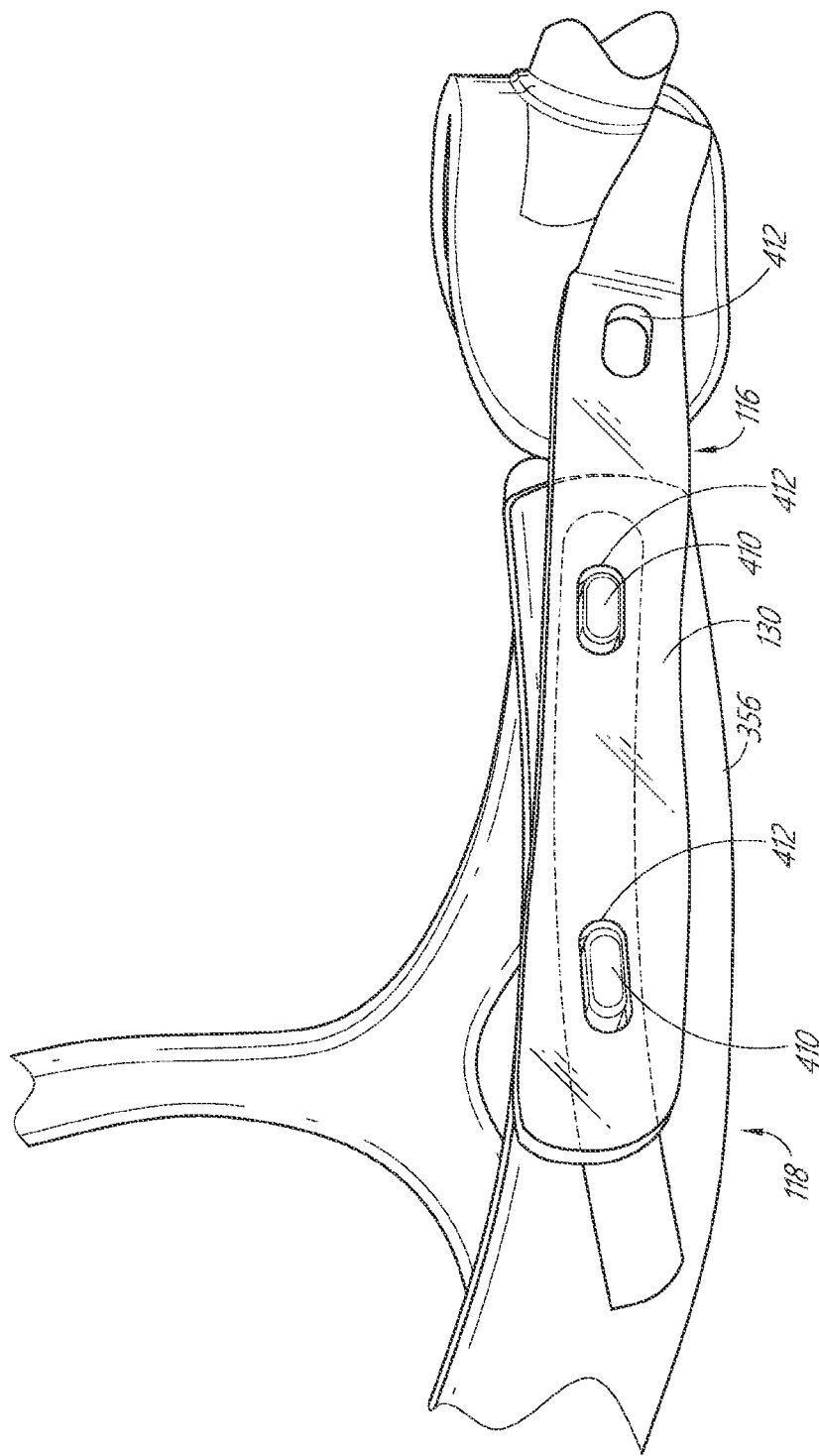
FIG. 30 is a side view of an alternative connection between the mask frame and the headgear in a connected configuration.
Figure 31:
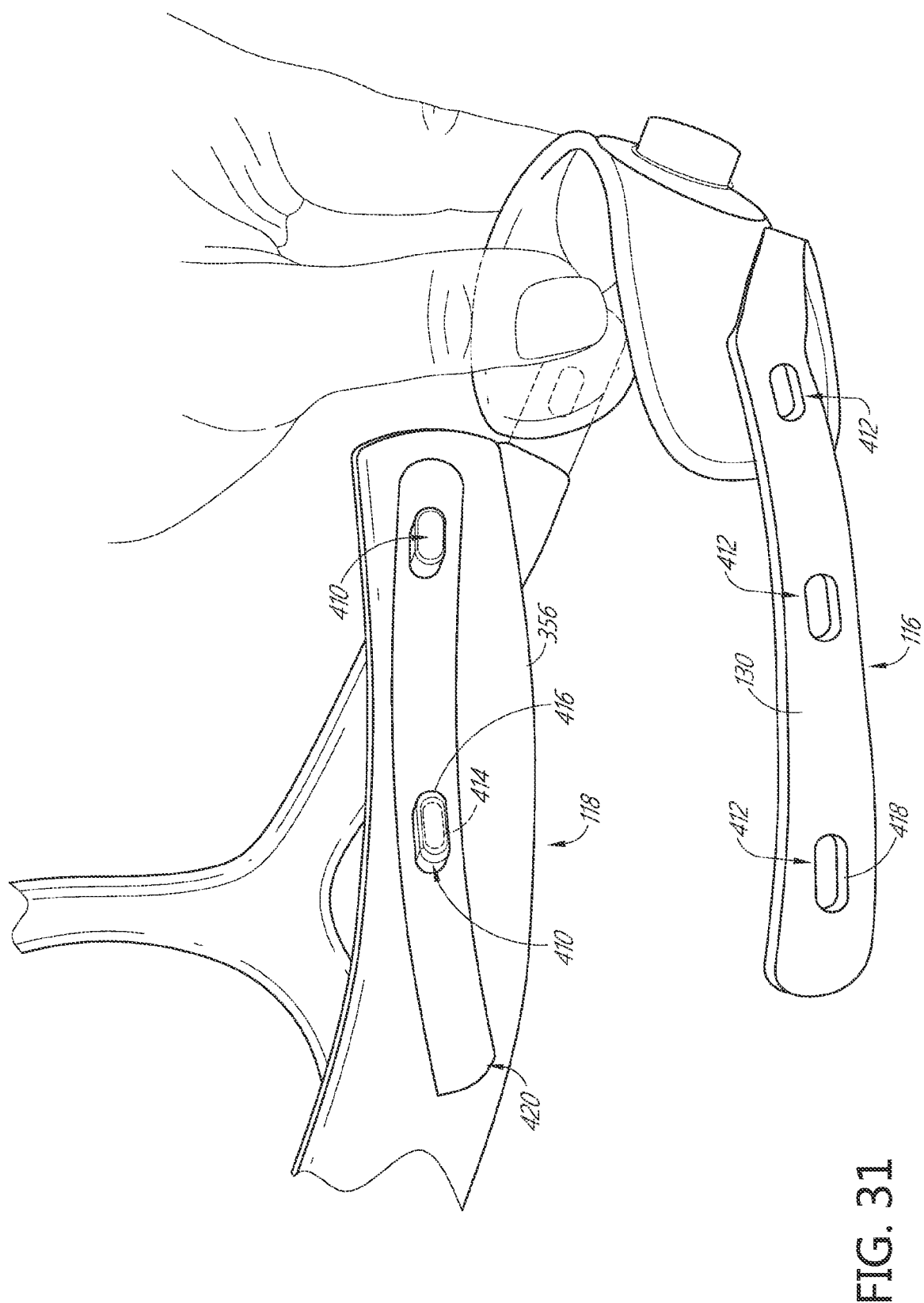
FIG. 31 is a side view of the connection of FIG. 30 in a disconnected configuration.

FIGS. 30 and 31 illustrate an alternative connection arrangement between the headgear 118 and the frame 116 (or other portion of the mask 112). In the illustrated arrangement, the forward extension straps 356 of the headgear 118 overlap the side arms 130 of the frame 116. In the illustrated arrangement, the forward extension straps 356 can be positioned to the inside of the side arms 130; however, in other arrangements, this arrangement can be reversed and the forward extension straps 356 can be positioned to the outside of the side arms 130.

In some configurations, the position of the headgear 118 relative to the frame 116 is adjustable such that the amount of overlap between the forward extension straps 356 can be adjusted. Such adjustment varies an effective circumferential length of the interface 110. In some configurations, the headgear 118 and the frame 116 are adjustable into a selected one of two or more discrete adjustment positions. Any suitable coupling arrangement between the headgear 118 and the frame 116 can be used. In the illustrated arrangement, the headgear 118 comprises one or more posts 410 located on the forward extension straps 356 and the frame 116 comprises one or more corresponding openings 412 located on the side arms 130 and configured to removably receive the posts 410. In the illustrated arrangement, the headgear 118 comprises two posts 410 on each side and each side arm 130 of the frame 116 comprises three openings 412. Thus, the headgear 118 and frame 116 have two different length adjustment positions. However, in other arrangements, other numbers of adjustment positions can be provided.

The posts 410 and openings 412 are similar in structure and function to a baseball-cap style size adjustment arrangement. Each of the posts 410 comprises a stem 414 and a head or cap 416. The illustrated posts 410 are generally T-shaped; however, other shapes can also be used, such as a cylindrical stem 414 and disc-shaped or spherical head 416, for example. The openings 412 are sized, shaped and/or otherwise configured to allow the heads 416 of the posts 410 to pass therethrough and to retain the posts 410 once passed through the openings 412, at least in response to normal or expected forces. However, the posts 410 can be deliberately removed from the openings 412 to permit separation of the headgear 118 and the frame 116. Passing of the posts 410 through the openings 412 can be accomplished by deformation of one or both the posts 410 and openings 412. That is, the heads 416 of the posts 410 can flex or otherwise deform and the openings 412 can stretch or enlarge to facilitate passage of the heads 416 of the posts 410.

In the illustrated arrangement, the openings 412 are elongated and each comprise a recessed flange 418 that is spaced inwardly from the outer surface of the side arms 130 of the frame 116. The recessed flange 418 can extend around a portion or an entirety of a periphery of the openings 412. The recessed flange 418 can be continuous or interrupted. For example, the recessed flange 418 can comprise portions on each end of the elongated opening 412, wherein those portions are separate from one another. The recessed flange 418 can be configured to contact and retain a head 416 of the associated post 410.

The posts 410 can be formed by or connected to the headgear 118 by any suitable arrangement. For example, the posts 410 can be unitarily formed with a base member 420 that is coupled to the headgear 118, such as by sewing, RF welding, adhesives or another suitable coupling arrangement. In some configurations, the posts 410 can be unitarily formed with a plastic core of the headgear 118.

Figure 32:
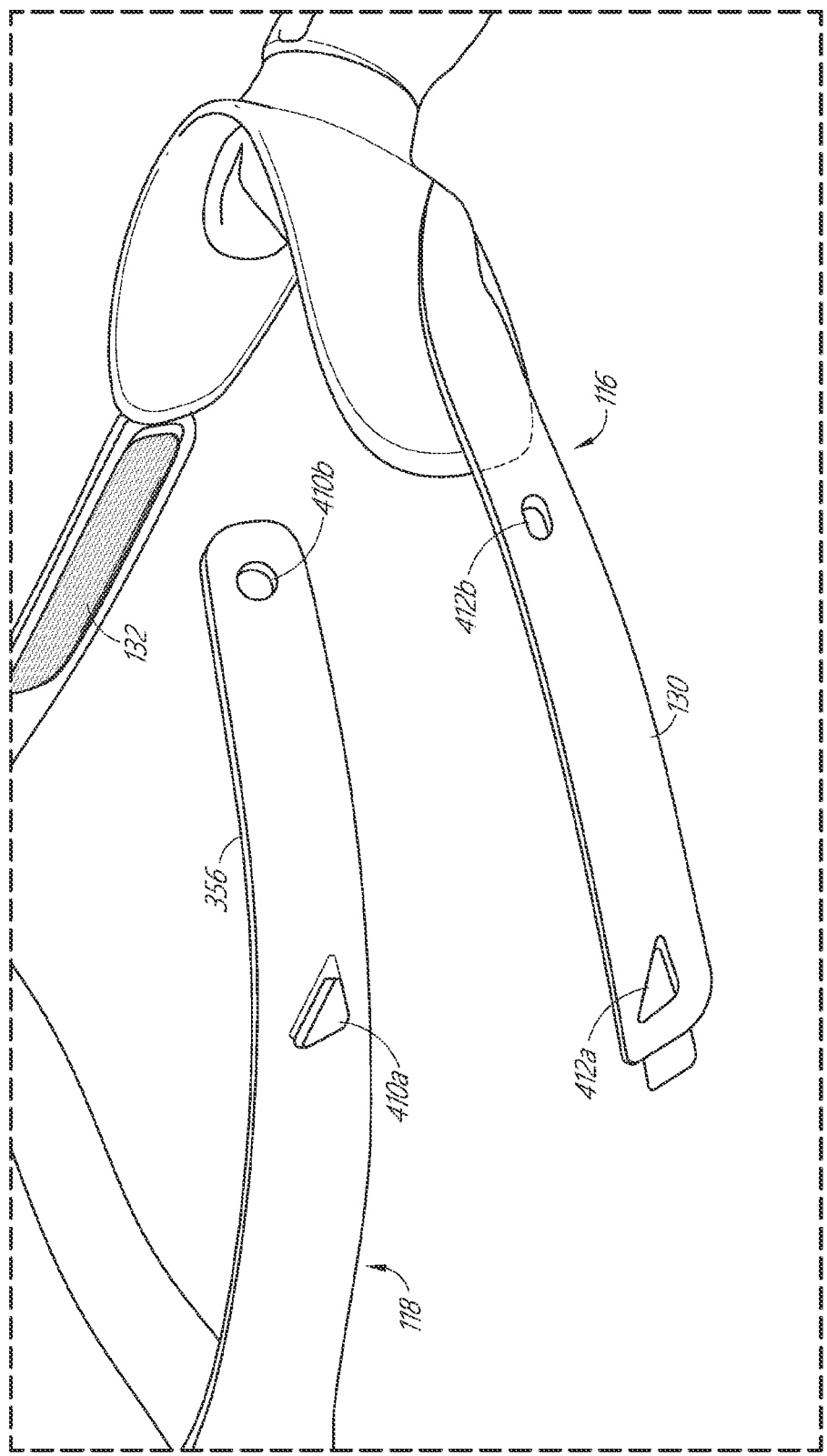
FIG. 32 is a side view of another alternative connection between the mask frame and the headgear in a disconnected configuration.
Figure 33:
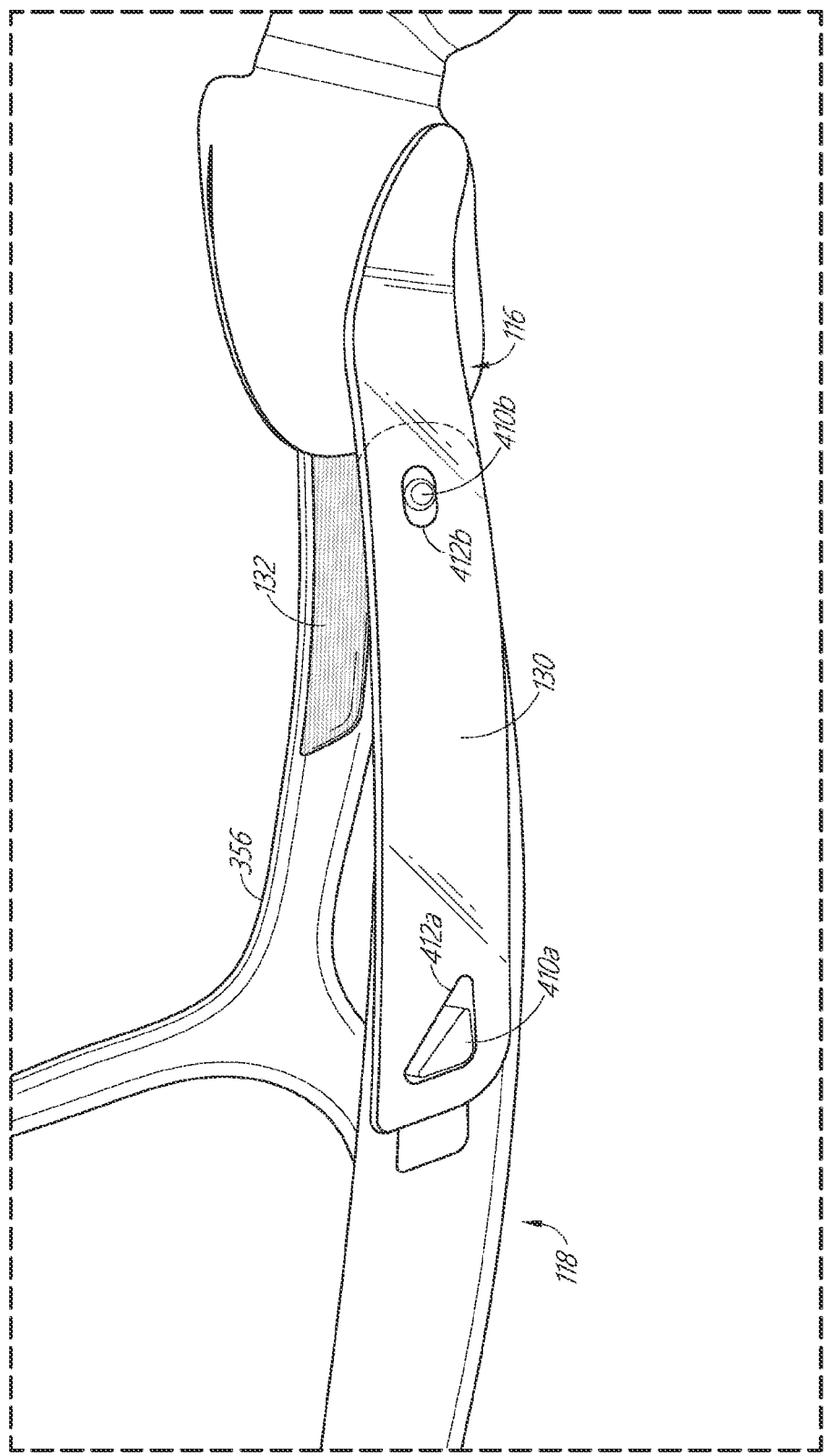
FIG. 33 is a side view of the connection of FIG. 32 in a connected configuration.

FIGS. 32 and 33 illustrate yet another alternative connection arrangement between the headgear 118 and the frame 116 (or other portion of the mask 112). In the illustrated arrangement, the forward extension straps 356 of the headgear 118 overlap the side arms 130 of the frame 116. In the illustrated arrangement, the forward extension straps 356 can be positioned to the inside of the side arms 130; however, in other arrangements, this arrangement can be reversed and the forward extension straps 356 can be positioned to the outside of the side arms 130.

In the illustrated configuration, the position of the headgear 118 relative to the frame 116 is fixed or non-adjustable when the frame 116 is connected to the headgear 118. In alternative arrangements, the position of the headgear 118 relative to the frame 116 can be adjustable such that the effective circumferential length of the interface 110 can be adjusted. Any suitable coupling arrangement between the headgear 118 and the frame 116 can be used. In the illustrated arrangement, the headgear 118 comprises one or more posts 410 located on the forward extension straps 356 and the frame 116 comprises one or more corresponding openings 412 located on the side arms 130 and configured to removably receive the posts 410. In the illustrated arrangement, the headgear 118 comprises two posts 410a, 410b on each side and each side arm 130 of the frame 116 comprises two complementary openings 412a, 412b. In some configurations, the two posts 410a and 410b are different from one another at least in shape. Similarly, the two openings 412a and 412b are different from one another at least in shape. In the illustrated arrangement, the rearward post 410a is generally triangular in shape and the forward post 410b is generally circular in shape. Similarly, the rearward opening 412a is generally triangular in shape and the forward post 412b is generally circular in shape. However, other suitable shapes can also be used. Furthermore, the shapes of different posts and/or openings can be the same or different.

Similar to the arrangement of FIGS. 30 and 31, the posts 410a, 410b and openings 412a, 412b of FIGS. 32 and 33 are similar in structure and function to a baseball-cap style size adjustment arrangement. Each of the posts 410a, 410b comprises a stem (not shown, but similar to stem 414 of FIGS. 30 and 31) and a head or cap (visible portion of the posts 410a, 410b). The openings 412a, 412b are sized, shaped and/or otherwise configured to allow the heads of the posts 410a, 410b to pass therethrough and to retain the posts 410a, 410b once passed through the openings 412a, 412b, at least in response to normal or expected forces. However, the posts 410a, 410b can be deliberately removed from the openings 412a, 412b to permit separation of the headgear 118 and the frame 116. Passing of the posts 410a, 410b through the openings 412a, 412b can be accomplished by deformation of one or both the posts 410a, 410b and openings 412a, 412b. That is, the heads of the posts 410a, 410b can flex or otherwise deform and the openings 412a, 412b can stretch or enlarge to facilitate passage of the heads of the posts 410a, 410b.

In some configurations, the openings 412a, 412b can each comprise a recessed flange that is spaced inwardly from the outer surface of the side arms 130 of the frame 116. The recessed flange can extend around a portion or an entirety of a periphery of the openings 412a, 412b. The recessed flange can be continuous or interrupted. For example, the recessed flange 418 can comprise portions on each end of the elongated opening 412a, 412b, wherein those portions are separate from one another. The recessed flange can be configured to contact and retain the head of the associated post 410a, 410b. In other configurations, the heads of the posts 410a, 410b can abut against an outer surface of the side arms 130 (or other portion of the frame 116) adjacent the openings 412a, 412b instead of a recessed flange.

The posts 410a, 410b can be formed by or connected to the headgear 118 by any suitable arrangement. For example, the posts 410a, 410b can be unitarily formed with a base member that is coupled to the headgear 118, such as by sewing, RF welding, adhesives or another suitable coupling arrangement. In some configurations, the posts 410a, 410b can be unitarily formed with a plastic core of the headgear 118.

Figure 34:
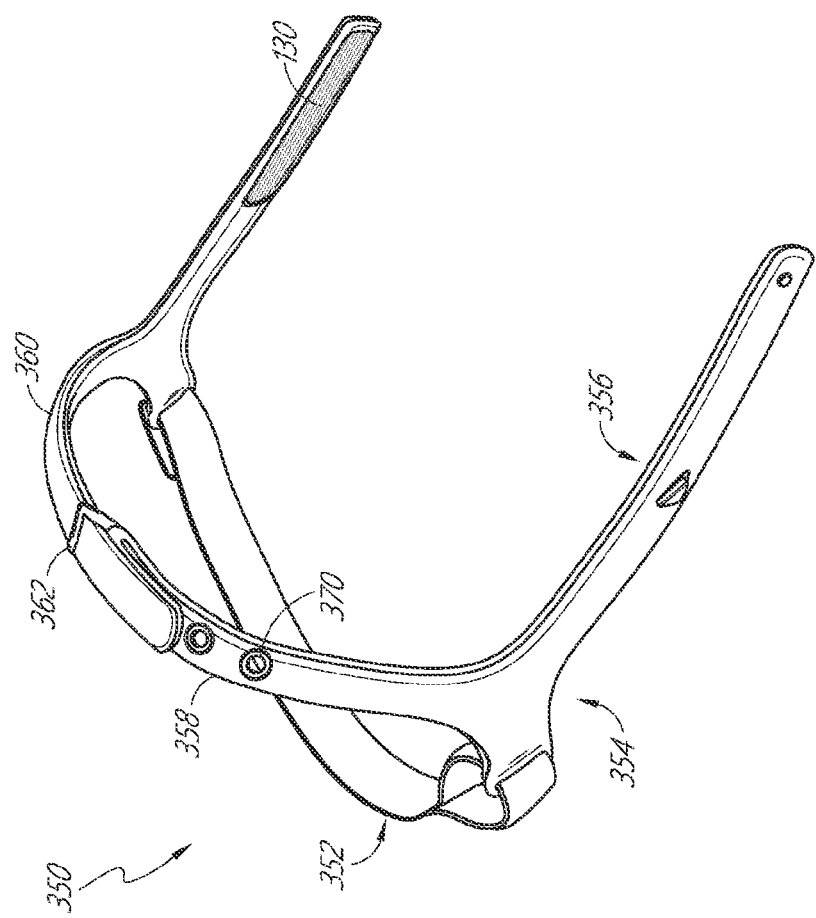
FIG. 34 is a perspective view of the entire headgear of FIGS. 32 and 33.

FIG. 34 illustrates an alternative arrangement of a headgear 118, which can be similar in many respects to the headgear 118 of FIGS. 3 and 23. Accordingly, aspects of the headgear 118 not specifically described below can be assumed to be the same as or similar to the headgear 118 of FIGS. 2 and 23, or can be of any other suitable arrangement. In the arrangement of FIG. 34, the headgear 118 comprises a bifurcated headgear arrangement having a top or upper strap portion 350 and a rear strap portion 352. The upper strap portion 350 is configured to pass over the top of the user's head from one side to the other. In some configurations, the upper strap portion 350 is a crown strap that lies over the parietal bone or at or near a junction between the parietal bone and the frontal bone. In other configurations, the upper strap portion 350 can comprise a forehead strap that lies over the frontal bone of the user.

The rear strap portion 352 passes around the back of the user's head and, in some configurations, lies over the occipital bone of the user. However, in other configurations, the rear strap portion 352 could be positioned higher or lower on the head and/or neck of the user. In the illustrated arrangement, the upper strap portion 350 and the rear strap portion 352 join one another on each side of the headgear 118 at a junction 354. Each one of a pair of forward extension straps 356 extends forwardly from the junction 354 toward and connects to a respective one of the side arms 130 of the frame 116.

In some configurations, at least some portions of the headgear 118 are rigid, semi-rigid, inelastic or substantially inextensible in response to normal or expected forces acting on the headgear 118 and other portion of the headgear 118 are elastic or extensible in response to normal or expected forces. In some configurations, one or more of the upper strap portion 350, junctions 354 and forward extension straps 356 are rigid, semi-rigid, inelastic or substantially inextensible. In the illustrated configuration, each of the upper strap portion 350, junctions 354 and forward extension straps 356 are rigid, semi-rigid, inelastic or substantially inextensible. In the illustrated configuration, the rear strap portion 352 is elastic or extensible. Such an arrangement allows the rear strap portion 352 to stretch to adjust a circumferential length of the headgear 118. The amount of stretch of the rear strap portion 352 can be limited.

In some configurations, the rear strap portion 352 can also be adjustable in length. In some configurations, it is preferable for circumferential length adjustment to occur at the back of the user's head, which is less susceptible to lengthening in response to blow-off forces. The rigid, semi-rigid, inelastic or substantially inextensible nature of the junctions 354 and forward extension straps 356 positioned on the side and forward portions of the user's head assists in maintaining a desired circumferential length of the headgear 118 despite the elastic nature of the rear strap portion 352. In some cases, frictional forces between the portions of the headgear 118 and the side and forward portions of the user's head inhibit movement or lengthening of the headgear 118 in response to blow-off forces. However, in other arrangements, the rear strap portion 352 can be rigid, semi-rigid, inelastic or substantially inextensible and, in such cases, may be adjustable in length.

The upper strap portion 350 can comprise a length adjustment arrangement. In the illustrated arrangement, the upper strap portion 350 comprises a first portion 358 and a second portion 360 that are separate from one another and are capable of being adjustably connected to one another. A free end of the first portion 358 comprises a loop 362 through which the second portion 360 can pass. Thus, the first portion 358 and the second portion 360 can be slid relative to one another to vary an overlapping distance of the portions 358, 360 and, thus, vary a length of the upper strap portion 350. The second portion 360 can be coupled to the first portion 358 to secure the upper strap portion 350 in a desired adjusted length. In the illustrated arrangement, an inner surface of the second portion 360 can comprise at least one protrusion (not shown), which can be similar to any of the posts 410, and the outer surface of the first portion 358 can comprise a plurality of openings 370 configured to removably receive the protrusion to provide a number of discrete adjustment positions. This arrangement can also be reversed.

With the above-described arrangement, for a particular user, the upper strap portion 350 can be adjusted to an appropriate length such that the junctions 354 and/or forward extension straps 356 sit above the user's ears. Once adjusted, the upper strap portion 350 can be maintained in the adjusted position during donning and doffing of the headgear 118 and associated interface 110. In other words, preferably, the first portion 358 and the second portion 360 do not have to be separated from one another for the user to put on or take off the interface 110. Rather, the headgear 118 allows the interface 110 to be donned ('like a cap') by holding the frame 116 at the seal 114 or near the seal 114 (as one would hold a cap at its peak when lifting or flipping it onto the head) and moving the rear strap portion 352 over and to the rear of the user's head. The stretchable or extensible rear strap portion 352 can facilitate the passing of the headgear 118 over the user's head without opening the headgear 118 by separating the portions 358, 360 of the upper strap portion 350 or separating one or both ends of the rear strap portion 352 from a remainder of the headgear 118. The headgear 118 may be removed or doffed in a reverse action.

In the illustrated configuration, the rear strap portion 352 is connected to each of the junctions 354 by an end portion of the rear strap portion 352 that is passed through a loop 364 carried by the junction 354 and doubled back on itself. The end portion of the rear strap portion 352 can be coupled to a relatively more central portion of the rear strap portion 352 by a suitable fastener, such as a book-and-loop fastener, for example. The rear strap portion 352 can be adjustable at one or both ends.

Figure 35:
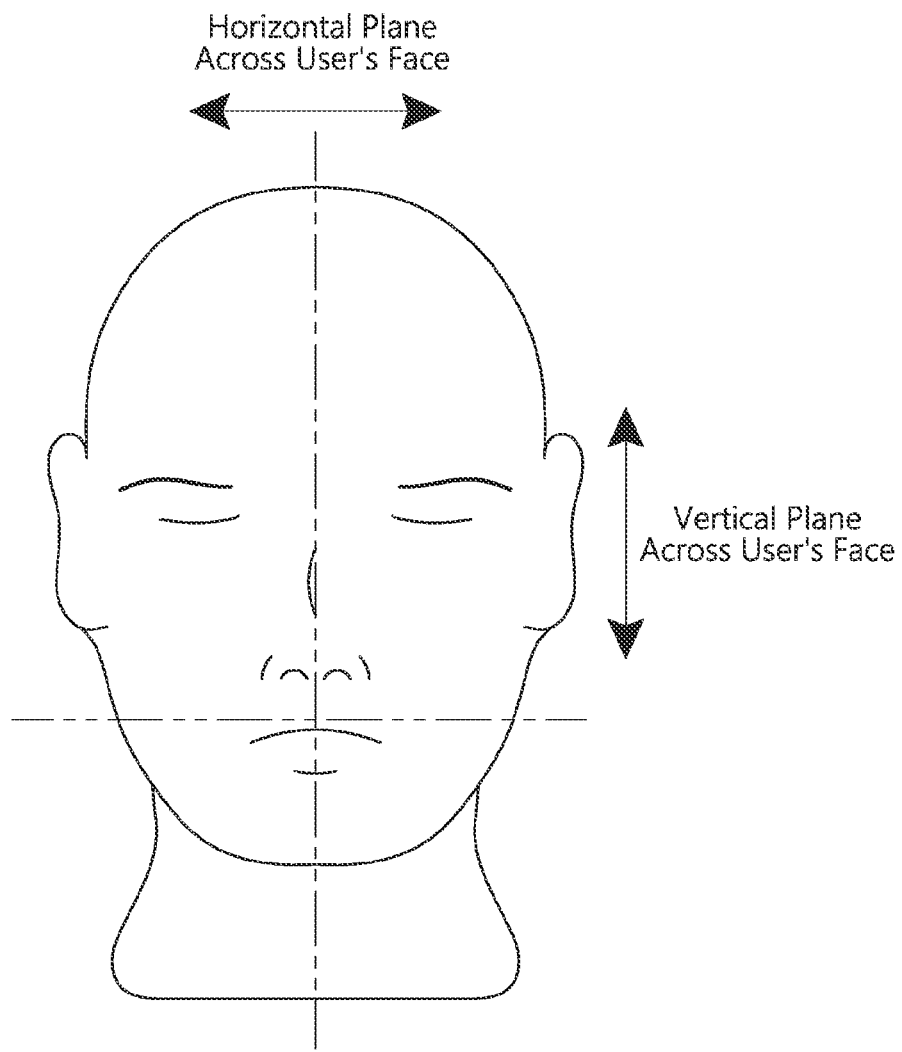
FIG. 35 is an illustration indicating horizontal and vertical planes across a user's face.

FIGS. 36A to 40C illustrate interface arrangements having alternative side arm arrangements which are rotatable or compliant along a horizontal plane (i.e., horizontally across the user's face), substantially rigid along a vertical plane (i.e., vertically across the user's face). The horizontal and vertical planes across a user's face are illustrated in FIG. 35. Providing side arms that are compliant along a horizontal plane allows the side arms to conform to the geometry of the user's face and/or change shape so as to not disturb the position of the seal on the user's face when external horizontal forces are applied to the side arms, for example, when the user sleeps on his/her side (e.g., a pillow contacting and exerting forces on the side arm). Further, providing side arms that are compliant along a horizontal plane allows the seal to be decoupled from the side arms and the frame such that the seal can be correctly positioned on the user's face and will not move due to movement of the side arms. That is, external forces are not transmitted directly to the seal which allows the seal to be maintained in the correct operational position. The following illustrated interface arrangements provide side arms that are substantially rigid across a vertical plane to resist or inhibit rotation or rocking of the seal relative to the side arms, the headgear and the user's face caused by a blow-off force, thereby, ensuring a seal against the user's nose. In addition, the side arm arrangements in FIGS. 36A to 40C also limit or inhibit twist of the side arms which limits or inhibits rotation of the interface arrangements relative to the user's face (i.e., along an axis that is generally parallel to a plane that is perpendicular to both the horizontal and vertical planes, as shown in FIG. 35). More specifically, the side arms may be substantially rigid such that each side arm resists torsional bending along its length (i.e., about an axis defined by a lengthwise direction of the side arm). In some configurations, the side arms may allow a limited range of twist or rotation of the interface arrangements relative to the user's face to provide an amount of compliance which may improve user comfort while ensuring that the interface seals against the user's face.

FIGS. 36A to 36D illustrate an interface 500 having a side arm arrangement having hinges 510 which allow the side arms 130 to rotate along a horizontal plane while remaining substantially rigid along a vertical plane (i.e., resisting bending caused by vertical forces). The side arms 130 may be formed from an injection moulded plastic material and are illustrated as having a rectangular cross-sectional shape. The rectangular cross-sectional shape of the side arms 130 have a height substantially greater than a thickness such that the resistance to bending in a direction parallel to the height direction is substantially greater than the resistance to bending in a direction parallel to the thickness direction. Accordingly, in the illustrated configuration and orientation of the side arms 130 in FIGS. 36A to 36D, the side arms 130 are substantially rigid along a vertical plane relative to the user and semi-rigid along a horizontal plane relative to the user (i.e., due to the rectangular cross-sectional shape). In some configurations, the side arms 130 may be rigid in both vertical and horizontal planes relative to the user. In addition, the geometry of the side arm, the cross-sectional shape and the type of material used to form the side arms may be configured to limit or inhibit twist of the side arms such that rotation of the interface arrangements relative to the user's face is limited or prevented.

Figure 36B:
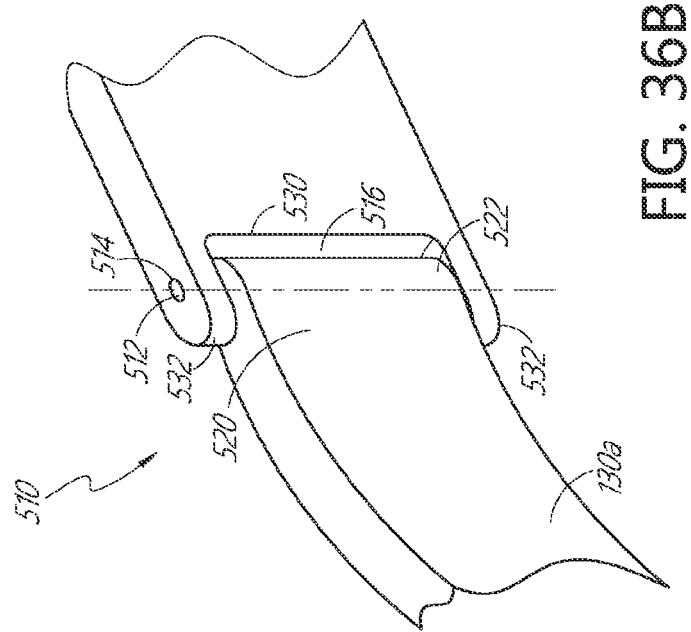
FIG. 36B is a close-up side perspective view of a hinge of the interface of FIG. 36A.
Figure 36A:
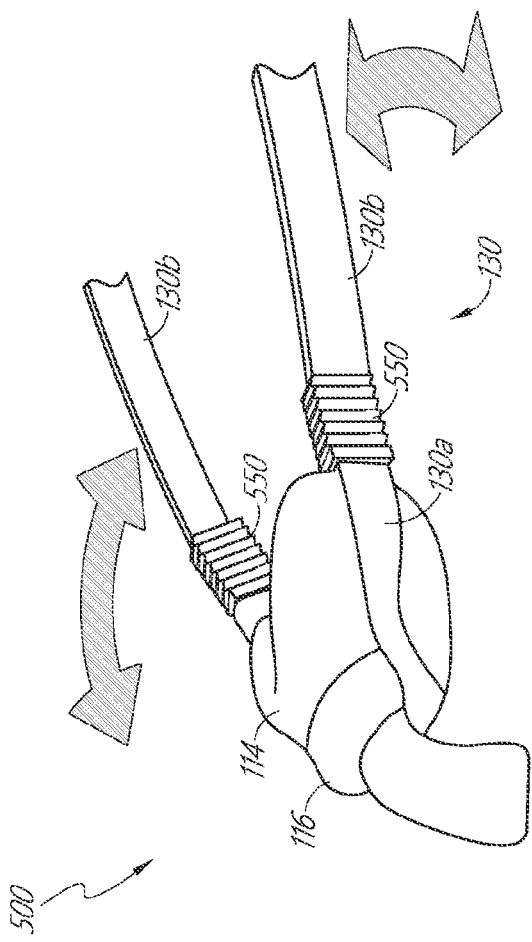
FIG. 36A is a side perspective view of an interface with a side arm arrangement having hinges wrapped in concertina covers.

As shown FIGS. 36A and 36B, the side arms 130 have a two-piece design in which a seal-connecting portion 130A of the side arm 130 is connected to a headgear-connecting portion 130B of the side arm 130 by a hinge 510. The seal-connecting portion 130A is connected to the frame 116 of the seal 114 and the headgear-connecting portion 130B is connected to the headgear (not shown). The seal-connecting portion 130A may be permanently or removably coupled to the frame 116 such that the seal 114 is rigidly attached to the seal-connecting portion 130A. With such an arrangement, the seal 114 is less likely to rotate or rock relative to the seal-connecting portion 130A. The seal-connecting portion 130A on both the left side and the right side of the seal 114 may be formed with the frame 116 as a single unitary component. The seal 114 may be connected to the frame 116 using any of the seal and frame connection arrangements previously disclosed. Similarly, the headgear-connecting portion 130B may be permanently or removably coupled to the headgear using any of the side arm and headgear connection arrangements previously disclosed.

As illustrated in FIG. 36B, the hinge 510 comprises a pin 512 that extends through holes 514 within the ends of the seal-connecting portion 130A and the headgear-connecting portion 130B. The end of the headgear-connecting portion 130B has a female connection portion 530 that includes outer knuckles 532 which define a slot 516 therebetween. The seal-connecting portion 130A has a male connection portion 520 that includes an inner knuckle 522 which is positioned within the slot 516 between the outer knuckles 532. As illustrated in FIG. 36A, the pin 512 and holes 514 are aligned with the height direction of the rectangular cross-section of the side arms 130, which is also substantially aligned with a vertical plane relative to the user. As such, the seal-connecting portion 130A and the headgear-connecting portion 130B rotate relative to each other about the pin 512. In other words, the seal-connecting portion 130A and the headgear-connecting portion 130B are rotatable across the user's face in the horizontal direction.

The hinge 510 and a portion of the side arms 130 are covered by a concertina cover 550. In some configurations, the concertina cover 550 provides resistance to rotation such that the seal-connecting and headgear-connecting portions 130A, 130B maintain their relative rotated positions. The concertina cover 550 may be formed from a semi-rigid plastic and have a deformable accordion-like geometry with ridges and bellows formed along its length. The concertina cover 550 may have a length that covers a portion of both the seal-connecting and headgear-connecting portions 130A, 130B. The concertina cover 550 has an inner cavity 552 through which the side arms 130 extend. The concertina cover 550 may have a size, shape and geometry similar to the side arms 130 such that the concertina cover 550 is tightly wrapped over the hinge 510 and around the side arms 130. Inner ridges 554 of the inner cavity 552 may have a tight fit or interference fit with the side arms 130 so as to contact and be tightly wrapped around the outer surface of the side arms 130. Accordingly, by having the concertina cover 550 wrapped around the side arms 130 and positioned over the hinge 510, the concertina cover 550 resists rotation between the seal-connecting and headgear-connecting portions 130A, 130B until a predetermined threshold amount of force is applied to the side arm 130 which causes the concertina cover 550 to bend and deform to allow the seal-connecting and headgear-connecting portions 130A, 130B to rotate relative to each other.

The hinge 510 is depicted as a butt- or mortise-type hinge having the inner knuckle 512 positioned between the outer knuckles 514. However, it should be known to one of ordinary skill in the art that the hinge 510 may include different knuckle and/or hinge arrangements. Further, it should be known to one of ordinary skill in the art that the illustrated arrangement is not limited to a single hinge and may include multiple hinges and concertina covers. Even further, the illustrated arrangement is not limited to a hinge arrangement having a pin. Other hinge arrangements may be used such as, a protrusion that engages and rotates about a receptacle.

Figure 37A:
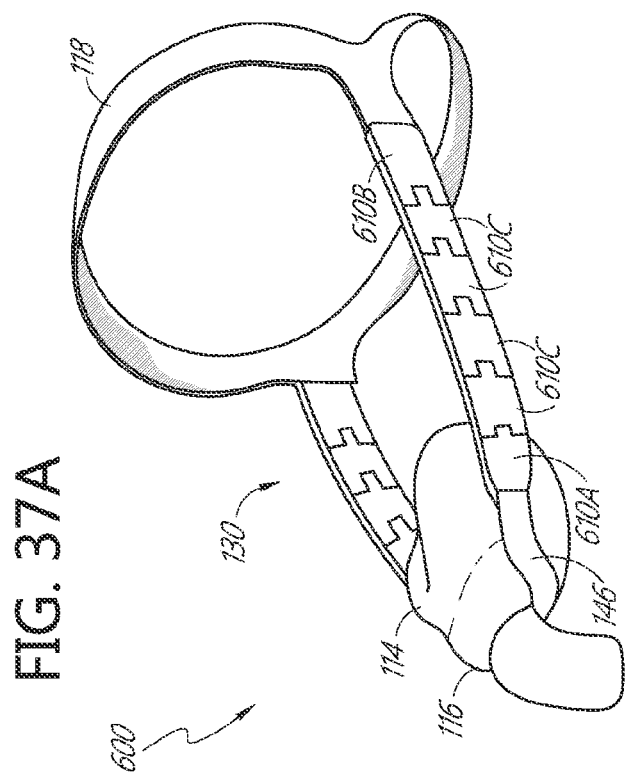
FIG. 37A is perspective view of an interface having a side arm arrangement having modular segments.
Figure 37B:
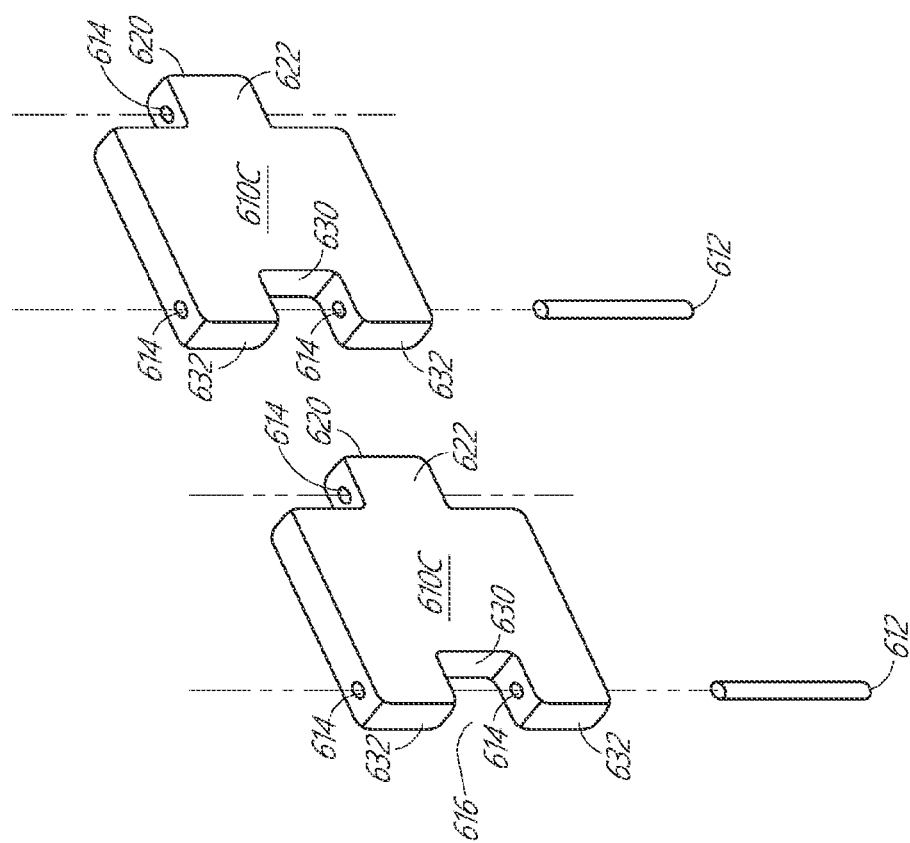
FIG. 37B is a close-up side perspective view of the modular segments of the interface of FIG. 37A.
Figure 37C:
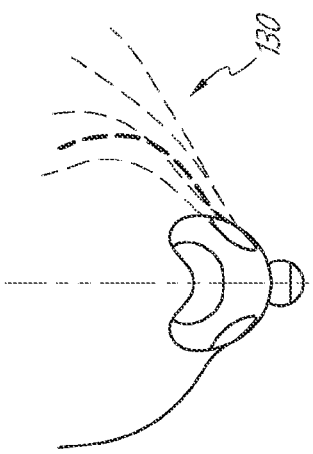
FIG. 37C is a top view of the interface of FIG. 37A illustrating the articulation of the side arm.

FIGS. 37A to 37C illustrate an interface 600 having a side arm arrangement having side arms 130 formed from modular segments 610A, 610B, 610C that are interlocked similar to a wristwatch band. Similar to the side arm arrangement in FIGS. 36A to 36D, a plurality of interlocking modular segments 610A, 610B, 610C allow the side arms 130 to rotate along a horizontal plane while remaining substantially rigid along a vertical plane. More specifically, the segments 610A, 610B, 610C allows the side arm 130 to articulate incrementally and conform to the shape of the user's face when an external horizontal force is applied, as depicted in FIG. 37C. Further, the plurality of segments 610A, 610B, 610C allow localized shape changes to the side arms 130 such that the side arms 130 conform to facial features or landmarks on a user's face. Similar the interface 500, the segments 610A, 610B, 610C of the side arm 130 resist rotation or rocking of the seal 114 caused by vertical forces acting on the seal 114 (e.g., the blow-off force). The segments 610A, 610B, 610C may be formed from an injection moulded plastic material and have a rectangular cross-sectional shape similar to the side arms 130 in FIGS. 36A to 36D.

As illustrated in FIG. 37A, the segment 610A may be permanently or removably coupled on one end to a connector portion or connector 146 of the seal frame 116. The segment 610A has a male connection portion 620 that includes an inner knuckle 622 positioned on an end opposite to the frame 116. Similarly, the segment 610B may be permanently or removably coupled to the headgear 118 on one end and has a female connection portion 630 on an end opposite the headgear 118 which includes outer knuckles 632 that define a slot 616 therebetween. In some configurations, the segments 610A and 610B are connected together by one or a series of segments 610C. Each segment 610C has a male connecting portion 620 on one end and a female connecting portion 630 on the opposite end in a lengthwise direction of the segment 610C. The inner knuckle 622 of the male connecting portion 620 of each segment 610A, 610C is positioned within the slot 616 between the outer knuckles 632 of the female connection portion 630 of segments 610B, 610C. The male and female connecting portions 620, 630 are connected by a pin 612 fitted within through holes 614 extending through the male and female connecting portions 620, 630. As illustrated in FIG. 37B, the pins 612 and holes 614 are aligned with the height direction of the rectangular cross-section of the side arms 130, which is also substantially aligned with a vertical plane relative to the user.

Similar to a wristwatch band, the pins 612 may be removable to allow segments 610C to be added or removed such that the length of the side arms 130 may be adjusted. It should be known to one of ordinary skill in the art that the segments are not limited to male and female connection portions 620, 630 having pins inserted through inner and outer knuckles 622, 632 and may include alternative modular and interlocking connection arrangements.

FIGS. 38A to 38D illustrate an interface 700 having a side arm arrangement having spring-loaded side arms 130 that deform or deflect to provide a temporary shape change when a momentary external horizontal force is applied to the side arms 130. When the momentary external horizontal force is removed, the side arms 130 return back to or toward an undeformed shape. Further, the spring-loaded side arms 130 are extensible to extend and contract which allow the interface 700 to accommodate a wider range of facial geometries as well as to account for blow off force in the mask. The side arms 130 have a spring portion 710 positioned between a seal-connecting portion 130A and a headgear-connecting portion 130B. The seal-connecting portion 130A may be permanently or removably coupled to the frame 116 such that the seal 114 is rigidly attached to the seal-connecting portion 130A such that seal 114 does not rotate or rock relative to the seal-connecting portion 130A. Similarly, the headgear-connecting portion 130B may be permanently or removably coupled to the headgear. The seal-connecting portion 130A, the headgear-connecting portion 130B and the spring portion 710 may be unitarily-formed as integral one-piece side arms. The side arms 130 may be formed from an injection moulded plastic material and are illustrated as having a rectangular cross-sectional shape similar to the side arm arrangements in FIGS. 36A-D and 37A-C.

Figure 38C:
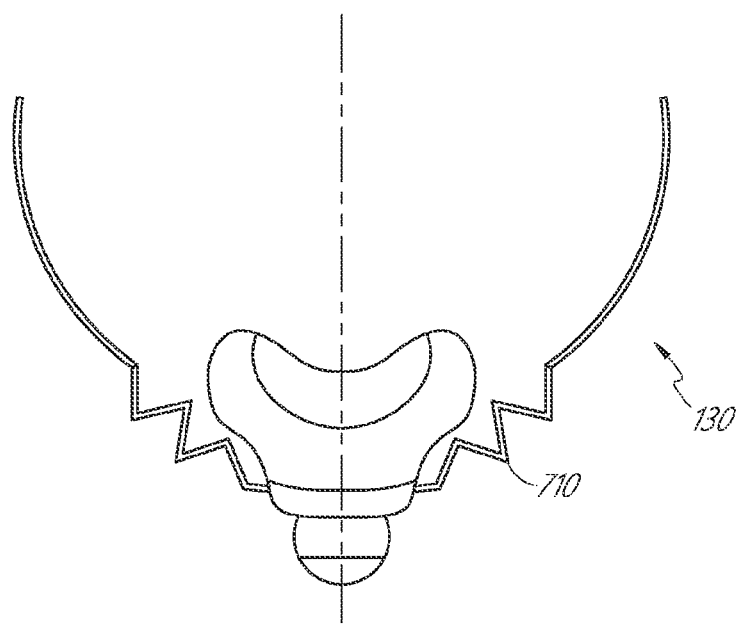
FIG. 38C is a top view of the interface of FIG. 38A illustrating the side arms in an undeformed shape.
Figure 38D:
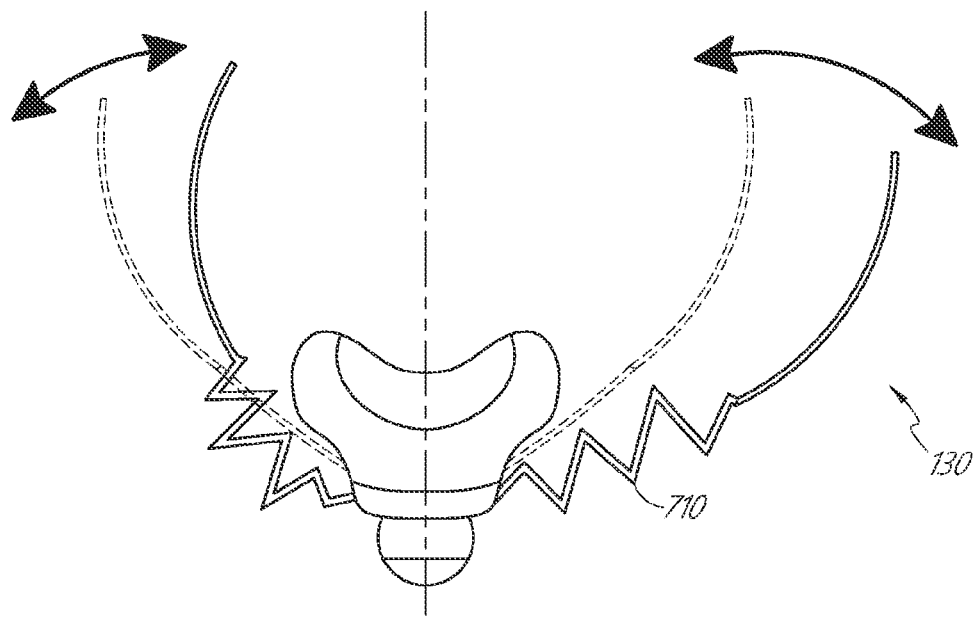
FIG. 38D is a top view of the interface of FIG. 38A illustrating the articulation of the side arms.

As illustrated in FIG. 38B, the spring portion 710 is illustrated as a linear accordion flat spring that is compressible, extendible, and horizontally rotatable. The spring portion 710 is formed as a series of straight segments 712 connected by bends 714. The bends 714 may form an acute angle between the straight segments 712 as to allow the spring portion 710 to bend, shorten in length or extend in length. FIGS. 38C and 38D illustrate the spring portion 710 bending, shortening and lengthening along a horizontal plane to allow the side arms 130 to move relative to the seal 114 when a momentary external horizontal force is applied to the side arms 130. The spring portion 710 absorbs at least a portion of and does not transfer an entirety of the momentary external horizontal force to the seal 114 such that the position of the seal 114 on the user's face remains undisturbed or is disturbed less than with other frame designs. The spring portion 710 may have an undeformed shape (i.e., when no momentary external horizontal force is applied) in which the seal-connecting portion 130A and the headgear-connecting portion 130B are substantially in-line or parallel on average in a length direction. However, the spring portions 710 may be formed so as to have a curved or non-linear undeformed shape on average in a length direction.

Similar to FIGS. 38A to 38D, FIGS. 39A and 39B illustrate an alternative spring-loaded side arm arrangement which also deforms to provide a temporary shape change when a momentary external horizontal force is applied to the side arms 130. However, in contrast to the side arms 130 in FIGS. 38A to 38D, the seal-connecting portion 130A and headgear-connecting portion 130B are connected to elastic segments 810 which provide a spring-loading effect similar to the spring portion 710. The elastic segments 810 may be formed from rubber or Thermoplastic polyurethane (TPU). The elastic segments 810 are positioned between the seal-connecting portion 130A and the headgear-connecting portion 130B and separated by a rigid segment 812. The seal-connecting portion 130A and headgear-connecting portion 130B are also rigid. As such, the elastic segments 810 bend and deform to allow the side arms 130 to be compliant within a horizontal plane to allow the side arms 130 to move relative to the seal 114 when a momentary external horizontal force is applied. That is, the elastic segment 810 absorbs at least a portion of and does not transfer an entirety of the momentary external horizontal force to the seal 114 such that the position of the seal 114 on the user's face remains undisturbed or is disturbed less than with other frame designs. Further, when the momentary external horizontal force is removed, the elastic segments 810 return back to their neutral undeformed shape.

Figure 39B:
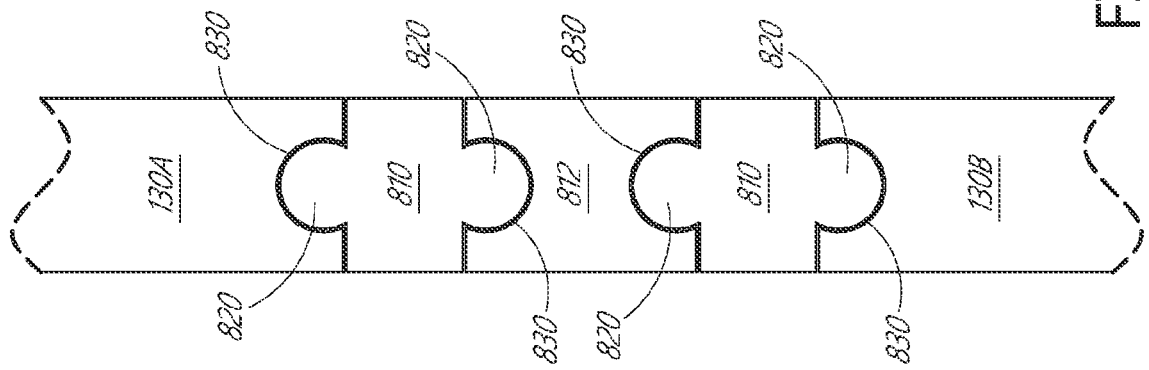
FIG. 39B is a top view of the elastic and rigid segments in FIG. 39A.
Figure 39A:
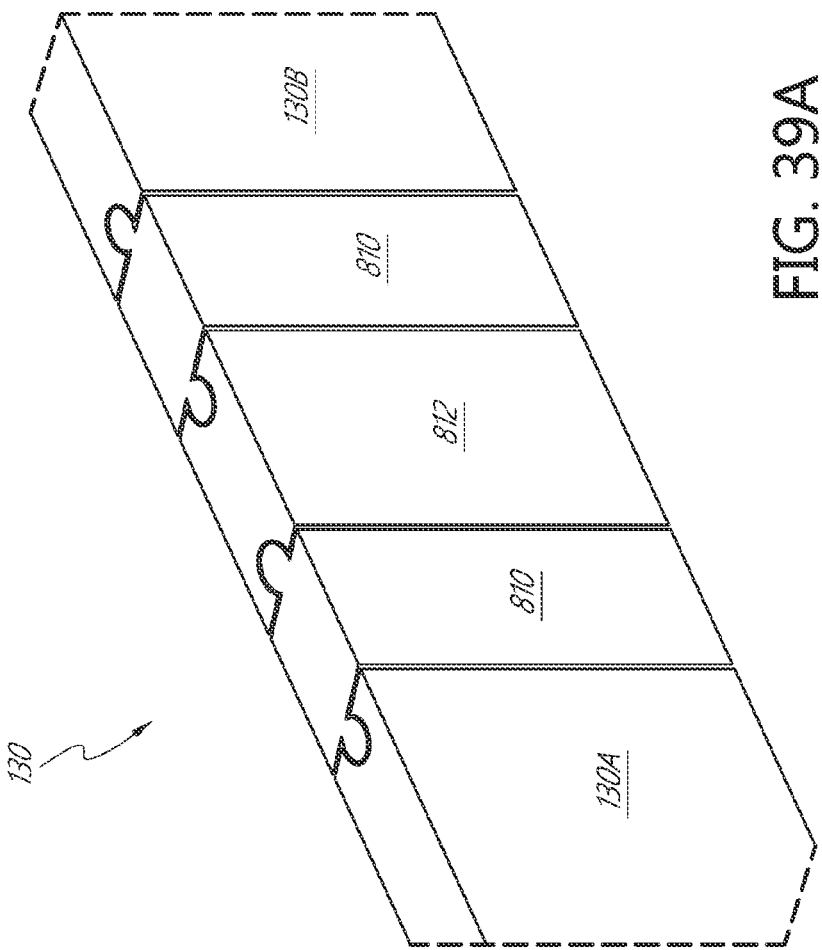
FIG. 39A is a close-up side perspective view of an alternative spring-loaded side arm arrangement having elastic and rigid segments.

As illustrated in FIG. 39B, the elastic segments 810 have male connection portions 820 on each end and the rigid segment(s) 812 have female connection portions 830 on each end. An elastic segment 810 is connected to a rigid segment 812 by positioning the male connection portion 820 into the female connection portion 830. The male connection portion 820 has a corresponding shape and size as the female connection portion 830 such that the male and female connection portions 820, 830 are connected by a tight fit or interference fit. The seal-connecting portion 130A and headgear-connecting portion 130B each have a female connection portion 830 positioned on the end facing the rigid segment 812. The rigid segment 812 has female connection portions 830 positioned on both ends. In some configurations, additional elastic and rigid segment 810, 812 may be added or removed to adjust the length of the side arms 130. Further, the male connection portion 820 is depicted as a cylindrical post and the female connection portion 830 is depicted as a cylindrical slot. It should be understood to one of ordinary skill in the art that the male and female connection portions 820, 830 is not limited to cylindrical posts and slots and may include alternative connection arrangements.

FIGS. 40A to 40E illustrate an interface 900 having a side arm arrangement having flexible side arms 130 that deform to provide a temporary shape change when a momentary external horizontal force is applied to the side arms 130 while remaining substantially rigid along a vertical plane. The side arms 130 have one or both of outer kerfing 910 and inner kerfing 920 along the length of the side arms 130. The outer kerfing 910 is positioned on an outer surface of the side arm 130 (i.e., facing away from the user) and is positioned closest to the seal 114. The inner kerfing 910 is positioned on an inner surface of the side arm 130 (i.e., facing toward the user) and is positioned closest to the headgear 118. The side arms 130 is formed from an injection moulded plastic material and the kerfing 910, 920 may be integrally and unitarily formed into the side arms 130. Alternatively, the kerfing 910, 920 may be formed by cutting, molding or otherwise creating vertical slots into the side arms 130. As shown, the side arms 130 have a rectangular cross-sectional shape similar to the side arm arrangements in FIGS. 36A-D and 37A-D. Cheek pads 950 may be attached to the side arms 130 over the inner kerfing 920 to prevent the inner kerfing 920 from contacting the user's face. The cheek pads 950 may be formed from a soft padding material.

Figure 40E:
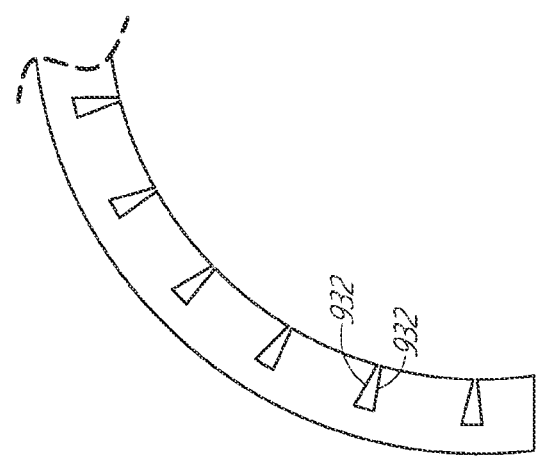
FIG. 40E is a close-up top view of the interface of FIG. 40A illustrating the articulation of the kerfing portions.
Figure 40D:
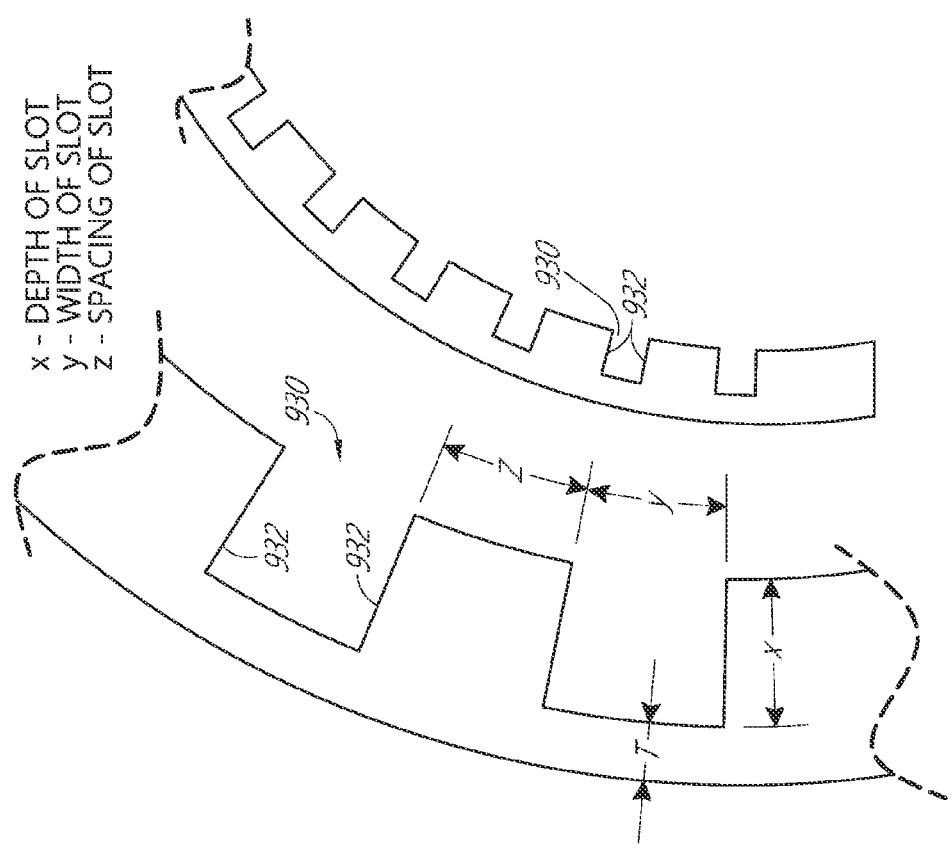
FIG. 40D is a close-up top view of the side arm kerfing on the interface of FIG. 40A.

As illustrated in FIGS. 40D and 40E, the kerfing 910, 920 consists of a series of live hinges or slots 930 recessed into the side arms 130 along a thickness direction of the side arms 130. The slots 930 extend through an entire width of the side arms 130. Accordingly, the thickness of the side arms 130 is thinner at portions having slots 930 than at portions between the slots 930. As a result, the side arm 130 is able to bend and rotate about the slots 930 when a momentary external horizontal force is applied to the side arms 130. Further, the kerfing 910, 920 allows the side arms 130 to return back to or toward an undeformed shape when the momentary external horizontal force is removed. As shown in FIG. 40D, the slots 930 have a depth X, a width Y and are spaced apart by a spacing distance Z. The return force for urging the side arm 130 to return back to or toward its undeformed neutral shape (i.e., also the amount of resistance to bending) is controlled by, at least in part or primarily, the depth X of the slot 930 (i.e., relative to the thickness of the side arm 130). Slots 930 having a greater depth X cause the side arm 130 to have a thinner thickness T at positions where the slots 930 are located. As a result, the thinner thickness T provides less resistance to bending and a smaller return force for returning the side arm 130 to an undeformed shape than slots 930 having a smaller depth X. The maximum amount of bending provided by a slot 930 is controlled by, at least in part or primarily, the width Y of the slot 930. Generally, a slot 930 having a greater width Y allows a greater amount of bending of the side arm 130 about the slot 930. The maximum amount of bending allowed by a slot 930 occurs when the slot 930 narrows in width until the sidewalls 932 of the slot 930 contact each other, as shown in FIG. 40E. Accordingly, providing slots 930 with a greater width Y provides a greater distance between the sidewalls 932. However, the amount of bending may be limited to prevent the side arms 130 from contacting the user's face or detaching from the headgear 118. FIG. 40C illustrates the maximum amount of bending provided by both the inner and outer kerfing 910, 920 relative to an undeformed shape shown in FIG. 40B. The rate of bending of the side arm 130 (i.e., gradual or acute bending) is controlled by, at least in part or primarily, the spacing distance Z and the quantity of slots 930. Closely spaced slots 930 having a narrow spacing distance Z will allow a greater rate of bending of the side arm 130 than widely spaced slots 930 having a wider spacing distance Z. As such, the amount and rate of curvature of the side arms 130 is determined by the depth X, width Y and spacing distance Z of the slots 930. Further, although the side arms 130 are depicted as having slots 930 with identical geometry, in some configurations, the slots 930 may have varying depth X, width Y and spacing distance Z along the length of the side arms 130 such that the side arms 130 have variable amounts and rates of curvature and return force along its length. Further, the slots 930 are not limited to rectangular shapes and may include a variety of shapes such as trapezoidal, curved, or semicircular shapes.

Figure 41B:
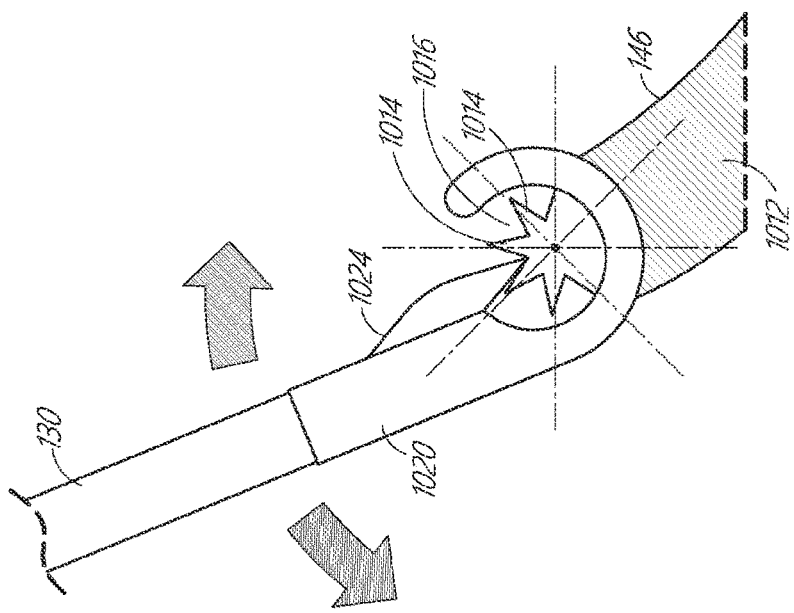
FIG. 41B is a close-up top view of a hook and a post connector in FIG. 41A.
Figure 41C:
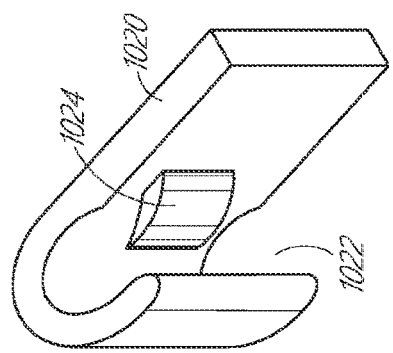
FIG. 41C is a close-up perspective view of the hook connector in FIG. 41A.
Figure 41A:
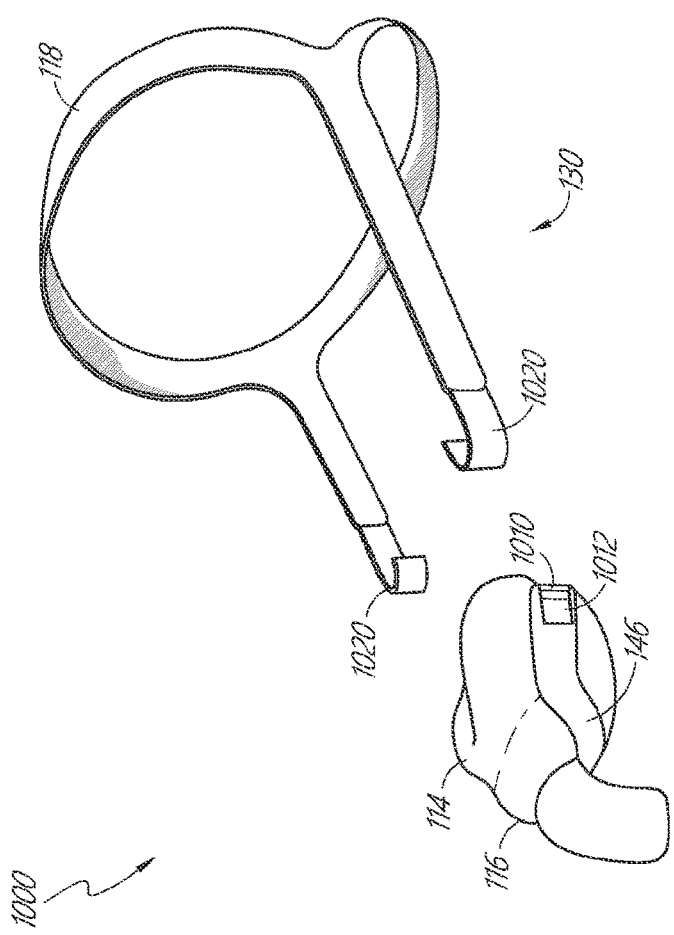
FIG. 41A is perspective view of an interface having a hook and post connector arrangement.

FIGS. 41A to 41C illustrate an interface 1000 having a hook and post connector arrangement that allows rotation and retains a rotation position between the seal 114 and the side arms 130 of the headgear 118. In the illustrated configuration, the headgear 118 is separable from the seal 114. The headgear 118 has a hook-shaped connector 1020 on each end of the side arms 130. The hook-shaped connector 1020 may be unitarily-formed as integral with the side arms 130. The side arms 130 and hook-shaped connector 1020 may be formed from an injection moulded plastic material and are illustrated as having a rectangular cross-sectional shape similar to the side arm arrangements in FIGS. 36A-D and 37A-D. The connector 146 of the frame 116 has a post 1010 on each end. The seal 114 is connected to the headgear 118 by attaching the hook-shaped connector 1020 to the post 1010. The hook-shaped connector 1020 has a cavity 1022 which receives the post 1010 such that the hook-shaped connector 1020 wraps over and around the post 1010. In other words, the post 1010 is positioned within the cavity 1022. In the illustrated configuration, the connector 146 has an opening 1012 adjacent to the post 1012 through which the hook-shaped connector 1020 extends through to wrap around the post 1010.

As illustrated in FIG. 41B, the post 1010 has teeth 1014 extending radially outward from the post 1010. The hook-shaped connector 1020 has a pawl 1024 that extends in a direction towards the cavity 1022. The pawl 1024 engages a valley 1016 between adjacent teeth 1014 such that rotation of the post 1010 within the cavity (i.e., rotation between the post 1010 and the hook-shaped connector 1020) is inhibited or obstructed by the pawl 1024. The pawl 1024 is semi-rigid and deflectable to allow rotation of the hook-shaped connector 1020 around the post 1010 (i.e., including rotation of the side arm 130 within a horizontal plane) when an external horizontal force is applied to the side arms 130. That is, when the yield strength of the pawl 1024 is overcome by an external horizontal force applied to the side arms 130, the pawl 1024 will deform and slide up the tooth 1014 from the valley 1016 as the hook-shaped connector 1020 rotates about the post 1010. The pawl 1024 slides up and over the tooth 1014 and down an adjacent valley 1016. The shape, thickness and geometry of the teeth 1014 and pawl 1024 may be varied to customize the force profile for allowing rotation of the post 1010 relative to the hook-shaped connector 1020. Further, due to the teeth 1014 extending radially outward from the post 1010, the hook-shaped connector 1020 may rotate clockwise or counterclockwise relative to the post 1010. In the illustrated configuration, the teeth 1014 are formed on only the side or portion of the post 1010 that faces the headgear 118 to provide the post 1010 with a smooth corresponding surface in contact with the inner surface of the hook-shaped connector 1020. In alternative configurations, the teeth 1014 may be formed entirely around the post 1010. The hook and post connector arrangement provides rotational resistance between the post 1010 and the hook-shaped connector 1020 such that the user may put on or remove the interface using traditional broken-loop don and doff methods. Further, the hook and post connector arrangement may also allow for alternative type don and doff methods, such as, a swing-fit type don and doff methods where one end of the headgear/frame is connected to the mask, and the other end of the headgear/frame is swung around the head and connected to the mask. The hook and post connector arrangement accommodates a variety of don and doff methods to improve usability of the interface.

Figure 42A:
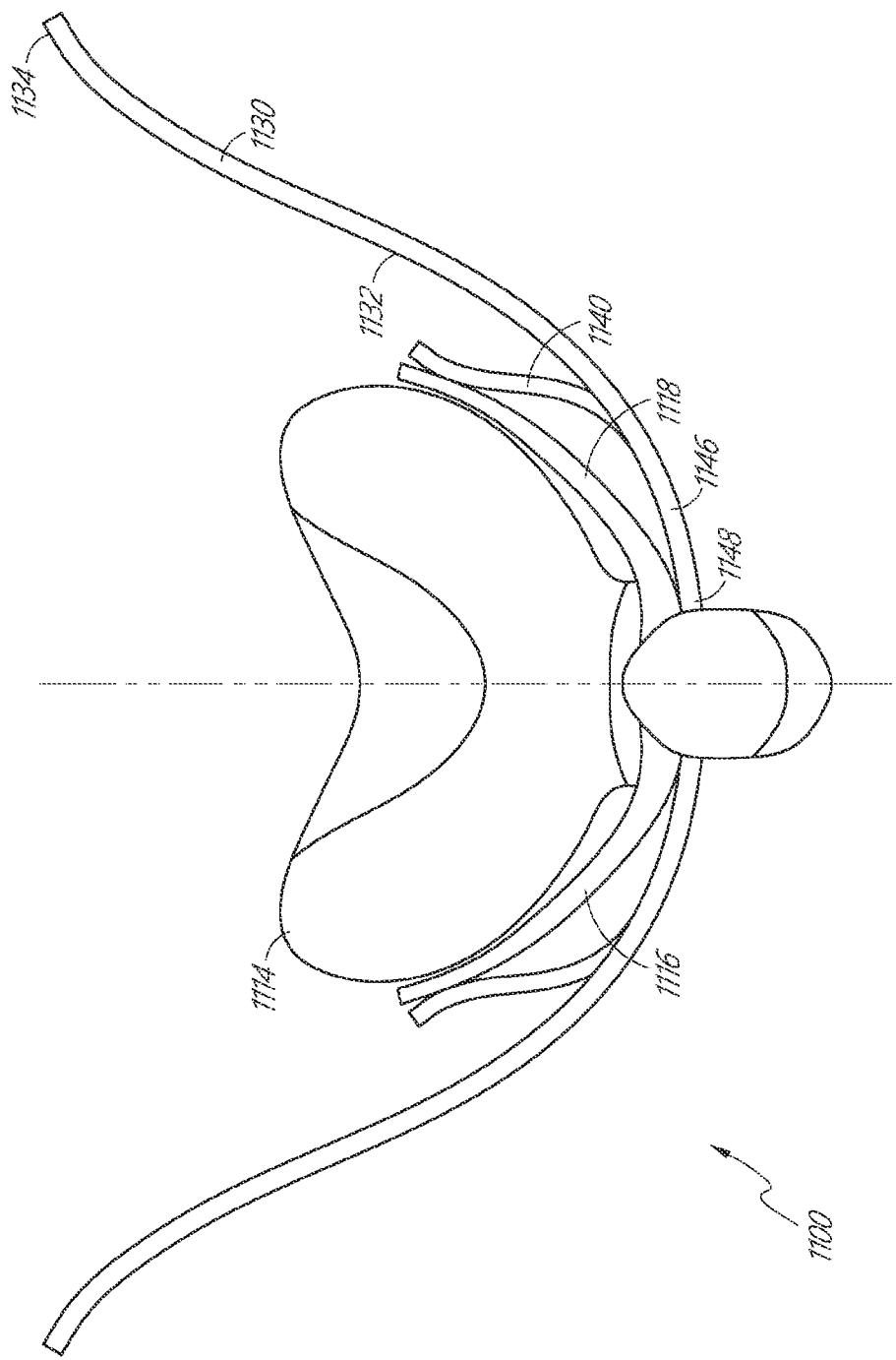
FIG. 42A is top view of an interface having a biased side arm arrangement.
Figure 42C:
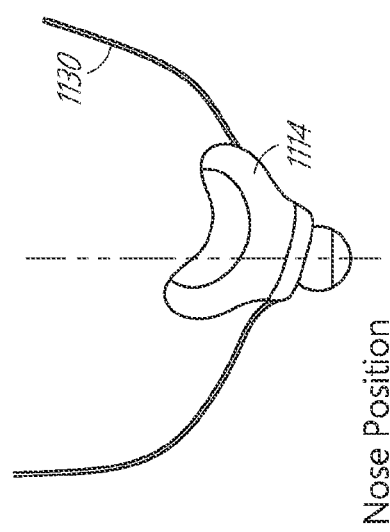
FIG. 42C is top view of the interface of FIG. 42A illustrating the orientation of the side arms when the interface is positioned on a user having a crooked nose.
Figure 42B:
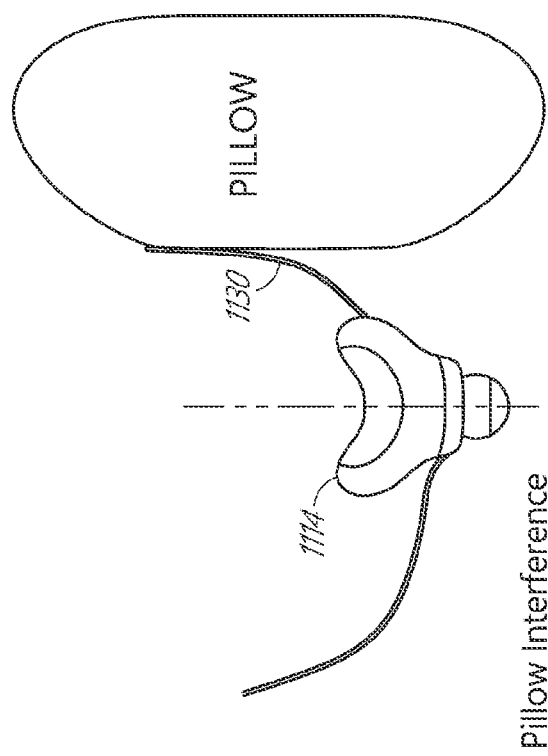
FIG. 42B is top view of the interface of FIG. 42A illustrating the orientation of the side arms when the interface is positioned on a user lying against a pillow.

FIGS. 42A to 42D illustrates an alternative interface assembly or interface 1100 having a seal 1114 that rotates horizontally relative to side arms 1130 (i.e., across the user's face) and is biased to a rotatably centered position between the side arms 1130 by leaf springs 1140. The rotating seal 1114 and the leaf springs 1140 allow the interface 1100 to absorb external horizontal forces to inhibit or prevent dislodging of the seal 1114 from under the user's nose, for example, when the user sleeps on his/her side and the interface 1100 is contacted by a pillow, as shown in FIG. 42B. Further, the rotating seal 1114 allows the interface 1110 to fit users having crooked noses, as shown in FIG. 42C. Similar to the above disclosed interfaces, the interface 1100 prevents or inhibits the seal 1114 from rotating along a vertical plane (i.e., vertically across the user's face). Further, the leaf springs 1140 center the seal 1114 when the external horizontal forces are removed.

Similar to the interface 110 in FIGS. 1 to 11, the interface comprises a seal 1114 attached to a frame assembly or frame 1116. The frame 1116 supports the seal 1114. A connector portion or connector 1146, which includes the side arms 1130, is attached to the frame 1116. The frame 1116 and the connector 1146 may be formed from a relatively rigid, semi-rigid or rigid material, such as polycarbonate, for example. Thus, in at least some configurations, the frame 1116 and the connector 1146 are more rigid than the seal 1114.

Similar to the connector 146 in FIGS. 1 to 11, the connector 1146 is a generally U-shaped member from a top-down view comprising the side arms 1130 and a central portion 1148 that connects the two side arms 1130 to one another. That is, side arms 1130 may be unitarily-formed as integral one-piece with the connector 1146 which provides greater vertical stability (i.e., resisting of movement of the seal vertically across the user's face). In contrast to the connector 146 in FIGS. 1 to 11, the connector 1146 is pivotally attached to the frame 1116 to allow the frame 1116 to rotate relative to the connector 1146 about a vertical axis such that that the frame 1116 rotates along a horizontal plane. The connector 1146 may be pivotally connected to the frame 1116 by a pivoting mechanism such as, for example, a cylindrical post positioned vertically within a socket.

As illustrated, the side arms 1130 extend outwardly (away from each other), rearwardly and upwardly at a shallow angle, past left and right extremities of the seal 1114 and along the left and right cheeks and in particular cheekbones of a user to connect to the headgear (not shown) for holding the seal 1114 on the face of a user. At their outer or free ends, the side arms 1130 include connector portions 1134 for detachably connecting the side arms 1130 to the headgear (not shown). The side arms 1130 are relatively inflexible in a horizontal and vertical plane (when worn).

Figure 42D:
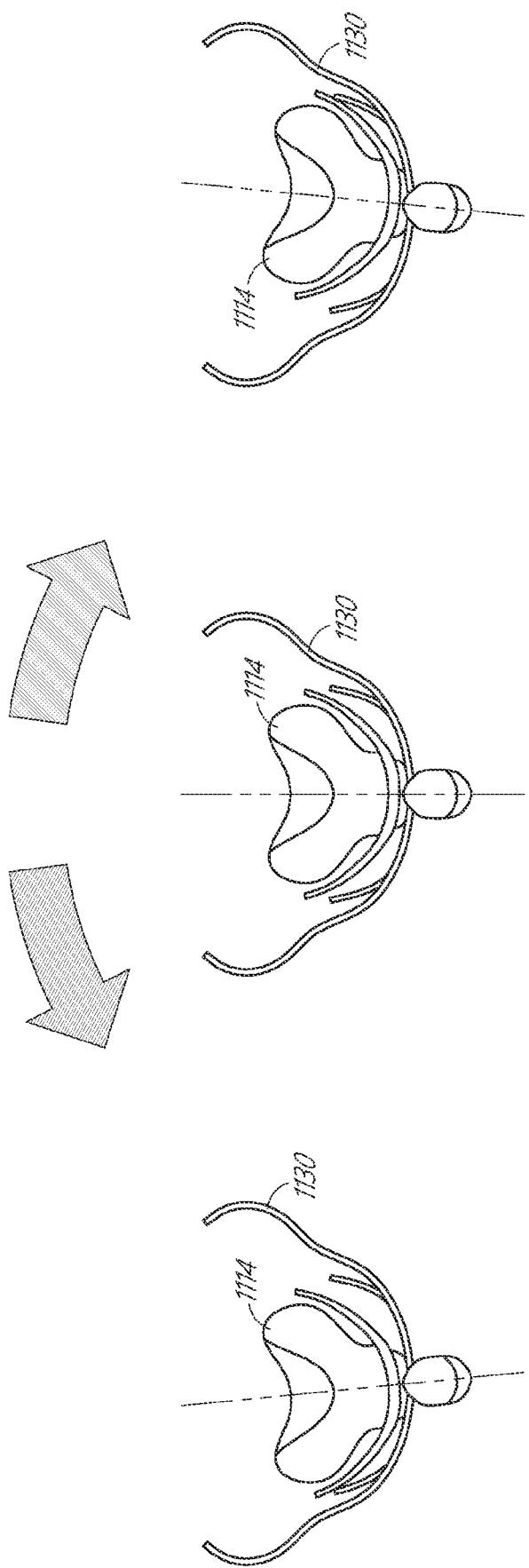
FIG. 42D is top view of the interface of FIG. 42A illustrating the range of the side arm positions.

As shown in FIG. 42A, each side arm 1130 has a leaf spring 1140 attached to and extending from an inner surface 1132 of the side arm 1130. The leaf springs 1140 extend a distance toward the frame 1116 so as to be in slidingly contact with an outer surface 1118 of the frame 1116 when the frame 1116 is centered between the side arms. The leaf springs 1140 are positioned along the inner surface 1132 such that both the leaf springs 1140 contact the outer surface 1118 of the frame 1116 when the frame 1116 is rotatably centered between the side arms 1130. The leaf springs 1140 act as cantilever springs to bias the frame 1116 away from the side arms 1130. In other words, the leaf springs 1140 bias the frame 1116 such that the seal 1114 is rotationally centered relative to the connector 1146. FIG. 42D (center) illustrates a neutral position of the frame 1116 relative to the side arms 1130 that is maintained by the leaf springs 1140. When the frame 1116 is centered between the side arms 1130, the leaf springs 1140 may be in slight contact with the frame 1116 so as to be unloaded. However, in some configurations, both leaf springs 1140 may be preloaded when the frame 1116 is centered between the side arms 1130 or slightly biased toward one of the side arms 1130.

When the seal 1114 and the frame 1116 are rotated from the centered position relative to the connector 1146, the leaf springs 1140 provide a return force to center the seal 1114 and the frame 1116. FIG. 42D (left, right) illustrates the seal 1114 and the frame 1116 rotated from the centered position relative to the connector 1146. The leaf spring 1140, which the frame 1116 rotates towards, deflects and exerts a return force to center the seal 1114 and the frame 1116.

In the illustrated configuration, the leaf springs 1140 only slidingly contact with the frame 1116. That is, the leaf springs 1140 are not fixed to the frame 1116. As such, the leaf spring 1140, which the frame 1116 is rotating away from, is not in contact with the frame 1116 and remains undeflected. In some configurations, the leaf springs 1140 may be attached to both the connector 1146 and the frame 1116 such that both leaf springs 1140 exert a return force on the frame 1116 to center the frame 1116 relative to the connector 1146. The leaf springs 1140 may have a smooth curved shape and sliding surface to reduce sliding friction between the leaf springs 1140 and the frame 1116. Further, the leaf springs 1140 may also be curved or include fillets or buttressing at the connection with the inner surface 1132 of the side arm 1130 to reinforce the connection between the side arm 1130 and the leaf springs 1140. Even further, the shape and geometry of the leaf springs 1140 may be modified to provide various force profiles for biasing the frame 1116. Still further, it should be understood to one of ordinary skill in the art that a variety of spring types may be used to absorb forces and bias the frame 1116. In other words, the interface 1100 is not limited to use of only leaf springs 1140 and may employ alternative biasing arrangements such as coil springs or elastically deforming cushions, airbags, pads, etc.

Figure 43A:
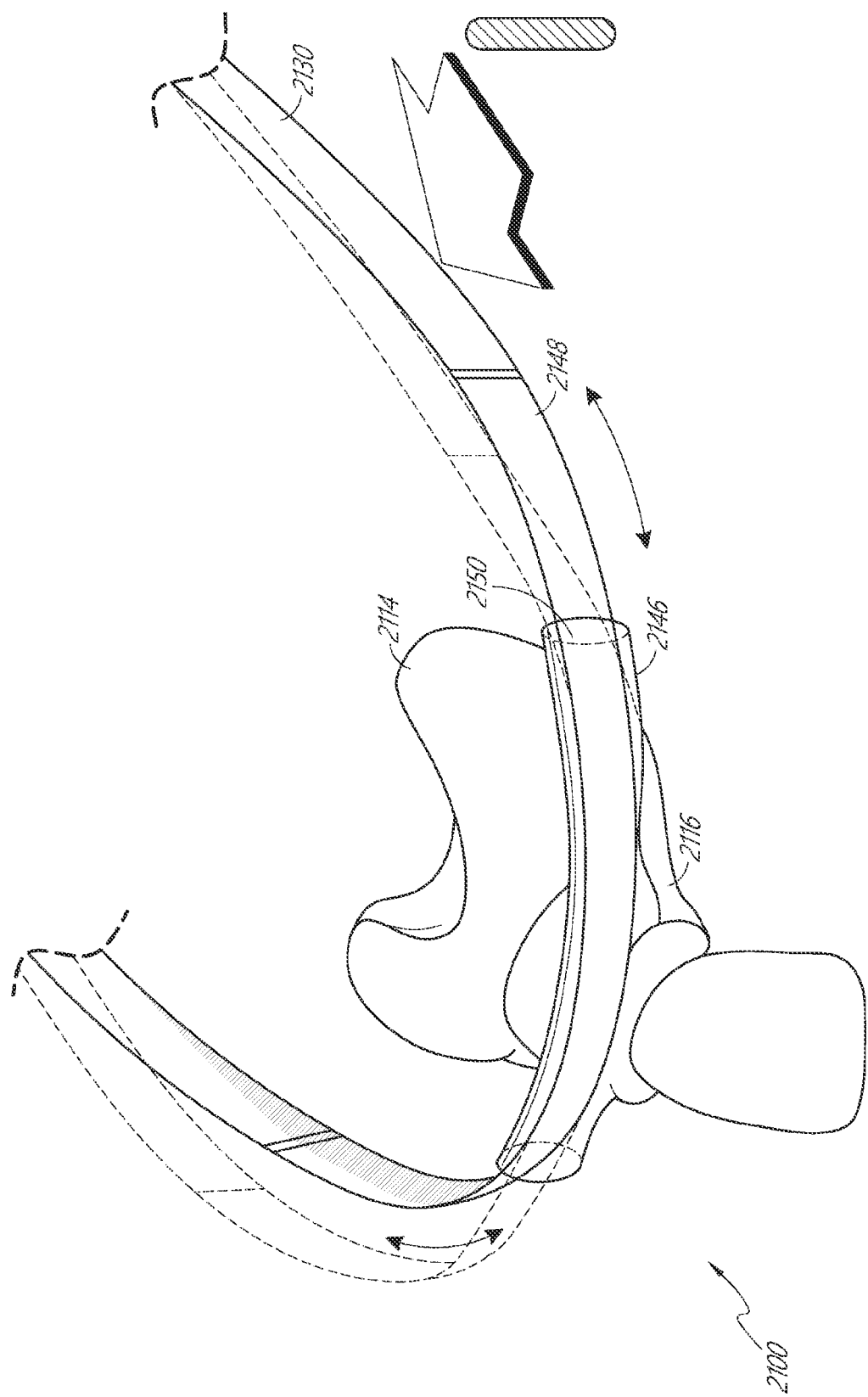
FIG. 43A is perspective view of an interface having a sliding seal arrangement.
Figure 43B:
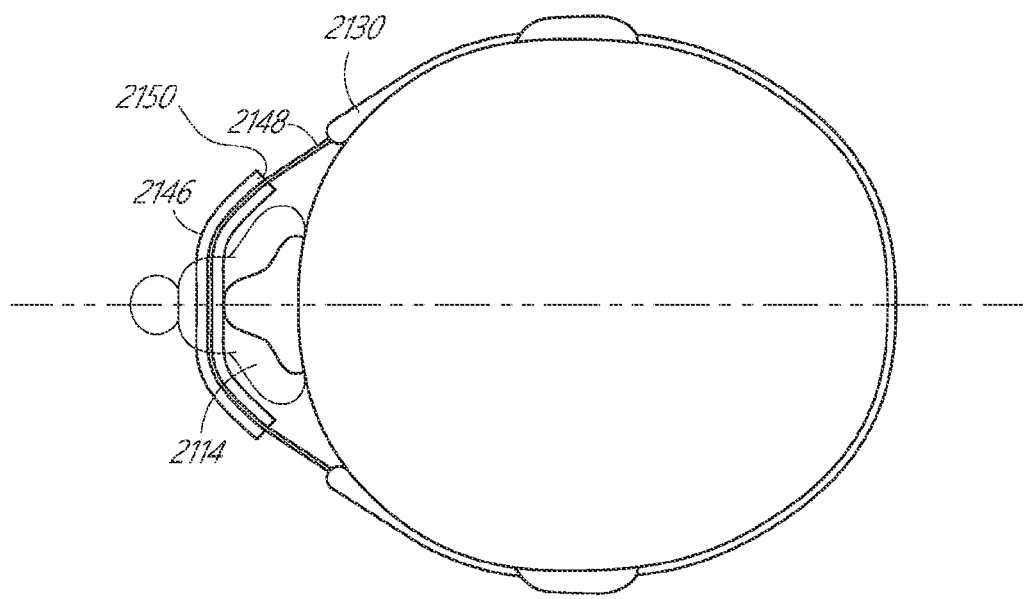
FIG. 43B is top view of the interface of FIG. 43A illustrating the orientation of the seal positioned in an undisturbed position on the user.
Figure 43C:
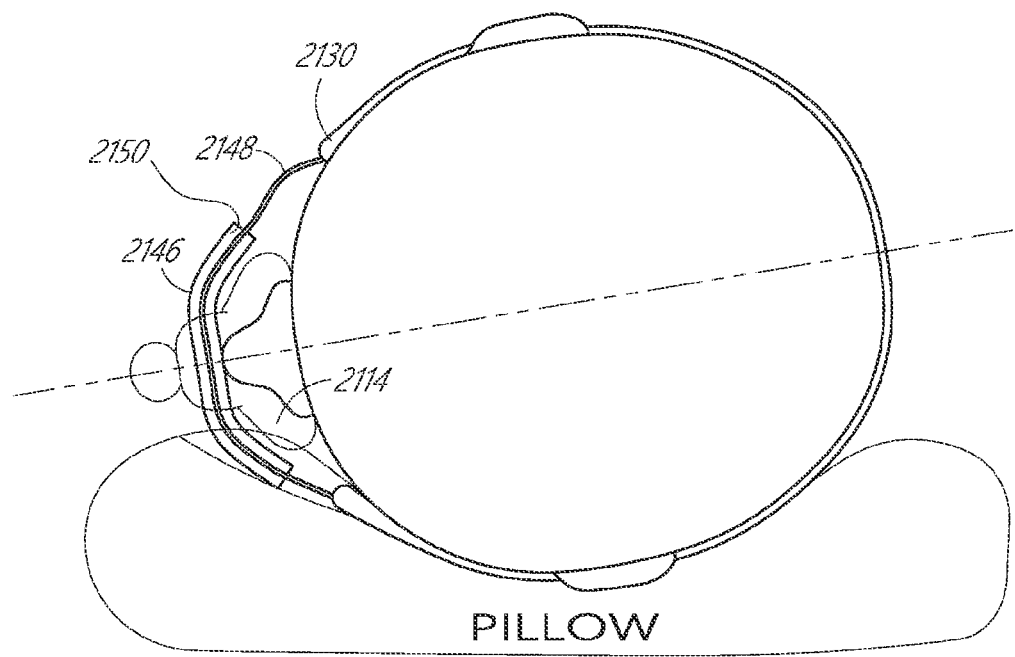
FIG. 43C is top view of the interface of FIG. 43A illustrating the orientation of the seal when the interface is positioned on a user lying against a pillow.

FIGS. 43A to 43C illustrate an alternative interface assembly or interface 2100 having a seal 2114 that slides horizontally or laterally between side arms 2130 (i.e., across the user's face). In contrast to the interface 1100 in FIGS. 42A to 42D, the seal 2114 slides horizontally or laterally across the user's face as opposed to rotating horizontally about an axis across the user's face. Having the seal 2114 slide horizontally between side arms 2130 allows the interface 2100 to absorb and adjust to external horizontal forces to inhibit or prevent dislodging of the seal 2114 from under the user's nose, for example, when the user sleeps on his/her side and the interface 2100 is contacted by a pillow, as illustrated in FIGS. 43B and 43C. Similar to the above disclosed interfaces, the interface 2100 prevents or inhibits the seal 1114 from rotating or flexing along a vertical plane (i.e., vertically across the user's face).

As shown in FIG. 43A, the side arms 2130 are connected to each other by a bridge or central portion 2148. That is, each side arm 2130 is connected to the central portion 2148 at its end, thereby forming a closed-loop with the headgear 2118. The side arms 2130 may be permanently or removably coupled to the headgear 2118. The side arms 2130 may be unitarily-formed as integral one-piece with the connector 2146 from a material such as polycarbonate such that the side arms 2130 and the central portion 2148 are rigid. Similar to the above-disclosed interfaces, the side arms 2130 and the central portion 2148 have an elongate cross-section having a height substantially greater than a thickness such that the side arms 2130 and the central portion 2148 resist vertical rotation (i.e., vertically across the user's face). The side arms 2130 and the central portion 2148 are connected to the frame 2116 by a connector portion or connector 2146. The connector 2146 has a channel 2150 through which the central portion 2148 slides within. The channel 2150 has a corresponding shape and size with the side arms 2130 and the central portion 2148 such that the side arms 2130 and the central portion 2148 are able to slide within and travel through the channel 2150. In operation, when the user sleeps on his/her side and the interface 2100 is contacted by a pillow which exerts a force on the side arms 2130, the side arms 2130 and the central portion 2148 are shifted and pushed through the channel 2150 of the connector 2146 such that the seal 2114 does not move and the position of the seal 2114 on the user's nose is undisturbed.

In some configurations, the range of travel between the side arms 2130 may be limited by varying the cross-sectional size and shape of the central portion 2148 or the side arms 2130 such that enlarged regions of the central portion 2148 or the side arms 2130 are unable to enter the connector 2146. For example, the height and/or the thickness of the end portions of the central portion 2148 may be increased such that the end portions of the central portion 2148 are larger than the height and/or width of the channel 2150. Accordingly, the range of travel of the frame 2116 would be limited to between the ends of the central portion 2148. In alternative configurations, protrusions extending from the surface of the central portion 2148 or the side arms 2130 may also be used to obstruct the central portion 2148 or the side arms 2130 from entering the connector 2146 such that the range of travel is limited.

FIGS. 44A to 49C illustrate nasal seals having features that inhibit or preferably prevent incorrect fitment of the nasal seal and also indicate to the user that the seal is incorrectly fitted. A common fitment mistake is for users to insert their nose into the nasal port of the seal. As a result, the seal will not properly seal around the user's nose and the mask may not function properly. Further, the mask is uncomfortable to wear and the user may be discouraged from continuing to wear the mask. The features of the nasal seals of FIGS. 42A to 49C indicate to the user that the nasal seal is incorrectly fitted, prevent or inhibit the user from incorrectly fitting the nasal seal, or provide the user with guidance on how the nasal seal should be properly fitted.

The illustrated configuration in FIGS. 44A to 44D depicts a nasal seal 114 that provides physical feedback indicating to the user that the seal 114 is incorrectly fitted which discourages the user from continuing to wear the seal 114 incorrectly. The nasal seal 114 is similar to the seal described in FIGS. 1-22 and, therefore, redundant discussion of similar structures will be largely omitted. The seal 114 has an inward or rearward-facing central portion 204 that faces or contacts the user during use of the seal 114. The central portion 204 has a nasal opening or aperture 128 defined by an upper edge 234, a lower edge 236, and side edges 238. As illustrated, the seal 114 has a thickened flange 1210 that causes the flange 1210 to be stiffer than the central portion 204 of the seal 114. The flange 1210 is formed along the upper portion of the aperture 128 to define the upper edge 234 of the aperture 128 and extends toward an interior or dead space 228 of the seal 114 when the seal is not worn by the user and undeformed. The ends of the flange 1210 may extend so as to be connected to the side edges 238, which may also increase the stiffness of the flange 1210. In some configurations, the flange 1210 may extend to include the lower edge 236 to substantially or completely surround the nasal aperture 128. The flange 1210 has a thickness that is greater than along the central portion 204 of the seal 114 such that the flange is stiffer and more rigid than the central portion 204. The flange 1210 is illustrated as having a constant thickness but the thickness of the flange 1210 may vary along its length. The flange 1210 may be integrally formed with the seal 114. The flange 1210 extends downward into the dead space 228 of the seal 114. In some configurations, the nasal aperture 128 has an edge that includes a thickened bead at the upper edge 234 of the nasal aperture 128.

Figure 44B:
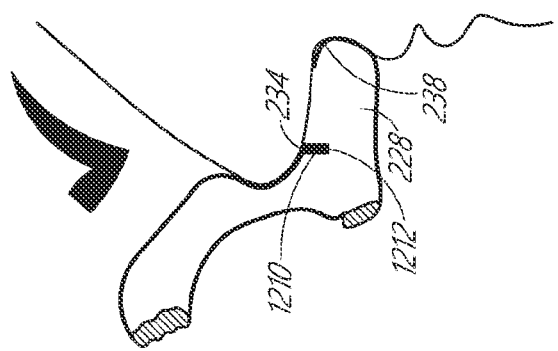
FIG. 44B is side cross-sectional view of the seal in FIG. 44A positioned correctly on a user.

FIG. 44B illustrates the seal 114 correctly fitted to the user. As shown, the user's nose is positioned on top of the seal 114 with the aperture 128 being positioned below the nares of the user and the tip of the user's nose being in contact with the central portion 204 of the seal. Further, the flange 1210 is not in contact with the user when the seal 114 is correctly fitted to the user. More specifically, the flange 1210 is positioned below the nares of the user's nose and extends in a direction away from the nose and into the seal 114.

Figure 44C:
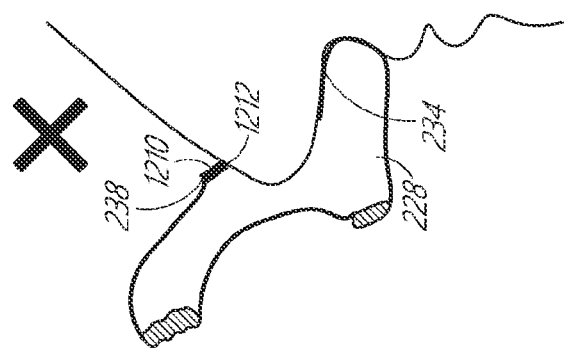
FIG. 44C is side cross-sectional view of the seal in FIG. 44A positioned incorrectly on a user.
Figure 44A:
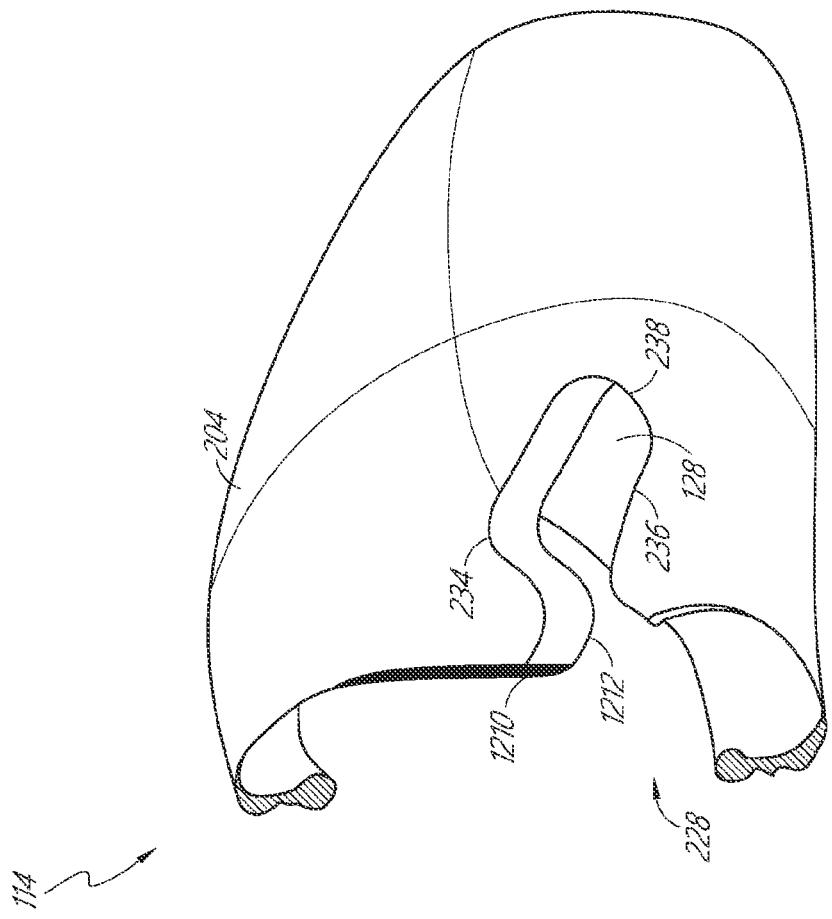
FIG. 44A is perspective cross-sectional view of a seal having a flange to indicate to the user that the seal is incorrectly fitted.

FIG. 44C illustrates the seal 114 incorrectly fitted to the user. In contrast to FIG. 42B, the user's nose extends through the aperture 128 and is positioned inside the seal 114. With the user's nose extending through the aperture 128, the flange 1210 is positioned on top of the user's nose with a bottom edge 1212 of the flange 1210 pressing into the tip, supra tip or bridge of the user's nose. The stiffness of the flange 1210 (i.e., due to its thickness and having ends attached to the side edges 238 of the aperture 128) prevents the flange 1210 from deforming or collapsing inward into the seal 114 due to the force of the user's nose pushing into the aperture 128. As such, the user will physically feel the flange 1210 pressing against his/her nose and causing discomfort which will provide haptic feedback or indication to the user that the seal is not correctly fitted. In other words, the discomfort caused by the flange 1210 that is felt by the user will be perceived as an indication that seal 114 is incorrectly fitted. The flange 1210 also prevents blow out because the flange 1210 is formed from thicker silicone and, therefore, stiffer and better able to hold its shape under blow out force applications.

Figure 44E:
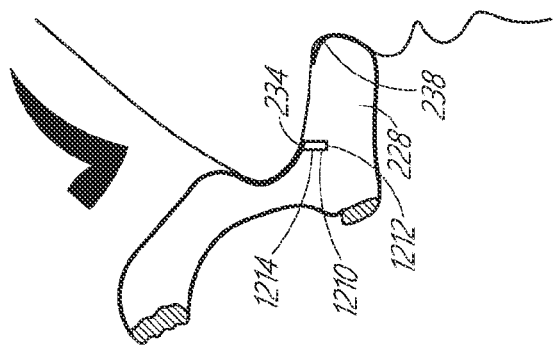
FIG. 44E is side cross-sectional view of the seal in FIG. 44D positioned correctly on a user.
Figure 44F:
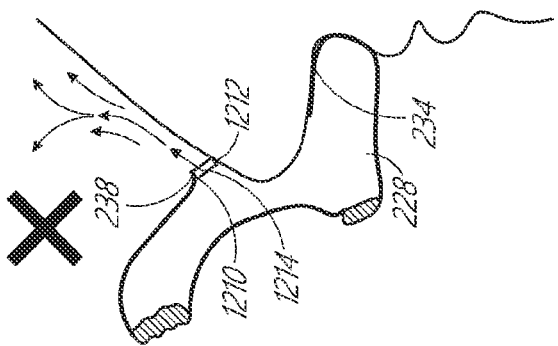
FIG. 44F is side cross-sectional view of the seal in FIG. 44D positioned incorrectly on a user.
Figure 44D:
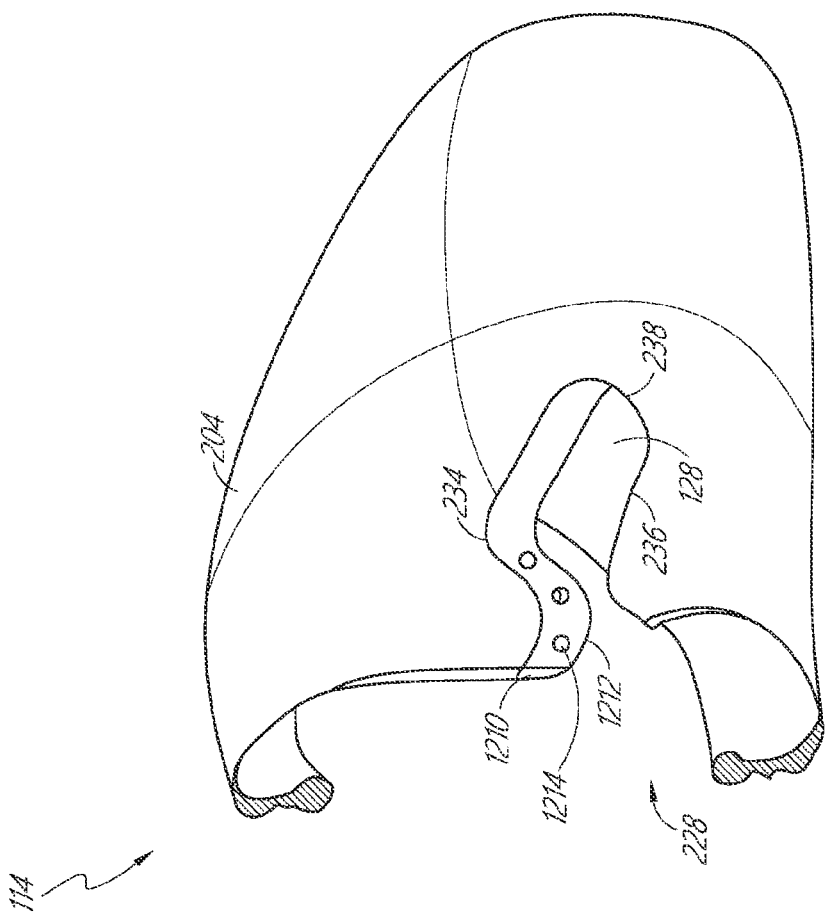
FIG. 44D is perspective cross-sectional view of a seal having a flange with blow holes to indicate to the user that the seal is incorrectly fitted.

FIGS. 44D to 44F illustrate an alternative flange configuration comprising a flange 1210 with through-holes or blow holes 1214 that extend through the flange 1210. The blow holes 1214 provide a pathway for pressurized air to escape from inside the seal to outside of the seal. Similar to FIG. 44B, when the seal 114 is correctly fitted to the user as shown in FIG. 44E, the user's nose is positioned on top of the seal 114 and the flange 1210 is not in contact with the user when the seal 114 is correctly fitted to the user. As shown in FIG. 44F, when the seal 114 is incorrectly fitted to the user, the user's nose is pressed into the aperture 128 such that the bottom edge 1212 of the flange 1210 presses into the user's nose, similar to FIG. 44C. In operation, when the seal 114 is filled with air under positive pressure, the pressurized air will flow through the blow holes 1214. The flange 1210 and blow holes 1214 are positioned slightly above the user's nose such that the user will feel the flow of pressurized air blowing through the blow holes 1214. Therefore, in addition to the discomfort of the flange 1210 pressing into the user's nose, the user will also feel the flow of air escaping the seal just above his/her nose. In some configurations, the blow holes may be positioned and/or angled such that the blow holes 1214 direct the flow of pressurized air towards the user's eyes. Further, the size and shape of the blow holes 1214 may be tuned to provide an audible sound such that the user is provided with an audible indicator when the seal 114 is incorrectly fitted. It should be understood to one of ordinary skill in the art that the blow holes 1214 are not limited to circular cross-sections and may be formed in various cross-sectional shapes and sizes.

Figure 44G:
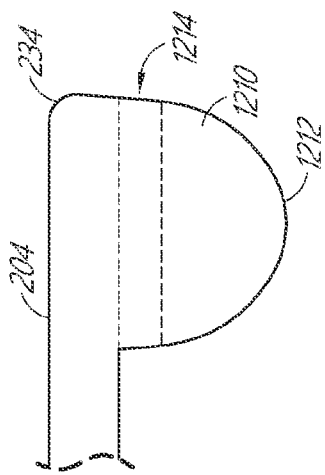
FIG. 44G is side cross-sectional view of an alternative flange arrangement having a rounded flange.
Figure 44H:
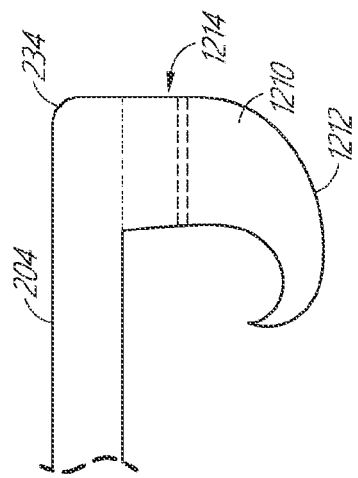
FIG. 44H is side cross-sectional view of an alternative flange arrangement having a rounded edge.

FIGS. 44G and 44H illustrate alternative flange configurations comprising a flange 1210 having a rounded bottom edge 1212. Similar to the flanges in FIGS. 44A-F, when the user's nose is pressed into the aperture 128, the flange 1210 presses into the user's nose and the blow holes 1214 direct pressurized air towards the user's eyes to indicate to the user that the seal 114 is not correctly fitted. However, in contrast to the flange 1210 in FIGS. 44A-F, the rounded bottom edge 1212 may provide a wider and rounded surface that contacts the user's nose without leaving a mark or indentation on the user's nose. FIG. 44G illustrates a flange 1210 having a semi-circular cross-section. FIG. 44H illustrates a flange 1210 having an upper portion that is rectangular in cross-section while the bottom portion of the flange is rounded. The rectangular upper portion allows the flange 1210 to flex such that the amount of force pressing down on the user's nose by the flange 1210 is distributed over a greater area so as to not leave a mark or indentation on the user's nose.

Figure 44I:
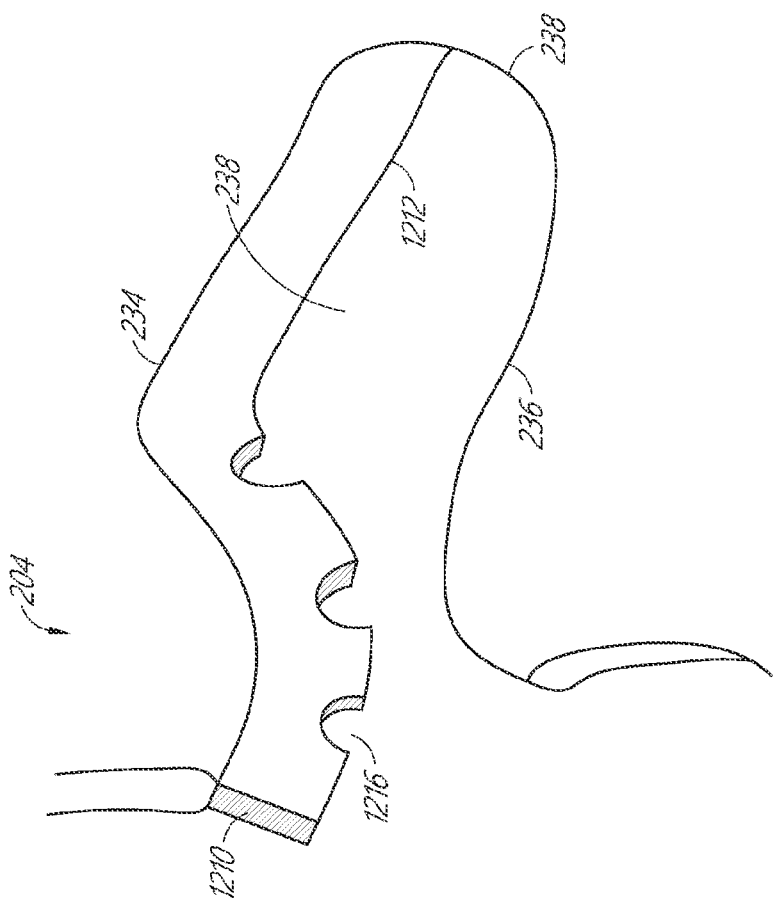
FIG. 44I is perspective cross-sectional view of a seal having a flange with recesses to indicate to the user that the seal is incorrectly fitted.

FIG. 44I illustrates an alternative flange configuration comprising a flange 1210 with recesses 1216 instead of the blow holes 1214 in FIGS. 44D-F. The recesses 1216 may be formed into the bottom edge 1212 of the flange 1210 such that pressurized air will flow through the recesses 1216 when the user's nose is pressed into the aperture 128 and the seal 114 is pressurized (i.e., the seal 114 is incorrectly fitted to the user).

Figure 45C:
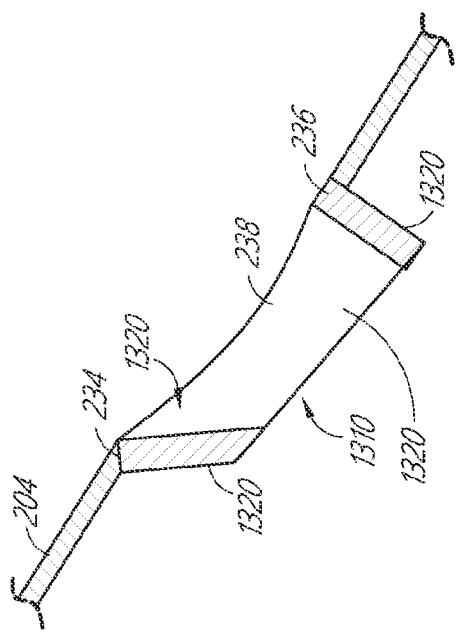
FIG. 45C is side cross-sectional view of the seal of FIG. 45B.
Figure 45D:
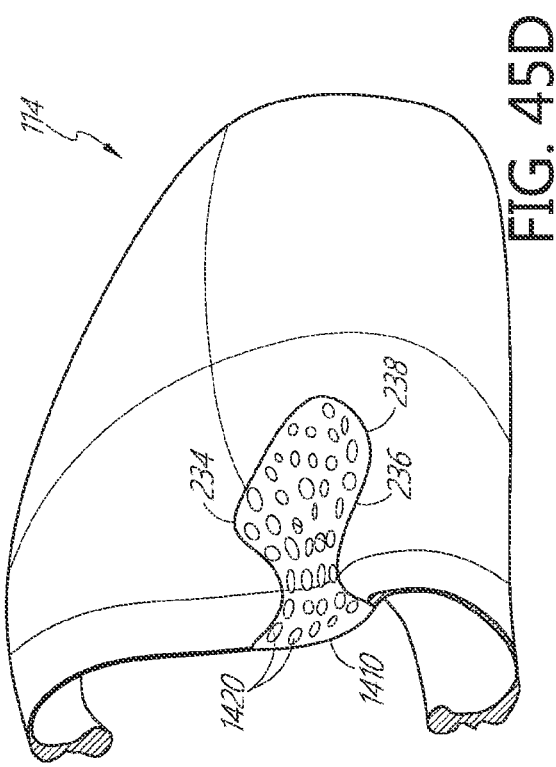
FIG. 45D is perspective cross-sectional view of an alternative seal arrangement having an aperture cover to physically prevent or inhibit the user from incorrectly wearing the seal.
Figure 45A:
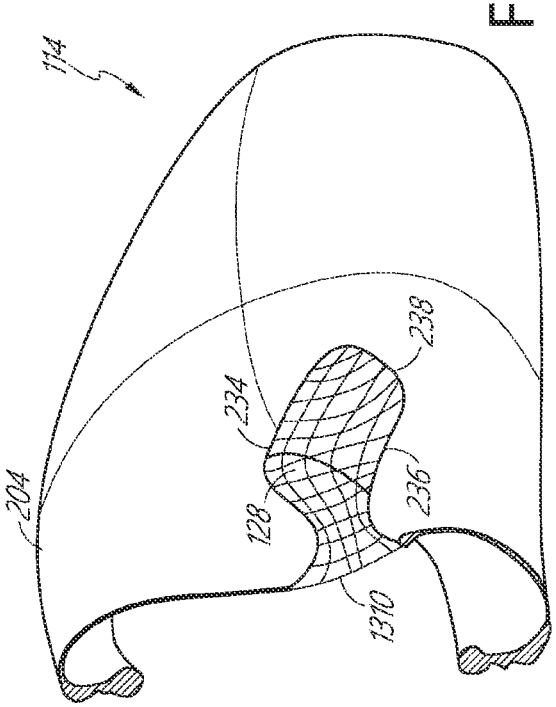
FIG. 45A is perspective cross-sectional view of a seal arrangement having a woven mesh over an aperture to physically prevent or inhibit the user from incorrectly wearing the seal.
Figure 45B:
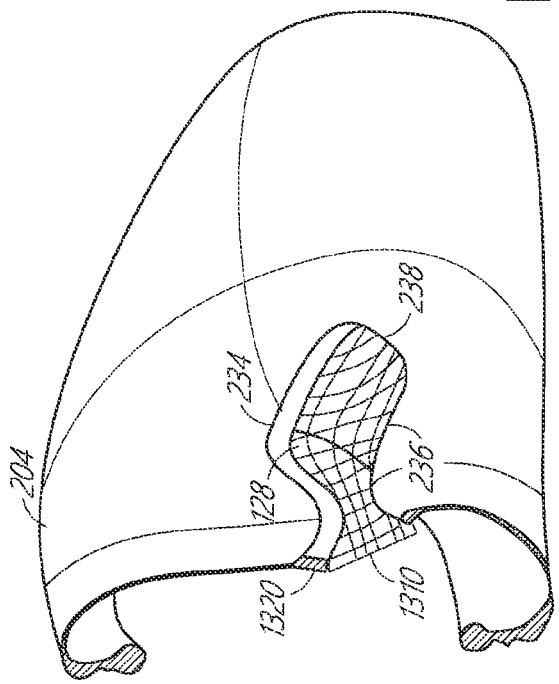
FIG. 45B is perspective cross-sectional view of an alternative seal arrangement having a woven mesh offset from an aperture to prevent direct skin contact with the woven mesh.

The illustrated configuration in FIGS. 45A to 45C depicts a nasal seal 114 that physically prevents or inhibits the user from incorrectly wearing the seal 114. More specifically, the seal 114 obstructs the user's nose from being inserted into the seal 114 through the aperture 128. The nasal seal 114 is similar to the seal described in FIGS. 1-22 and FIGS. 44A-I and, therefore, redundant discussion of similar structures will be largely omitted. As illustrated in FIG. 45A, the seal 114 has a woven mesh 1310 over-moulded or otherwise affixed onto the upper, lower, and side edges 234, 236, 238 of the aperture 128 such that the woven mesh 1310 is flush with the sealing surface of the seal 114. The woven mesh 1310 spans across and covers the aperture 128. The woven mesh 1310 allows air to flow through the aperture 128 while preventing or inhibiting the user from inserting his/her nose into the aperture 128. The woven mesh 1310 may be over-moulded from a silicone material onto the aperture 128. The woven mesh 1310 may be elastic to conform to the shape of the aperture 128 and deform with the seal 114. However, the woven mesh 1310 may be taut so as to prevent or inhibit the user's nose from entering the seal 114. Further, the strand width and the coarseness or fineness of the woven mesh 1310 may be varied so as to provide strength to withstand the force of the user's nose pushing into the aperture 128 while also minimizing any pressure drop caused by the woven mesh 1310 restricting the flow of air through the aperture 128.

FIGS. 45B and 45C illustrate an alternative configuration of a nasal seal 114 having a woven mesh 1310 offset inward into the seal 114 by an offset flange 1320. As shown in FIG. 45C, the outer edges of the offset flange 1320 may be attached to the upper, lower, and side edges 234, 236, 238 of the aperture 128 and the offset flange 1320 extends inward in a direction towards the interior of the seal 114. The inner edges of the offset flange 1320 are attached to the woven mesh 1310. The offset flange 1320 positions the woven mesh 1310 away from the sealing surface so that the user's nose is not in direct skin contact with the woven mesh 1310 when the user's nose is positioned over the aperture 128.

FIGS. 45D and 45E illustrates an alternative configuration of a nasal seal 114 that obstructs the user's nose from being inserted into the seal 114 through the aperture 128. In contrast to the woven mesh 1310 of FIGS. 45A-C, the seal 114 has an aperture cover 1410 with an array of holes 1420 extending through the aperture cover. Similar to the woven mesh 1310, the aperture cover 1410 obstructs the user's nose from being inserted into the seal 114 through the aperture 128. The aperture cover 1410 is attached onto the upper, lower, and side edges 234, 236, 238 of the aperture 128 such that the aperture cover 1410 is flush with the sealing surface of the seal 114. The aperture cover 1410 may be unitarily or integrally formed with the seal 114. The holes 1420 extend through and are uniformly distributed across the aperture cover 1410. The holes 1420 allow air to flow through the aperture cover 1410 while preventing or inhibiting the user from inserting his/her nose into the aperture 128. The diameters and spacing of the holes 1420 may be configured to minimize noise and pressure drop. It should be understood to one of ordinary skill in the art that the holes 1420 may include an unlimited combination of holes having various shapes, sizes, and arrangements. FIG. 45E illustrates examples of holes 1420 arranged on the aperture cover 1410, such as, a combination of large and small holes, polygonal-shaped boles, wide holes spanning across the aperture, holes arranged in a fan configuration across the aperture.

FIGS. 46A to 46D also illustrate an alternative configuration of a nasal seal 114 that obstructs the user's nose from being inserted into the seal 114 through the aperture 128. In contrast to the woven mesh 1310 of FIGS. 45A-C and the aperture cover 1410 of FIGS. 45D-E, the aperture 128 has a series of tethers 1510 that are attached to the perimeter of the aperture 128 along the upper, lower, and side edges 234, 236, 238 of the aperture 128. When the user attempts to insert his/her nose into the aperture 128, the user's nose will contact one or more of the tethers 1510 which will indicate to the user that the seal 114 is not correctly fitted. If the user continues to insert his/her nose into the aperture 128, the tethers 1510 will block or obstruct the user from pushing further into the aperture 128.

The tethers 1510 extend downward into the seal 114 and are attached to an inner surface 1520 of a bottom wall of the seal. The tethers 1510 are formed from elongated string-like strands of silicone that are bonded or integrally molded with a component part of the seal 114 or to the seal 114 itself. The tethers 1510 are evenly spaced around the perimeter of the aperture 128.

Figure 46A:
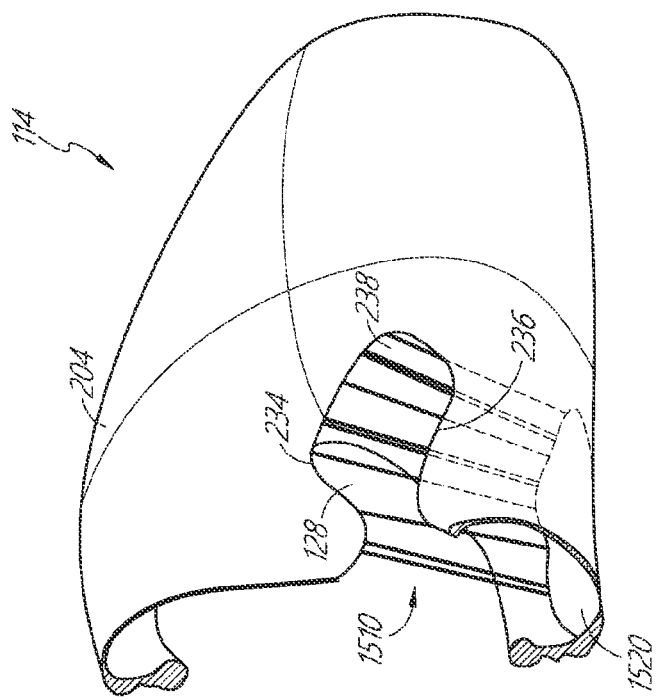
FIG. 46A is perspective cross-sectional view of a seal arrangement having tethers to physically prevent or inhibit the user from incorrectly wearing the seal.
Figure 46B:
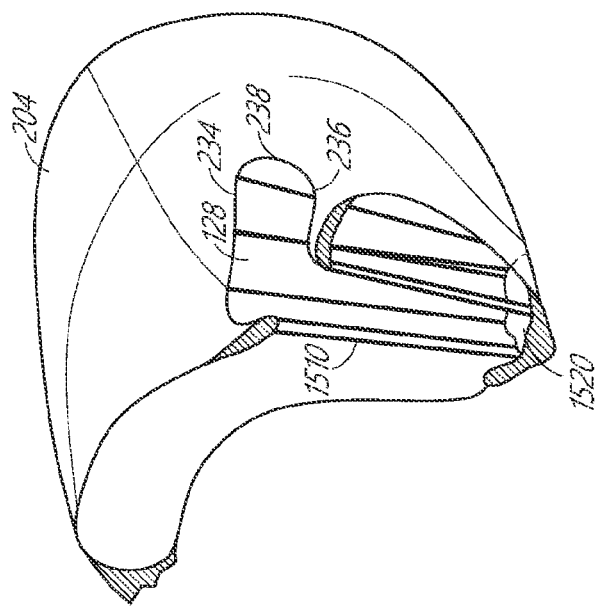
FIG. 46B is side cross-sectional view of the seal arrangement in FIG. 46A.
Figure 46C:
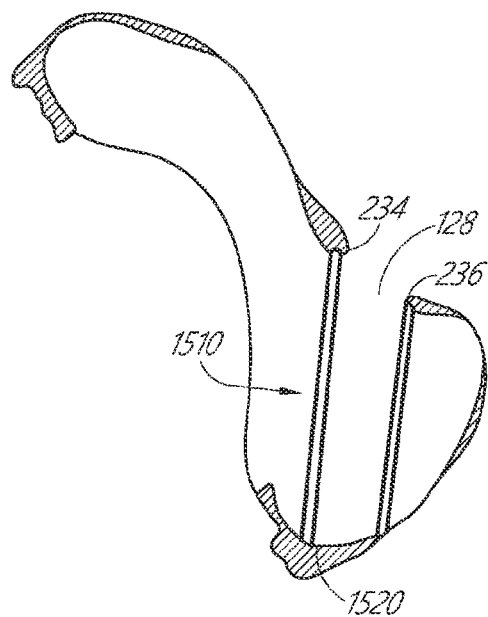
FIG. 46C is side cross-sectional view of the seal of FIG. 46A illustrating the seal in an undeformed shape.
Figure 46D:
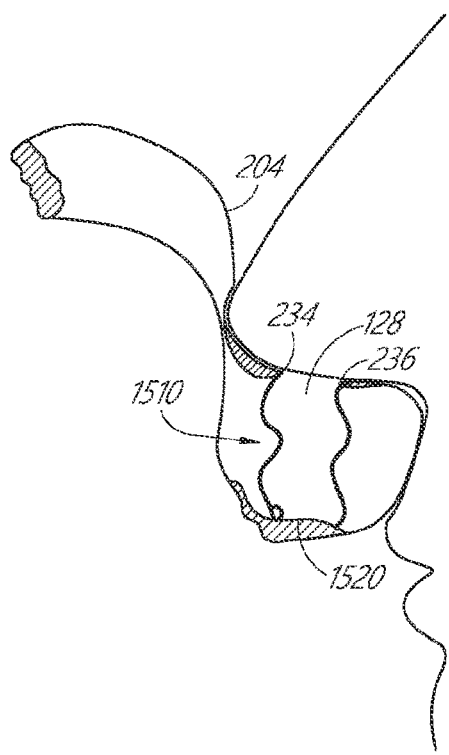
FIG. 46D is side cross-sectional view of the seal of FIG. 46A illustrating the seal correctly fitted to a user.

As illustrated in FIG. 46C, the tethers 1510 are taut (i.e., tension within the tethers 1510) when the seal 114 is undeformed (i.e., the seal 114 is not fitted on the user). As a result, the tethers 1510 anchor the central portion 204 of the seal 114 to an inner surface 1520 at the bottom of the seal 114 which allows the seal 114 to hold its undeformed shape. As such, the undeformed position of the edges of the aperture 128 may be controlled and maintained. As illustrated in FIG. 46D, the tethers 1510 are slackened (i.e., no tension within the tethers 1510) when the seal 114 is properly fitted to the user. That is, when the seal 114 is worn by the user, the seal 114 is compressed such that the distance decreases between the aperture 128 and the inner surface 1520 at the bottom of the seal 114. As a result, the tethers 1510 are compressed and slackened.

Figure 46F:
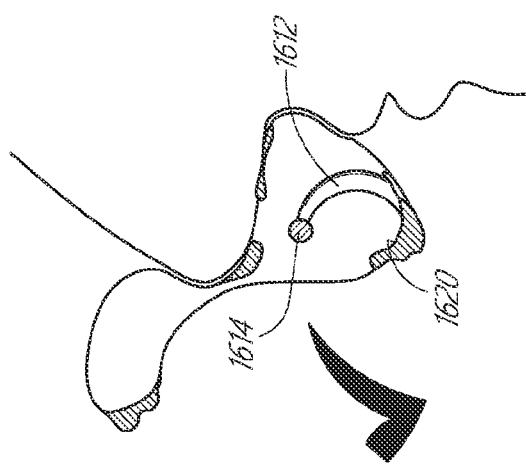
FIG. 46F is side cross-sectional view of the seal of FIG. 46E illustrating the seal correctly fitted to a user.
Figure 46G:
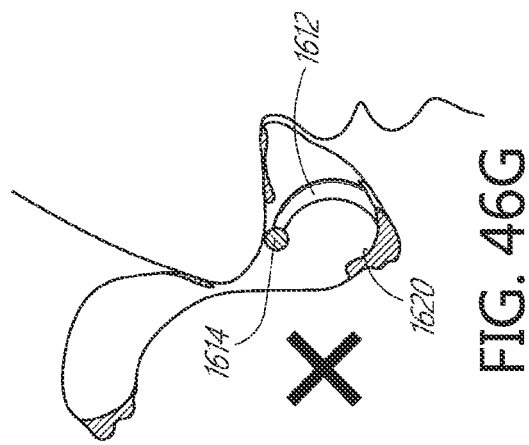
FIG. 46G is side cross-sectional view of the seal of FIG. 46B illustrating the seal incorrectly fitted to a user.
Figure 46E:
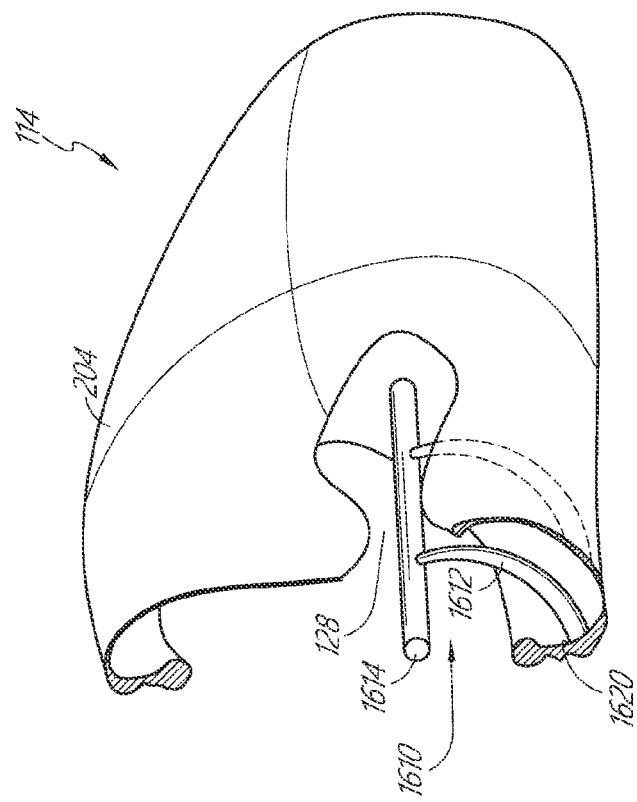
FIG. 46E is perspective cross-sectional view of a seal arrangement having a bumper to physically prevent or inhibit the user from incorrectly wearing the seal.

FIGS. 46E to 46H illustrate another alternative configuration of a nasal seal 114 that obstructs the user's nose from being inserted into the seal 114 through the aperture 128. In contrast to the tethers 1510 of FIGS. 46A-D, the seal 114 has a bumper 1610 attached to the inner surface 1620 at the bottom of the seal 114 and positioned immediately below the aperture 128. As illustrated in FIG. 46F, when the user attempts to insert his/her nose into the aperture 128, the seal 114 will compress and the user's nose will contact the bumper 1610. When contacting the bumper 1610, the user is provided feedback such that the user may realize that his/her nose should not be inserted into the aperture 128 and will try to refit the seal 114 with the user's nose positioned outside of the aperture 128.

The bumper comprises a vertical strut 1612 and a lateral beam 1614. The strut 1612 is positioned below the aperture 128 and attached to the inner surface 1620 at the bottom of the seal 114. The strut 1612 extends vertically upward towards the aperture 128. The upper end of the strut 1612 is attached to the beam 1614. The beam 1614 has an elongated shape that extends laterally across the width of the aperture 128.

The strut 1612 has a height such that the beam 1614 is positioned a distance below the aperture 128 when the seal 114 is correctly fitted to the user, as shown in FIG. 46C. In other words, the beam 1614 is not in contact with the user's nose when the seal 114 is correctly fitted to the user. The seal 114 may compress slightly due to the force required to provide an airtight seal around the user's nose. However, strut 1612 has a height such that the beam 1614 is not in contact with the user's nose despite the seal 114 being compressed. The strut 1612 and beam 1614 may be formed from a silicone material such that the strut 1612 and the beam 1614 are flexible and do not cause pain or injury when contacting the user's nose. The strut 1612 and beam 1614 may be bonded or integrally molded with a component part of the seal 114 or the seal 114 itself. Further, the strut 1612 may have a curved shape such that the shape of the strut 1612 may provide an amount of flexibility so that the strut 1612 deforms when contacting the user's nose.

Figure 46H:
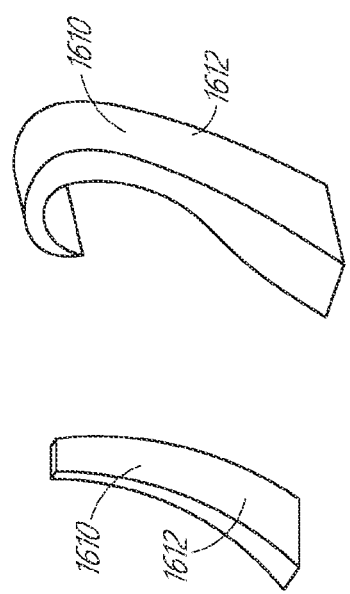
FIG. 46H illustrates alternative bumper arrangements.

The beam 1614 is illustrated as having a straight and elongated cylindrical shape. However, it should be understood to one of ordinary skill in the art that the beam 1614 may be one of a variety of shapes that obstruct the user's nose or other objects from descending deeper into the seal 114 through the aperture 128. Further, in some configurations, the seal 114 may have a strut 1612 without a beam 1614 attached to the upper end of the strut 1612. FIG. 46H illustrates examples of strut arrangements having a strut 1612 without a beam.

Figure 47C:
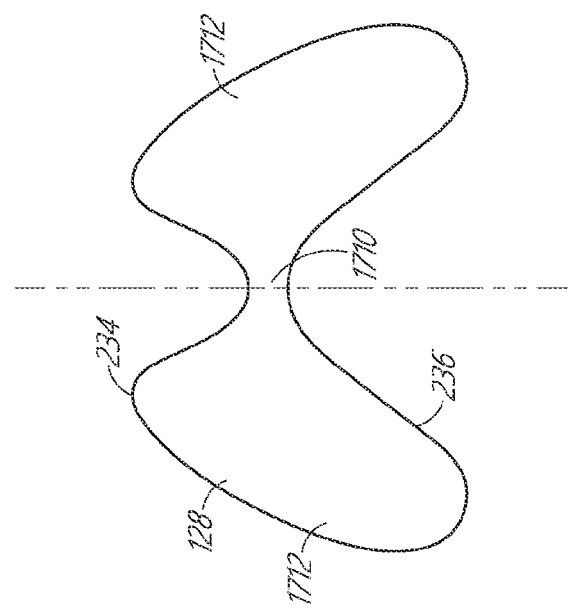
FIG. 47C illustrates an alternative configuration of an aperture for a seal that prevents or inhibits the user's nose from being inserted into the aperture.
Figure 47B:
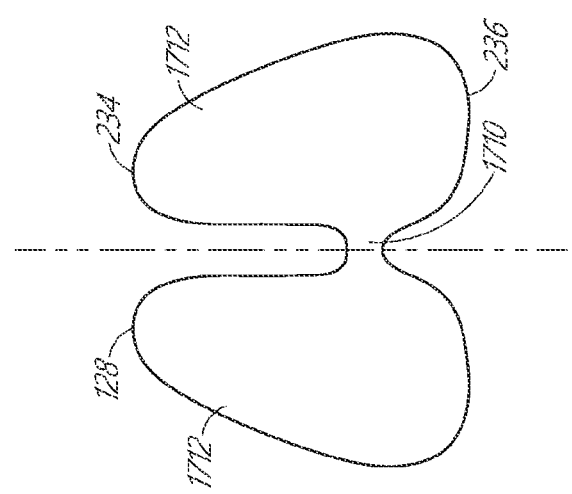
FIG. 47B illustrates an alternative configuration of an aperture for a seal that prevents or inhibits the user's nose from being inserted into the aperture.
Figure 47A:
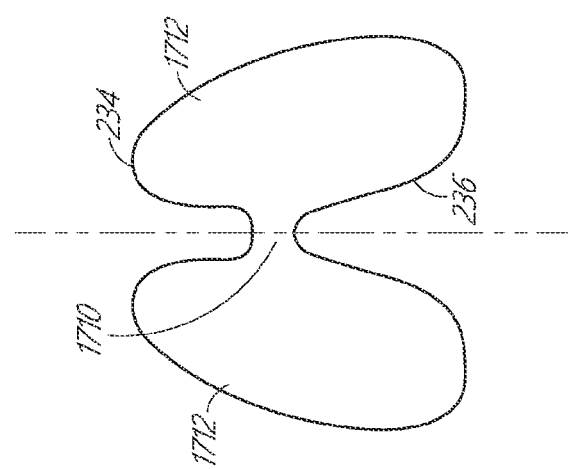
FIG. 47A illustrates an alternative configuration of an aperture for a seal that prevents or inhibits the user's nose from being inserted into the aperture.

FIGS. 47A to 47G illustrate alternative configurations of an aperture 128 for a seal (not shown) that inhibits or prevents the user's nose from being inserted into the aperture 128 by providing distinct locations for the user's left and right nares over the aperture 128. As shown, the upper and lower 234, 236 edges of the aperture 128 narrow at a lateral midpoint of the aperture 128 to form a narrow central portion 1710 of the aperture 128 that is positioned between a left and right nares 1712. The widest distance between the upper and lower 234, 236 edges of the aperture 128 at the narrow central region 1710 is substantially narrower than the widest distance between the upper and lower 234, 236 edges at the left and right nares 1712. As a result, the narrow central portion 1710 defines distinct left and right nares 1712 such that the user may intuitively and unmistakably recognize that his/her nares should be positioned over the left and right nares 1712 because the user will recognize that the aperture 128 is too narrow at the narrow central portion 1710 for his/her nose to be inserted. Further, if the user attempts to insert his/her nose into the aperture 128, portions of the seal 114 around the narrow central portion 1710 will contact the tip or septum of the user's nose to obstruct or block insertion into the aperture 128. The left and right nares 1712 may be ovular in shape. The aperture 128 may be formed in a variety of shapes such as, but not limited to, a kidney shape (FIGS. 47A-D) or a crescent shape (FIG. 47E). The left and right nares 1712 may be angled toward each other such that the upper-most edges of the left and right nares 1712 are closer together than the lower-most edges of the left and right nares 1712. In some configurations, the left and right nares 1712 may be angled away from the narrow central region 1710. Each of the left and right nares 1712 may have a shape such that a width of the upper-most portion of the left and right nares 1712 is narrower than a width of the lower-most portion of the left and right nares 1712. In some configurations, the narrow central region 1710 may be positioned closer to the upper edge 234 of the aperture 128, as shown in FIGS. 47A, 47C and 47D. In other configurations, the narrow central region 1710 may be positioned closer to the lower edge 236 of the aperture 128, as shown in FIG. 47B.

As illustrated in FIGS. 47A to 47F, the position, shape and size of the narrow central region 1710 may vary between the upper and lower 234, 236 edges of the aperture 128 according to the size and shape of the user's nose and nares. Similarly, the size and shapes of the left and right nares 1712 may also vary according to the size and shape of the user's nose and nares. FIGS. 47F and 47G illustrate an aperture 128 having overlapping upper and lower edges 234, 236. As shown, the lower edge 236 extends over the upper edge 234 such that the left and right nares 1712 are entirely separated. Separate left and right nares 1712 provides explicitly distinct locations for placement of the user's left and right nares over the aperture 128.

In some configurations, the seal 114 may be configured such that an aperture 128 having overlapping upper and lower edges 234, 236 provides a flush seating surface for the user's nose to be seated on. As illustrated in FIG. 47G, an upper portion 1730 of the seal 114 may have a recess 1732 that receives a lower portion 1740 of the seal 114 such that the seating surface at the intersection of the upper and lower portions 1730, 1740 is substantially flat. A substantially flat seating surface at the intersection of the upper and lower portions 1730, 1740 inhibits or prevents a portion of the user's nose from becoming pinched in between the upper and lower portions 1730, 1740. The lower portion 1740 may also have a protrusion 1742 having a corresponding shape with the recess 1732 such that the upper and lower portions 1730, 1740 are interlocked and provide a substantially flat seating surface when the seal 114 is fitted to the user.

Figure 48D:
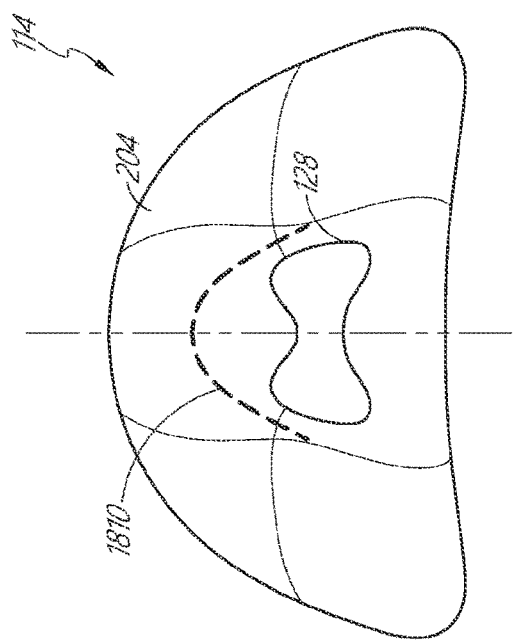
FIG. 48D depicts an alternative marking indicating correct nose alignment and position.
Figure 48B:
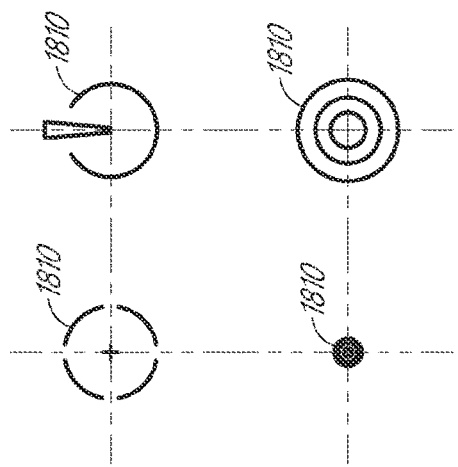
FIG. 48B depicts alternative marking arrangements.
Figure 48C:
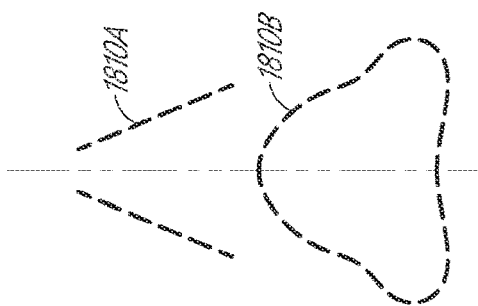
FIG. 48C depicts an alternative combination marking indicating correct nose alignment and position.
Figure 48A:
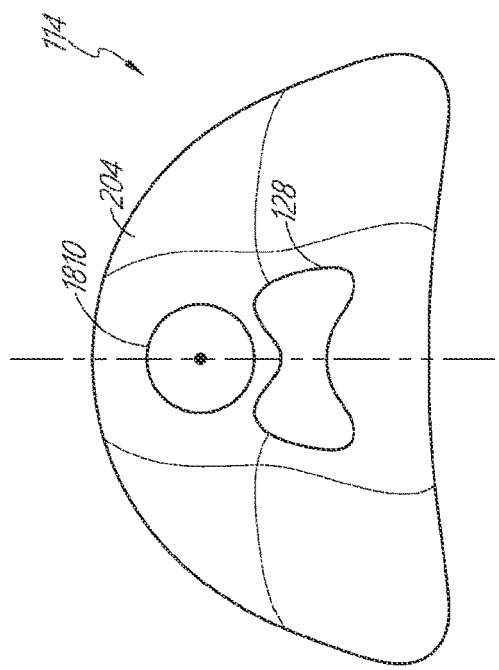
FIG. 48A is a rear view of a nasal seal arrangement having visual markings to indicate correct nose position.

FIGS. 48A to 48D illustrate an alternative configuration of a nasal seal 114 that provides the user with visual guidance regarding how the seal 114 should be properly fitted to the nose. As illustrated in FIG. 48A, the seal 114 has markings 1810 to visually indicate to the user where to position his/her nose over the aperture 128. The markings 1810 are depicted as a circular target with a center "bullseye". The markings 1810 are positioned on the central portion 204 of the seal 114 at a position where the tip of the user's nose should be positioned. The markings 1810 may be printed with ink on the inner or outer surface of the seal 114. In some configurations, the ink may be a water-based washable ink that may be removed with water such that the user may remove the markings 1810 once learning how the seal 114 should be correctly fitted. In other configurations, the markings 1810 may be a sticker that is applied with an adhesive onto or on an interior surface of the seal 114 within the dead space such that the markings 1810 are visible through the surface of the seal 114. FIG. 48B illustrates alternative target-type markings 1810. FIG. 48C illustrates a combination of markings including markings 1810A indicating the alignment of the user's nose on the seal 114 and markings 1810B indicating the position of the underside of the user's nose on the aperture 128. FIG. 48D illustrates markings 1810 depicting an outline of the user's nose to indicate both the alignment of the user's nose on the seal 114 and the position of the user's nose over the aperture 128.

Figure 48F:
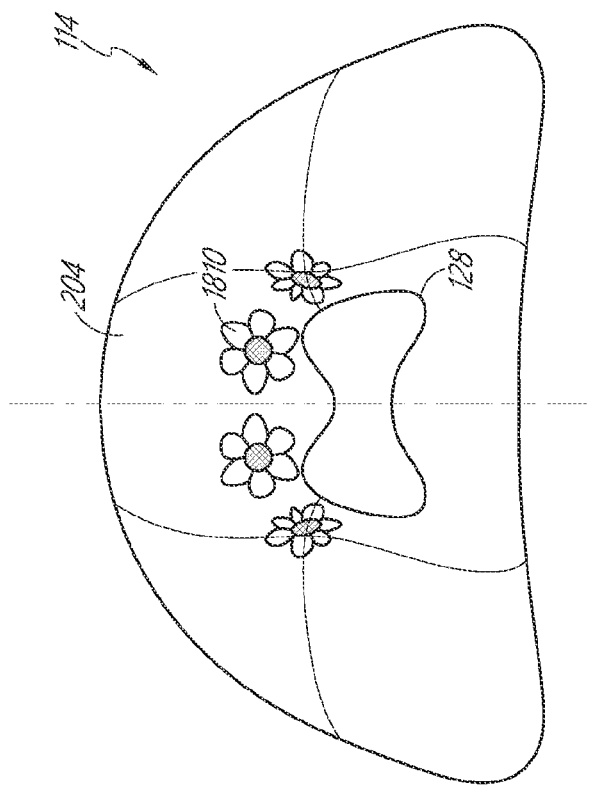
FIG. 48F is a rear view of an alternative scented marking arrangement.
Figure 48E:
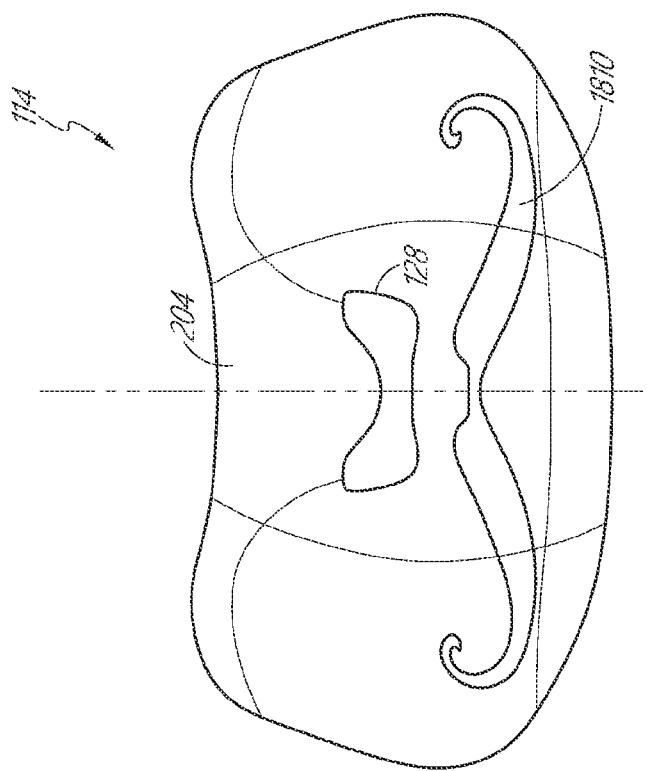
FIG. 48E is a rear view of an alternative marking arrangement.

In contrast to explicit images indicating the exact position, placement, and/or alignment of the user's nose, the markings 1810 may include amusing or comical images to communicate the location of the seal 114 on the user's face. FIG. 48E depicts markings 1810 in the form of a mustache that is printed below the aperture 128 onto the central portion 204 of the seal 114 that is positioned under the user's upper lip. The image of a mustache provided by the markings 1810 would indicate to the user where his/her upper lip should be positioned. Similarly, FIG. 48F depicts markings 1810 in the form of flowers that are printed above the aperture 128 onto the central portion 204 of the seal 114 that is positioned under the user's nose. In some configurations, the markings 1810 may also be scented (e.g., a floral scent) to further indicate how the seal 114 should be fitted. In other configurations, the markings 1810 may be a sticker that is applied with an adhesive onto the seal 114. In other configurations, the markings 1810 may be applied using ink or stickers that change according to temperature such that regions of the seal 114 may change colors (e.g., red or green) when the seal 114 is incorrectly or correctly fitted. The changing colors may provide positive or negative feedback regarding the user's behavior.

In contrast to printed markings 1810, FIGS. 48G to 48I illustrate markings 1910 formed in frosted silicone. The markings 1910 may be integrally and unitarily molded into the seal 114 to provide frosted silicone markings 1910 having an opaque appearance that contrasts from the translucent appearance of the remaining portions of the seal 114. Similar to FIG. 48D, FIG. 48O illustrates a frosted silicone marking 1910 that indicates both the position and alignment of the user's nose on the seal 114 and the position of the user's nares on the aperture 128. FIG. 48H illustrates a frosted silicone marking 1910 that indicates the position of the user's nares on the aperture 128 by outlining the shape of the user's nares in frosted silicone. Similar to FIG. 48A, FIG. 48I illustrates target-type markings 1910 in frosted silicone that may indicate where on the seal 114 the tip of the user's nose should be positioned.

Figure 49B:
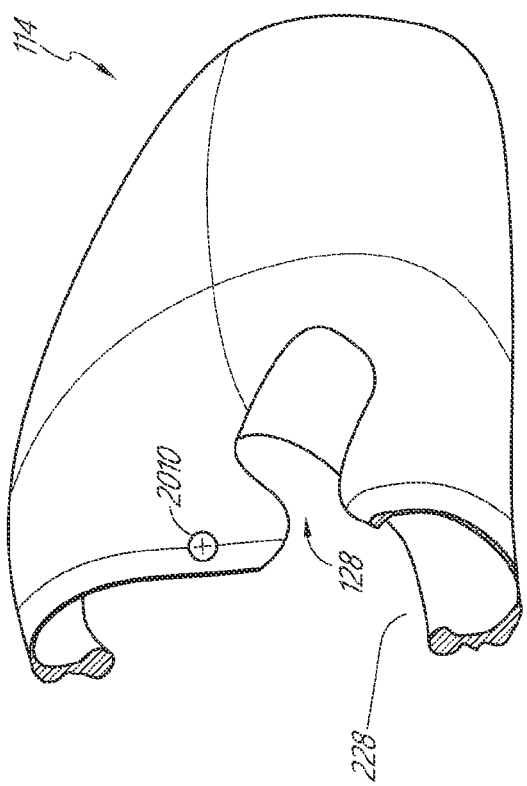
FIG. 49B is a perspective cross-sectional view of the nasal seal arrangement of FIG. 49A.
Figure 49C:
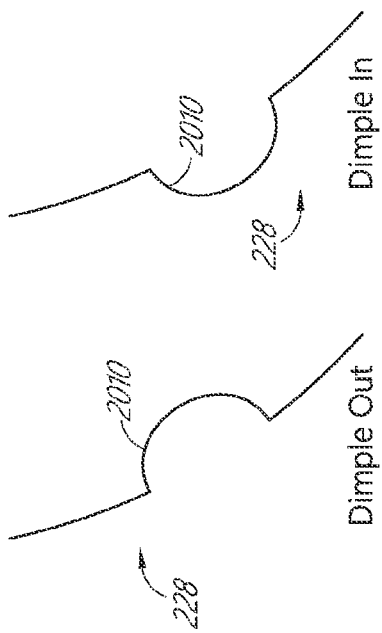
FIG. 49C is a side cross-sectional view of the positions of the depressible dimple of the nasal seal arrangement of FIG. 49A.
Figure 49A:
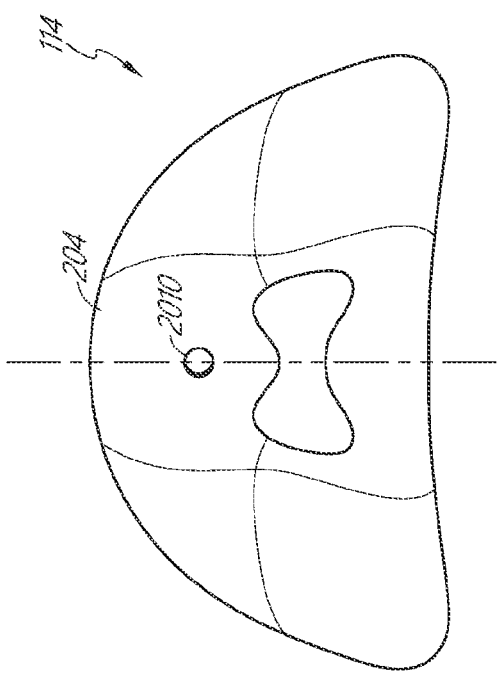
FIG. 49A is a rear view of a nasal seal arrangement having a depressible dimple to indicate correct nose position.

As another alternative to printed markings, FIGS. 49A to 49C illustrate a deformable marking or depressible dimple 2010 that deforms to indicate that the seal 114 is correctly fitted on the user. Similar to the markings 1810 in the shape of a target or "bulls-eye", the dimple 2010 is positioned on the central portion 204 of the seal 114 at a position where the tip of the user's nose should be positioned. As illustrated in FIG. 49C, the dimple 2010 deforms inward toward the inner cavity or dead space of the seal 114 when depressed. Accordingly, when the tip of the user's nose is positioned over the dimple 2010, the dimple 2010 will deform inward to provide haptic positive feedback to the user that the seal 114 is positioned correctly. The dimple 2010 may also make an audible "popping" noise when the dimple 2010 deforms inward. The dimple 2010 may be reset to extend outward (i.e., away from an interior or dead space of the seal 114) when the seal 114 is removed from the user's face such that dimple 2010 is repositioned for the next fitting. The dimple 2010 provides an easily recognizable mechanism for indicating where the user's nose should be placed on the seal 114 since deformable dimples are also used on consumer products (e.g., takeaway coffee lids).

The dimple 2010 may also be used to indicate whether the seal 114 is sufficiently tight on the user. For example, the force profile or threshold amount of force required to deform the dimple 2010 may be determined based on the proper tightness of the seal 114 against the user's nose or face. Accordingly, the dimple 2010 will not deform unless a threshold force is applied which will indicate to the user whether the seal 114 is sufficiently tight against the user's nose or face.

FIGS. 50A to 50F illustrate alternative configurations of an interface 3110 that adjusts the angle of the nasal seal 3114 according to the user's nose angle to comfortably fit user's noses within a wide range of upward or downward angles and minimize the amount of force applied to the user's subnasal region. Generally, the subnasal region of a user is sensitive to the upward force applied by the seal. However, in order to inhibit or prevent the seal from leaking, the seal must apply an upward force to the user's nose that is greater than the blow-off force. The blow-off force varies according to the upward or downward angle of the user's nose. As such, a seal that comfortably fits a user having an upwardly angled nose (i.e., by applying a minimum amount of force to the subnasal region of the user) may be uncomfortable for a user with a downwardly angled nose because the seal will not be aligned with the blow-off force thereby applying a greater amount of force to the subnasal region of the user. Therefore, to reduce or minimize the amount of force applied to the subnasal region, the interface 3110 provides a seal 3114 that is rotatable depending on the upward or downward angle of the user's nose to provide a sealing force that is aligned with and directly opposes the user's blow-off force which reduces or minimizes the amount of force applied to the user's subnasal region.

Figure 50A:
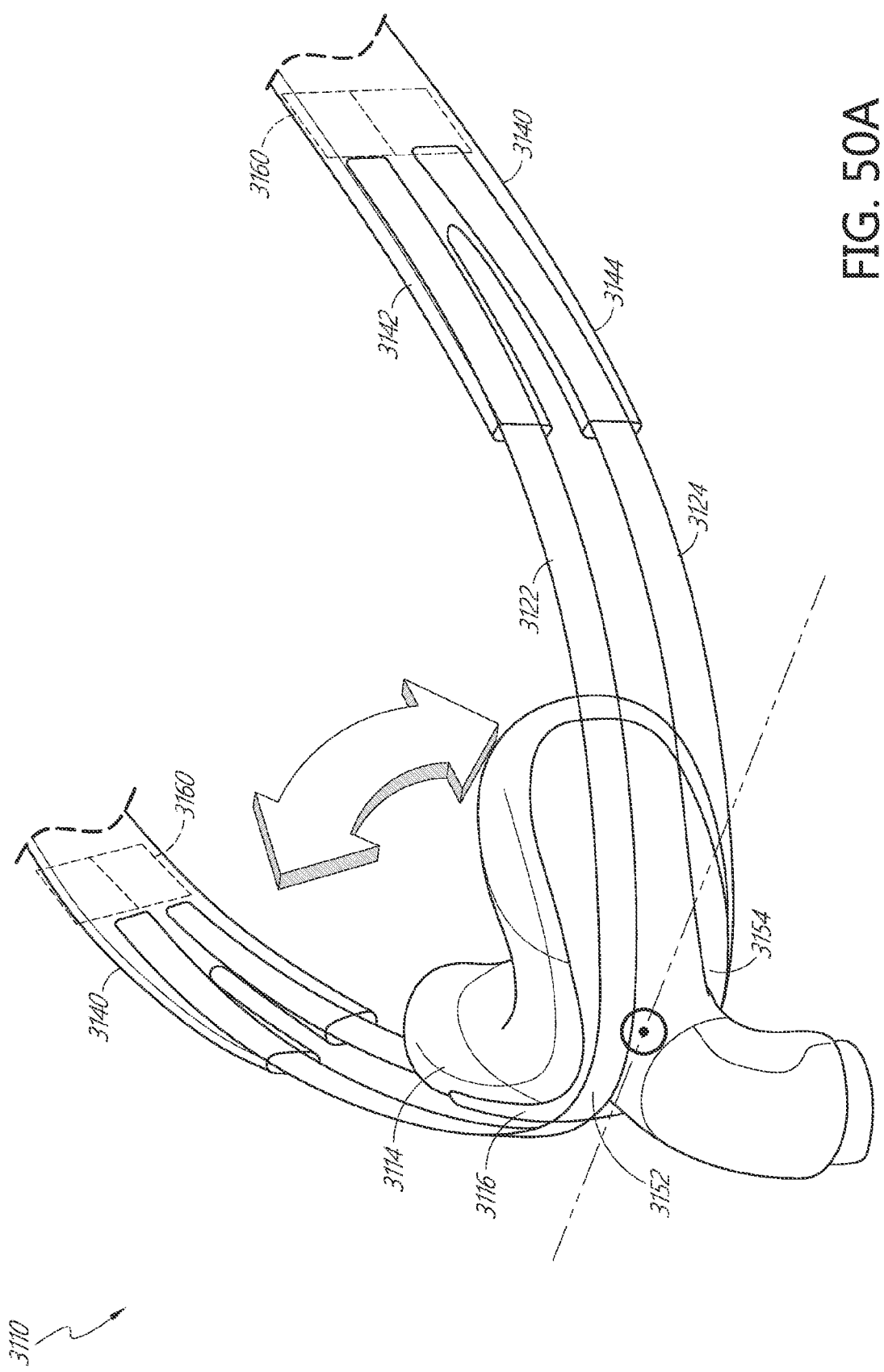
FIG. 50A is a perspective view of an interface arrangement having a rotatable nasal seal.

In FIG. 50A, the interface 3110 has a seal 3114 that is attached to a frame 3116. The seal 3114 and frame 3116 are similar to the seal 114 and frame 116 described in FIGS. 1-22 and, therefore, redundant discussion of similar structures will be largely omitted. The frame 3116 is rotatably attached to an upper frame rail 3122 at an upper connection portion 3152 and rotatably attached to a lower frame rail 3124 at a lower connection portion 3154. That is, the frame 3116 rotates relative to the upper frame rail 3122 about the upper connection portion 3152 and the frame 3116 also rotates relative to the lower frame rail 3124 about the lower connection portion 3154. The upper and lower frame rails 3122, 3124 may be formed from a relatively rigid, semi-rigid or rigid material, such as polycarbonate, for example. The ends of the upper and lower frame rails 3122, 3124 are attached to forward straps 3140 of the headgear 3118. That is, the ends of the upper frame rail 3122 are attached to an upper headgear strap 3142 and the ends of the lower frame rail 3124 are attached to a lower headgear strap 3144. As such, the seal 3114 is supported at the upper and lower connection portions 3152, 3154 by the headgear 3118.

Figure 50B:
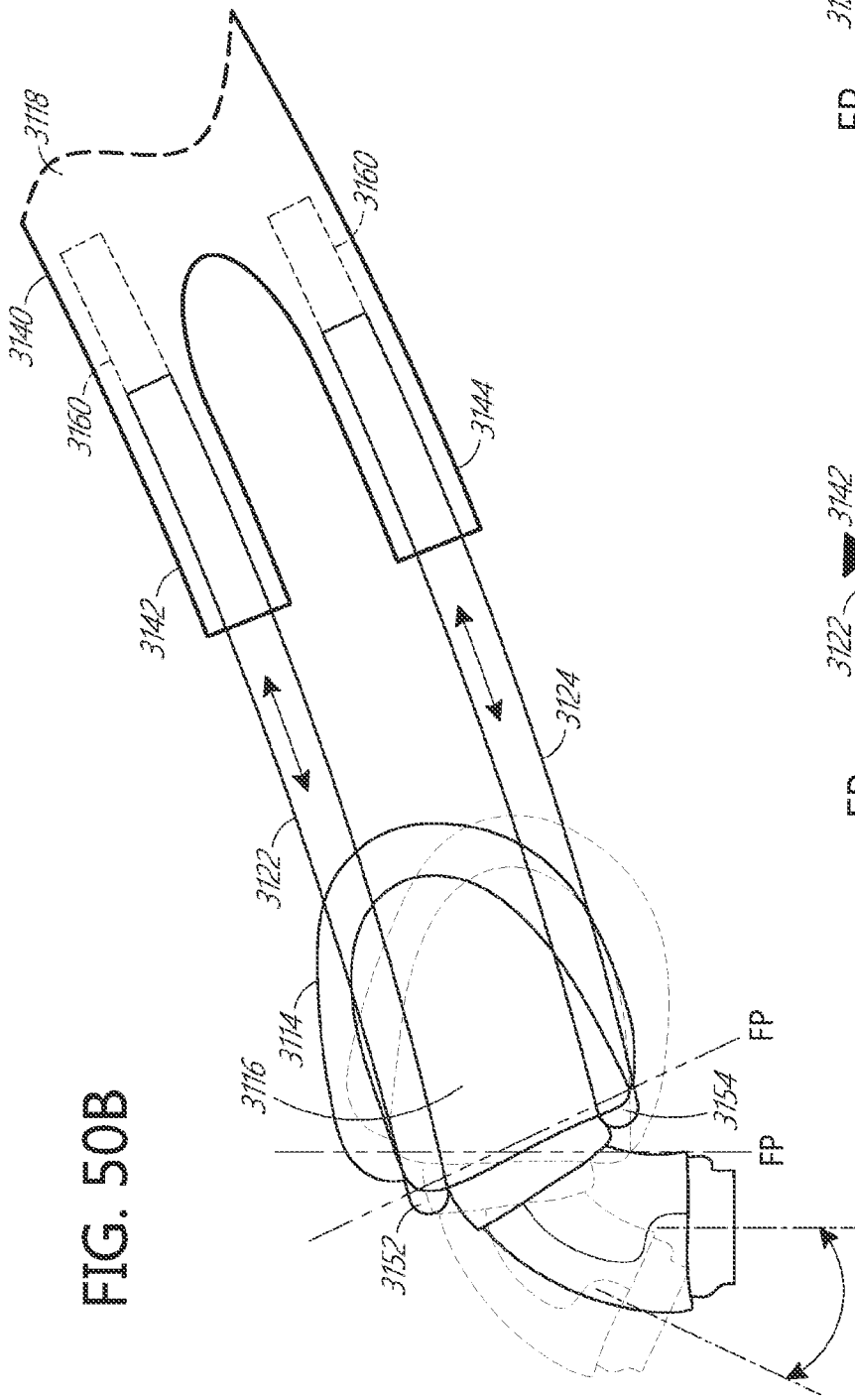
FIG. 50B is a side view of the interface arrangement of FIG. 50A illustrating the range of rotation of the rotatable nasal seal.

The upper and lower frame rails 3122, 3124 may be attached to the upper and lower headgear straps 3142, 3144 by a connection mechanism 3160 such that the upper and lower frame rails 3122, 3124 may extend or retract relative to the headgear 3118, as illustrated in FIG. 50B. More specifically, the extension or retraction of the upper and lower frame rails 3122, 3124 changes the relative positions of the upper and lower connection portions 3152, 3154 which causes rotation of the seal 3114 and allows rotational adjustability of the seal 3114 within a range of angular rotation. A rotated position of the seal 3114 is depicted in dashed lines in FIG. 50B.

Figure 50C:
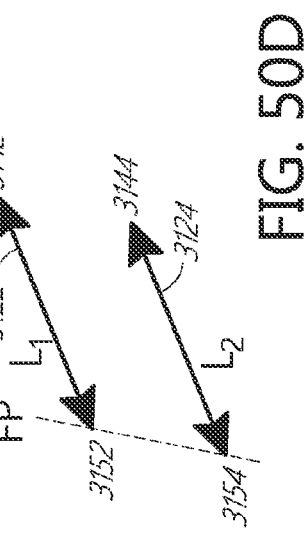
FIGS. 50C and 50D are schematic side views illustrating the extended and retracted positions of the frame rails causing rotation of a front plane projection line of the rotatable nasal seal of the interface arrangement of FIG. 50A.
Figure 50D:
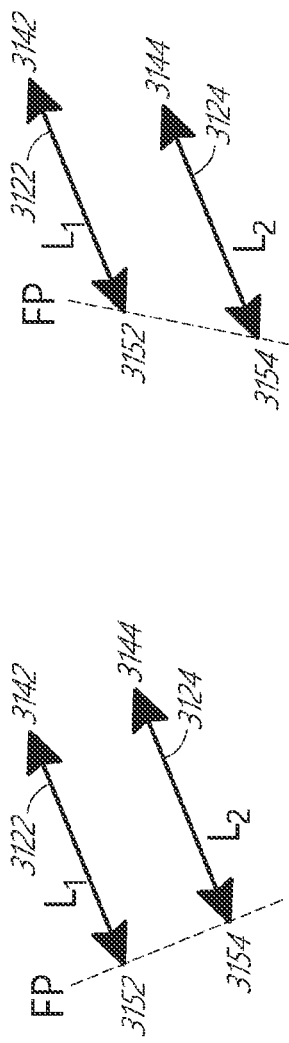

For illustration, FIGS. 50C and 50D are schematic side views of the upper and lower frame rails 3122, 3124 to show changes to the respective positions of the upper and lower connection portions 3152, 3154 when the upper and lower frame rails 3122, 3124 are extended or retracted from the upper and lower headgear straps 3142, 3144. As shown, a length L1 is measured as a distance between the upper connection portion 3152 and an end of the upper headgear strap 3142. Similarly, a length L2 is measured a distance between the lower connection portion 3154 and an end of the lower headgear strap 3144. Accordingly, extending or retracting the upper or lower frame rails 3122, 3124 relative to the upper and lower connection portions 3152, 3154 changes the lengths L1, L2. To further illustrate the effect of extending and retracting the upper and lower headgear straps 3142, 3144, a front plane projection line FP defined by the upper and lower connection portions 3152, 3154 represents a front plane of the frame 3116. As such, the angle of the front plane projection line FP changes depending upon the lengths L1, L2 of the upper and lower frame rails 3122, 3124.

When comparing FIGS. 50C and 50D, the length L1 does not change between FIGS. 50C and 50D. However, the length L2 increases from FIG. 50C to FIG. 50D. That is, the length L2 in FIG. 50D is greater than in FIG. 50C. As a result, the lower connection portion 3154 is positioned further away from the headgear 3118 than in FIG. 50C which causes the seal 3114 to rotate downward, as depicted by the clockwise rotation of the front plane projection line FP in FIG. 50D. Similarly, although not depicted, the extension of the upper frame rail 3122 and the retraction of the lower frame rail 3124 would causes the seal 3114 to rotate upward and the front plane projection line FP to rotate counter clockwise. The range of angular rotation provided by the upper and lower frame rails 3122, 3124 may depend upon the amount or range of extension and retraction provided to by the upper and lower frame rails 3122, 3124 by both the connection mechanism 3160. Accordingly, rotation of the seal 3114 within the range of angular rotation allows the seal 3114 to comfortably fit user's noses within a wide range of positive or negative nose angles in order to minimize the amount of force applied to the user's subnasal region.

Figure 50F:
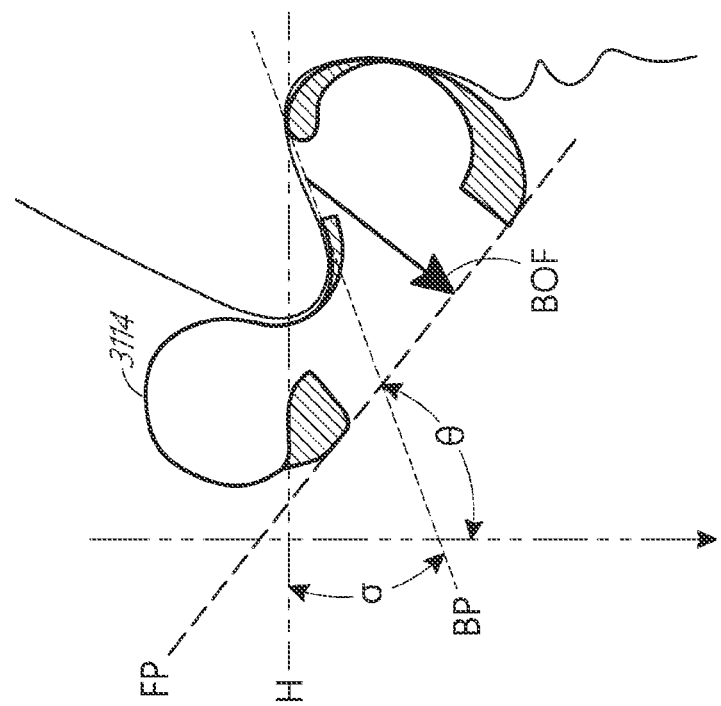
FIG. 50F is a side cross-sectional view of the rotatable nasal seal of FIG. 50A fitted to a user having a negative nose angle.
Figure 50E:
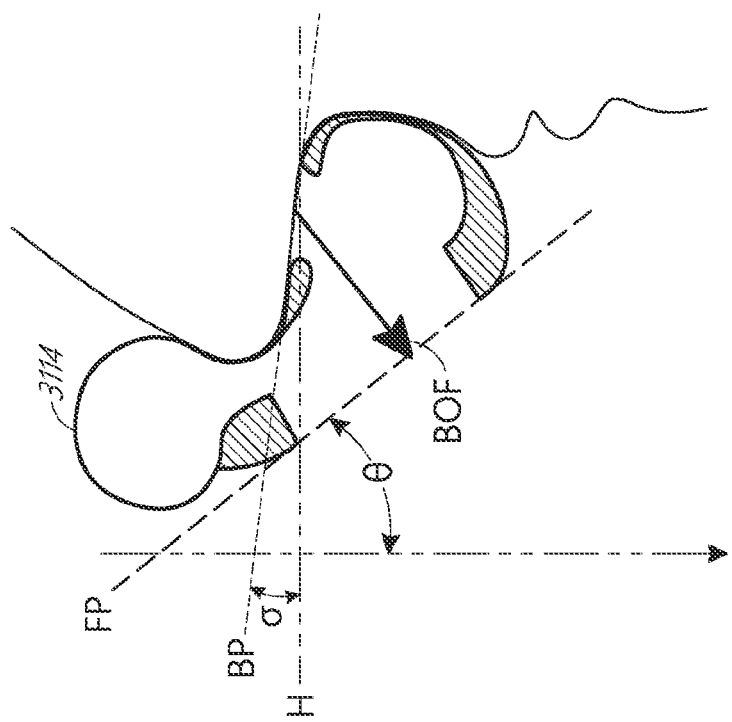
FIG. 50E is a side cross-sectional view of the rotatable nasal seal of FIG. 50A fitted to a user having an positive nose angle.

To illustrate the effect of the rotational adjustability of the seal 3114 provided by the interface 3110, FIG. 50E illustrates a cross-sectional view of the seal 3114 fitted to the nose of a user with a positive nose angle and FIG. 50F illustrates a cross-sectional view of the seal 3114 fitted to the nose of a user with a negative nose angle. The nose angle is determined based an angle σ between a bottom plane BP of the user's nose and a horizontal reference plane H. A positive nose angle is defined as an angle σ above the horizontal reference plane H. A negative nose angle is defined as an angle σ below the horizontal reference plane H. FIGS. 50E-F also depict the blow-off force vector BOF for both positive and negative nose angles. As shown, the blow-off force vector BOF for the positive nose angle is angled closer to a horizontal plane than the blow-off force vector BOF for the negative nose angle. FIGS. 50E-F also depict the front plane projection line FP, which is defined by the upper and lower connection portions 3152, 3154 and represents a front plane of the frame 3116, illustrated in FIGS. 50A-D. The interface 3110 accommodates blow-off force vectors BOF of varying angles that are caused by positive and negative nose angles by allowing the seal 3114 to rotate according to the nose angle such that the front plane projection line FP is perpendicular to the blow-off force vector BOF. Aligning the front plane projection line FP to be perpendicular to the blow-off force vector BOF minimizes the amount of force applied to the user's subnasal region.

As illustrated in FIG. 50E, the seal 3114 fitted to the positive nose angle is rotated clockwise compared to the seal 3114 fitted to the negative nose angle (FIG. 50F) such that the front plane projection line FP is perpendicular to the blow-off force. As a result, the amount of force applied to the user's subnasal region for the seal 3114 to seal against the user's nose is minimized. In FIG. 50F, the seal 3114 fitted to the negative nose angle is rotated counterclockwise compared to the seal 3114 fitted to the positive nose angle in FIG. 50E such that the front plane projection line FP is also perpendicular to the blow-off force. As a result, the amount of force applied to the user's subnasal region to provide a seal against the user's nose is minimized. To further illustrate the difference in rotation angle of the front plane projection line FP, an angle θ is shown between the front plane projection line FP and vertical reference plane V. As shown, the angle θ of the front plane projection line FP for the seal 3114 fitted to the positive nose angle in FIG. 50E is less than the angle θ of the front plane projection line FP for the seal 3114 fitted to the negative nose angle in FIG. 50F.

The seal 3114 may be rotatably attached to the upper frame rail 3122 and the lower frame rail 3124 by any connection arrangement that allows rotation of the frame 3116. In other words, the upper and lower connection portions 3152, 3154 may include a variety of any connection arrangement that allows rotation of the frame 3116. In some configurations, the frame 3116 may have loops or through holes positioned on a front portion of the frame 3116 through which the upper frame rail 3122 and the lower frame rail 3124 pass through, thereby, allowing the frame 3116 to rotate about the upper and lower frame rails 3122, 3124.

The connection mechanism 3160 may include any connection mechanism arrangement between the headgear 3118 and the upper and lower frame rails 3122, 3124 that provide extension and retraction of the upper and lower frame rails 3122, 3124 such that the seal 3114 is rotatable through a range of angular rotation. The connection mechanism 3160 may include the rigid adjustment mechanisms as described in U.S. provisional patent application 61/261,715, which is incorporated herein by reference.

Figure 51C:
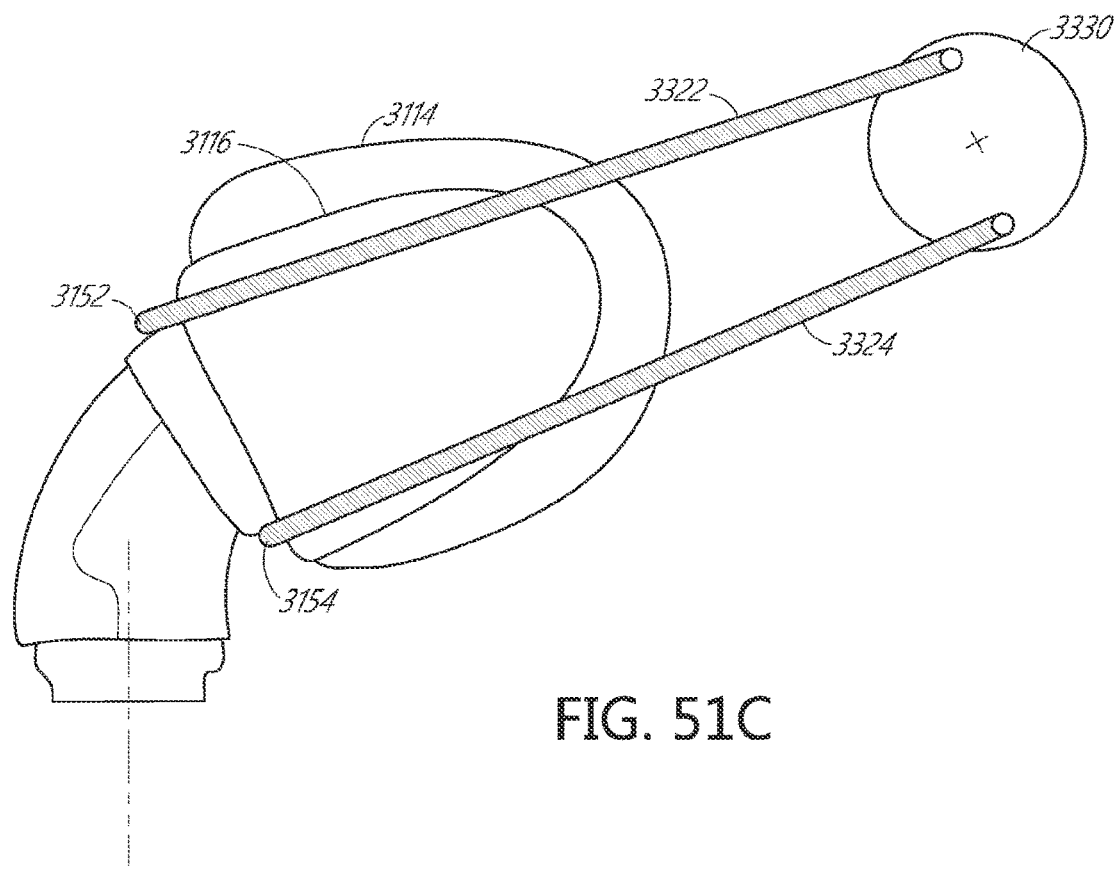
FIGS. 51C and 51D are side views of the alternative interface arrangement of FIG. 51A illustrating various rotation positions of the nasal seal.

FIGS. 51A to 51G illustrate alternative connection mechanisms that allow the seal 3114 to rotate through a range of angular rotation. FIGS. 51A-B illustrate a connection mechanism 3260 comprising an endless or closed-loop cable 3220 and pulleys 3230. The closed-loop cable 3220 has an upper loop portion 3222 and a lower loop portion 3224. Similar to the upper and lower frame rails 3122, 3124, the closed-loop cable 3220 is connected to the frame 3116 at upper and lower connection portions 3152, 3154. The upper and lower connection portions 3152, 3154 may comprise loops or through holes positioned on a front portion of the frame 3116 through which the closed-loop cable 3220 passes therethrough, thereby, allowing the frame 3116 to rotate about the upper and lower frame rails 3222, 3224.

As shown in FIGS. 51A-B, the closed-loop cable 3220 is wrapped around the pulleys 3230. The pulleys 3230 are attached to forward straps 3240 of the headgear 3118. The pulleys 3230 rotate clockwise or counterclockwise to allow the upper and lower loop portions 3222, 3224 to increase or decrease in length such that the seal 3114 rotates. That is, rotation of the pulleys 3230 pulls the upper or lower connection portions 3152, 3154 closer to the headgear 3118. Accordingly, the user may rotate the pulleys 3230 to rotate and adjust the seal 3114 until the seal 3114 is comfortably fitted.

In some configurations, the pulley 3230 may have a recessed groove around its circumference to receive the closed-loop cable 3220. Further, the user may don and doff the seal 3114 by separating the closed-loop cable 3220 from the pulley 3230. Even further, the pulleys 3230 may be adjustably attached to the forward straps 3240 of the headgear 3118 to allow the slack within the closed loop cable 3220 and, hence, the tightness of the seal 3114 against the user's face, to be adjusted. More specifically, the position of the pulleys 3230 may be moved along the forward straps 3240 (i.e., closer or further away from the frame 3114) such that the tightness of the seal 3114 against the user's face may be adjusted. Alternatively, closed-loop cable 3220 having different lengths may be provided such that the tightness of the seal 3114 against the user's face may be adjusted.

Figure 51D:
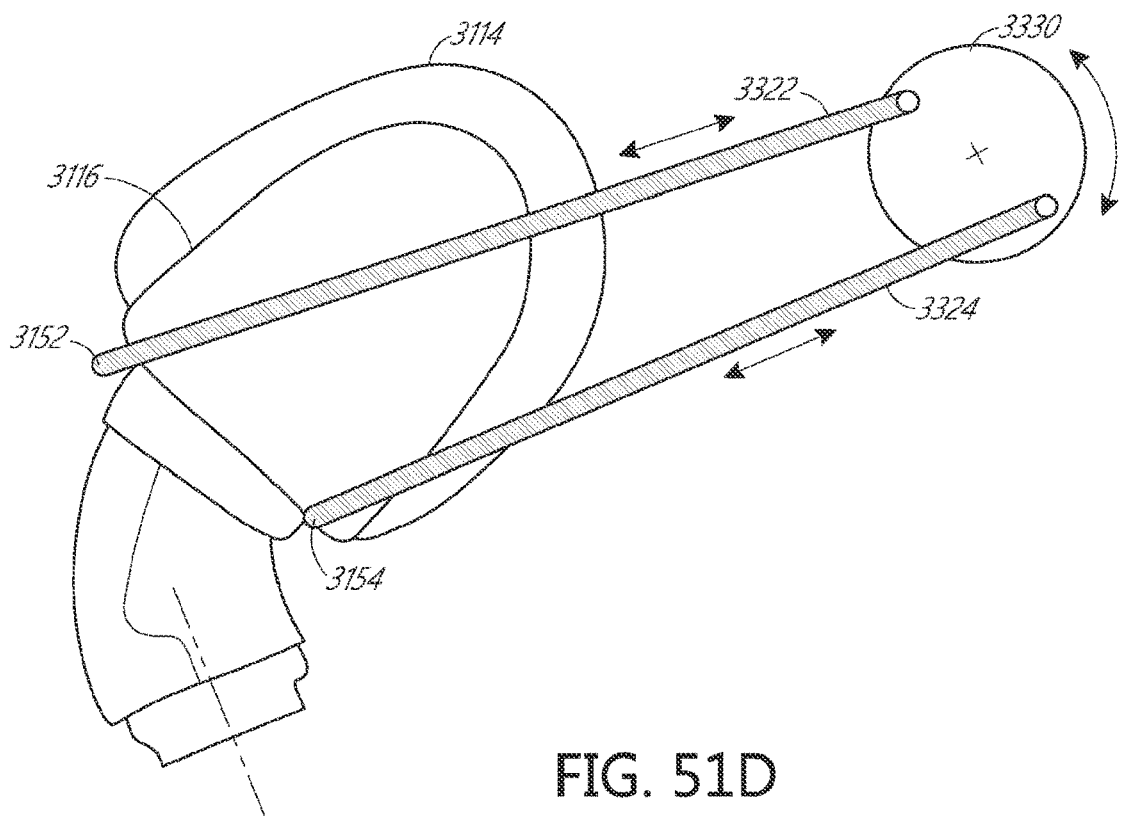

FIGS. 51C-D illustrate an alternative connection mechanism comprising upper and lower yokes 3322, 3324 that are attached to a pulley 3330. In contrast to the closed-loop cable 3220, the upper and lower yokes 3322, 3324 have fixed lengths and may be rigid or semi-rigid in construction. As a result, the upper and lower yokes 3322, 3324 may be sufficiently rigid to resist yielding to vertical forces such as, for example, vertical components of the blow-off force. The upper and lower yokes 3322, 3324 are rotatably attached to the pulley 3230 to allow the upper and lower yokes 3322, 3324 to rotate relative to the pulley 3230. As shown, the user may rotate the pulley 3230 to rotate the seal 3114 in a clockwise or counterclockwise direction. More specifically, rotation of the pulley 3230 may push or pull the upper and lower yokes 3322, 3324 which pushes or pulls the upper and lower connection portions 3152, 3154 further or closer to the headgear 3118. As a result, the seal 3114 rotates upward or downward.

Figure 51E:
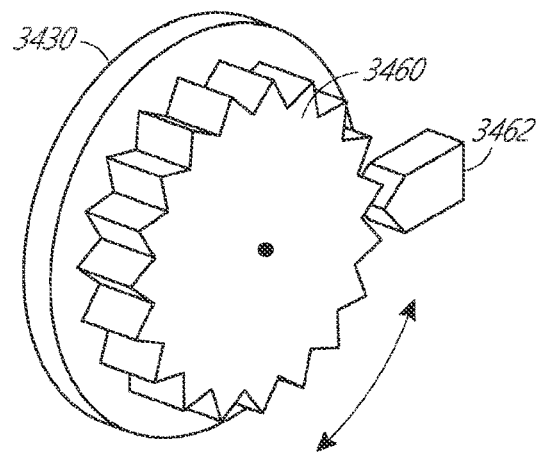
FIG. 51E is a side perspective view of a geared pulley for retaining the rotation position of the nasal seal.

As shown in FIG. 51E, the pulley 3430 may have a gear 3460 positioned on a side of the pulley 3430. The gear 3460 may engage a tooth 3462 that is attached to the headgear 3118. The tooth 3462 engages the teeth of the gear 3460 to inhibit or prevent rotation of the pulley 3430 such that the rotational orientation of seal 3114 is maintained. In some configurations, the pulley 3460 may have a toothed outer circumference. The pulley 3430 and the tooth 3462 may be formed from plastic such as Thermoplastic polyurethane (TPU).

Figure 51F:
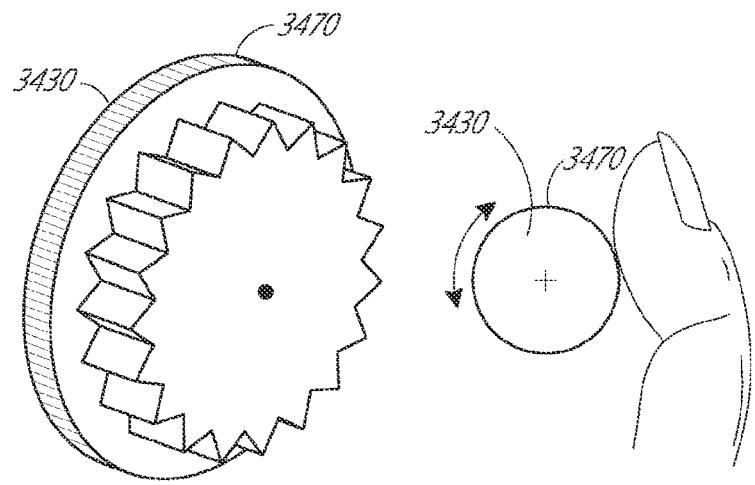
FIG. 51F is a side perspective view of a geared pulley having a knurled outer surface.
Figure 51G:
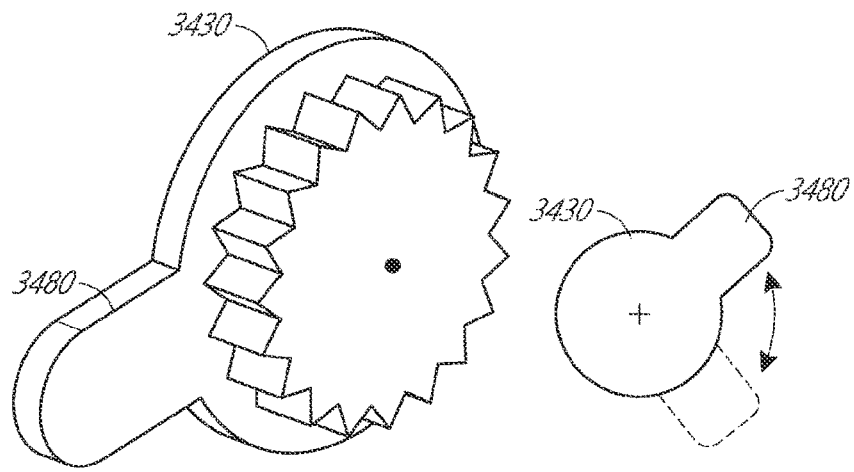
FIG. 51G is a side perspective view of a geared pulley having a lever.

FIG. 51F illustrates a pulley 3430 having a knurled outer circumference 3470. The texture provided by the knurled outer circumference 3270 provides increased grip to allow the user to overcome the retaining force of the tooth 3462 and rotate the pulley 3430. Similarly, FIG. 51G illustrates a pulley 3430 having a lever 3480 extending radially outward from a perimeter of the pulley 3430. Accordingly, the pulley 3430 may be rotated by turning the lever 3480.

Figure 52B:
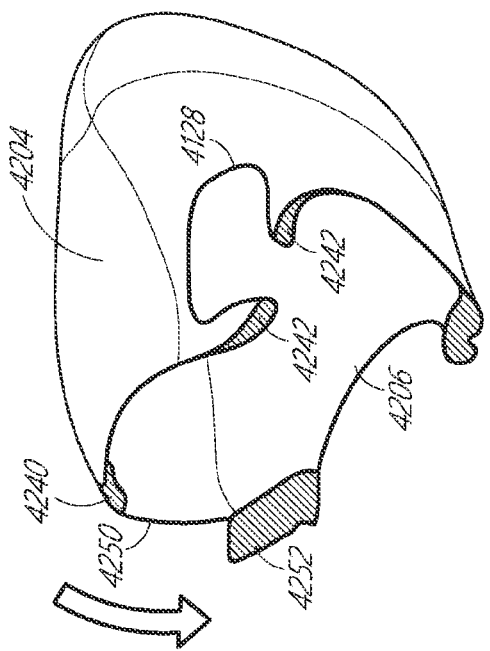
FIG. 52A is a perspective view of a rolling nasal seal.
Figure 52C:
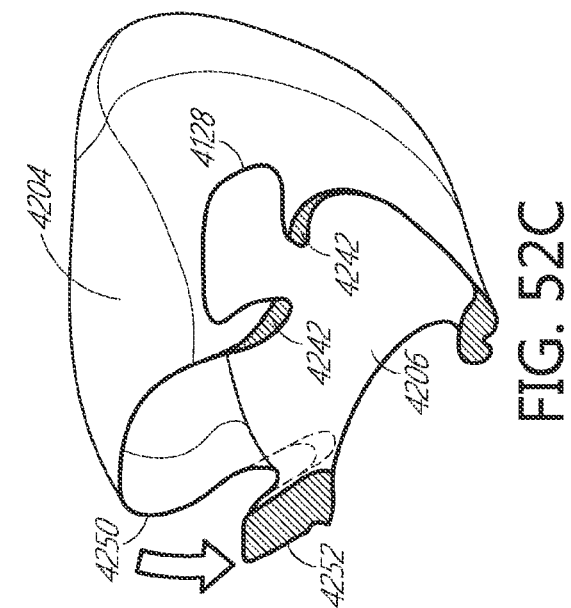
Figure 52A:
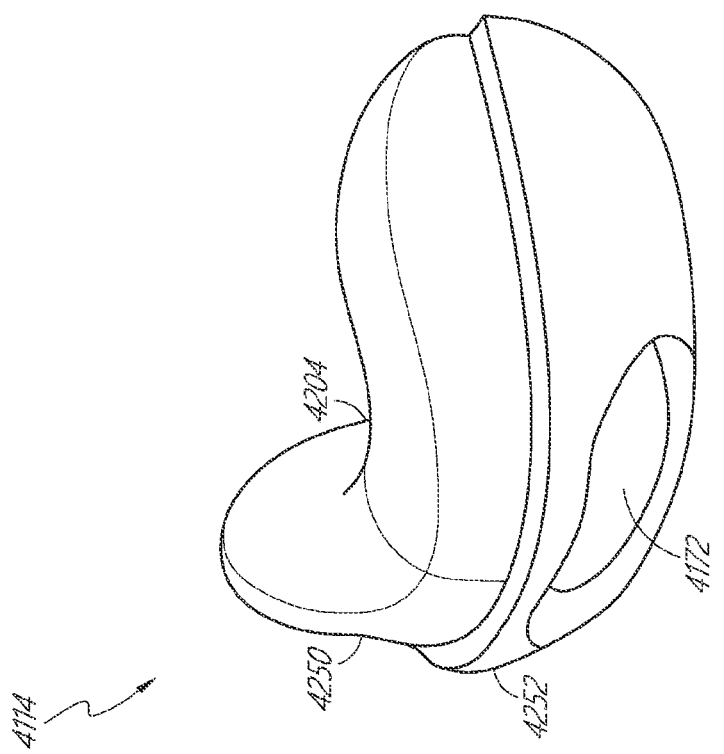

FIGS. 52A to 52C illustrate an alternative configuration of a rolling seal 4114 that deforms to comfortably fit user's noses within a wide range of upwardly or downwardly angles in order to minimize the amount of force applied to the user's subnasal region. In contrast to a mechanism that rotates the seal upward or downward in alignment with the angle of user's nose, the seal 4114 deforms and rolls downward over onto itself, which allows the seal 4114 to conform to the shape and angle of the user's nose. More specifically, the seal 4114 has regions of varying thickness or stiffness such that the deformation of the seal 4114 may be controlled and provided in predetermined regions of the seal 4114 when force is applied to the seal 4114 thereby minimizing the amount of force applied to the user's subnasal region. When the seal 4114 is removed, the upper outer peripheral region 4250 reverts back to its undeformed shape.

The seal 4114 has an aperture 4128 surrounded by an inward or rearward-facing central portion 4204 that faces or contacts the lower portion of the user's nose during use of the seal 4114. The central portion 4204 is connected to an upper outer peripheral region 4250 that surrounds the central portion 4204 and extends along lateral portions of the outer periphery of the seal 4114. A lower outer peripheral region 4252 is positioned below the upper outer peripheral region 4250 and also extends along a lower lateral portion of the outer periphery of the seal 4114. The upper outer peripheral region 4250 is connected to an inner upper edge of the lower outer peripheral region 4252 that is adjacent to the dead space 4206 of the seal 4114. A seal port 4172 may be formed at a center midpoint region of the lower outer peripheral region 4252.

FIG. 52B illustrates a vertical cross-section of the seal 4114. As shown, the thickness of the lower outer peripheral region 4252 (i.e., wall thickness of the seal 4114 at the lower outer peripheral region 4252) is much greater than the thickness of the upper outer peripheral region 4250. Accordingly, the lower outer peripheral region 4252 has significantly greater stiffness and rigidity than the upper outer peripheral region 4250. In some configurations, the lower outer peripheral region 4252 may be formed from a rigid plastic material upon which silicone portions of the seal 4114 is overmoulded thereon. As a result, when a downward force is applied to the central portion 4204 of the seal 4114 (i.e., if the user has a downwardly angled nose), the upper outer peripheral region 4250 rolls inward and downward onto itself and/or the lower outer peripheral region 4252, as shown in FIG. 52C. More specifically, the central portion 4204 moves downward and/or inward into the dead space 4206 of the seal 4114 in reaction to the force applied, which causes the upper outer peripheral region 4250 to collapse and roll inward into the dead space 4206 of the seal 4114 and downward onto itself and/or the lower outer peripheral region 4252. The rolling of the upper outer peripheral region 4250 allows the seal 4114 to move downward and/or inward to conform to the shape and angle of the bottom plane of the user's nose such that the force applied to the subnasal region of the user is reduced. In addition, by adjusting the thickness and stiffness of the upper outer peripheral region 4250, the force required to induce rolling of the upper outer peripheral region 4250 can be controlled, which controls the force applied against the nose of the user. For example, by progressively varying the thickness or stiffness, rolling of the upper outer peripheral region 4250 can become increasingly or decreasingly resisted over the range of movement.

The seal 4114 may include a stiffening portion or thickened band 4240 positioned between the upper outer peripheral region 4250 and the central portion 4204. The band 4240 may extend along the upper outer edge of the central portion 4204 on an inner wall of the seal 4114. The band 4240 reduces the prevalence of ballooning and provides additional structure between the upper outer peripheral region 4250 and the central portion 4204 to inhibit or prevent rolling of the central portion 4204 and facilitate rolling of the upper outer peripheral region 4250. The band 4240 can be a component formed of a material that is more rigid than, or that features increased stiffness relative to, the silicone or other material forming the seal 4114.

The seal 4114 may also include a thickened or stiffened aperture region 4242 around the aperture 4128. The reinforced aperture region 4242 may extend around or enclose the aperture 4128 to inhibit or prevent the edges of the aperture 4128 from deforming and collapsing into the dead space 4206 of the seal 4114. Further, the reinforced aperture region 4242 may also aid in transferring the downward force applied by the user's nose to the upper outer peripheral region 4250. Similar to the band 4240, the reinforced aperture region 4242 can be a component formed of a material that is more rigid than, or that features increased stiffness relative to, the silicone or other material forming the seal 4114.

In the illustrated configuration, the thickness of the upper outer peripheral region 4250 may be similar in thickness compared to the central portion 4204 and other regions of the seal 4114, except the lower outer peripheral region 4252 which is significantly thicker. However, in such a case, the central portion 4204 is reinforced by the thickened band 4240 to inhibit or prevent collapsing or rolling of the central portion 4204. In some configurations, the thickness of the seal 4114 along the upper outer peripheral region 4250 may be thinner than all other portions of the seal 4114 to provide a region of reduced stiffness relative to all other regions of the seal 4114 such that deformation and rolling is limited to only the upper outer peripheral region 4250.

While the illustrated configuration uses regions of varying thickness, other methods for providing regions of varied stiffness also can be used to induce rolling of the seal 4114. For example, the material of the seal 4114 can be configured to have regions of relative increased or decreased stiffness through material selection or material properties. In addition, a composite of materials can be used to provide regions of varying stiffness or rigidity. Moreover, a combination of any suitable techniques can be used. Nevertheless, the upper outer peripheral region 4250, which is configured with decreased thickness, provides a simple manner of achieving the region of increased stiffness.

FIGS. 53A to 53D illustrates an alternative configuration of a rolling seal 5114 that adjusts by deforming to accommodate users having a wide range of under nose angles, which is a combination of a user's nose angle and upper lip angle. Similar to the seal 4114 in FIGS. 52A-C, the seal 5114 has an upper outer peripheral region 5250 that rolls downward onto itself to accommodate users with negative nose angles. However, the seal 5114 also has a lower outer peripheral region 5252 that rolls upward onto itself to accommodate users with a protruding upper lip angle. That is, the upper and lower outer peripheral region 5250, 5252 rolls downward and upward, respectively, such that the seal 4114 is compressed to fit between the space between the user's nose and upper lip. When the seal 4114 is removed from the space between the user's nose and upper lip, the upper and lower outer peripheral region 5250, 5252 revert back to their undeformed shape.

The upper and lower outer peripheral regions 5250, 5252 may be separated by a rigid frame portion 5260. The rigid frame portion 5260 may be formed from thick silicone such the rigid frame portion 5260 is substantially inflexible. Alternatively, the rigid frame portion 5260 may be formed from a rigid plastic material upon which the upper and lower outer peripheral regions 5250, 5252 may be overmoulded thereon from a flexible material such as silicone. A seal port 5172 may be formed at a center midpoint region of the frontal region of rigid frame portion 5260. The rigid frame portion 5260 is illustrated as recessed inward relative to the outer lateral perimeter of the upper and lower outer peripheral regions 5250, 5252. However, in some configurations, it should be understood to one of ordinary skill in the art that the rigid frame portion 5260 may be flush with or protruding from the outer lateral perimeter of the upper and/or lower outer peripheral regions 5250, 5252.

Figure 53B:
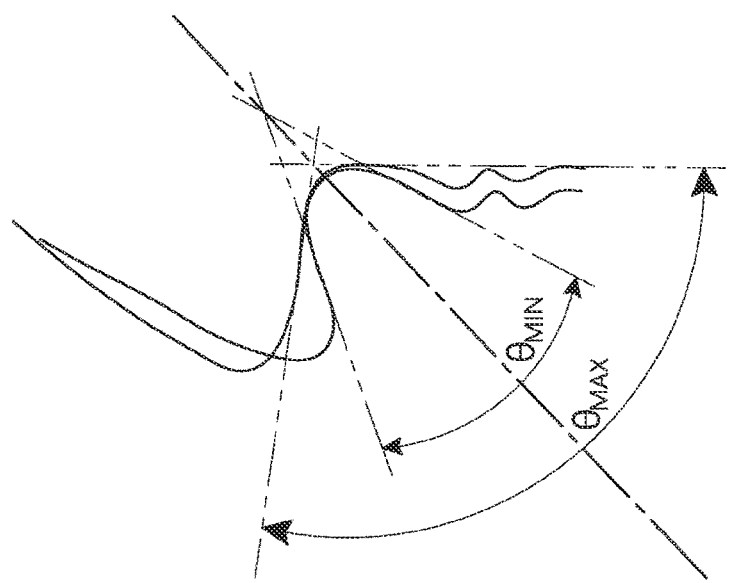
Figure 53A:
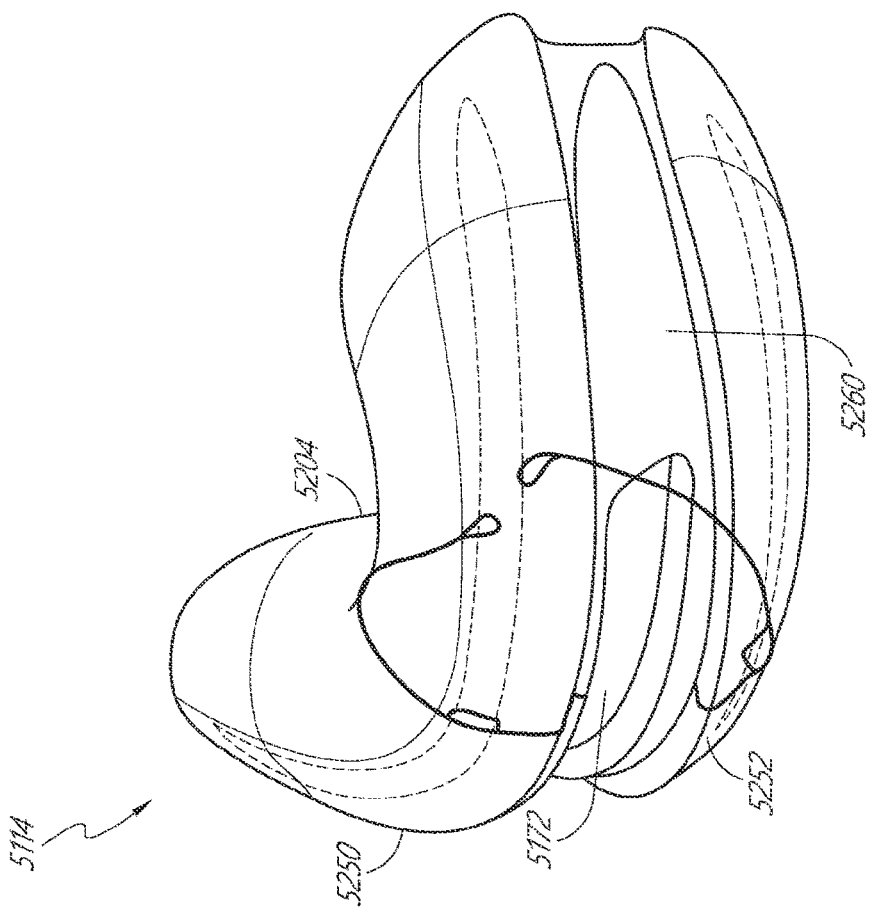

The seal 5114 having rolling upper and lower outer peripheral regions 5250, 5252 accommodates users having a wide range of under nose angles (i.e., nose angle and upper lip angle combinations). FIG. 53B is a comparative illustration showing a side profile of a user having a positive nose angle and a shallow upper lip angle that is overlaid over a side profile of a user having a negative nose angle and a protruding upper lip angle. An under nose angle is measured between the subnasal region and the upper lip. The user having a positive nose angle and a shallow upper lip angle is shown as having an under nose angle of $\theta_{MAX}$. The user having a negative nose angle and a protruding upper lip angle is shown as having an under nose angle of $\theta_{MIN}$. In other words, the under nose angle is greater for users having a positive nose angle and a shallow upper lip angle than for users having a negative nose angle and a protruding upper lip angle.

Figure 53D:
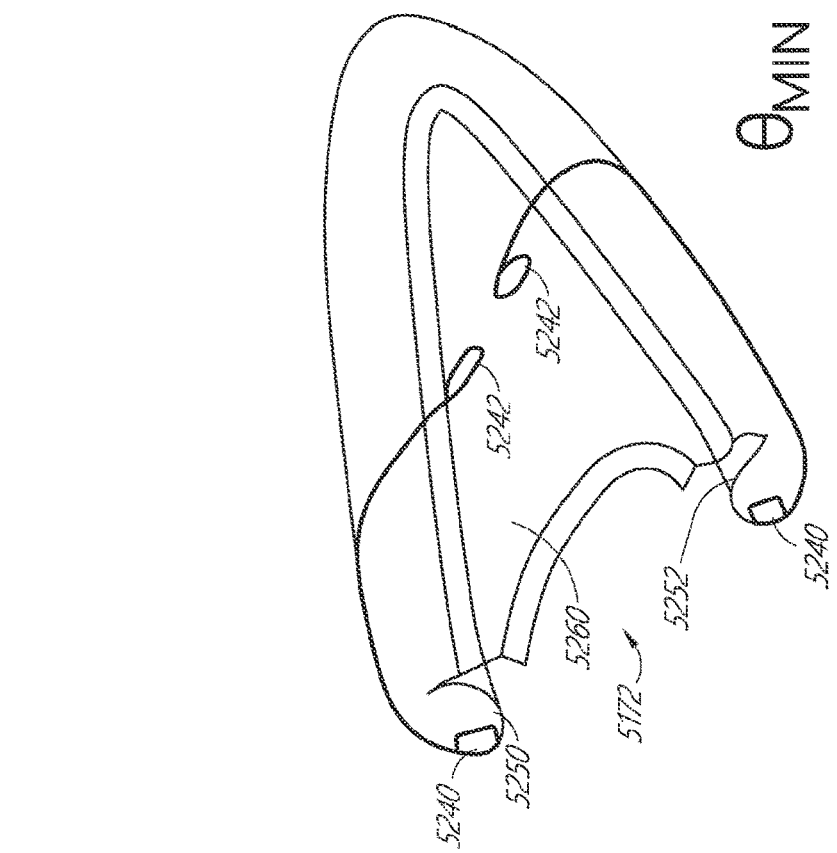
Figure 53C:
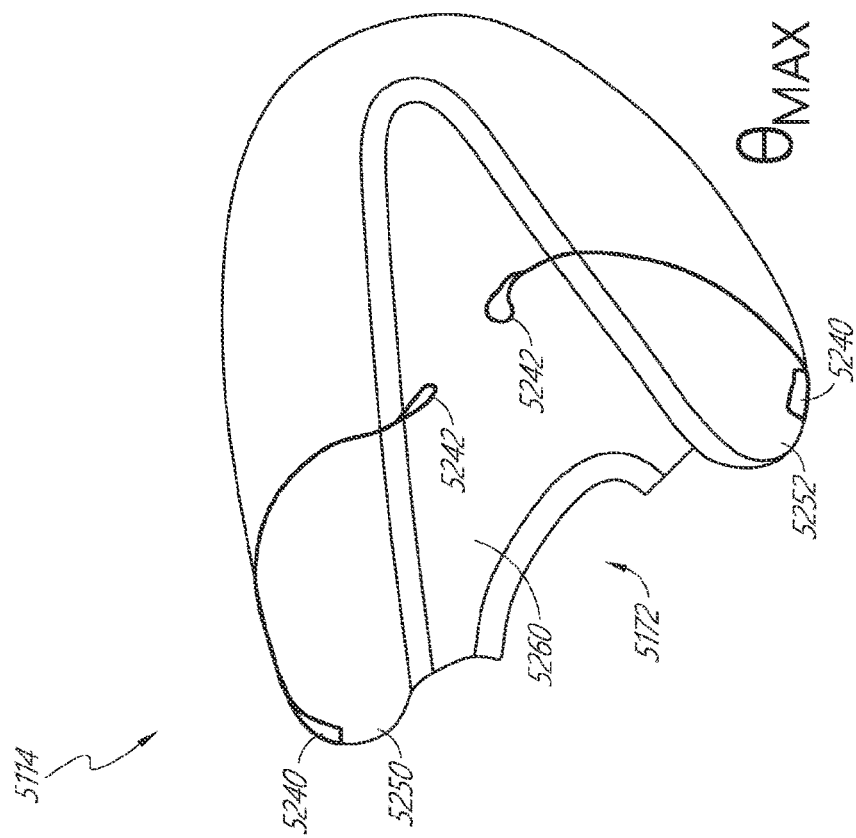

The seal 5114 accommodates users having under nose angles within the range of $\theta_{MIN}$ to $\theta_{MAX}$. FIG. 53C is a side view orientation of the seal 5114 configured to fit a user having an under nose angle $\theta_{MAX}$. As illustrated, the upper and lower outer peripheral regions 5250, 5252 are undeformed such that the seal 5114 may span the under nose angle $\theta_{MAX}$ and seal against the user's nose. FIG. 53D is a side view orientation of the seal 5114 configured to fit a user having an under nose angle $\theta_{MIN}$. In contrast, the upper and lower outer peripheral regions 5250, 5252 are deformed and rolled onto themselves such that the seal 5114 conforms to fit the under nose angle $\theta_{MIN}$ and seal against the user's nose while minimizing the amount of force applied to the user's subnasal region.

The upper and lower outer peripheral regions 5250, 5252 may be substantially similar in structure with the upper outer peripheral region 4250 and each other. As such, the upper and lower outer peripheral regions 5250, 5252 may deform similarly under similar forces. Accordingly, the seal port 5172 is balanced between the upper and lower outer peripheral regions 5250, 5252. Further, sustained vertical external forces are absorbed by the upper and lower outer peripheral regions 5250, 5252 as they roll and equalize at a new position. Temporary vertical external forces caused by, for example, incidental hose pulls, are absorbed by the upper and lower outer peripheral regions 5250, 5252 and the upper and lower outer peripheral regions 5250, 5252 will return toward or to their equalized position. In some configurations, the upper and lower outer peripheral regions 5250, 5252 may have different size, geometry and/or structure such that the upper outer peripheral region 5250 may provide a different force profile than the lower outer peripheral region 5252.

Figure 53E:
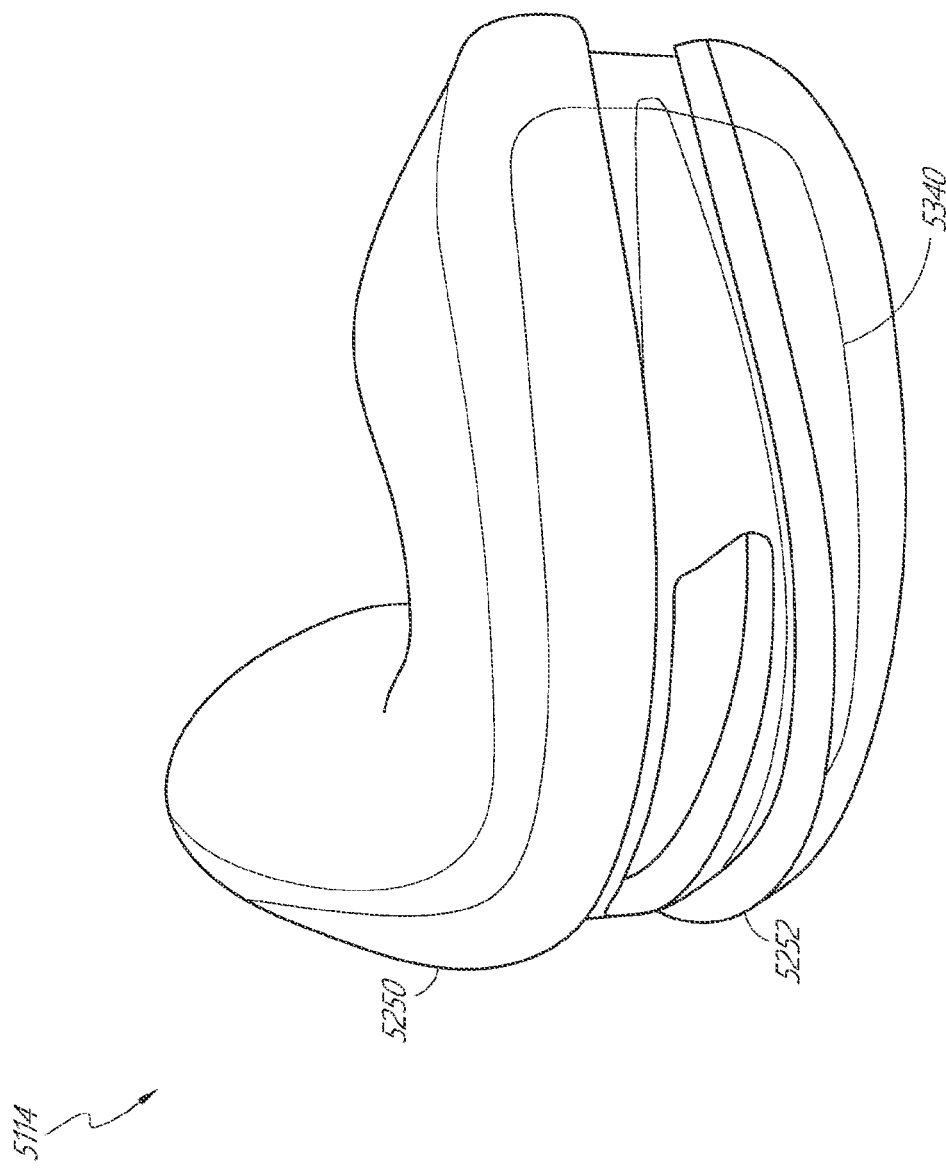

Similar to the seal 4114, stiffening portions or thickened bands 5240 extend around the outer uppermost edge of the upper outer peripheral region 5250 and the outer lowermost edge of the lower outer peripheral region 5252 on inner walls of the seal 5114. Further, the seal 5114 may also include a thickened or stiffened aperture region 5242 around the aperture 5128. The bands 5240 and the stiffened aperture region 5242 aid in transferring force applied by the user's nose and upper lip to the upper and lower outer peripheral regions 5250, 5252. FIG. 53E illustrates an alternative to the stiffening bands 5240. As shown, the seal 5114 may have a spring steel strip 5340 upon which the upper and lower outer peripheral regions 5250, 5252 are overmoulded. The spring steel strip 5340 facilitates rolling of the upper outer peripheral region 4250 by inhibiting or preventing rolling at other regions of the seal 5114.

FIGS. 54A to 54G illustrates an alternative configuration of a seal 6114 having a bellowing region 6202 that allows the seal 6114 to adjust to fit a range of nose lengths. The bellowing region 6202 is a deformable region of the seal 6114 that receives the user's nose and deforms to accommodate the length and shape of the user's nose and bellows outward and/or upward to relieve and reduce the amount of force acting against the user's nose. As shown in FIGS. 54A-B, the bellowing region 6202 is a flexible region formed from a thin-walled portion of the seal 6114. The bellowing region 6202 may have the thinnest wall thickness compared to all other portions of the seal 6114 such that the deformation occurs only in the bellowing region 6202. The thin wall thickness provides flexibility which allows the bellowing region 6202 to change shape by deforming inward and expanding outward. The bellowing region 6202 may include the central portion 6204 such that the bellowing region 6202 surrounds the aperture 6128. Further, the bellowing region 6202 may extend to include portions of the upper outer peripheral regions 6250. The seal 6114 may also include a thickened or stiffened aperture region 6242 around the aperture 6128. That is, the aperture 6128 may have thickened or stiffened aperture region 6242 that is formed from thickened silicone (i.e., relative to other portions of the seal 6114) such that the aperture 6128 is stiffened and strengthened so as to inhibit or prevent collapsing of the seal 6114 around the aperture 6128. Accordingly, the stiffened aperture region 6242 may ensure that the bellowing region 6202 of the seal 6114 deforms, as opposed to the regions around the aperture 6128, when the seal 6114 is fitted to the user.

FIG. 54C is a comparative illustration showing a side cross-sectional view of the seal 6114 fitted to a user having a longer nose overlaid over a side cross-sectional view of the seal 6114 fitted to a user having a shorter nose with an upward angle. As illustrated, the longer nose extends deeper into the seal 6114 compared to the shorter nose. As a result, the bellowing region 6202L deforms inward to receive the longer nose. Further, the bellowing region 6202L protrudes outwardly in forward and upward directions to increase the volume within the seal 6114 such that a pressure increase inside the seal 6114 is minimized. As a result, the amount of force acting against the longer nose decreases which increases comfort of the seal 6114. In addition, the thin surface provided by the bellowing region 6202L that extends up the user's nose improves the comfort of the seal 6114 because the amount of force is distributed over a greater amount of contact area with the nose. In contrast, the bellowing region 6202S inflates or extends toward the user to receive the shorter nose. The shorter nose does not extend deep into the seal 6114. As such, the bellowing region 6202S does not protrudes outwardly in forward and upward directions as the bellowing region 6202L.

FIG. 54D illustrates the seal 6114 fitted to a user having a longer nose with a level plane nose angle. FIG. 54E illustrates the seal 6114 fitted to a user having a longer nose with a negative nose angle. As shown, the bellowing region 6202 of the seal 6114 protrudes outwardly in forward and upward directions to accommodate both nose angles. Similarly, FIG. 54F illustrates the seal 6114 fitted to a user having a shorter nose with a positive nose angle. FIG. 54G illustrates the seal 6114 fitted to a user having a shorter nose with a negative nose angle. As shown, the bellowing region 6202 of the seal 6114 extends in the upward directions to accommodate both nose angles. In some configurations, the thickness and stiffness along the bellowing region 6202 may vary such that the seal 6114 may initially bellow or protrude upward along the user's nose improve comfort of the seal 6114 against the user's nose. After a threshold pressure or force is applied, the bellowing region 6202 may then bellow or protrude forward to relieve pressure within the seal 6114.

The comfort of a nasal pillow seal can be improved by avoiding having the nasal seal protrude into the nostrils of the user. Nasal seals that do not protrude into the user's nostrils may form a seal with the user by having surfaces that compress against the lower portion of the user's nose and upper lip. This can give the nasal seal a larger profile compared to a seal that protrudes into the nostrils of the patient. A problem with large-profile nasal pillow seals is that the seal can dislodge if the seal comes into contact with another surface, for example, when the user changes position onto their side. Reducing the profile of the nasal seal can reduce the perceived obtrusiveness of the seal and can reduce the negative effects experienced when sleeping on one's side. As a low-profile respiratory interface is smaller, it is less likely to come into contact with a pillow or another surface associated with sleeping that may dislodge the respiratory interface and break the seal on the patient's nose. However, a low-profile respiratory interface may have less surface area to form a seal with the user's skin. The respiratory interfaces disclosed herein provide a low-profile nasal seal that is comfortable to wear and maintains a good seal between the interface and the user.

FIG. 55 is a perspective view of another example of an interface assembly or respiratory mask system 110 that can be used with or incorporated into the system 10 of FIG. 1. The mask system 110 can be similar in at least some respect to the mask system 110 of FIGS. 2-22 and is described in the context of differences relative to the prior mask system 110. Components or features of the present mask system 110 that are not discussed in detail can be the same as or similar to the corresponding components or features of the prior mask system 110, or can be of another suitable arrangement. Accordingly, in some instances, the same reference numerals are used to refer to the same, corresponding or similar components or features. The respiratory mask system 110 comprises a mask 112, which in some configurations includes a seal 114 and a frame assembly or frame 116. The seal 114 can be connected to the frame 116 by a connector 7222. The respiratory mask system 110 also includes headgear 118 for securing the mask 112 to the user. The headgear 118 can include a yoke 127 that extends along the front of the mask 112. The yoke 127 can be integrally formed with the headgear 118. In some embodiments, the yoke 127 is removably connected to the frame 116. In certain variants, the yoke 127 is integrated with the frame 116. In the illustrated embodiment, the headgear 118 forms a closed loop from behind the head of the user to the front of the frame 116 and/or from the front of the frame 116 to the top of the head of the user. In preferred embodiments, the respiratory mask system 110 does not comprise a T-piece from the frame 116 extending upwardly (when worn) to connect to the headgear 118 at the user's forehead. However, if desired, aspects, features or components of the disclosed respiratory mask system 110 can be utilized in a design that incorporates a T-piece. The seal 114 does not rest on the bridge of the nose, thereby reducing the size and profile of the seal and making the seal less obtrusive. Also, by not resting on the bridge of the nose, the seal 114 is adapted to reduce any chance of pressure damage on the sensitive nasal bridge region.

In some configurations, the respiratory mask system 110 also comprises a short flexible tube or gas delivery conduit 120 that allows fluid communication with an interior of the seal 114 and which connects to the supply conduit 12 of the CPAP system 10 or other respiratory system. The gas delivery conduit 120 is connected to the mask 112 either directly or via a suitable connector, such as a hollow connector 122, which can be of any desirable or suitable shape, such as curved or bent (e.g., an elbow) or straight. In some configurations, the connector 122 can swivel about one or more swivel axes relative to the mask 112 so that the path of the gas delivery conduit 120 relative to the positioning of the mask 112 on the face of the user can adapt to the sleeping position of the user. However, in other arrangements, the connector 122 can be integral or unitary with the mask 112. In the illustrated embodiment, there is no connector 122, and the gas delivery conduit 120 is fixedly connected to the frame 116. The end of the gas delivery conduit 120 opposite the connector 122 can comprise a suitable connector 124 for connecting the gas delivery conduit 120 to the supply conduit 12. In some configurations, the connector 124 can be or comprise a swivel connector that allows relative rotation between the gas delivery conduit 120 and the supply conduit 12.

The respiratory mask system 110 preferably includes a limited flow outlet or bias flow vent 126 for providing gas washout from the respiratory mask system 110. In some configurations, the bias flow vent 126 is in the form of a collection of small apertures. The bias flow vent 126 may be provided in the frame 116, as shown, in the connector 122 or elsewhere on the respiratory mask system 110.

In some configurations, the mask 112 can comprise the seal 114, the frame 116, and the connector 122. In some configurations, the frame 116 (and, if desired, the connector 122) can be stiffer than at least a portion of the seal 114, such as the portion that defines a user-contacting surface. In some configurations, the seal 114 is removably coupled to the frame 116 around a passage through the frame 116 from the interior of connector 122. In the illustrated embodiment, the frame 116 acts as a hub or a connector between the seal 114, the gas delivery conduit 120, and the headgear 118. The frame 116 also provides rigid support to the seal 114 and/or connector 122. The frame 116 is preferably rigid or semi-rigid, and can also be formed from a thickened silicone or other plastic material. Thus, the seal 114 and the frame 116 together can form an enclosure having a gas flow inlet from the CPAP system 10 and an aperture 7128 (see, e.g., FIG. 58A) through the seal 114 to the user.

In some configurations, the headgear 118 comprises side arms 130 that extend outwardly (away from each other), rearwardly and upwardly at a shallow angle, past left and right extremities of the seal 114 and along the left and right cheeks and in particular cheekbones of a user to connect to the headgear 118 for holding the seal 114 on the face of a user. Such side arms 130 may be longer than they are deep or thick and may be resiliently flexibly connected to the frame and/or resiliently flexible along their length (width-wise but not heightwise). In some configurations, the side arms 130 extend toward or to a location between the ears and eyes of the user and/or to or near the temple of the user. In some embodiments, the side arms 130 extend along the cheeks and upward toward the top of the head to form a closed-loop headgear 118.

FIG. 56 shows an embodiment of the seal 114 and the frame 116. For clarity, the yoke 127 retaining structure is not shown. The yoke 127 would extend across the front or distal-facing surface of the frame 116. In the illustrated arrangement, the frame 116 defines a general U-shape when viewed from above. As discussed below, a connector 7222 can connect the seal 114 to the frame 116. The connector 7222 can function to provide support to the seal 114 and can resist deformation of the seal 114 when the seal 114 is under positive pressure in use.

FIG. 57 depicts a non-limiting embodiment of the frame 116. FIGS. 58A-C depict non-limiting embodiments of a seal 114. With reference to FIG. 57, the central portion of the frame 116 defines an aperture 7170 through which gases can flow. A first annular wall surrounds the aperture 7170 and projects in a rearward direction to define a support or connector 7172 for the seal 114. A second annular wall (containing the bias flow vent 126 and shown in FIG. 56) of the frame 116 surrounds the aperture 7170 and projects in a forward direction to define a support for the connector 122. With reference to FIGS. 58A-C, the seal 114 defines a gas inlet aperture 7175 configured to receive the connector 7172 of the frame 116. The seal 114 and the frame 116 can be removably coupled by any suitable arrangement, such as a friction-fit or snap-fit, for example. In the illustrated arrangement, the connector 7172 includes one or more recesses 7176 configured to receive a corresponding protrusion (not shown) of the seal 114 to create a snap-fit engagement between the seal 114 and the frame 116. However, this arrangement could also be reversed. Moreover, the entire arrangement could be reversed between the seal 114 and the frame 116 in that the seal 114 could include a male connector portion and the frame 116 could include a corresponding female connector portion. In some configurations, the seal 114 can include a connector 7222, as shown in FIGS. 72 and 73, that is formed around the gas inlet aperture 7175 of the seal 114. The connector 7222 can be formed from a rigid plastic (e.g., polycarbonate). The connector 7222 can be formed as part of the seal 114. For example, the seal 114 can be overmolded onto the connector 7222. In some embodiments, the connector 7222 is adhered to the seal 114 with adhesive or is connected to the seal 114 with a coupling or a fastener. In some configurations, the connector 7222 includes multiple pieces that capture the seal 114 therebetween. The connector 7222 allows connection between the frame 116 and the seal 114. In some embodiments, the frame 116 does not provide structural support for the seal 114. Rather, the frame 116 acts as a manifold that enables the headgear 118, gas delivery conduit 120, and the seal 114 in combination with the connector 7222 to be combined into a single respiratory mask system 110. The structural support for the seal 114 is provided on the distal face of the seal 114 by the connector 7222.

Preferably, the seal 114 and the frame 116 include an alignment or key arrangement such that the seal 114 and the frame 116 can only be assembled in the correct orientation relative to one another. Any suitable arrangement can be used. For example, the seal connector 7172 can include a recess 7180 configured to receive a key or protrusion (not shown) of the seal 114. The recess 7180 and protrusion can be located on an upper, central portion of the aperture 7170 and/or other locations along the perimeter of the aperture 7170. This arrangement could also be reversed. Moreover, other suitable arrangements could also be used, such as a non-circular shape of the connector 7172 and the gas inlet aperture 7175, for example. In some embodiments, the gas inlet aperture 7175 can have a general D-shape, with a bottom portion of the gas inlet aperture 7175 being flattened or closer than the other portions of the gas inlet aperture 7175 to a central point of the gas inlet aperture 7175. The frame 116 can include a D-shaped seal connector 7172 that mates with the D-shaped gas inlet aperture 7175 to ensure correct alignment and prevent rotation of the seal 114 relative to the frame 116. The D-shaped or non-circular gas inlet aperture 7175 can also reduce the overall height of the respiratory mask system 110, thereby making the respiratory mask system 110 less obtrusive and more desirable to use.

In the embodiment of FIG. 58A, the gas inlet aperture 7175a of the seal 114a is largely circular in shape with a diameter of about 29.7 mm to accommodate a circular gas delivery conduit. In some variants, the gas inlet aperture 7175a is between 28-34 mm. In the embodiment of FIG. 58B, the gas inlet aperture 7175b is largely circular in shape with a diameter of about 26.5 mm, but the lower edge of the gas inlet aperture 7175b includes a truncated portion 7177 having a marginally reduced diameter (FIG. 59B). This truncated portion 7177 can provide an intuitive indication of the orientation of a seal connector (FIGS. 72 and 73), discussed below. The truncated portion 7177 can be located on either or both lateral edges of the gas inlet aperture 7175, the upper edge, or any location about the perimeter of the gas inlet aperture 7175. In some variants, the gas inlet aperture 7175b is between 26-30 mm. In the embodiment of FIG. 58C, the gas inlet aperture 7175c is largely circular in shape with a diameter of about 28.4 mm. The lower edge of the gas inlet aperture 7175c includes a truncated portion 7177, discussed above. In some variants, the gas inlet aperture 7175c is between 28-32 mm.

The seal 114 has a hollow interior which is filled with air under positive pressure in use and is configured to seal under the nose of the user, along a portion of the face extending lateral to the nose, as well as along the upper lip of the user (FIGS. 63A-C). FIGS. 58A-C depict non-limiting embodiments of the seal 114. The seal 114 comprises at least one nasal opening or aperture 7128. The nasal aperture 7128 communicates between the hollow interior of the seal 114 and the rear wall 7202 (FIG. 66A-C) of the seal 114. The gas inlet aperture 7175 provides an opening between the hollow interior of the seal 114 and the front wall 7212 of the seal 114. In some configurations, the seal 114 can comprise more than one nasal aperture 7128. In some configurations, the seal 114 can comprise apertures 7128 defined within superstructures, such as pillows, prongs or the like. In some configurations, the nasal aperture 7128 can be defined by a nasal cushion or insert, which can be over-molded or otherwise secured to a base structure of the seal 114. Examples of suitable arrangements of the seal 114 are disclosed in Applicant's publication no. WO 2014/077708, the entirety of which is incorporated by reference herein.

As discussed in more detail below, the seal 114 can be designed so that the seal has a low-profile and maintains good sealing characteristics under positive pressures up to and including 18-20 mm $H_2O$. The profile of the seal 114 can be characterized by the distance the seal 114 extends beyond the user's nose. Generally speaking, the seal 114 in FIG. 58C has a lower profile compared to the seal 114 in FIG. 58A. The profile of the seal 114 of FIG. 58B is intermediate to the profiles of the seals in FIGS. 58A and 58C.

FIGS. 59A-C show front views of the seals 114 shown in FIGS. 58A-C. The seal 114 can have an overall height 7140 and an overall width 7142, as shown in FIGS. 59A-C. FIGS. 60A-C show left views of the seals 114 of FIGS. 59A-C. The seal 114 can have an overall depth 7144, as shown in FIGS. 60A-C. In some embodiments, the profile of the seal 7144 can be reduced by reducing one or more of the overall height 7140, overall width 7142, and/or overall depth 7144 of the seal 114. While specific dimensions are discussed herein, the proportions of the specific dimension relative to one another are considered within the scope of the present disclosure as well. For example, a disclosure of a height and a depth includes a disclosure of the ratio of the height to the depth.

In the illustrated embodiment of FIGS. 59A and 60A, the overall height 7140*a* is 42.1 mm, the overall width 7142*a* is 75.8 mm and the overall depth 7144*a* is 45.6 mm. In some configurations, the overall height 7140*a* is between 37-47 mm, between 40-44 mm, or is about 42 mm. In some configurations, the overall width 7142*a* of the seal 114*a* is between 72-82 mm, between 75-77 mm, or is about 76 mm. In some embodiments, the overall depth 7144*a* is between 40-50 mm, between 44-48 mm, or is about 46 mm.

In the illustrated embodiment of FIGS. 59B and 60B, the overall height 7140*b* is 41.0 mm, the overall width 7142*b* is 59.0 mm and the overall depth 7144*b* is 43.0 mm. In some configurations, the overall height 7140*a* is between 36-46 mm, between 39-43 mm, or is about 41 mm. In some configurations, the overall width 7142*b* of the seal 114*b* is between 54-64 mm, between 57-61 mm, or is about 59 mm. In some embodiments, the overall depth 7144 is between 38-48 mm, between 41-45 mm, or is about 43 mm.

In the illustrated embodiment of FIGS. 59C and 60C, the overall height 7140*c* is 35.6 mm, the overall width 7142*c* is 59.0 mm and the overall depth 7144*c* is 43.2 mm. In some configurations, the overall height 7140*c* is between 30-40 mm, between 33-37 mm, or is about 35 mm. In some configurations, the overall width 7142*c* of the seal 114*c* is between 54-64 mm, between 57-61 mm, or is about 59 mm. In some embodiments, the overall depth 7144*c* is between 38-48 mm, between 41-45 mm, or is about 43 mm.

In some configurations, the seal 114 is sized to fit different nasal structures. For example, the seal 114 can be provided in Small, Medium, Large, and Wide Models. In some embodiments, the seal 114 can be sized to fit the nasal structures of different ethnicities (e.g., Caucasians, Asians, African Americans). The aforementioned overall height 7140, width 7142, and depth 7144 ranges can be representative of a Medium Model of the different embodiments shown in FIGS. 59A-C. For the embodiment shown in FIG. 59C, the overall width 7142*c* may be from about 45 mm for a Small model to about 80 mm for a Large Model. The Large Model of the embodiment in FIG. 59C can have a similar height 7140*c* and depth 7144*c* as those of the Medium Model shown in FIG. 59C. In certain variants, the Large Model of the embodiment in FIG. 59C has a larger height 7140*c* and/or depth 7144*c* compared to the Medium Model shown in FIG. 59C. The Small Model of the embodiment in FIG. 59C can have a similar width 7142*c* as the Medium Model shown in FIG. 59C. In certain variants, the Small Model has a smaller width 7142*c*, height 140*c* and/or depth 7144*c* compared to the Medium Model shown in FIG. 6C. The Wide Model of the embodiment in FIG. 59C can have a width 7142*c* between 70-80 mm, between 73-77, or about 75 mm. The Wide Model of the embodiment of FIG. 59C can have a larger height 7140*c* and/or depth 7144*c* that is similar to those of the Medium model shown in FIG. 59C.

Referring to FIGS. 60A-C, the uppermost point 7182 of the gas inlet aperture 7175 can be disposed distal to the bottommost point 7184 of the gas inlet aperture 7175 when the bottom wall of the seal 114 is horizontal. As illustrated, a line passing through the uppermost and bottommost points 7182, 7184 of the gas inlet aperture 7175 can form an angle 7186 with a vertical line passing through the bottommost point 7184. This angle 7186 can be referred to as the gas inlet angle 7186. In the embodiment of FIG. 60A the gas inlet angle 7186*a* is 8.75° and the uppermost point 7182*a* is 4.65 mm distal of the bottommost point 7184*a*. In the embodiment of FIG. 60B the gas inlet angle 7186*b* is 13.2° and the uppermost point 7182*b* is 7.1 mm distal of the bottommost point 7184*b*. In the embodiment of FIG. 60C the gas inlet angle 7186*c* is 15.5° and the uppermost point 7182*c* is 8.1 mm distal of the bottommost point 7184*c*.

In some configurations, the gas inlet angle 7186 can range from between 5-30°, between 7-20°, or between 8-16°. In some variants, the gas inlet angle 7186 can be selected to reduce the volume within the hollow interior space of the seal 114. Reduction of the volume within the hollow interior space of the seal 114 can reduce the obtrusiveness of the seal 114. The volume within the hollow interior of the seal 114 can also be known as dead space. Reduction of the dead space can improve the flushing of expired air and carbon dioxide. The gas inlet angle 7186 can be selected to tilt the gas inlet aperture 7175 (and the gas delivery conduit that protrudes therefrom) toward the horizontal axis. Angling the gas delivery conduit that protrudes from the mask 112 toward the horizontal axis can allow the gas delivery conduit 120 to be connected to the supply conduit 12 without the use of an elbow connector. Angling the gas delivery conduit 120 toward the horizontal axis can reduce hose pull.

In addition to reducing the overall height 7140, width 7142, and depth 7144 dimensions of the seal 114, the profile of the seal 114 can be reduced by changing the shape of the seal 114. FIGS. 61A-C are rear views of the seals 114 shown in FIGS. 58A-C. Referring to FIGS. 61A-C, the rear wall 7202*c* of the embodiment of FIG. 61C has a more triangular shape compared to the rear surfaces 7202*a,b* of the embodiments of FIGS. 61A and 61B. As shown in FIGS. 61A-C, a rearward projection of the rear wall 7202 can define a perimeter that circumferentially surrounds the nasal aperture 7128. This perimeter can be referred to as a rear perimeter. The seal 114 shown in FIG. 61C has a rear perimeter that is smaller than that of the seal shown in FIG. 61A. In some variants, the profile of the seal 114 is reduced by reducing the rear perimeter of the seal 114.

The nasal aperture 7128 of the seal 114 is disposed in a central portion of the rear wall 7202. The central portion of the rear wall 7202 is distal to the lateral portions of the rear wall 7202, thereby forming a nasal recess 7214. In use, the nasal recess 7214 receives the tip portion of the user's nose. The seal 114 has a bottom wall 7216 that extends proximally upward to meet the rear wall 7202. In the embodiments of FIGS. 61B and 61C, the bottom wall 7216b,c and the rear wall 7202b,c meet to form a shelf 7218b,c near the bottom of the nasal recess 7214. The seal shown in FIG. 61A has a less well defined shelf. As described below, a more defined shelf 7218 can reduce the profile of the seal 114 by allowing the bottom portion of the seal 114 to tilt closer to the user's face, as shown in FIGS. 63A-C. A well-defined shelf 7218 can allow the volume of the hollow interior of the seal 114 to be reduced, thereby reducing the profile of the seal 114. The shelf 7218 can also improve the stability of the seal 114, allowing the size of the seal 114 to be reduced while maintaining good performance (e.g., sealing) of the seal 114.

FIGS. 62A-C are top views of the seals 114 shown in FIGS. 58A-C. Referring to FIGS. 62A-C, the rear wall 7202c of the embodiment of FIG. 62C extends distally further than do the rear surfaces 7202a,b of embodiments of FIGS. 62A and 62B. When the seal 114 is viewed from the top, the aperture 7128c of the seal 114c shown in FIG. 62C is closer to a distal-most point 7230c of the seal 114c than to a proximal-most point 7232c of the seal 114c. In the embodiment of FIG. 62A, the aperture 7128a is closer to a proximal-most point 7232a of the seal 114a than to a distal-most point 7230a of the seal 114a. In the embodiment shown in FIG. 62A, the front wall 7212a flares out more as it extends in the rear-ward direction compared to the front surfaces 7212b,c of the seals 114b,c shown in FIGS. 62B and 62C. The front surfaces 7212b,c maintain a parabolic form as the front surfaces 7212b,c extend in the rear-ward direction and, in some configurations, may continuously curve in one direction without a point of inflection. In contrast, the front wall 7212a of the seal 114a has a point of inflection 7201, as indicated in FIG. 62A. In some configurations, the proximal-most point of the rear surface 7202c is located within a distal half of the seal 114c or is located less than halfway from the distal-most point 7230c to the proximal-most point 7232a in a fore-aft direction of the seal 114c. In some configurations, the proximal-most point of the rear surface 7202c is located between about 30-50% or at about 40% of the distance from the distal-most point 7230c to the proximal-most point 7232a FIGS. 63A-C are side views of the seals 114 of FIGS. 58A-C positioned in use on a user's face. The seal 114 advantageously does not require contact with the bridge of the nose of the user. In the illustrated configuration, the seal 114 does not extend over the bridge of the nose of the user. More particularly, the illustrated seal 114 does not contact the bridge of the nose of the user.

With continued reference to FIGS. 63A-C, the profile of the seal 114 can be lowered by aligning the seal 114 along the base of the user's nose within the space between the user's nose and check. In the embodiment of FIG. 63C, the lateral portions of the seal 114c tuck further up into the space between the user's cheek and nose than do the lateral portions of the embodiments of the seal 114a,b shown in FIGS. 63A and 63B. In addition or in the alternative, a lower portion of the seals 114b and 114c are positioned closer to the face (e.g., upper lip) of the user in use than the lower portion of the seal 114a (with the lower portion of seal 114c being closer than the lower portion of seal 114b). Such an arrangement can provide for an advantageous orientation or angle of a gases delivery tube or conduit and/or of the frame or headgear. The orientation of the gas inlet aperture 7175 can be characterized by an angle 7240, also referred to as the use angle 7240. The use angle 7240 is the angle between the horizontal axis and a line that is normal to the line that extends between the uppermost and bottommost points 7182, 7184 of the gas inlet aperture 7175 when the nasal aperture 7128 is directed towards the nasal passage of the user. In the embodiment of the seal 114a of FIG. 63A, the use angle 7240a is about 30.0°. In other arrangements, such as the embodiments of FIGS. 63B and 63C, the use angle 7240b,c is greater than about 35° or greater than about 40°. In the embodiment of FIG. 63B, the use angle 7240b is about 43.7°. In the embodiment of FIG. 63C, the use angle 7240c is about 45.6°. Due to the variety of nasal shapes among the human population, the use angle 7240 may be subject to significant variation for a given seal. For example, the use angle 7240 can vary from about 0° to about 70°. However, it can be advantageous for the use angle 7240 to be relatively large to reduce the negative effects of hose pull. In some variants, the use angle 7240 can range from about 70° to about 90°.

The seal 114 can have an effective taper that is defined as a ratio of the depth 7144 (FIGS. 60A-C) of the seal 114 to the projected area of the lateral portion of the front wall 7212 when the seal 114 is viewed from the side. In calculating the effective taper, the front wall 7212 is considered to extend to the line extending between the uppermost and bottommost points 7182, 7184 of the gas inlet aperture 7175. In the embodiment of FIG. 63A, the effective taper has a value of about 0.37. In the embodiment of FIG. 63C, the effective taper has a value of about 0.39. In some variants, the profile of the seal 114 is reduced by increasing the use angle 7240, and/or by increasing the effective taper of the seal 114.

Referring to FIG. 64, the seal 114 can have a variable wall thickness. The thickened wall portions can be designed to provide a support structure that helps the seal 114 maintain contact with the user's skin when the seal 114 is in use. In some variants, the thickened wall portions help the seal 114 resist deformation when the seal 114 is in use. The thickened wall portions can allow less material to be used to make the seal 114, thereby reducing the profile of the seal 114. The thickened wall portions can extend into the hollow interior of the seal. For example, the thickened wall portions may extend proximally from the front wall 7212 and/or distally from the rear wall 7202.

The seal 114 can have regions of varying thickness. For example, each lateral side portion of the seal 114 can have a top region 7302, a back region 7304, a front region 7306, and a central region 7308. Only one side portion has the regions identified in FIG. 11. The regions of the other side can be a mirror image of the illustrated side. The back region 7304 can have a thickness that is greater than the thickness of all the other regions. The top region 7302 and/or the central region 7308 can have a thickness that is less than the thickness of all other regions. In the illustrated embodiment, the top region 7302 and the central region 7308 have a thickness of about 0.3 mm, the front region 7306 has a thickness of about 2.6 mm and the back region 7304 has a thickness of about 3.9 mm.

FIGS. 65A and 65B show the thickened wall portions or regions of the embodiment of the seal 114c shown in FIG. 58C. The regions shown in FIGS. 65A and 65B can be the same as or similar to the regions shown in FIG. 64. The thickened wall portions extend into the hollow interior of the seal 114c. In FIG. 65A, the outline of the seal 114c profile is shown for clarity. The top region 7302c and the central region 7308c have a thickness of about 0.3 mm, and the front region 7306c has a thickness of about 1.0 mm. The back region 7304c has a variable thickness, with a maximum thickness of about 1.45 mm. In some variants, the thickness of the top region 7302c and the central region 7308c is between about 0.2 mm and about 0.4 mm. The thickness of the front region 7306c is between about 0.7 mm and about 1.3 mm. The maximum thickness of the back region 7304c is between about 1.2 mm and about 1.7 mm.

As shown in FIGS. 65A and 65B, the back region 7304c is the shape of a "U" with the bottom of the "U" being disposed near the proximal-most point of the front wall 7212. The front region 7306c extends across the top of the "U"-like structure formed by the back region 7304c. The central region 7308c is enclosed by the front region 7302c and the back region 7304c. The top region 7302c extends from the back region 7304c away from the central region 7308c.

The thickness of the thickened wall portions in the seal 114c shown in FIG. 58C have been decreased compared to those of the seal 114a shown in FIG. 58A. Reducing the thickness of the wall portions assists in reducing the weight and/or the obtrusiveness of the seal 114. The thickness of the thickened wall portions can be increased to increase rigidity and friction between the seal 114 and the frame 116. In some variants, the thickness of the thickened wall portions is increased to increase the vertical stability of the seal 114.

FIGS. 66A-C show a sagittal cross-sectional view of the seal 114. In particular, FIGS. 66A-C show the seal 114c; however, certain features can be found in other arrangements of the seal 114, such as seals 114a and 114b. For the sake of comparison, the seals 114a, b, c are illustrated in FIGS. 67A-C. The thickness of the bottom wall 7216 of the seal 114 can vary. The bottom wall 7216 can have a distal thickness 7316 near the front wall 7212. The bottom wall 7216 can have a proximal thickness 7318 near the rear wall 7202. The bottom wall 7216 can have a central thickness 7320 disposed within a longitudinally central portion of the bottom wall 7216. In some arrangements, two or more of the distal thickness 7316, the proximal thickness 7318 and the central thickness 7320 vary relative to one another.

FIGS. 67A-C show sagittal cross-sectional views of the seal embodiments depicted in FIGS. 58A-C. The seal 114a shown in FIG. 67A has a distal thickness 7316a of about 1.5 mm and a central thickness 7320a of about 0.3 mm. The seal 114b shown in FIG. 67B has a distal thickness 7316b of about 2.4 mm and a central thickness 7320b of about 0.5 mm, and a proximal thickness 7318b of about 2.9 mm. The seal 114c shown in FIG. 67C has a distal thickness 7316c of about 1.35 mm and a central thickness 7320c of about 0.5 mm, and a proximal thickness 7318c of about 3.1 mm. As mentioned above, the seals 144b,c shown in FIGS. 67B and 67C have a clear distinction between the bottom wall 7216 and the rear wall 7202, forming a shelf 7218 in the form of a rounded edge on the proximal side of the bottom wall 7216. The seal 144a in FIG. 67A has a curved bottom wall 7216a with no clearly defined interface with the rear wall 7202a.

With continued reference to FIGS. 67A-C, the rear wall 7202 can have a thickened portion 7330 that surrounds the nasal aperture 7128. The thickened portion 7330 can extend distally from the distal-facing surface of the rear wall 7202 and can have a maximum thickness 7332. The thickened portion 7330 can be adapted to prevent the edges of the aperture 7128 from deforming (e.g., "blowing out") when the seal 114 is under pressure in use. Deformation of the aperture 7128 can reduce the effectiveness of the seal 114 and increase discomfort of the user. The thickened portion 7330 can improve effectiveness of the seal 114.

The seal 114a in FIG. 67A has an oval, pad-like thickened portion 7330a. The thickened portion 7330a has a maximum thickness 7332a of about 1.5 mm. The thickened portion 7330a gradually tapers as it extends away from the nasal aperture 7128. The seal 114b in FIG. 67B has a thickened portion 7330b that is similar to the thickened portion 7330a of the seal 114a shown in FIG. 67A.

Referring to FIG. 68, the seal 114b can include a thickened ridge 7340 that extends distally about 1.0 mm from the distal-facing surface of the rear wall 7202b. The ridge 7340 can be disposed between the interface of the thickened portion 7330b and the top region 7302b of the seal 114b. In some variants, the ridge 7340 reinforces the seal 114b to prevent the seal 114b from creasing as air pressure is increased in the hollow interior of the seal 114b. In some embodiments, the thickened portion 7330 can contribute to some distortion of the seal 114b as it is inflated. The ridge 7340 can allow the seal 114b to inflate smoothly. In some embodiments, the seal 114 having a thickened portion 7330 can inflate smoothly without the seal 114 having a ridge 7340. In certain variants, the seal 114c that has a thickened portion 7330c that closely matches the nasal aperture 7128 can inflate smoothly without the seal 114c having a ridge 7340.

FIG. 69 shows in greater detail the thickened portion 7330b of the seal 114b in FIG. 14B. The thickened portion 7330b extends a maximum distance 7334b of about 7.9 mm from the edge of the nasal aperture 7128. The thickened portion extends from the distal-facing surface of the rear wall 7202 a maximum thickness 7332b of about 1.5 mm.

FIG. 70 shows a detailed front view of the thickened portion 7330c of the seal 114c shown in FIG. 67C. The thickened portion 7330c matches the periphery of the nasal aperture 7128 more closely than do the thickened portions 7330a,b shown in FIGS. 67A and 67B. The thickened portion 7330c extends distally into the hollow interior of the seal 114c from the rear wall 7202c. The thickened portion 7330c has a maximum width of about 3.3 mm.

In many embodiments, the surface portion of the seal 114 surrounding or defining the nasal aperture 7128 is not in direct contact with the nose of the user. Instead, a volume of air separates the surface portion of the seal 114 surrounding or defining the nasal aperture 7128 and the portion of the user's nose that is within nasal recess 7214 of the seal 114. This separation between the seal 114 and the user's nose allows the area of the nasal aperture 7128 to be reduced without users feeling that the flow through the aperture 7128 is constricted. Referring to FIGS. 71A-C, the area of the nasal aperture 7128 can be evaluated by comparing the areas of rear-ward projections of the nasal aperture 7128. The rear-ward projection of the nasal aperture 7128 can have a minimum height 7342, a maximum height 7344, and an overall width 7346. The seal 144a in FIG. 71A has a minimum height 7342a of about 4.0 mm, a maximum height 7344a of about 12.0 mm, and an overall width 7346a of about 18.8 mm. The seal 144b in FIG. 71B has a minimum height 7342b of about 4.0 mm, a maximum height 7344b of about 11.0 mm, and an overall width 7346b of about 17.1 mm. The seal 144c in FIG. 71C has a minimum height 7342c of about 4.5 mm, a maximum height 7344c of about 11.0 mm, and an overall width 7346c of about 16.9 mm. Each of these aforementioned minimum heights 7342, maximum heights 7344, and overall widths 7346 can be increased or reduced by at least 20% in certain variants.

Another method of comparing the reduction in size of the nasal aperture 7128 for the seals 114 shown in FIGS. 71A-C is by comparing the surface area changes between the aperture 7128a shown in FIG. 71A to that of the aperture 7128c shown in FIG. 71C. The surface area of the aperture 7128 can be measured along the curved surface of the nasal recess 7214 to get a more accurate measurement than that obtained from the 2D rearward projection data discussed above. For the seal 114a in FIG. 71A, the surface area of the aperture 7128a along the curved surface of the nasal recess 7214a is approximately 161 mm². For the seal 114c in FIG. 71C, the surface area of the aperture 7128c along the curved surface of the nasal recess 7214c is approximately 141 mm². In some configurations, the surface area of the aperture 7128 is less than or equal to about 160 mm², less than or equal to about 150 mm² or less than or equal to about 141 mm² or 140 mm².

With reference to FIGS. 72 and 73, the seal 114 can include a connector 7222 (also referred to as a seal clip) that couples to the seal 114. In some embodiments, the connector 7222 can be a portion of the frame 116. For example, the connector 7222 can be a portion of the frame 116 that is permanently integrated with the seal 114 (e.g., overmolding the seal 114 over the connector 7222 portion of the frame 116). In certain embodiments, the connector 7222 includes a clip portion that allows connection to another frame 116 or to the yoke 127 or headgear 118. The connector 7222 can be configured to provide lateral support to the seal 114. The connector 7222 can have a front flange 7224, a rear flange 7226, and a hub portion 7228 disposed between the front and rear flanges 7224, 7226. The connector 7222 can be configured to capture a portion of the seal 114 between the front flange 7224 and the rear flange 7226. In some embodiments, the connector 7222 is over-molded onto the seal 114. In some embodiments, the seal 114 is over-molded onto the connector 7222. In some configurations, the front flange 7224 can connect to the rear flange 7226 by a snap-fit arrangement, which can be a permanent or removable connection.

When the connector 7222 is assembled to the seal 114, the rear flange 7226 is positioned within an interior of the seal 114 and the hub portion 7228 extends through the gas inlet aperture 7175 of the seal 114. The front flange 7224 of the connector 7222 is positioned on the exterior of the seal 114. The seal 114 can comprise an annular rim that encircles the gas inlet aperture 7175 and is configured to be captured by the front flange 7224 and the rear flange 7226 of the connector 7222.

The connector 7222 can have a central opening 7250 that aligns with the gas inlet aperture 7175 of the seal 114 when the connector 7222 is attached to the seal 114. The central opening 7250 can be configured to couple to a frame 116, a gas delivery conduit 120, an elbow connector 122, or other suitable means for connecting the connector 7222 to a CPAP system.

The connector 7222 can have side arms 7252 that extend proximally and laterally from the central opening 7250. The side arms 7252 can be configured to be more resistant to lateral deformation than the seal 114. The side arms 7252 can provide lateral support for the seal 114. The connector 7222 can ensure the seal 114 maintains its shape under pressure, enabling the seal 114 to effectively encompass the nose of the patient. In some variants, the front wall 7212 of the seal 114 may include a recess for receiving the side arms 7252 of the connector 7222. The profile of the seal 114 can be reduced by positioning the side arms 7252 to sit within the recess on the front wall 7212 of the seal 114. In some embodiments the side arms 7252 can be overmolded, chemically bonded or otherwise affixed to the seal 114. The side arms 7252 prevent the seal 114 from over expanding and losing a seal with the patient's nose. The side arms 7252 can prevent the seal 114 from severely deforming due to inflation from the pressure from the gases flowing through the patient interface 112.

FIG. 74 shows another embodiment of a seal 114d that is similar to the seal 114, 144a, 114b, 114c except as described differently below. The features of the seal 114d can be combined or included with the seal 114 or any other embodiment discussed herein. The illustrated embodiment has a connector 7222d attached to the seal 114d. The connector 7222d is similar to the connector 7222 except as described differently below. As discussed, the connector 7222d has side arms 7252d that extend proximally and laterally from the central opening 7250d and provide lateral support to the seal 114d. The connector 7222d has a rear flange 7226d that is positioned within an interior of the seal 114d. In the illustrated embodiment, the rear flange 7226d has a blue color and is visible through the translucent seal 114d. The color of the rear flange 7226d can help guide a user to connect properly the seal 114d with another component of the interface (e.g., gas delivery conduit 120). For example, the color of the rear flange 7226d may match the color of a portion of the gas delivery conduit 120, making intuitive for a user the connection of the gas delivery conduit 120 to the connector 7222d. In some embodiments, it is intended for coloring to be used as an indication of components in the seal 114. For example, the front flange 7224d can be completely transparent while the rear flange 7226d can be colored a transparent blue.

FIG. 75 shows another embodiment of a connector 7222e attached to a seal 114e. The seal 114e is similar to the seal 114 or any other embodiment discussed herein except as described differently below. The connector 7222e is similar to the connector 7222 or any other embodiment discussed herein except as described differently below. The features of the seal 114e and connector 7222e can be combined or included with the seal 114, or the connector 7222, or any other embodiment discussed herein. In the illustrated embodiment, a front wall 7254e of the connector 7222e is substantially flush with the front wall 7212e of the seal 114e. In some embodiments, at least a portion of the front wall 7254e of the connector 7222e can protrude laterally and/or distally beyond the front wall 7212e of the seal 114e. In some embodiments, at least a portion of the front wall 7212e of the seal 114e can protrude laterally and/or distally beyond the front wall 7254e of the connector 7222e.

As discussed above, the seal 114 can be made in different sizes to allow at least one of the seals 114 to fit a wider variety of nasal structures. For example, the seal 114 can be made in four different sizes: small, medium, large, and wide. The four sizes of the seal 114 can be configured to allow one or more of the available seals 114 to be suitable for as wide a variety of users. In some configurations, the four seal sizes can allow the seal 114 to be viable for a substantial portion or a maximum portion of the population. The seal 114 can be made in more than four different sizes (e.g., extra-large, medium-wide, extra-small).

FIGS. 76A-E show different views of the medium-sized seal 114e that is shown in FIG. 75. FIG. 76A is a front view of the seal 114e and is similar to the view shown in FIGS. 59A-C for the seals 114a-c. FIG. 76B is a left, side view of the seal 114e and is similar to the view shown in FIGS. 60A-C for the seals 114a-c. FIG. 76C is a rear view of the seal 114e and is similar to the view shown in FIGS. 61A-C for the seals 114*a-c*. FIG. 76D is a top view of the seal 114*e* and is similar to the view shown in FIGS. 62A-C for the seals 114*a-c*. FIG. 76E is a bottom view of the seal 114*e*.

As shown in FIG. 76A, the seal 114*e* can be symmetric relative to a vertical axis 7256. The vertical axis 7256 passes through a midline of the seal 114*e* and aligns with a sagittal plane that extends from the front of the seal to the rear of the seal 114*e*. As discussed above, the front wall 7212*e* of the seal 114*e* can have a recessed portion 7258*e*. The recessed portion 7258*e* can be configured to receive a portion of the connector 7222*e*. For example, the recessed portion 7258*e* can receive the front flange 7224 of the connector 7222. Referring to FIGS. 76A-B, the seal 114*e* can have an overall height 7140*e*, an overall width 7142*e*, and an overall depth 7144*e* that are similar to those described for the seals 114*a-c* shown in FIGS. 59A-7C above. Table 1 below shows an example of the approximate dimensions of the overall height 7140, the overall width 7142, and the overall depth 7144 for different sizes (e.g., small, medium, large, wide) of the seal 114. In some embodiments, one or more of the dimensions of a seal 114 may vary by ±10% of the dimension listed in Table 1. The present disclosure includes the ratios that can be derived from the dimensions herein disclosed. For example, the present disclosure includes not only the disclosed overall widths of the small and large seals but also the ratio of the width of the small seal to the width of the large seal and any other ratio that can be derived from the dimensions disclosed herein.

TABLE 1

Approximate dimensions of Small, Medium, Large, and Wide seal sizes.

| Seal Size | Overall Height (mm) | Overall Width (mm) | Overall Depth (mm) |
|---|---|---|---|
| Small | 36.2 | 59.0 | 43.2 |
| Medium | 38.0 | 58.6 | 41.2 |
| Large | 38.0 | 72.0 | 42.7 |
| Wide | 38.0 | 72.0 | 43.9 |

In some embodiments, the small- and medium-sized seals 114 are designed to be appropriate for approximately the same nose widths (also referred to herein as breadths), and are tailored to size experimentally according to a subnasal to pronasal dimension. For example, the small-sized seal 114 has a greater width than the medium-sized seal 114 because users of the small-sized seal 114 tend to have similar width or wider noses than users of the medium-sized seal 114. However, in the embodiments presented in Table 1, the difference in the overall widths 7142 between the small- and medium-sized seals 114 is minimal (0.4 mm).

FIG. 77 shows a perspective view of the medium-sized seal 114*e* shown in FIG. 76A. FIG. 78 shows a perspective view of an embodiment of a wide-sized seal 114*f*. As shown in FIGS. 77 and 78, the recessed portion 7258*e* of the medium-sized seal 114*e* can be more blunted compared to the recessed portion 7258*f* of the wide-sized seal. For example, in the illustrated embodiments, the recessed portions 7258*e,f* of the medium- and wide-sized seals 114*e,f* can be said to have a height dimension that is measured parallel to the vertical axis 7256. Compared to the height dimension of the medium-sized seal 114*e*, the height dimension of the wide-sized seal 114*f* decreases more slowly toward the lateral aspect 7260*e,f* of the recessed portion 7258*e,f*.

FIGS. 79A-B are left, side views of the medium-sized seal 114*e* shown in FIG. 77. Referring to FIG. 79A, a gas inlet angle 7186*e* can be formed by the vertical axis 7256 and the line passing through the uppermost point 7182*e* and the bottommost point 7184*e* of the gas inlet aperture 7175*e* when the bottom wall 7216*e* is aligned approximately horizontally, as described above with regard to FIGS. 60A-C. Because the bottom wall 7216*e* is curved, the whole bottom wall 7216*e* is not aligned horizontally, nor is the entire forward portion of the bottom wall 7216*e*. In the illustrated embodiment, the gas inlet angle 186*e* is 14.0°. In some embodiments, the gas inlet angle 7186*e* can be an angle other than 14.0°. A front wall distal displacement 7261*e* can be defined as the distance of a distal-most point of the seal 114*e* (which corresponds to the uppermost point 7182*e* in the illustrated arrangement) from the vertical axis 7256. In the illustrated embodiment, the front wall distal displacement 7261*e* is 7.9 mm. In some embodiments, the front wall distal displacement 7261*e* can be a value other than 7.9 mm. Angling the gas inlet aperture 7175 downward helps resist hose tug when the seal 114 is in use. For example, angling the gas inlet aperture 7175 downward can reduce tug from a gas delivery conduit 120 that is connected to the seal 114.

FIG. 79B illustrates another way of characterizing the size or shape of the seal 114 relative to the gas inlet aperture 7175. In FIG. 79B, the seal 114*e* is rotated to align the uppermost point 7182*e* and the bottommost point 7184*e* of the gas inlet aperture 7175*e* along the vertical axis 7256. A perpendicular distance 7262*e* (or another way to characterize a depth of the seal 114*e*) can be defined as the distance of a proximal-most point 7232*e* of the seal 114*e* from the vertical axis 7256. In the illustrated embodiment, the perpendicular distance 7262*e* is 35.2 mm. In some embodiments, the perpendicular distance 7262*e* can be a value other than 35.2 mm.

Table 2 shows a comparison of approximate perpendicular distances 7262 for seals 114 of different sizes (e.g., small, medium, large, wide). In some embodiments, one or more of the dimensions of a seal 114 may vary by +10% of the dimension listed in Table 2. As discussed above, the present disclosure includes the ratios that can be derived from the dimensions disclosed herein. As with Table 1 above, the medium-sized seal 114 can have a slightly smaller perpendicular distance 7262 compared to that of the small-sized seal 114 due to the applied anthropometric data set.

TABLE 2

Approximate front wall displacement for Small, Medium, Large, and Wide seal sizes.

| Seal Size | Front Wall Displacement (mm) |
|---|---|
| Small | 36.2 |
| Medium | 35.2 |
| Large | 37.0 |
| Wide | 37.2 |

FIG. 80 depicts a side view of the seal 114*e* positioned in use on a user's face. As described above with regard to FIGS. 63A-C, the orientation of the gas inlet aperture 7175*e* can be characterized by a use angle 7240*e*. The use angle 7240*e* can characterize the angle the seal 114 sits at on a user's nose with respect to the transverse plane of the user's head. In the illustrated embodiment, the use angle 7240*e* is approximately 45°. In other embodiments, the gas inlet aperture 7175*e* can be at different orientations. In some variants, the orientation of the gas inlet aperture 7175e can be dependent on the user's nose size and physical characteristics.

FIG. 81 shows a front view of the seal 114e shown in FIG. 76A. The orientation of the front view shown in FIG. 81 is different from the front view of the seal 114e shown in FIG. 76A because the view shown in FIG. 81 is aligned with a plane that is perpendicular to the axial direction of the gas inlet aperture 7175e. As discussed in more detail below, the seal 114e can include a connector engagement structure or a connector retaining structure 7262e that surrounds the gas inlet aperture 7175e. The other embodiments of the seal 114 disclosed herein can also include a connector retaining structure 7262 that is similar to the connector retaining structure 7262e described below. The connector retaining structure 7262e defines the gas inlet aperture 7175e and provides a structure that allows the connector 7222 (shown in FIG. 72) to be connected to the body of the seal 114.

The gas inlet aperture 7175e can include a truncated portion 7177e, as described with regard to FIGS. 59B and 59C. The truncated portion 7177e can provide an intuitive indication for the orientation of the connector 7222 of the seal 114. In the illustrated embodiment, the truncated portion 7177e is positioned on the bottom edge of the connector retaining structure 7262e. In some embodiments, the truncated portion 7177e can be positioned on the top edge of the connector retaining structure 7262e, on either or both of the lateral edges of the connector retaining structure 7262e, or on any combination thereof.

Because of the truncated portion 7177e of the connector retaining structure 7262e, the gas inlet aperture 7175e can have a vertical dimension 7264e that is different from a lateral dimension 7266e of the gas inlet aperture 7175e. For example, in FIG. 81, the truncated portion 7177e is positioned on the bottom edge of the connector retaining structure 7262e making vertical dimension 7264e of the gas inlet aperture 7175e smaller than the lateral dimension 7266e of the gas inlet aperture 7175e. In the illustrated embodiment, the gas inlet aperture 7175e has a vertical dimension 7264e that is 26.5 mm and a lateral dimension 7266e that is 31.17 mm. However, these dimensions are illustrative only and not intended to be limiting. In some embodiments, the vertical dimension 7264e has a value other than 26.5 mm, and the lateral dimension 7266e has a value other than 31.17 mm.

The seal 114e can have regions of differing thickness, as describe above with regard to FIG. 64. FIG. 82A shows an isometric view of the seal 114e. FIG. 82B shows that the seal 114e can have an apical region 7268e, a core region 7270e, and an intermediate region 7272e disposed between the apical region 7268e and the core region 7270e. The apical region 7268e of the seal 114e can have a thickness of approximately 0.3 mm. In the illustrated embodiment, the thickness of the apical region 7268e is reduced compared to that of other embodiments of the seal 114 (e.g., the seal 114 of FIG. 64). In the illustrated embodiment, the reduced thickness of the apical region 7268e increases the extent the seal 114e can flex and be compressed in use. Reducing the thickness of the apical region 7268e can reduce the forces imposed on the face of the user by the seal 114 when the seal 114 is in use.

With continued reference to FIG. 82B, the thickness of the intermediate region 7272e can be non-constant. In some embodiments, the thickness of the intermediate region 7272e can increase non-linearly as the seal 114e is traversed laterally along the intermediate region 7272e from a first point 7276e near the top of the seal 114e to a second point 7278e near the bottom of the seal 114e. In the illustrated embodiment, the thickness of the intermediate region 7272e is approximately 0.3 mm at the first point 7276e and approximately 3.4 mm at the second point 7278e. In some embodiments, the thickness of the intermediate region 7272e may simply vary (e.g., increase and decrease multiple times along the path between the first point 7276e and the second point 7278e) between approximately 0.3 mm and approximately 3.8 mm at various locations along the profile of the intermediate region 7272e. In the illustrated embodiment, the core region 7270e corresponds to the recessed portion 7258e of the front wall 7212e and has a wall thickness of approximately 1.00 mm. The thicknesses indicated above are the seal thickness as measured in a direction that is normal to the surface of the seal 114e. In some embodiments, one or more of the aforementioned thicknesses can vary by ±10% of these stated values.

FIG. 83 shows a left side view of a cross-section of a lateral portion of the seal 114e. In FIG. 83, the front portion of the seal 114e is shown in light shading to indicate the location of the selected cross-section with respect to the rest of the seal 114e. FIG. 83 shows an inner surface 7274e of the front wall 7212e of the seal 114e. The inner surface 7274e faces the hollow interior space of the seal 7114e. The differing thicknesses of the apical region 7268e, the core region 7270e, and the intermediate region 7272e are viewable in the cross-section of the front wall 7212e. The thickness profile of the front wall 7212e of the illustrated seal 114e allows the seal 114e to perform better when in use, as discussed below. The thin regions of the seal 114e allow the seal 114e to deform where required to better fit a user's nose. The thick regions of the seal 114e provide and transmit reinforcement forces that keep the seal 114e from blowing out when the seal 114e is under pressure in use.

FIG. 84 shows a left side view of a sagittal cross-section of the seal 114e, as described above with regard to FIGS. 66A-67C. The seal 114e can include a thickened portion 7330e that encompasses the nasal aperture 7128e, as described above with regard to FIGS. 69 and 70.

FIG. 85 shows a front view of the inner surface of the rear wall of the seal 114e. In the illustrated embodiment, the thickened portion 7330e can closely approximates the contours of the nasal aperture 7128e at the lateral edges of the nasal aperture 7128e and extends further away from the nasal aperture 7128e at the medial portions of the nasal aperture 7128e. As discussed above, the thickened portion 7330e can assist in preventing blow out of the seal 114e when the seal 114e is under pressure in use.

Referring back to FIG. 84, the maximum thickness of the thickened portion 7330e of the illustrated embodiment is 1.8 mm and is located on the central axis of the seal 114e immediately adjacent to the nasal aperture 7128e. In some embodiments, the maximum thickness of the thickened portion 7330e is greater than 1.8 mm. In some embodiments, the maximum thickness of the thickened portion 7330e is less than 1.8 mm. The ratio of the maximum thickness of the thickened portion 7330e to the adjacent portion of the rear wall 7202e can be 1.8:0.3 or 6:1.

With continued reference to FIG. 84, the bottom wall 7216e of the seal 114e has a forward portion 7280e, a rear portion 7282e, and a central portion 7284e interposed between the forward portion 7280e and the rear portion 7282e. The forward portion 7280e is characterized by an area of relatively high thickness adjacent to the connector retaining structure 7262e. As discussed below, at least a portion of the central portion 7284e can be characterized by a region of relatively low thickness. The region of the central portion 7284e that characterized by a region of relatively low thickness is referred to herein as a sub-nasal window 7285e (shown in FIG. 87). The rear portion 7282e is characterized again by an area of relatively high thickness with respect to the central portion 7284e. In the illustrated embodiment, the rear portion 7282e forms a clear distinction between the bottom wall 7216e and the rear wall 7202e. In the illustrated embodiment, the thickness of the forward portion 7280e is 2.7 mm, the thickness of the central portion 7284e is 0.3 mm, and the thickness of the rear portion 7282e is 2.7 mm, where the thickness is measured along a direction that is normal to the outer surface of the bottom wall 7216e. In some embodiments, one or more of the aforementioned thicknesses can vary by +10% of these stated values.

The sub-nasal window 7285e (shown in FIG. 87) of the central portion 7284e can be said to be a recessed surface on the inner face of the bottom wall 7216e. In some embodiments, the central portion 7284e can include a band of decreased thickness along a portion of the surface of the bottom wall 7216e that faces the hollow interior of the seal 114e. In the illustrated embodiment, the central portion 7284e is recessed approximately 2.4 mm with respect to the forward portion 7280e and the rear portion 7282e at the central axis of the seal 114e. In some embodiments, the entire central portion 7284e can be recessed with respect to the forward portion 7280e and the rear portion 7282e by a constant dimension.

Reducing the thickness of the central portion 7284e can improve the comfort of the seal 114e during prolong use. An issue that can occur with some nasal seal designs or some users is sub-nasal discomfort after periods of extended use. It was found that reducing the thickness of the central portion 7284e of the bottom wall 7216e improved the comfort of the seal 114. As mentioned, the reduced thickness of the central portion 7284e creates a sub-nasal window 7285e between the thickened forward and rear portions 7280e, 7282e of the bottom wall 7216e. The sub-nasal window 7285e allows increased deformation of the bottom wall 7216e of the seal 114e during use and does not compromise the effectiveness of the seal 114e. The increased thickness of the forward portion 7280e and the rear portion 7282e of the bottom wall 7216e increases the structural integrity of the seal 114e and allows the formation of an approximately air-tight seal with the user's face. The rear portion 7282e of the bottom wall 7216e assists in the formation of this air-tight seal against the user's lip and/or sub-nasal region.

In some variants, the extent to which the central portion 7284e is recessed can vary. For example, the central portion 7284e can be recessed a maximum amount at the central axis (shown in cross-section in FIG. 84) and recessed a minimum amount at the lateral ends of the central portion 7284e. In some embodiments, the central portion 7284e can include a combination of regions of adjacent increased or decreased thickness, thereby creating a plurality of regions that are recessed to different extents with respect to the forward and rear portions 7280e, 7282e. The boundaries between these adjacent regions can resemble step-wise function (e.g., abrupt changes in thickness). The boundaries between the adjacent regions can be smooth curves that transition in a continuous fashion from one level of recess to another. In some embodiments, the central portion 7284e can have an undulating thickness as the central portion 7284e extends laterally away from the central axis. For another example, the central portion 7284e can include a plurality raised ridges that extend parallel to one another laterally away from the central axis.

FIG. 86 shows a bottom view of an embodiment of the seal 114g that is similar to the seal 114 or any other embodiment discussed herein except as described differently below. The sub-nasal window 7285g of the seal 114g can have a proximal dimension 7286g that extends along the medial plane of the seal 114g from the distal most point of the sub-nasal window 7285g to the proximal most point of the sub-nasal window 7285g, as shown in FIG. 86. The sub-nasal window 7285g can have a lateral dimension 7288g that extends from the right most point of the sub-nasal window 7285g to the left most point of the sub-nasal window 7285g, as shown in FIG. 86. In the illustrated embodiment, the seal 114g has a sub-nasal window 7285g that has a proximal dimension 7286g of approximately 15.72 mm and a lateral dimension 7288g of approximately 32.45 mm. The overall depth 7144g of the seal 114e is 41.2 mm, making the ratio between the proximal dimension 7286g and the overall depth 7144g of the illustrated embodiment 1:2.6. The proximal dimension 7286g constitutes approximately 38% of the overall depth 7144g of the seal 114g. The overall width 7142g of the seal 114g is 58.6 mm, making the ratio between the lateral dimension 7288g and the overall width 7142g of the illustrated embodiment 1:1.8. The lateral dimension 7288g constitutes approximately 55% of the overall width 7142g of the seal 114g. These dimensions are illustrative and not meant to be limiting. In some embodiments, the dimensions and ratios can alter depending on the size of the seal 114.

FIG. 87 shows a top view of a cross-section of the seal 114e shown in FIG. 76A. The top view is taken along a plane that is perpendicular to the sagittal plane. Accordingly, the surface of the bottom wall 7216e that faces the hollow interior of the seal 114e is viewable in FIG. 87. As shown, the sub-nasal window 7285e can have a first width 7290e that is a measurement of the length of the sub-nasal window 7285e that intersects a proximal axis 7292 that extends along the midline of the seal 114e from the front wall 7212e to the rear wall 7202e of the seal 114e. As illustrated in FIG. 87, a reference line 7296e can be defined normal to the proximal axis 7292 and passing through the rearmost point of the sub-nasal window 7285e that lies on the proximal axis 7292. The sub-nasal window 7285e can have a second width 7294e that is a measurement of the width of the sub-nasal window 7285e at the lateral most point of the sub-nasal window 7285e that lies on the reference line 7296e, with the second width 7294e being aligned to cross the sub-nasal window 7285e in as short a distance as possible, as shown in FIG. 87. In the illustrated embodiment, the first width 7290e is approximately 5.9 mm and the second width 7294e is approximately 7.1 mm, making the ratio of the first width 7290e to the second width 7294e 1.0:1.2. These dimensions correspond to a medium-sized seal 114 and are meant to be illustrative and non-limiting. In some embodiments, the dimensions and ratios can alter depending on the size (e.g., small, medium, large, wide) of the seal 114.

In some embodiments, the second width 7294e can be the maximum width of the sub-nasal window 7285e. As discussed, the second width 7294e can be measured at a point of the sub-nasal window 7285e that is laterally displaced from the proximal axis 7292. In some embodiments, the sub-nasal window 7285e can maintain approximately the same width as the sub-nasal window 7285e extends laterally away from the proximal axis 7292.

FIG. 88 shows a bottom view of an embodiment of the seal 114h that is similar to the seal 114 or any other embodiment discussed herein except as described differently below. The illustrated embodiment is a wide-sized seal 114h.

In the seal 114*h* shown in FIG. 88, the sub-nasal window 7285*h* spans the bottom wall 7216*h* of the seal 114*h*. Having the sub-nasal window 7285*h* extend across the entire length of the bottom wall 7216*h* can be beneficial when compared to a sub-nasal window 7285 that only partially spans the length of the bottom wall 7216 (e.g., the sub-nasal window 7285*e* shown in FIG. 87) because a sub-nasal window 7285*h* with a longer lateral profile allows a longer length of the seal 114*h* to be compressed when in use. Accordingly, this can assist to further reduce potential sub-nasal discomfort.

FIG. 89 shows a top view of a cross-section of an embodiment of a wide-sized seal 114*i*. The top view is taken along a plane that is perpendicular to the sagittal plane. Accordingly, the surface of the bottom wall 7216*i* that faces the hollow interior of the seal 114*i* is viewable in FIG. 89. The first width 7290*i* of the seal 114*i* that is shown in FIG. 89 is greater than the first width 7290*e* of the seal 114*e* that is shown in FIG. 87. In the illustrated embodiment, the first width 7290*i* can be approximately 6.9 mm. As shown in FIG. 89, the sub-nasal window 7285*i* spans the length of the bottom wall 7216*i*. The seal 114*i* is similar to the seal 114*e* or any other embodiment discussed herein except as described differently below. The features of the seal 114*i* can be combined or included with the seal 114*e* or any other embodiment discussed herein. Accordingly, the sub-nasal window 7285*i* can have absolute dimensions and/or ratios and/or configurations similar to those described for the sub-nasal window 7285*e* or any other embodiment discussed herein.

FIG. 90 shows a rear perspective view of an embodiment of a medium-sized seal 114*j*. The sub-nasal window 7285*j* shown in FIG. 90 is similar to the sub-nasal window 7285*h* shown in FIG. 89 in that the sub-nasal window 7285*j* spans across the length of the bottom wall 7216*j*. The recessed portion 7285*j* of the central portion 7284*j* (also referred to herein as the sub-nasal window 7285*j*) can be seen extending laterally along the bottom wall 7216*j* and into a region between the front wall 7212*j* and rear wall 7202*j* of the seal 114*j*. Accordingly, the sub-nasal window 7285*j* can be said to laterally extend beyond what could strictly be referred to as the bottom wall 7216*j* of the seal 114*j*.

FIG. 91 shows a top view of a cross-section of an embodiment of a seal 114*k*. The top view is taken along a plane that is substantially perpendicular to the sagittal plane. Accordingly, the surface of the bottom wall 7216*k* that faces the hollow interior of the seal 114*i* is viewable in FIG. 91. In the illustrated embodiment, the central portion 7284*k* includes three sub-nasal windows 7285*k* characterized by a reduced wall thickness of the bottom wall 7216*k* of the seal 114*k*. In the illustrated embodiment, the three sub-nasal windows 7285*k* are partitioned by two struts 7287*k*, which are characterized by regions of increased thickness. The partitioned sub-nasal windows 7285*k* can improve the behavior of the seal 114*k* when the seal 114*k* is under compression. The sub-nasal windows 7285*k*, being regions of reduced thickness, can compress when the seal 114*k* is worn, thereby reducing the pressure imposed on the upper lip of the user. The struts 7287*k*, being thickened portions, can improve the ability of the seal 114*k* to retain its shape when deformed around a user's nose in the distal-to-proximal direction. In the illustrated embodiment, the struts 7287*k* have the same wall thickness as the adjacent front and rear portions 7280*k*, 7282*k*. In some embodiments, the struts 7287*k* can have a wall thickness that is different than the wall thickness of the adjacent front and rear portions 7280*k*, 7282*k*. For example, the struts 7287*k* can have a wall thickness that is greater than or less than the adjacent front and rear portions 7280*k*, 7282*k*. In some embodiments, the wall thickness of the sub-nasal window 7285*k* can vary across the sub-nasal window 7285*k*. For example, the wall thickness of the sub-nasal window 7285*k* can gradually increase over the length of the sub-nasal window 7285*k* so that the region of the sub-nasal window 7285*k* that is adjacent to the strut 7287*k* has the same wall thickness as the strut 7287*k*. Accordingly, the transition of the wall thickness between the sub-nasal window 7285*k* and the strut 7287*k* can be gradual over a length of the bottom wall 7216*k* rather than step-wise as shown in the embodiment of FIG. 91. The illustrated embodiment, has three sub-nasal windows 7285*k*. However, some embodiments may have four or more sub-nasal windows 7285*k*. Additionally, the struts 7287*k* of the illustrated embodiment are of approximately constant width (e.g., the dimension of the strut 7287*k* adjacent the front wall 7212*k* of the seal 114*k* is approximately the same as the dimension of the strut 7287*k* adjacent the rear wall 7202*k* of the seal 114*k*). In some embodiments, the width of the struts 7287*k* may not remain approximately constant. For example, the dimension of the strut 7287*k* adjacent the front wall 7212*k* of the seal 114*k* can be smaller than the dimension of the strut 7287*k* adjacent the rear wall 7202*k* of the seal 114*k* (e.g., the width of the strut 7287*k* increases when translating from the front wall 7212*k* to the rear wall 7202*k* of the seal 114*k* along the bottom wall 7216*k* of the seal 114*k*). In some embodiments, the opposite could also be the case (e.g., the width of the strut 7287*k* decreases when translating from the front wall 7212*k* to the rear wall 7202*k* of the seal 114*k* along the bottom wall 7216*k* of the seal 114*k*).

As discussed above with regard to FIG. 55, the seal 114 can be attached to a connector 7222 that assists in providing structure to the seal 114 when the seal 114 is under pressure in use. In addition, the connector 7222 can provide a means for connecting the seal 114 to a frame 116 of a mask 112. As shown in FIG. 72, the connector 7222 can include a front flange 7224 and a rear flange 7226. The front flange 7224 and rear flange 7226 can include cooperating structures to retain between them the connector retaining structure 7262 of the seal 114.

FIGS. 92A-G show different views of the embodiment of a front flange 7224*e* shown in FIG. 75. The front flange 7224*e* is similar to the front flange 7224 except as described differently below. The features of the front flange 7224*e* can be combined or included with the front flange 7224 or any other embodiment discussed herein. FIG. 92A shows a front perspective view of the front flange 7224*e*. FIG. 92B shows a rear perspective view of the front flange 7224*e* shown in FIG. 92A.

As shown in FIG. 92A, the front flange 7224*e* can include a forward surface 7350*e*, a rearward surface 7352*e*, a central opening 7250*e*, and side arms 7252*e* that extend proximally and laterally away from the central opening 7250*e*. In the illustrated embodiment, the front flange 7224*e* is symmetric with respect to a sagittal plane of the front flange 7224*e*. As shown in FIG. 92B, the front flange 7224*e* can include a first clip retaining projection 7354*e* and a second clip retaining projection 7356*e*. In the illustrated embodiment, the first and a second clip retaining projections 7354*e*, 7356*e* have a semi-circular shape and are located on the rearward surface 7352*e*, adjacent to the central opening 7250*e* of the front flange 7224*e*. The first clip retaining projection 7354*e* is spaced apart vertically from a second clip retaining projection 7356*a*. The rearward surface 7352*e* of the side arms 7252*e* is configured to cooperate with the recessed portion 7258*e* of the seal 114*e*. As shown, each of the side arms 7252*e* twists slightly as it extends proximally away from the central opening 7250e. The twist of the side arms 7252e is configured to match the profile of the recessed portion 7258e of the seal 114e. As discussed above, the side arms 7252e of the front flange 7224e act to provide rigidity and a form of structural integrity to the seal 114e.

FIG. 92C is a front view of the front flange 7224e. FIG. 92D is a left side view of the front flange 7224e. FIG. 92E is a rear view of the front flange 7224e. As shown in FIG. 92E, the front flange 7224e can include a rim 360e that surrounds the central opening 7250e of the front flange 7224c. FIG. 92F is a top view of the front flange 7224e. FIG. 92G is a bottom view of the front flange 7224c.

FIGS. 93A-G show different views of an embodiment of a rear flange 7226e. The rear flange 7226e is similar to the rear flange 7226 except as described differently below. The features of the rear flange 7226e can be combined or included with the rear flange 7226 or any other embodiment discussed herein. FIG. 93A shows a front perspective view of the rear flange 7226e. FIG. 93B shows a rear perspective view of the rear flange 7226e shown in FIG. 93A.

Referring to FIGS. 93A-B, the rear flange 7226e can include a collar 7362e, a first clip retaining recess 7364e, a second clip retaining recess 7336e, a plurality of locating features 7368e, a plurality of frame retaining members 7370e, and a rim 7372e to secure the seal 114e. In the illustrated embodiment, the locating features 7368e are similarly sized. However, this does not need to be the case. In some embodiments, the locating features 7368e are shaped differently from one another. In some embodiments, the locating features 7368e can be shaped differently from each other to reduce material used in manufacturing. The first clip retaining recess 7364e and the second clip retaining recess 7336e are adapted to cooperate with the first clip retaining projections 7354e and the second clip retaining projections 7356e respectively to allow the front and rear flanges 7224e, 7226e to be aligned and secured together with the correct spacing between the front and rear flanges 7224c, 7226e. The front and rear flanges 7224e, 7226e can then be welded together. In some embodiments, the first clip retaining projection 7354e is sized differently than the second clip retaining projection 7356e to prevent inversion or positioning upside down of the rear flange 7226e relative to the front flange 7224e.

The orientation of one or more of the clip retaining projections and recesses can be reversed, with one or more of the projections being disposed on the rear flange 7226e and one or more of the recesses being disposed on the front flange 7224e. In some embodiments, the rear flange 7226e can include retaining projections instead of retaining recesses, and the front flange 7224e can include cooperating retaining recesses. In certain variants, there can be less than two corresponding recesses and projections to secure the front and rear flanges 7224e, 7226e.

The frame retaining members 7370e allow the frame 116 (shown in FIG. 55) to be secured to the connector 7222e and the seal 114e via a push fit or interference fit system. The front flange 7224e and the rear flange 7226e can be closed together so that they secure the connector retaining structure 7262e of the seal 114e within the connector 7222e, as described below. In at least one embodiment, the rear flange 7226e can include only one frame retaining member 7370e. In some embodiments, the rear flange 7226e can include 3 or more frame retaining members 7370e.

The locating features 7368e assist the manufacturing of the completed seal 114e and frame 116. The locating features 7368e fit into corresponding recesses adjacent to the perimeter of the gas inlet aperture 7175e of the seal 114e. The presence of these cooperating features allows the rear flange 7226e and the seal 114e to be easily aligned with one another. In at least one embodiment, the rear flange 7226e can include 2 or less locating features 7368e. In some embodiments, the rear flange 7226e can include 4 or more locating features 7368e.

In at least one embodiment, after the rear flange 7226e, the seal 114e, and the front flange 7224e have been secured together, the rear flange 7226e can be bonded to the front flange 7224e so that the configuration of the connector 7222e and the seal 114e is substantially difficult to disassemble. The rear flange 7226e and the front flange 7224e can be bonded together through any appropriate means (e.g., RF welding, adhesive bonding, etc.).

Figure 93E:
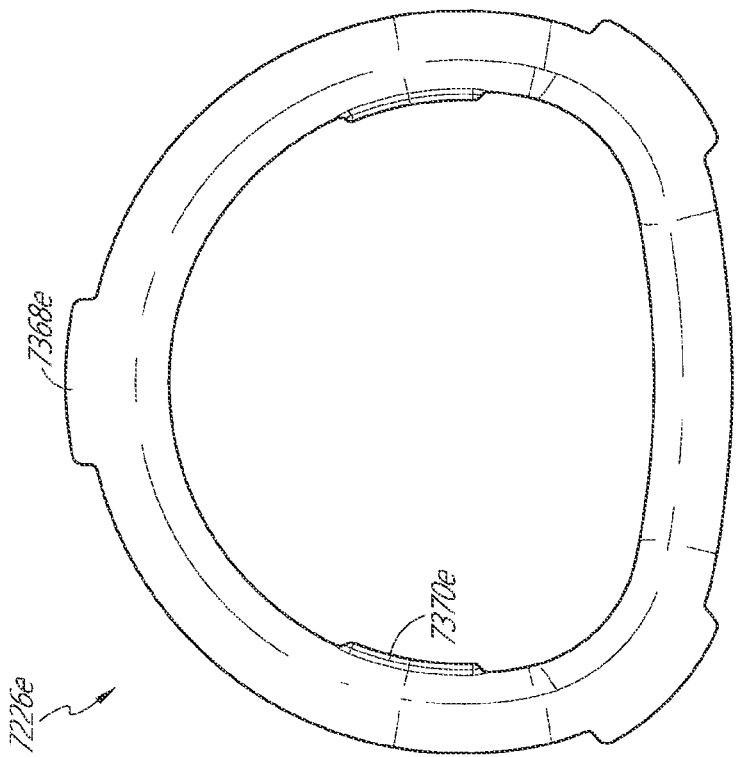

FIG. 93C is a front view of the rear flange 7226e. FIG. 93D is a left side view of the rear flange 7226e. FIG. 93E is a rear view of the rear flange 7226e. FIG. 93F is a top view of the rear flange 7226e. FIG. 93G is a bottom view of the rear flange 7226e.

FIG. 94 shows a rear perspective view of the front flange 7224e attached to the rear flange 7226e. In the illustrated embodiment, the connector 7222e is formed by assembling the front flange 7224e and the rear flange 7226e. The seal 114e is not shown in FIG. 94.

FIG. 95 shows a left side view of a cross-section of the assembled seal 114e and connector 7222e. The cross-sectional plane is the sagittal plane described above with regard to FIGS. 65A-C and 84. As shown in FIG. 95, the connector retaining structure 7262e of the seal 114e is secured between the front flange 7224e and the rear flange 7226e when the connector 7222e is assembled onto the seal 114e.

FIG. 96 shows a zoomed in cross-section of an embodiment of the seal 114m on a plane parallel to the sagittal plane of a user. In the illustrated embodiment, the front flange 7224m and the rear flange 7226m fit together to secure the connector retaining structure 7262m of the seal 114m via interference fit. As a result, a user can disassemble the seal 114m, the front flange 7224m, and the rear flange 7226m as desired.

FIG. 97 shows a cross section of an embodiment of a seal 114n, a front flange 7224n, and a rear flange 7226n. In the illustrated embodiment, the rear flange 7226n is welded to the front flange 7224n as shown by the weld 7380n. The connector 7222n is designed to be assembled in such a way that no plastic parts can break in normal use. This reduces the risk that a plastic component could break and be inhaled. The weld 7380n assists this because the connector 7222n must be broken to detach the connector 7222n from the seal 114n. The rear flange 7226n is sized such that an interference fit 7382n is formed with the seal 114n as indicated. The seal 114n is compressed at the indicated point of the interference fit 7382n to form the fit. This fit is beneficial in preventing foreign material from becoming lodged in crevasses of the apparatus. The weld 7380n shown in FIG. 97 can be a "shear weld."

FIG. 98 shows a cross section of an embodiment of a seal 114p, a front flange 7224p, and a rear flange 7226p. The rear flange 7226p is welded to the front flange 7224p, however the weld 7380p in the illustrated embodiment is a "face weld."

FIG. 99 shows a cross section of an embodiment of a seal 114q, a front flange 7224q, and a rear flange 7226q. The rear flange 7226q is welded to the front flange 7224q, however the weld 7380q is configured as shown. In the illustrated embodiment, the weld 7380q is a "shear weld."

A benefit of the connectors 7222 shown in FIGS. 96 and 97 is that gas flowing through central opening 7250 of the front flange 7224 can enter and exit the hollow interior of the seal 114 without encountering a ledge of the rear flange 7226. By contrast, in the connectors 7222 shown in FIGS. 98 and 99, gas flowing through the central opening 7250 of the front flange 7224 will encounter a ledge or gap formed between the front flange 7224 and the rear flange 7226 in the vicinity of the weld 7380.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A nasal seal, comprising:
    a seal body defining a breathing chamber, the seal body configured to receive a user's nose and sealingly contact an underside of the user's nose;
    a nasal port in the seal body positioned beneath the nares of wearer; and
    wherein the nasal seal comprises a pair of thickened wall portions that, in use, contact the user's cheeks, wherein the pair of thickened wall portions each extend into a bottom wall of the seal body, the thickened wall portions each having a wall thickness that is greater than a wall thickness of adjacent portions of the seal body, the thickened wall portions each comprising a groove defined within the thickened wall portion that allows decoupled movement of portions of the thickened wall portion on opposing sides of the groove, wherein each groove extends laterally into and has an end located within the bottom wall of the seal body, wherein the ends of the grooves are separated from one another by a region of increased thickness in the bottom wall.

2. The nasal seal of claim 1, wherein the nasal port comprises a central portion positioned between a pair of lateral portions, the nasal port further comprising an upper edge and a lower edge; wherein the lower edge defines an inwardly projecting portion within the central portion.

3. The nasal seal of claim 2, wherein the inwardly projecting portion is curved.

4. The nasal seal of claim 1, wherein the nasal port is kidney-shaped or bowtie-shaped.

5. The nasal seal of claim 1, further comprising a thickened rim portion extending around a portion or an entirety of a periphery of the nasal port, the thickened rim portion having a larger wall thickness than a portion of the seal body immediately adjacent the thickened rim portion.

6. The nasal seal of claim 1, wherein the seal body comprises a central portion positioned between a pair of lateral portions, wherein in use the seal body is configured such that the lateral portions move inwardly when pressure is applied to the central portion by a user.

7. The nasal seal of claim 1, wherein a user-facing surface of the nasal seal comprises a thinned wall portion.

8. The nasal seal of claim 7, wherein the thinned wall portion of the user-facing surface has or is equal to the smallest wall thickness of the seal body.

9. The nasal seal of claim 1, wherein the wall thickness of the thickened wall portions define or are equal to a largest wall thickness of the seal body.

10. The nasal seal of claim 1, further comprising a connector configured to allow the nasal seal to be coupled to a frame, wherein the connector comprises a first portion within the seal body and a second portion outside of the seal body, wherein the first portion and the second portion are coupled to one another.

11. The nasal seal of claim 10, wherein the first portion comprises a flange and a hub, wherein the hub extends through an aperture of the seal body and wherein the second portion is coupled to the hub of the first portion.

12. The nasal seal of claim 11, wherein the seal body comprises a rim extending partially or entirely around the aperture, wherein the rim is captured between the first portion and the second portion.

13. The nasal seal of claim 12, wherein the rim comprises a generally T-shaped cross-section having a base, a first lobe extending in a first direction from the base and a second lobe extending in a second direction from the base opposite the first direction.

14. The nasal seal of claim 13, wherein each of the first portion and the second portion of the connector comprises a recess configured to receive a respective one of the first lobe and the second lobe.

15. The nasal seal of claim 10, wherein the seal body and the connector comprise interfering portions that inhibit or prevent relative rotation between the seal body and the connector.

16. The nasal seal of claim 1, wherein the seal body has a first texture on a user-contacting side and a second texture on the opposite side, wherein the second texture is different from the first texture.

17. The nasal seal of claim 1, wherein a portion of each of the thickened wall portions define a rearward-facing surface of the seal body configured to contact the user's cheeks.

18. The nasal seal of claim 1, wherein a depth of the groove is less than the wall thickness of the thickened wall portion.

19. The nasal seal of claim 1, wherein the region of increased thickness in the bottom wall comprises a pair of struts.

20. The nasal seal of claim 19, wherein each of the pair of struts is located at the end of one of the grooves.

21. The nasal seal of claim 20, further comprising a sub-nasal groove located in the bottom wall of the seal body between the pair of struts.

22. The nasal seal of claim 19, wherein each of the pair of struts has a wall thickness that is different than a wall thickness of an adjacent portion of a front wall and a rear wall of the seal body.

* * * * *